(12) United States Patent
Hildebrand et al.

(10) Patent No.: US 9,110,080 B2
(45) Date of Patent: Aug. 18, 2015

(54) EPITOPE TESTING USING SOLUBLE HLA

(75) Inventors: William H. Hildebrand, Edmond, OK (US); Rico Buchli, Edmond, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 1029 days.

(21) Appl. No.: 13/116,808

(22) Filed: May 26, 2011

(65) Prior Publication Data
US 2014/0093973 A1 Apr. 3, 2014

Related U.S. Application Data

(63) Continuation of application No. 11/451,567, filed on Jun. 12, 2006, now abandoned, which is a continuation-in-part of application No. 11/257,286, filed on Oct. 24, 2005, now abandoned, which is a continuation of application No. 10/095,818, filed on Mar. 11, 2002, now abandoned, said application No. 11/257,286 is a continuation-in-part of application No. 09/974,366, filed on Oct. 10, 2001, now Pat. No. 7,541,429, and a continuation-in-part of application No. 10/022,066, filed on Dec. 18, 2001, now abandoned.

(60) Provisional application No. 60/689,179, filed on Jun. 10, 2005, provisional application No. 60/274,605, filed on Mar. 9, 2001, provisional application No. 60/362,799, filed on Mar. 7, 2002, provisional application No. 60/256,410, filed on Dec. 18, 2000.

(51) Int. Cl.
*G01N 33/68* (2006.01)
*G01N 33/569* (2006.01)
*G01N 33/533* (2006.01)

(52) U.S. Cl.
CPC ...... *G01N 33/6878* (2013.01); *G01N 33/56977* (2013.01); *G01N 2333/70539* (2013.01)

(58) Field of Classification Search
None
See application file for complete search history.

(56) References Cited

U.S. PATENT DOCUMENTS

| | | | |
|---|---|---|---|
| 4,683,202 A | 7/1987 | Mullis | |
| 5,256,541 A | 10/1993 | Pouletty et al. | |
| 5,270,169 A | 12/1993 | Chang et al. | |
| 5,292,641 A | 3/1994 | Pouletty | |
| 5,482,841 A | 1/1996 | Buelow | |
| 5,582,031 A | 12/1996 | Rathbone | |
| 5,710,248 A | 1/1998 | Grose | |
| 5,750,367 A | 5/1998 | Chan | |
| 5,776,746 A | 7/1998 | Denney, Jr. | |
| 5,798,209 A | 8/1998 | Chan | |
| 5,830,995 A | 11/1998 | Shoyab et al. | |
| 6,001,365 A | 12/1999 | Peterson et al. | |
| 6,232,445 B1 | 5/2001 | Rhode et al. | |
| 6,255,073 B1 | 7/2001 | Cai et al. | |
| 2003/0096298 A1 | 5/2003 | Barnea et al. | |
| 2003/0124613 A1* | 7/2003 | Hildebrand et al. | 435/7.1 |
| 2006/0040310 A1 | 2/2006 | Hildebrand et al. | |

FOREIGN PATENT DOCUMENTS

| | | |
|---|---|---|
| WO | WO93/17095 | 9/1993 |
| WO | WO 95/11702 | 5/1995 |
| WO | WO 97/46256 | 12/1997 |
| WO | WO 98/06749 | 2/1998 |
| WO | WO 00/23053 | 4/2000 |

OTHER PUBLICATIONS

Buchli et al (Biochemistry, 2004, 43(46): 14852-14863).*
"Molecular Cloning a Laboratory Manual", Maniatis et al., Selected Text "RNA-Dependent DNA Polymerase" p. 129, "Isolation of mRNA from Mammalian Cells" pp. 191-193, Cold Harbor Spring Laboratory (1982).
"HIV-1 Reverse Transcriptase Is a Target for Cytotoxic T Lymphocytes in Infected Individuals", Walker et al., Science, 240(4848):64-66 (1988).
"Assembly of MHC Class I Molecules Analyzed in Vitro", Townsend et al., Cell, 62(6):285-295 (1990).
"Allele-Specific Motifs Revealed by Sequencing of Self-Peptides Eluted From MHC Molecules", Falk et al., Nature, 351(6324):290-296, (1991).
"Characterization of Peptides Bound to the Class I MHC Molecule HLA-A2.1 by Mass Spectrometry", Hunt et al., Science, 255(5049):1261-1263 (1992).
"Peptide Binding to HLA-A2 and HLA-B27 Isolated From *Escherichia coli*", Parker et al., The Journal of Biological Chemistry, 267(8):5451-5459 (1992).
"Endogenous Peptides of Soluble Major Histocompatibility Complex Class I Molecule, H-2Lds: Sequence Motif, Quantitative Binding, and Molecular Modeling of the Complex", Corr et al., J. Exp. Med., 176(6):1681-1692 (1992).
"The Specificity and Efficiency of Endogenous Peptides in the Induction of HLA Class I Alpha Chain Refolding", Tanigaki, Eur J. Immunol., 22(8):2177-2180 (1992).
"Can One Predict Antigenic Peptides for MHC Class I-Restricted Cytotoxic T Lymphocytes Useful for Vaccination?", Calin-Laurens et al., Vaccine, 11(9): 974-978 (1993).
"Direct Identification of an Endogenous Peptide Recognized by Multiple HLA-A2.1-Specific Cytotoxic T Cells", Henderson et al., Proc. Natl. Acad. Sci. USA, 90:10275-10279 (1993).

(Continued)

*Primary Examiner* — Gerald R Ewoldt
*Assistant Examiner* — Marianne Dibrino
(74) *Attorney, Agent, or Firm* — Dunlap Codding, P.C.

(57) ABSTRACT

The present invention relates generally to a methodology for assaying the binding of a peptide to an individual, specific, soluble HLA molecule using fluorescence polarization. The peptides utilized in the method may be identified by indirect methods utilizing T lymphocytes, or by a direct method of epitope discovery described herein.

12 Claims, 60 Drawing Sheets

(56) References Cited

OTHER PUBLICATIONS

"Characterization of Endogenous Peptides Eluted From the Class I MHC Molecule HLA-B7 Determined by Mass Spectrometry and Computer Modeling", Huczko et al., J. Immunol., 151(5):2572-2587 (1993).

"Peptide Binding to the Most Frequent HLA-A Class I Alleles Measured by Quantitative Molecular Binding Assays", Sette et al., Molecular Immunology, 31(11): 813-822 (1994).

"Binding of a Peptide Antigen to Multiple HLA Alleles Allows Definition of an A2-Like Supertype", del Guercio et al., J Immunol., 154(2):685-693 (1995).

"An HLA Class I Peptide-Binding Assay Based on Competition for Binding to Class I Molecules on Intact Human B Cells Identification of Conserved HIV-I Polymerase Peptides Binding to HLA-A*0301", van der Burg et al., Human Immunology, 44:189-198 (1995).

"Measuring Interactions of MHC Class I Molecules Using Surface Plasmon Resonance", Khilko et al., J. Immunol. Methods, 183(1):77-94 (1995).

"Peptide Motifs of HLA-B58, B60, B61, and B62 Molecules", Falk et al., Immunogenetics, 41(2-3):165-168 (1995).

"An Empirical Method for the Prediction of T-Cell Epitopes", Davenport et al., Immunogenetics, 42(5):392-397 (1995).

"Detailed Motifs for Peptide Binding to HLA-A*0201 Derived From Large Random Sets of Peptides Using Cellular Binding Assay", Drijfhout et al., Human Immunology, 43(1):1-12, (1995).

"Analysis of the Structure of Naturally Processed Peptides Bound by Class I and Class II Major Histocompatibility Complex Molecules", Appella et al., EXS., 73:105-119 (1995).

"Mapping and Ranking of Potential Cytotoxic T Epitopes in the p53 Protein: Effect of Mutations and Polymorphism on Peptide Binding to Purified and Refolded HLA Molecules", Gnjatic et al., Eur. J. Immunol., 25(6):1638-1642 (1995).

"Simplified High-Sensitivity Sequencing of a Major Histocompatibility Complex Class I-Associated Immunoreactive Peptide Using Matrix-Assisted Laser Desorption/Ionization Mass Spectrometry", Woods et al., 226(1):15-25 (1995).

"Probing HLA-B7 Conformational Shifts Induced by Peptide-Binding Groove Mutations and Bound Peptide With Anti-HLA Monoclonal Antibodies", Smith et al., 157(6):2470-2478 (1996).

"HLA Allele Selection for Designing Peptide Vaccines", Kamalakar et al, Genetic Analysis: Biomolecular Engineering, 13:81-86 (1996).

"Class I-Restricted Presentation of an HIV-1 gp41 Epitope Containing an N-Linked Glycosylation Site. Implications for the Mechanism of Processing of Viral Envelope Proteins", Ferris et al., J Immunol., 156(2):834-840 (1996).

"Evaluation of Hollow Fiber Bioreactors as an Alternative to Murine Ascites Production for Small Scale Monoclonal Antibody Production", Jackson et al., J. Immunol. Methods, 189(2):217-231 (1996).

"T-Cell Epitope Determination", Walden, Curr Opin Immunol., 8(1):68-74 (1996).

"Large-Scale Production of Class I Bound Peptides: Assigning a Signature to HLA-B*1501", Prilliman et al., Immunogentics, 45(6):379-385 (1997).

"HLA Class I Binding Motifs Derived From Random Peptide Libraries Differ at the COOH Terminus From Those of Eluted Peptides", Davenport et al., J. Exp. Med., 185(2): 367-371 (1997).

"Stability of Emtpy and Peptide-Loaded Class II Major Histocompatibility Complex Molecules at Neutral and Endosomal pH: Comparison to Class I Proteins", Reich et al., Proc. Natl. Acad. Sci. USA, 94:2495-2500 (1997).

"Human Peptide Transporter Deficiency: Importance of HLA-B in the Presentation of Tap-Independent EBV Antigens", de la Salle et al., J. Immunol., 158(10):4555-4563 (1997).

"A Novel, Highly Efficient Peptide-HLA Class I Binding Assay Using Unfolded Heavy Chain Molecules: Identification of HIV-1 Derived Peptides That Bind to HLA-A*0201 and HLA-A*0301", Tan et al., J. Immunol. Methods, 205(2): 201-209 (1997).

"Synthetic Peptides Based on *Chlamydia trachomatis* Antigens Identify Cytotoxic T Lymphocyte Responses in Subjects From a Trachoma-Endemic Population", Holland et al., Clin. Exp. Immunol., 107(1):44-49 (1997).

"Complexity Among Constituents of the HLA-B*1501 Peptide Motif", Prilliman et al., Immunogenetics, 48:89-97 (1998).

"A Microcapillary Column Switching HPLC—Electrospray Ionization MS System for the Direct Identification of Peptides Presented by Major Histocompatibility Complex Class I Molecules", van der Heeft et al., Anal. Chem., 70:3742-3751 (1998).

"Synthetic Peptides of Human Papillomavirus Type 18 E6 Harboring HLA-A2.1 Motif Can Induce Peptide-Specific Cytotoxic T-Cells From Peripheral Blood Mononuclear Cells of Healthy Donors", Yoon et al., Virus Research, 54:23-29 (1998).

"MHCPEP, A Database of MHC-Binding Peptides: Update 1997", Brusic et al., Nucleic Acids Research, 26(1): 368-371 (1998).

"Prediction of MHC Class II-Binding Peptides Using an Evolutionary Algorithm and Artificial Neural Network", Brusic et al., Bioinformatics, 14(2): 121-130 (1998).

"Efficient Generation of Major Histocompatibility Complex Class I-Peptide Complexes Using Synthetic Peptide Libraries", Stevens et al., The Journal of Biological Chemistry, 273(5):2874-2884 (1998).

"Neural Network-Based Prediction of Candidate T-Cell Epitopes", Honeyman et al., Nat. Biotechnol., 16(10): 966-969 (1998).

"Direct Identification of Major Histocompatibility Complex Class I-Bound Tumor-Associated Peptide Antigens of a Renal Carcinoma Cell Line by a Novel Mass Spectrometric Method", Flad et al., Cancer Research, 58(24):5803-5811 (1998).

"Structure and Function of a Membrane-Bound Murine MHC Class I Molecule", Celia et al., Proc. Natl. Acad. Sci. USA, 96:5634-5639 (1999).

"Identification of HLA-A3 and -B7-Restricted CTL Response to Hepatitis C Virus in Patients With Acute and Chronic Heptitis C", Chang et al., J. Immunol., 162(2):1156-1164 (1999).

"HLA-B15 Peptide Ligands Are Preferentially Anchored at Their C Termini", Prilliman et al., J. Immunol., 162(12):7277-7284 (1999).

"Alpha-2 Domain Polymorphism and HLA Class I Peptide Loading", Prilliman et al., Tissue Antigens, 54(5):450-460 (1999).

"Syfpeithi: A Database for MHC Ligands and Peptide Motifs", Rammensee et al., Immunogenetics, 50:213-219 (1999).

"Peptide Motif of the Class I Molecule HLA-B*1503", Prilliman et al., Immunogenetics, 49:144-146 (1999).

"Clad Against All Clades—Can Vaccinomics Build a World HIV Vaccine?", Holton, The Scientist, 14(18):1 (2000).

"Human Immunology—26$^{th}$ Annual ASHI Meeting Abstracts 2000", 61: Supplement 2 (2000).

"C-Terminal Epitope Tagging Facilitates Comparative Ligand Mapping From MHC Class I Positive Cells", Hickman et al., Human Immunology, 61:1339-1346 (2000).

"FIMM, a database of functional molecular immunology", C Schonbach et al., Nucleic Acids Research, vol. 28, No. 1, Jan. 2000, pp. 222-224, XP002242984 Oxford, UK figure 1; table 1.

"Rapid Determination of HLA B*07 Ligands From the West Nile Virus NY99 Genome", De Groot et al., Emerging Infectious Diseases, 7(4):706-713 (2001).

"Examination of Possible Structural Constraints of MHC-Binding Peptides by Assessment of Their Native Structure Within Their Source Proteins", Schueler-Furman et al., Proteins: Structure, Function, and Genetics, 45:47-54 (2001).

"Use of Fluorescence Polarization to Monitor MHC-Peptide Interactions in Solution", Dedier et al., Journal of Immunological Methods, 255:57-66 (2001).

"Neural Network Method for Predicting Peptides That Bind Major Histocompatibility Complex Molecules", Gulukota et al., Methods Mol. Biol., 156:201-209 (2001).

"Generic Liposome Reagent for Immunoassays", Plant et al., Analytical Biochemistry, vol. 176, Issue 2, pp. 420-426 (1989).

"Dissociation of the Peptide-MHC Class I Complex Limits the Binding Rate of Exogenous Peptide", Ojcius et al., Journal of Immunology, vol. 151, No. 11, pp. 6020-6026 (1993).

Dissociation of the Peptide/MHC Class I Complex: pH Dependence and Effect of Endogenous Peptides on the Activation Energy, Ojcius

(56) References Cited

OTHER PUBLICATIONS et al., Biochemical and Biophysical Research Communications, vol. 197, No. 3, pp. 1216-1222 (1993).
"Role of HLA-A Motifs in Identification of Potential CTL Epitopes Inhuman Papillomavirus Type 16 E6 and E7 Proteins", Kast et al., Journal of Immunology, vol. 152, No. 8, pp. 3904-3912 (1994).
"The Accessibility of Peptides Bound to the Mouse MHC Class II Molecule IE-d Studied by Fluorescence", de Kroon et al., Federation of European Biochemical Societies Letters, vol. 342, No. 3, pp. 230-234 (1994).
"A New Murine Lymphocytotoxic Monoclonal Antibody Recognizing HLA-A2, -A28 and -A9", Mizuno et al., Tissue Antigens, 48:224-227 (1996).
"The Use of Magnetic Beads Coated With Soluble HLA Class I or Class II Proteins in Antibody Screening and for Specificity Determination of Donor-Reactive Antibodies", Sumitran-Karuppan et al., Transplantation, 61(10):1539-1546 (1996).
"Antibody Screening by Enzyme-Linked Immunosorbent Assay Using Pooled Soluble HLA in Renal Transplant Candidates", Zaer et al., Transplantation, 63(1):48-51 (1997).
"A Mutant Human $B_2$-Microglobulin Can Be Used to Generate Diverse Multmeric Class I Peptide Complexes as Specific Probes Fort Cell Receptors", Walter et al., Journal of Immunological Methods 214:41-50 (1998).
"In Vitro Induction of Specific Cytotoxic T Lymphocytes Using Recombinant Single-Chain MHC Class I/Peptide Complexes", Lone et al., Journal of Immunotherapy, 21(4):283-294 (1998).
"In Vitro Peptide Binding to Soluble Empty Class I Major Histocompatibility Complex Molecules Isolated From Transfected *Drosophila melanogaster* Cells", Matsumura et al., The Journal of Biological Chemistry, vol. 267, ISS Nov. 25:23589-23595 (1992).
"Prediction of Well-Conserved HIV-1 Ligands Using a Matrix-Based Algorithm, Epimatrix", Schafer et al., Vaccine, 16(19):1880-1884 (1998).
"Molecular Cloning a Laboratory Manual", Maniatis et al., Selected Text "Synthesis and Cloning of DNA" vol. 1, pp. 211-246, Cold Harbor Spring Laboratory (1982).
"A Soluble Divalent Class I Major Histocompatibility Complex Molecule Inhibits Aloreactive T Cells At Nonmolar Concentrations", Dal Porto et al., Proc. Natl. Acad. Sci. USA, 90:6671-6675 (1993).
"Targeted Amplification of Alternatively Spliced Transcripts of Major Histocompatibility Complex Class I Heavy Chain", Yang et al., Journal of Immunological Methods, 175:265-279 (1994).
"Unisyn Strives for Flexibility and Scale", Prompt, Membrane and Separation Technology News, ISSN 0737-8483, Mar. 1, 1998.
"Thermal Stability Comparison of Purified Empty and Peptide-Filled Forms of a Class I MHC Molecule", Fahnstock et al., Science 258: 1658-1662 (1992).
"Prominent Role of Secondary Anchor Residues in Peptide Binding to HLA-A2.1 Molecules", Ruppert et al., Cell 74: 929-937 (1993).

Real-Time Measurement of Antigenic Peptide Binding to Empty and Preloaded Single-Chain Major Histocompatibility Complex Class I Molecules, Ojcius et al., Eur. J. Immunol. 23: 1118-1124 (1993).
pET System Manual. $6^{th}$ Edition., Novagen, pp. 2-8 and 22-23 (1995).
"Isolation and Rapid Identification of an Abundant Self-Peptide From Class II HLA-DRB1 *0401 Alleles Induced by Measles Vaccine Virus Infection", Ovsyannikova et al., J. Imm. Meth. 246: 1-12 (2000).
"The HLA-B14 Peptide Binding Site Can Accommodate Peptides With Different Combinations of Anchor Residues", J. Biol. Chem. 269 (1): 32426-32434 (1994), DiBrino et. al.
"Development and Validation of a Fluorescence Polarization-Based Competitive Peptide-Binding Assay for HLA-A *0201—A New Tool for Epitope Discovery", Buchli et al., *Biochemistry* 44:12491-12507 (2004).
"Competition-Based Cellular Peptide Binding Assay for HLA Class I", Kessler et al., Curr. Protocols in Immunol., 18.12.1-18.12-15 (2004).
"Efficient Site Specific Removal of a C-Terminal Flag Fusion From a FAB' Using Copper(II) Ion Catalysed Protein Cleavage", Humphreys et al., Protein Eng., 12)2): 179-184 (1999).
"Membrane-Type 1 Matrix Metalloproteinase Cytoplasmic Tail-Binding Protein-1 Is a New Member of the Cupin Superfamily a Possible Multifunctional Protein Acting as an Invasion Suppressor Down-Regulated in Tumors", Uekita et al., J. Biol. Chem., 279:12734-12743 (2004).
"Focis Abstract Supplement", VanGundy et al., Clin. Immunol., 115:S3-S282, Abstract Sa2.82 (2005).
Heterogeneous Expression of the Tumor-Associated Antigens Rage-1, Prame, and Glycoprotein 75 in Human Renal Cell Carcinoma: Candidates for T-Cell-Based Immunotherapeis?, Neumann et al., Canc. Res. 58: 4090-4095 (1998).
Yang et al.; "Targeted amplification of alternatively spliced transcripts of major histocompatibility complex class I heavy chain"; J Immunol Methods, vol. 176, pp. 265-270 (1994).
Fujii et al.; "A soluble form of the HLA-G antigen is encoded by a messenger ribonucleic acid containing intron 4"; J Immunol Methods, vol. 153, pp. 5516-5524 (1994).
Johnson et al.; "Rapid cloning of HLA class I cDNAs by locus specific PCR"; J Immunol Methods, vol. 233, pp. 119-129 (Jan. 2000).
Bainbridge et al.; "The short forms of HLA-G are unlikely to play a role in pregnancy because they are not expressed at the cell surface"; J Reprod Immunol, vol. 47, pp. 1-16 (May 2000).
Cereb et al.; "Induction of microvariant specific CTL lines reactive to a single amino acid mismatch in bulk cultures using a transfectant expressing a single HLA class I molecule"; J Immunol, vol. 156, pp. 18-26 (1996).
Office Action, dated Mar. 12, 2012 from co-pending Canadian Application No. 2,438,376.

\* cited by examiner

B2M QUALITY CONTROL
Dose-response curve of sHLA-A*3101T (E15) using 2.2 nM of FITC-labeled peptide P2(A*0301) b2m (FITZ3)

B2M QUALITY CONTROL

Dose-response curve of sHLA-A*4301T (1272) using 2.0 nM of FITC-labeled peptide P2(A*0101) b2m (FITZ3)

B2M QUALITY CONTROL

Dose-response curve of sHLA-A*6801T (5130) using 2.6 nM of FITC-labeled peptide P2(A*0301) b2m (FITZ3)

B2M QUALITY CONTROL
Dose-response curve of sHLA-A*7401T (G17)
using 2.3 nM of FITC-labeled peptide P2(A*0301)
b2m (FITZ3)

B2M QUALITY CONTROL
Dose-response curve of sHLA-B*1501T (1876) using 2.1 nM of FITC-labeled peptide P2(A*0101) b2m (FITZ3)

B2M QUALITY CONTROL
Dose-response curve of sHLA-B*1801T (2568) using 1.8 nM of FITC-labeled peptide P2(B*4402) b2m (FITZ3)

B2M QUALITY CONTROL
Dose-response curve of sHLA-B*3505T (C20) using 4.1 nM of FITC-labeled peptide P1(A*0201) b2m (FITZ3)

B2M QUALITY CONTROL
Dose-response curve of sHLA-B5602T (1182) using 4.1 nM of FITC-labeled peptide P1(A*0201) b2m (FITZ3)

B2M QUALITY CONTROL
Dose-response curve of sHLA-Cw*0801T (3427) using 3.4 nM of FITC-labeled peptide P1(A*0201) b2m (FITZ3)

FIGURE 62

| Supertypes | | | | | | | | | | | |
|---|---|---|---|---|---|---|---|---|---|---|---|
| A1 | | A2/B62 | | A3 | | A24 | | B7 | | B44 | |
| Overview | | | | | | | | | | | |
| A1 Peptide | | A2 Peptides | | A3 Peptides | | A24 Peptide | | B7 Peptides | | B44 Peptides | |
| A*0101 | (2/2) | A*0201 | (4/4) | A*1102 | (3/3) | A*2402 | (1/1) | B*0702 | (2/2) | | |
| A*2902 | (2/2) | B*1302 | (4/4) | A*6801 | (2/3) | | | B*3505 | (2/2) | | |
| A*3601 | (1/2) | Cw*0801 | (4/4) | A*0301 | (3/2) | | | B*5301 | (1/2) | | |
| | | A*4301 | (2/4) | A*3402 | (2/3) | | | B*5602 | (2/2) | | |
| | | A*6901 | (3/4) | A*3101 | (2/3) | | | | | | |
| | | B*5602 | (2/4) | | | | | | | | |
| | | | | | | | | | | | |
| A*1102 | (1/2) | B*1501 | (2/4) | A*2902 | (1/3) | A*2902 | (1/1) | B*5501 | (1/2) | B*1801 | (11/12) |
| A*2601 | (1/2) | A*2902 | (1/4) | A*6601 | (1/3) | A*2301 | (1/1) | B*1508 | (1/2) | B*4002 | (8/12) |
| B*1501 | (1/2) | A*1102 | (1/4) | B*1501 | (1/3) | A*6601 | (1/1) | | | B*3701 | (2/12) |
| A*4301 | (1/2) | B*3505 | (1/4) | | | Cw*0801 | (1/1) | | | B*4001 | (8/12) |
| | | B*1512 | (2/4) | | | B*4501 | (1/1) | | | B*1501 | (1/1) |
| | | B*4002 | (2/4) | | | | | | | | |
| | | A*2601 | (1/4) | | | | | | | | |
| | | Cw*0304 | (1/4) | | | | | | | | |
| | | | | | | | | | | | |
| B*1516 | (1/1) | A*2402 | (1/4) | A*7401 | (2/3) | B*1501 | (1/1) | B*0801 | (1/2) | | |
| A*3402 | (1/1) | B*5101 | (1/4) | A*2501 | (1/3) | | | | | | |

BOLD  Sette agreement

EPITOPE TESTING USING SOLUBLE HLA

CROSS-REFERENCE TO RELATED APPLICATIONS

This application is a continuation of U.S. Ser. No. 11/451,567, filed Jun. 12, 2006, now abandoned; which claims benefit under 35 U.S.C. 119(e) of provisional application U.S. Ser. No. 60/689,179, filed Jun. 10, 2005; the contents of which are hereby expressly incorporated herein by reference in their entirety.

This application is also a continuation-in-part of U.S. Ser. No. 11/257,286, filed Oct. 24, 2005, now abandoned; which is a continuation of U.S. Ser. No. 10/095,818, filed Mar. 11, 2002, now abandoned; which claims priority under 35 U.S.C. §119(e) of provisional U.S. Ser. No. 60/274,605, filed Mar. 9, 2001, and provisional U.S. Ser. No. 60/362,799, filed Mar. 7, 2002. Said application U.S. Ser. No. 11/257,286 is also a continuation-in-part of U.S. Ser. No. 09/974,366, filed Oct. 10, 2001, now U.S. Pat. No. 7,541,429, issued Jun. 2, 2009; and is also a continuation-in-part of U.S. Ser. No. 10/022,066, filed Dec. 18, 2001, now abandoned; which claims benefit of provisional application U.S. Ser. No. 60/256,410, filed Dec. 18, 2000. The contents of each of the above-listed patent applications are hereby expressly incorporated in their entirety by reference.

STATEMENT REGARDING FEDERALLY SPONSORED RESEARCH OR DEVELOPMENT

Not Applicable.

BACKGROUND OF THE INVENTION

1. Field of the Invention

The present invention relates generally to a methodology of epitope testing for the identification of peptides that bind to an individual soluble MHC Class I or Class II molecule.

2. Description of the Background Art

Class I major histocompatibility complex (MHC) molecules, designated HLA class I in humans, bind and display peptide antigen ligands upon the cell surface. The peptide antigen ligands presented by the class I MHC molecule are derived from either normal endogenous proteins ("self") or foreign proteins ("nonself") introduced into the cell. Nonself proteins may be products of malignant transformation or intracellular pathogens such as viruses. In this manner, class I MHC molecules convey information regarding the internal fitness of a cell to immune effector cells including but not limited to, CD8$^+$ cytotoxic T lymphocytes (CTLs), which are activated upon interaction with "nonself" peptides, thereby lysing or killing the cell presenting such "nonself" peptides.

Class II MHC molecules, designated HLA class II in humans, also bind and display peptide antigen ligands upon the cell surface. Unlike class I MHC molecules which are expressed on virtually all nucleated cells, class II MHC molecules are normally confined to specialized cells, such as B lymphocytes, macrophages, dendritic cells, and other antigen presenting cells which take up foreign antigens from the extracellular fluid via an endocytic pathway. The peptides they bind and present are derived from extracellular foreign antigens, such as products of bacteria that multiply outside of cells, wherein such products include protein toxins secreted by the bacteria that often times have deleterious and even lethal effects on the host (e.g., human). In this manner, class II molecules convey information regarding the fitness of the extracellular space in the vicinity of the cell displaying the class II molecule to immune effector cells, including but not limited to, CD4$^+$ helper T cells, thereby helping to eliminate such pathogens the examination of such pathogens is accomplished by both helping B cells make antibodies against microbes, as well as toxins produced by such microbes, and by activating macrophages to destroy ingested microbes.

Class I and class II HLA molecules exhibit extensive polymorphism generated by systematic recombinatorial and point mutation events; as such, hundreds of different HLA types exist throughout the world's population, resulting in a large immunological diversity. Such extensive HLA diversity throughout the population results in tissue or organ transplant rejection between individuals as well as differing susceptibilities and/or resistances to infectious diseases. HLA molecules also contribute significantly to autoimmunity and cancer. Because HLA molecules mediate most, if not all, adaptive immune responses, large quantities of pure isolated HLA proteins are required in order to effectively study transplantation, autoimmunity disorders, and for vaccine development.

There are several applications in which purified, individual class I and class II MHC proteins are highly useful. Such applications include using MHC-peptide multimers as immunodiagnostic reagents for disease resistance/autoimmunity; assessing the binding of potentially therapeutic peptides; elution of peptides from MHC molecules to identify vaccine candidates; screening transplant patients for preformed MHC specific antibodies; and removal of anti-HLA antibodies from a patient. Since every individual has differing MHC molecules, the testing of numerous individual MHC molecules is a prerequisite for understanding the differences in disease susceptibility between individuals. Therefore, purified MHC molecules representative of the hundreds of different HLA types existing throughout the world's population are highly desirable for unraveling disease susceptibilies and resistances, as well as for designing therapeutics such as vaccines.

Class I HLA molecules alert the immune response to disorders within host cells. Peptides, which are derived from viral- and tumor-specific proteins within the cell, are loaded into the class I molecule's antigen binding groove in the endoplasmic reticulum of the cell and subsequently carried to the cell surface. Once the class I HLA molecule and its loaded peptide ligand are on the cell surface, the class I molecule and its peptide ligand are accessible to cytotoxic T lymphocytes (CTL). CTL survey the peptides presented by the class I molecule and destroy those cells harboring ligands derived from infectious or neoplastic agents within that cell.

While specific CTL targets have been identified, little is known about the breadth and nature of ligands presented on the surface of a diseased cell. From a basic science perspective, many outstanding questions have permeated through the art regarding peptide exhibition. For instance, it has been demonstrated that a virus can preferentially block expression of HLA class I molecules from a given locus while leaving expression at other loci intact. Similarly, there are numerous reports of cancerous cells that fail to express class I HLA at particular loci. However, there is no data describing how (or if) the three classical HLA class I loci differ in the immunoregulatory ligands they bind. It is therefore unclear how class I molecules from the different loci vary in their interaction with viral- and tumor-derived ligands and the number of peptides each will present.

Discerning virus- and tumor-specific ligands for CTL recognition is an important component of vaccine design. Ligands unique to tumorigenic or infected cells can be tested and incorporated into vaccines designed to evoke a protective CTL response. Several methodologies are currently employed to identify potentially protective peptide ligands. One approach uses T cell lines or clones to screen for biologically active ligands among chromatographic fractions of eluted peptides (Cox et al., Science, 264:716-719 (1994), which is expressly incorporated herein by reference in its entirety). This approach has been employed to identify peptides ligands specific to cancerous cells. A second technique utilizes predictive algorithms to identify peptides capable of binding to a particular class I molecule based upon previously determined motif and/or individual ligand sequences (De Groot et al., Emerging Infectious Diseases, 7:4 (2001), which is expressly incorporated herein by reference in its entirety). Peptides having high predicted probability of binding from a pathogen of interest can then be synthesized and tested for T cell reactivity in precursor, tetramer or ELISpot assays.

However, there has been no readily available source of individual HLA molecules. The quantities of HLA protein available have been small and typically consist of a mixture of different HLA molecules. Production of HLA molecules traditionally involves growth and lysis of cells expressing multiple HLA molecules. Ninety percent of the population is heterozygous at each of the HLA loci; codominant expression results in multiple HLA proteins expressed at each HLA locus. To purify native class I or class II molecules from mammalian cells requires time-consuming and cumbersome purification methods, and since each cell typically expresses multiple surface-bound HLA class I or class II molecules, HLA purification results in a mixture of many different HLA class I or class II molecules. When performing experiments using such a mixture of HLA molecules or performing experiments using a cell having multiple surface-bound HLA molecules, interpretation of results cannot directly distinguish between the different HLA molecules, and one cannot be certain that any particular HLA molecule is responsible for a given result. Therefore, prior to the present invention, a need existed in the art for a method of producing substantial quantities of individual HLA class I or class II molecules so that they can be readily purified and isolated independent of other HLA class I or class II molecules. Such individual HLA molecules, when provided in sufficient quantity and purity as described herein, provides a powerful tool for studying and measuring immune responses.

Therefore, there exists a need in the art for improved methods of assaying binding of peptides to class I and class II MHC molecules to identify epitopes that bind to specific individual class I and class II MHC molecules, as well as methods of detecting overlapping peptide binding capacities of multiple MHC molecules. The present invention solves this need by coupling the production of soluble HLA molecules with epitope isolation, discovery, and testing methodologies.

BRIEF DESCRIPTION OF THE DRAWINGS

FIG. 15 illustrates the screening of HLA A, B and C alleles for cross-reactivity evaluation. A panel of 48 distinct sHLA alleles was tested to determine the specificity of the present invention's designed peptides to sHLA-A*0201 and to elaborate cross-reactivity to other sHLA allele specificities. FP values are obtained using a more simplified binding protocol without addition of β2m. Each peptide candidate (10 nM) was incubated with 100 μg/ml of activated sHLA and peptide/HLA interaction was monitored over time. Final equilibrium polarization levels indicating the extent of binding to each allele after incubation with each of the five test peptides is shown. A threshold line of 29.3 mP was introduced, which corresponds to the completely free state (and lowest polarization value) of the labeled ligand. (A) In this graph, twenty HLA-A, and two HLA-C were tested of which sHLA-A*0201, and sHLA-Cw*0801 showed highest reactivity followed by less effective binders such as sHLA-A*4301, sHLA-A*6801 and sHLA-A*6901. The insert visualizes the time-course of association for peptide P3 to sHLA-A*0201(‡) and P5 to sHLA-A*1102(*). (B) No significant binding was detected to any of the B-alleles tested.

FIG. 62 illustrates the classification of a variety of peptides into six supertypes, A1, A2, A3, A24, B7, and B44, based on the result of a FP-based peptide binding assay binding assay in which the variety of peptides were FITC-labeled and tested against 53 MHC class I molecules.

DETAILED DESCRIPTION OF THE INVENTION

Figure 1:
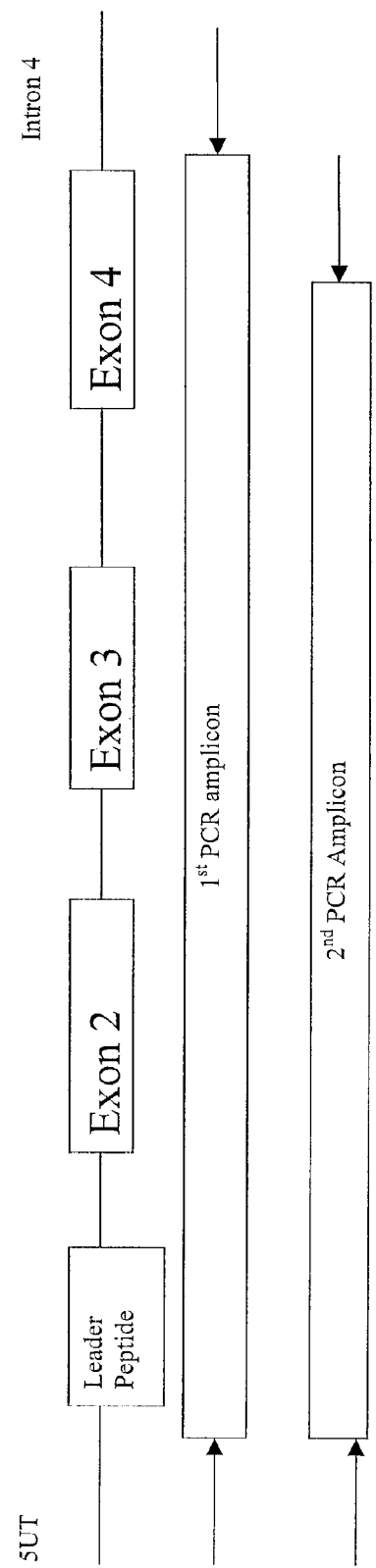
FIG. 1 is an overview of a two stage PCR strategy to amplify a truncated version of the human class I MHC.

Before explaining at least one embodiment of the invention in detail by way of exemplary drawings, experimentation, results, and laboratory procedures, it is to be understood that the invention is not limited in its application to the details of construction and the arrangement of the components set forth in the following description or illustrated in the drawings, experimentation and/or results. The invention is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

The present invention combines methodologies for assaying the binding of peptide epitopes to individual, soluble MHC molecules with methodologies for the production of individual, soluble MHC molecules and with a method of epitope discovery and comparative ligand mapping (including methods of distinguishing infected/tumor cells from uninfected/non-tumor cells). The method of production of individual, soluble MHC molecules has previously been described in detail in parent application U.S. Ser. No. 10/022,066, filed Dec. 18, 2001, entitled "METHOD AND APPARATUS FOR THE PRODUCTION OF SOLUBLE MHC ANTIGENS AND USES THEREOF," the contents of which have previously been expressly incorporated in their entirety by reference. The method of epitope discovery and comparative ligand mapping has previously been described in detail in parent application U.S. Ser. No. 09/974,366, filed Oct. 10, 2001, entitled "COMPARATIVE LIGAND MAPPING FROM MHC CLASS I POSITIVE CELLS", the contents of which have previously been expressly incorporated in their entirety by reference. A brief description of each of these methodologies is included herein below for the purpose of exemplification and should not be considered as limiting.

The present invention is related to a method of assaying a peptide for binding to an individual class I molecule. The method includes providing a peptide of interest and providing individual soluble class I molecule-endogenous peptide complexes in which individual soluble class I molecules have endogenous peptides loaded therein. The peptide of interest and the individual soluble class I molecules are mixed together, and individual soluble class I molecule-peptide of interest complexes, wherein the individual soluble class I molecules have the peptide of interest loaded therein, are identified. The individual soluble class I molecule-endogenous peptide complexes may be treated under conditions that cause the individual soluble class I molecules to release the endogenous peptides prior to mixing the peptide of interest with the individual soluble class I molecules, and such method of treating may involve heating the individual soluble class I molecule-endogenous peptide complexes to cause the individual soluble class I molecules to release the endogenous peptides.

The peptide of interest may be labeled using a radiolabel or a fluorescent label to allow identification of individual soluble class I molecule-peptide of interest complexes from unbound peptide of interest. When a fluorescent label is utilized, the individual soluble class I molecule-peptide of interest complexes may be identified by any of the methods of fluorescence detection known in the art, such as by fluorescence polarization. Alternatively, the individual soluble class I molecule-fluorescence labeled peptide of interest may be isolated using an antibody against the individual soluble class I molecule. When a radiolabel is utilized, the individual soluble class I molecule-peptide of interest complexes may be isolated away from unbound peptide of interest, such as by gel filtration. Alternatively, the individual soluble class I molecule-peptide of interest complexes may be identified using an antibody that recognizes the individual soluble class I molecule having a peptide loaded therein.

To produce the individual soluble class I molecule-endogenous peptide complexes, genomic DNA or cDNA encoding at least one class I molecule is obtained, and an allele encoding an individual class I molecule in the genomic DNA or cDNA is identified. The allele encoding the individual class I molecule is PCR amplified in a locus specific manner such that a PCR product produced therefrom encodes a truncated, soluble form of the individual class I molecule. The PCR product is then cloned into an expression vector, thereby forming a construct that encodes the individual soluble class I molecule, and the construct is transfected into a cell line to provide a cell line containing a construct that encodes an individual soluble class I molecule. The cell line must be able to naturally process proteins into peptide ligands capable of being loaded into antigen binding grooves of class I molecules.

The cell line is then cultured under conditions which allow for expression of the individual soluble class I molecules from the construct, and these conditions also allow for endogenous loading of a peptide ligand into the antigen binding groove of each individual soluble class I molecule prior to secretion of the individual soluble class I molecules from the cell. The secreted individual soluble class I molecules having the endogenously loaded peptide ligands bound thereto are then isolated.

The construct that encodes the individual soluble class I molecule may further encode a tag, such as a HIS tail or a FLAG tail, which is attached to the individual soluble class I molecule and aids in isolating the individual soluble class I molecule.

The peptide of interest may be chosen based on several methods of epitope discovery known in the art. Alternatively, the peptide of interest may be identified by a method for identifying at least one endogenously loaded peptide ligand that distinguishes an infected cell from an uninfected cell. Such method includes providing an uninfected cell line containing a construct that encodes an individual soluble class I molecule, wherein the uninfected cell line is able to naturally process proteins into peptide ligands capable of being loaded into antigen binding grooves of class I molecules. A portion of the uninfected cell line is infected with at least one of a microorganism (such as HIV or HBV), a gene from a microorganism or a tumor gene, thereby providing an infected cell line, and both the uninfected cell line and the infected cell line are cultured under conditions which allow for expression of individual soluble class I molecules from the construct. The culture conditions also allow for endogenous loading of a peptide ligand in the antigen binding groove of each individual soluble class I molecule prior to secretion of the individual soluble class I molecules from the cell. The secreted individual soluble class I molecules having the endogenously loaded peptide ligands bound thereto are isolated from the uninfected cell line and the infected cell line, and the endogenously loaded peptide ligands are separated from the individual soluble class I molecules from both the uninfected cell line and the infected cell line. The endogenously loaded peptide ligands are then isolated from both the uninfected cell line and the infected cell line, and the two sets of endogenously loaded peptide ligands are compared to identify at least one endogenously loaded peptide ligand presented by the individual soluble class I molecule on the infected cell line that is not presented by the individual soluble class I molecule on the uninfected cell line, or to identify at least one endogenously loaded peptide ligand presented by the individual soluble class I molecule on the uninfected cell line that is not presented by the individual soluble class I molecule on the infected cell line.

Following identification of the peptide ligand that distinguishes an infected cell from an uninfected cell, a source protein from which the endogenously loaded peptide ligand is obtained can be identified. Such source protein may be encoded by at least one of the microorganism, the gene from a microorganism or the tumor gene with which the cell line was infected to form the infected cell line, or the source protein may be encoded by the uninfected cell line. When the source protein is encoded by the uninfected cell line, such protein may also demonstrate increased expression in a tumor cell line.

The present invention is also related to a method of assaying a peptide for binding to an individual class I molecule. The method includes providing a first peptide, wherein the first peptide is known to bind to a specific class I molecule, and labeling the first peptide. Individual soluble, specific class I molecules, as described herein above, are provided, and the labeled first peptide is mixed with the individual soluble, specific class I molecules to provide individual soluble, specific class I molecule-labeled first peptide complexes, which are isolated. A second peptide, which is a peptide of interest, is provided and mixed with the individual soluble, specific class I molecule-labeled first peptide complexes, and individual soluble, specific class I molecule-second peptide complexes are identified, wherein the second peptide has displaced the labeled first peptide and the individual soluble, specific class I molecule has the second peptide loaded therein.

The first peptide may be labeled with a radiolabel or a fluorescent label. When labeled with a fluorescent label, the individual soluble, specific class I molecule-second peptide complexes may be identified by fluorescence polarization.

Production of Individual, Soluble MHC Molecules

The methods of the present invention may, in one embodiment, utilize a method of producing MHC molecules (from genomic DNA or cDNA) that are secreted from mammalian cells in a bioreactor unit. Substantial quantities of individual MHC molecules are obtained by modifying class I or class II MHC molecules so that they are capable of being secreted, isolated, and purified. Secretion of soluble MHC molecules overcomes the disadvantages and defects of the prior art in relation to the quantity and purity of MHC molecules produced. Problems of quantity are overcome because the cells producing the MHC do not need to be detergent lysed or killed in order to obtain the MHC molecule. In this way the cells producing secreted MHC remain alive and therefore continue to produce MHC. Problems of purity are overcome because the only MHC molecule secreted from the cell is the one that has specifically been constructed to be secreted. Thus, transfection of vectors encoding such secreted MHC molecules into cells which may express endogenous, surface bound MHC provides a method of obtaining a highly concentrated form of the transfected MHC molecule as it is secreted from the cells. Greater purity is assured by transfecting the secreted MHC molecule into MHC deficient cell lines.

Production of the MHC molecules in a hollow fiber bioreactor unit allows cells to be cultured at a density substantially greater than conventional liquid phase tissue culture permits. Dense culturing of cells secreting MHC molecules further amplifies the ability to continuously harvest the transfected MHC molecules. Dense bioreactor cultures of MHC secreting cell lines allow for high concentrations of individual MHC proteins to be obtained. Highly concentrated individual MHC proteins provide an advantage in that most downstream protein purification strategies perform better as the concentration of the protein to be purified increases. Thus, the culturing of MHC secreting cells in bioreactors allows for a continuous production of individual MHC proteins in a concentrated form.

The method of producing MHC molecules utilized in the present invention and described in detail in U.S. Ser. No. 10/022,066 begins by obtaining genomic or complementary DNA which encodes the desired MHC class I or class II molecule. Alleles at the locus which encode the desired MHC molecule are PCR amplified in a locus specific manner. These locus specific PCR products may include the entire coding region of the MHC molecule or a portion thereof. In one embodiment a nested or hemi-nested PCR is applied to produce a truncated form of the class I or class II gene so that it will be secreted rather than anchored to the cell surface. FIG. 1 illustrates the PCR products resulting from such nested PCR reactions. In another embodiment the PCR will directly truncate the MHC molecule.

Locus specific PCR products are cloned into a mammalian expression vector and screened with a variety of methods to identify a clone encoding the desired MHC molecule. The cloned MHC molecules are DNA sequenced to ensure fidelity of the PCR. Faithful truncated clones of the desired MHC molecule are then transfected into a mammalian cell line. When such cell line is transfected with a vector encoding a recombinant class I molecule, such cell line may either lack endogenous class I MHC molecule expression or express endogenous class I MHC molecules. One of ordinary skill of the art would note the importance, given the present invention, that cells expressing endogenous class I MHC molecules may spontaneously release MHC into solution upon natural cell death. In cases where this small amount of spontaneously released MHC is a concern, the transfected class I MHC molecule can be "tagged" such that it can be specifically purified away from spontaneously released endogenous class I molecules in cells that express class I molecules. For example, a DNA fragment encoding a HIS tail may be attached to the protein by the PCR reaction or may be encoded by the vector into which the PCR fragment is cloned, and such HIS tail, therefore, further aids in the purification of the class I MHC molecules away from endogenous class I molecules. Tags beside a histidine tail have also been demonstrated to work, and one of ordinary skill in the art of tagging proteins for downstream purification would appreciate and know how to tag a MHC molecule in such a manner so as to increase the ease by which the MHC molecule may be purified.

Cloned genomic DNA fragments contain both exons and introns as well as other non-translated regions at the 5' and 3' termini of the gene. Following transfection into a cell line which transcribes the genomic DNA (gDNA) into RNA, cloned genomic DNA results in a protein product thereby removing introns and splicing the RNA to form messenger RNA (mRNA), which is then translated into an MHC protein. Transfection of MHC molecules encoded by gDNA therefore facilitates reisolation of the gDNA, mRNA/cDNA, and protein. Production of MHC molecules in non-mammalian cell lines such as insect and bacterial cells requires cDNA clones, as these lower cell types do not have the ability to splice introns out of RNA transcribed from a gDNA clone. In these instances the mammalian gDNA transfectants of the present invention provide a valuable source of RNA which can be reverse transcribed to form MHC cDNA. The cDNA can then be cloned, transferred into cells, and then translated into protein. In addition to producing secreted MHC, such gDNA transfectants therefore provide a ready source of mRNA, and therefore cDNA clones, which can then be transfected into non-mammalian cells for production of MHC. Thus, the present invention which starts with MHC genomic DNA clones allows for the production of MHC in cells from various species.

A key advantage of starting from gDNA is that viable cells containing the MHC molecule of interest are not needed. Since all individuals in the population have a different MHC repertoire, one would need to search more than 500,000 individuals to find someone with the same MHC complement as a desired individual—such a practical example of this principle is observed when trying to find a donor to match a recipient for bone marrow transplantation. Thus, if it is desired to produce a particular MHC molecule for use in an experiment or diagnostic, a person or cell expressing the MHC allele of interest would first need to be identified. Alternatively, in the method of the present invention, only a saliva sample, a hair root, an old freezer sample, or less than a milliliter (0.2 ml) of blood would be required to isolate the gDNA. Then, starting from gDNA, the MHC molecule of interest could be obtained via a gDNA clone as described herein, and following transfection of such clone into mammalian cells, the desired protein could be produced directly in mammalian cells or from cDNA in several species of cells using the methods of the present invention described herein.

Current experiments to obtain an MHC allele for protein expression typically start from mRNA, which requires a fresh sample of mammalian cells that express the MHC molecule of interest. Working from gDNA does not require gene expression or a fresh biological sample. It is also important to note that RNA is inherently unstable and is not as easily obtained as is gDNA. Therefore, if production of a particular MHC molecule starting from a cDNA clone is desired, a person or cell line that is expressing the allele of interest must traditionally first be identified in order to obtain RNA. Then a fresh sample of blood or cells must be obtained; experiments using the methodology of the present invention show that ≥5 milliliters of blood that is less than 3 days old is required to obtain sufficient RNA for MHC cDNA synthesis. Thus, by starting with gDNA, the breadth of MHC molecules that can be readily produced is expanded. This is a key factor in a system as polymorphic as the MHC system; hundreds of MHC molecules exist, and not all MHC molecules are readily available. This is especially true of MHC molecules unique to isolated populations or of MHC molecules unique to ethnic minorities. Starting class I or class II MHC molecule expression from the point of genomic DNA simplifies the isolation of the gene of interest and insures a more equitable means of producing MHC molecules for study; otherwise, one would be left to determine whose MHC molecules are chosen and not chosen for study, as well as to determine which ethnic population from which fresh samples cannot be obtained and therefore should not have their MHC molecules included in a diagnostic assay.

While cDNA may be substituted for genomic DNA as the starting material, production of cDNA for each of the desired HLA class I types will require hundreds of different, HLA typed, viable cell lines, each expressing a different HLA class I type. Alternatively, fresh samples are required from individuals with the various desired MHC types. The use of genomic DNA as the starting material allows for the production of clones for many HLA molecules from a single genomic DNA sequence, as the amplification process can be manipulated to mimic recombinatorial and gene conversion events. Several mutagenesis strategies exist whereby a given class I gDNA clone could be modified at either the level of gDNA or at the cDNA resulting from this gDNA clone. The process of producing MHC molecules utilized in the present invention does not require viable cells, and therefore the degradation which plagues RNA is not a problem.

Method of Epitope Testing

Utilizing the production of individual soluble MHC proteins described herein previously, a method of epitope testing has been developed. Such a method of epitope testing is advantageous because of the single specificities of the soluble HLA molecules produced in the manner described herein. Previous work in this area has used mixtures of different HLA molecules to purify or separate out individual class I or class II HLA molecules from the mixture. However, such purification steps result in selective purification of particular endogenously loaded peptide/HLA complexes while not purifying the same HLA molecule complexed with a different peptide. Such selective purification will bias the endogenously loaded peptides in the HLA molecules. For example, typical purification methods involve the use of antibodies, which may recognize certain peptides loaded in HLA molecules and not others. In addition, such purification steps may not remove all of the other class I and class II HLA molecules, leaving these proteins to skew data and its interpretation. Therefore, the antibody may not recognize all of a particular class I or class II HLA because of the peptide bound therein. Using individual, soluble HLA molecules produced in accordance with the present invention in the methods of epitope testing described herein, the individual, soluble HLA molecules are endogenously loaded with thousands of naturally produced peptides, and the pool of such individual, soluble HLA molecules is not biased in the peptide cargo loaded therein.

The goal of the epitope binding assay is to identify the affinity of peptide ligands for binding to particular HLA molecules. The initial HLA binding studies utilized detergent solubilized class I molecules from EBV transformed cell lines (Sette, A., et al., *Mol Immunol*, 31(11):813-22 (1994), which is hereby expressly incorporated herein by reference). One perceived advantage of utilizing HLA that is naturally loaded with thousands of endogenous peptide ligands inside the cell is that peptide binding competition assays actually utilize these thousands of naturally loaded peptides in the assay. In the competitive assay with naturally loaded HLA, the HLA molecule of interest can be purified away from other HLA molecules in the detergent lysate or be used in a mixture with other HLA molecules. Radiolabeled peptides are identified that have a high affinity for the HLA molecule in question. The affinity of additional "test" peptides for the HLA molecule in question is then determined by their ability to compete with the high affinity radiolabeled peptide.

Several challenges are associated with the isolation of HLA with naturally loaded peptides. One challenge is that most EBV cell lines express 6 different class I molecules. Purification of HLA molecules can result in the isolation of class I containing only a subset of the representative peptide ligands (Solheim, J. C., et al., *J. Immunol.*, 151(10):5387-5397 (1993); and Bluestone, J. A., et al., *Journal of Exp. Med.*, 176(6):1757-61 (1992), each of which are hereby expressly incorporated herein by reference). Alternatively, using a mixture of HLA molecules produces results where the investigator does not know which HLA molecule in the mixture actually bound the peptide. A third challenge is that isolation of HLA proteins from detergent cell lysates produces microgram quantities of peptide. When performing a peptide binding assay twice in triplicate with hundreds to thousands of peptides at several different concentrations for each peptide, HLA protein can be rapidly utilized in milligram quantities.

To circumvent this limitation in the amount of HLA protein available with naturally loaded ligands, two groups have reported producing HLA proteins in bacteria (Ostergaard Pedersen, L., et al., *Eur J Immunol*, 31(10):2986-96 (2001); and Dedier, S., et al., *J Immunol Methods*, 255(1-2):57-66 (2001), each of which are expressly incorporated herein by reference). The HLA produced in bacteria must then be refolded into a natural conformation consisting of class I heavy chain, beta-2-microglobulin light chain, and peptide ligand(s). While this method of class I protein production circumvents the limitations of detergent lysate HLA protein production, production in bacteria (or insect cells) introduces another set of challenges to obtaining HLA protein for a peptide binding study.

One challenge of producing non-native HLA heavy chains and then refolding in vitro is that refolding in vitro can be difficult. Discussions with Dr. John Altman at Emory University, The Beckman Tetramer Facility, and others who work with bacterial HLA indicates that the percentage of HLA that refolds into an intact trimolecular complex of heavy chain-light chain-peptide can range between 0 to 70%. Some HLA molecules come back together well while others do not. One factor in refolding HLA molecules in vitro is the peptide; high affinity peptides help to reform the complex while some peptides result in no HLA refolding. Using those that do refold with a high affinity peptide in a peptide binding assay can be difficult because displacing a single high affinity peptide can be difficult in the binding assay. This is in contrast to the various affinities of the thousands of endogenously loaded peptides. On the other hand, some HLA molecules cannot be refolded when made in bacteria. Finally, although much HLA heavy chain can be made, sometimes only a fraction of the protein will refold.

The method of producing sHLA with thousands of naturally loaded endogenous peptides as disclosed herein above allows for the production of milligram quantities of HLA in a natural form. Peptides produced in this manner have been characterized and shown to be the same as detergent solubilized HLA (Prilliman, K. R., et al, *Immunogenetics*, 45:379-

385 (1997); Prilliman, K. R., et al., *Immunogenetics*, 48:89-97 (1998); Prilliman, K. R., et al., *Tissue Antigens*, 54(5):450-60 (1999); and Prilliman, K. R., et al., *J Immunol*, 162(12): 7277-84 (1999), each of which are expressly incorporated herein by reference). By secreting HLA proteins, it is insured that only the desired HLA molecule is in solution. Such HLA molecules can then be purified without biasing the peptides in the HLA protein. It has also been shown that high-affinity peptides known to bind a particular HLA specificity bind the HLA molecule in question, while peptides known to bind other HLA molecules do not bind the HLA molecule in question. Additionally, it has been shown that the high affinity peptides can be labeled with fluorescent labels, and then a competition assay can be performed that demonstrates that other peptides can compete with the high affinity labeled peptide at increasing concentrations. The methods of the present invention thus produce substantial quantities of a sHLA reagent that is natural in its conformation and peptide cargo and that is useful for peptide binding assays. The plentiful amount of protein allows the screening of hundreds or thousands of peptides at different concentrations in multiple experiments. The naturally loaded peptide provides a true competitive reflection of the affinity of the labeled and test peptides for the HLA molecule in question.

Figure 3:
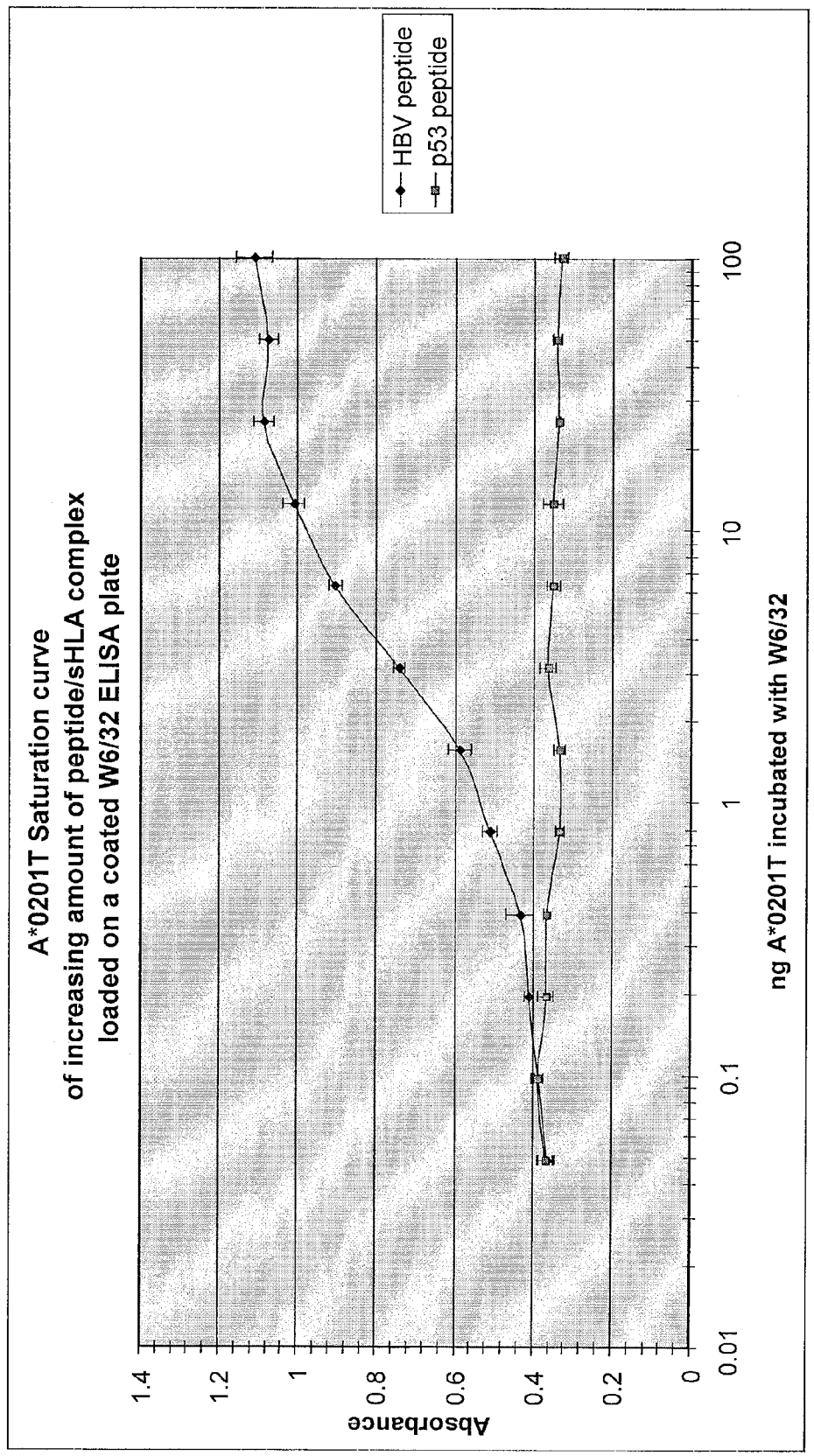
FIG. 3 illustrates an A*0201T saturation curve of increasing amount of peptide/sHLA complex loaded on a coated W6/32 ELISA plate.
Figure 4:
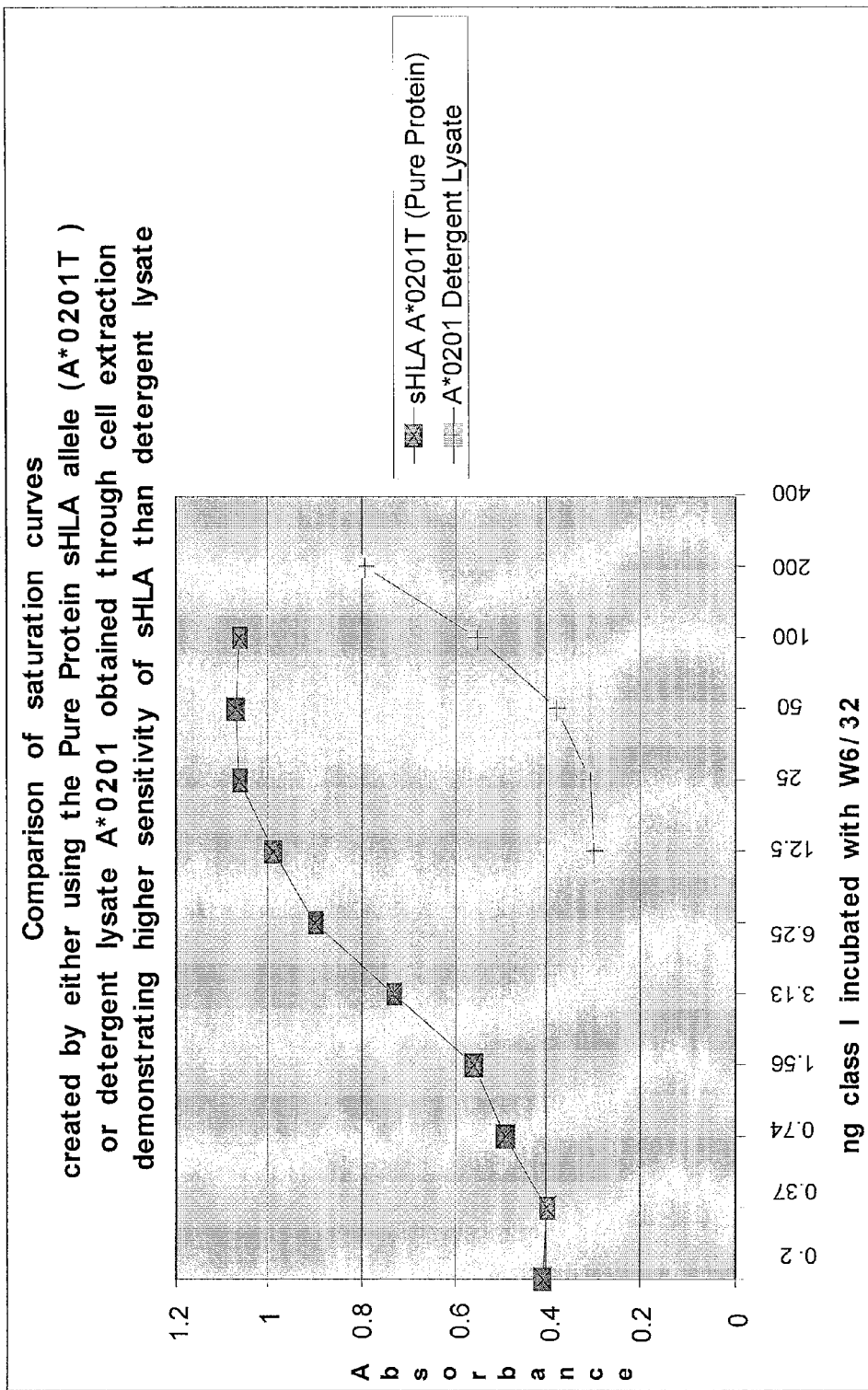
FIG. 4 illustrates a comparison of saturation curves created using either sHLA allele (A*0201T) or detergent lysate A*0201 obtained through cell extraction demonstrating higher sensitivity of sHLA than detergent lysate.

In one embodiment of the method of epitope testing, purified, individual, soluble HLA molecules containing endogenously loaded peptide ligands are mixed with a control peptide known to have high affinity for the HLA molecule and the peptide(s) of interest. A method of detection for binding of the known high affinity control peptide is provided, such as labeling of the control peptide, i.e., fluorescence or radiolabeling, or providing an antibody specific for the complex formed when the known high affinity control peptide binds to the individual HLA molecule (FIGS. 3 and 4). The detectable, high affinity control peptide will displace the endogenously loaded peptide ligands and bind to the individual soluble HLA molecule, as detected by measurement of the label on the control peptide or antibody binding to the control peptide/HLA complex, and the peptide(s) of interest will compete with the high affinity control peptides for displacement of the endogenously loaded peptides and binding to the individual soluble HLA molecules. A negative control used in such method would be a low affinity peptide which will not compete with the high affinity control peptide for displacement of the endogenously loaded peptide and binding to the individual soluble HLA molecules. Thus, epitope testing utilizing the soluble HLA molecules of the present invention, simply put, involves a competition between the control peptide and the test peptide by determining how well did the test peptide displace the control peptide from a soluble HLA molecule and/or displace an endogenously loaded peptide and competitively bind to a soluble HLA molecule.

The above-described assay will typically be performed in liquid phase; however, the method of epitope testing described herein is adaptable to solid phase assays. That is, the individual HLA molecules may be bound to a support. Methods of binding proteins to a support are known in the art and are adaptable to the assay methods described herein.

In yet another embodiment of a method of epitope testing using the individual soluble HLA molecules described herein, a number of individual, soluble HLA molecules may be bound to Luminex™ beads. In the Luminex™ technology, a series of 100 to 1000 beads are each provided with varying concentrations of two different dyes. For example, Bead A may comprise 10% Dye A and 90% Dye B, while Bead B comprises 15% Dye A and 85% Dye B, while Bead C comprises 20% Dye A and 80% Dye B, and Bead D comprises 25% Dye A and 75% Dye B, etc. A specific fluorescence detector can identify each specific bead by the amounts of Dye A and Dye B present in each bead. To each of the 100 to 1000 Luminex™ beads, a different individual class I or II HLA molecule can be bound. It has been demonstrated that the individual soluble HLA molecules of the present invention can be bound to the Luminex™ beads (U.S. Ser. No. 60/274,605, which has previously been incorporated herein by reference). Therefore, the fluorescence detector can identify specific individual HLA molecules by the specific amount of dyes in the bead to which such molecules are bound. All of the beads may be mixed together in one assay, such as one well on a 96 well plate. To the reaction, a detectable, high affinity control peptide as described above is added for each individual soluble HLA molecule bound to a bead, and the peptide of interest is also added to the reaction. The mixture is then passed through the fluorescence detector, which contains two different lasers. The first laser detects the amounts of dyes in the bead, that is, the first laser identifies which bead is passing the laser. The second laser is positioned so that upon identification of the specific bead passing the first laser, the second laser can detect whether or not the detectable high affinity control peptide is bound to the HLA molecule attached to the specific bead. As stated above, this detection may be a radiolabel or fluorescence label attached to the control peptide or a method of antibody binding which detects the control peptide/HLA complex. In this manner, 100 to 1000 binding tests can be run for each peptide of interest to determine which HLA molecules bind such peptide.

In another embodiment of the method of epitope testing, as HLA molecules are known to bind 9 amino acid peptides in the groove thereof, nonamer peptides may be tethered to a chip or other type of support to provide a peptide microarray. For example, PVDF membranes have been utilized to prepare protein microarrays, and such technology could be easily adaptable to the methods described herein. Such nonamers may consist of every possible combination of amino acids, and therefore $9^{20}$ combinations of nonamers would be utilized, or such nonamers may only differ at positions known to be important for binding to HLA molecules, for example, positions 2 and 9 (in this case, $2^{20}$ combinations would be required). The nonamers may be anchored to the chip or other type of support in any known manner. Preferably, the nonamers are anchored internally off side chains of amino acids not on the ends of the nonamers. Specific individual class I or class II HLA molecules could then be passed over the nonamer microarray and allowed to bind, and by detecting binding of specific class I or class II HLA molecules to certain peptides, a database of all peptides to which individual class I or class II HLA molecules bind could be formed (as described in U.S. Ser. No. 10/082,034, filed Feb. 21, 2002, entitled "SOLUBLE HLA LIGAND DATABASE UTILIZING PREDICTIVE ALGORITHMS AND METHODS OF MAKING AND USING SAME", the contents of which are hereby expressly incorporated in their entirety by reference). In this manner, rather than making all the different combinations of peptides produced from a specific virus, bacteria, tumor gene, etc. to determine which peptides bound to individual class I or class II MHC molecules, the genomic sequence of such virus, bacteria, etc. could be "blasted" against the data obtained above and located in the database to identify putative epitopes which could be utilized in the method of epitope testing described herein.

In another embodiment of the method of epitope testing, the above described technology could be "flipped", that is, the individual HLA molecules could be bound to the chip or other support to form an HLA protein microarray. Such method would be similar to the solid-phase assays described herein before.

Peptides Utilized in Epitope Testing

The peptides to be tested in the epitope binding assay of the present invention will be synthetic peptides and will have their sequence derived from portions of various host, viral and bacterial proteins. The proteins upon which the peptides are based can be identified in several ways. One method of identifying proteins that contain peptides that may or may not bind to HLA molecules is through the use of T lymphocytes. T lymphocytes are known to recognize specific peptides in the context of specific HLA molecules. Indeed, this is the mechanism whereby T lymphocytes specifically target antigens in adaptive immune responses.

There are several means of using T lymphocytes for identifying HLA holding peptides that trigger the T lymphocyte. One means is to separate the complex mixture of peptides eluted from HLA molecules into fractions or points in time. The peptides in the fractions are then loaded onto HLA molecules and the cells with the loaded peptides are exposed to T lymphocytes from a cancer patient, a virus infected person, or a person with a bacterial infection. The idea is that the T lymphocytes from a person with a disease controlled by T lymphocytes can be used to identify T lymphocyte peptide-HLA immune targets.

There are several ways to measure the recognition of HLA-peptide target cells using T lymphocytes. One method is to detect HLA/peptide target cell lysis by T lymphocytes, as disclosed in Smith, E. S., et al., *Lethality-based selection of recombinant genes in mammalian cells: application to identifying tumor antigens*. Nat Med, 2001. 7 (8): p. 967-72; Huczko, E. L., et al., *Characteristics of endogenous peptides eluted from the class I MHC molecule HLA-B7 determined by mass spectrometry and computer modeling*. J. Immunol., 1993. 151: p. 2572-2587; Scheibenbogen, C., et al., *Analysis of the T cell response to tumor and viral peptide antigens by an IFNg-ELISPOT assay*. Int. J. Cancer, 1997. 71: p. 932-936; and Rinaldo, C. R., Jr., et al., *Anti-human immunodeficiency virus type 1 (HIV-1) CD8(+) T-lymphocyte reactivity during combination antiretroviral therapy in HIV-1-infected patients with advanced immunodeficiency*. J Virol, 2000. 74 (9): p. 4127-38, all of which are incorporated herein expressly by reference. Using one or a combination of assays that detect T lymphocyte recognition of a target cell, experiments can be designed to identify HLA-peptide candidates that may trigger T lymphocytes.

In the above references, investigators using T lymphocytes to identify HLA-peptide targets do not know which peptide is stimulating T lymphocytes. For example, Zauderer et al. know that over-expression of a transfected "tumor" gene in a cell line is causing T lymphocytes from cancer patients to recognize that cell line. However, this assay cannot determine which peptide from the protein encoded by the transfected "tumor" gene is triggering T lymphocyte recognition. Moreover, the investigator does not know if a peptide derived from the protein encoded by the "tumor" gene is presented by HLA or if the gene is indirectly changing other proteins which may indirectly result in another protein's peptide being recognized in HLA.

Other uses of T lymphocytes indicate that HLA-peptide target complexes exist, but again, they do not specify which exact target peptide is in the HLA molecule. Using evidence from the T lymphocyte assay, an investigator will synthesize several peptides which are suspected to resemble the T lymphocyte target. These peptides can then be tested for their binding to HLA target molecules. Peptides that bind to the HLA molecules are detected in this binding assay. Such binding to an HLA molecule indicates that a peptide should next be tested for recognition by T lymphocytes. Peptides that do not bind can be eliminated from further characterization.

Use of T lymphocytes is one way to begin to sift through proteins and peptide mixtures for possible immune targets. Another way is to simply synthesize all the overlapping peptides in a target protein. These overlapping peptides can be tested for their binding to HLA proteins. Peptides that bind can then be tested for T lymphocyte recognition. This process eliminates T lymphocytes from the selection process.

A protein that an investigator wishes to target in a vaccine, diagnostic, or therapy can be selected in a number of ways. These protein selection mechanisms include T lymphocyte selection, microarray identification of upregulated genes, or simply testing immune responses to a protein of interest. These selection criteria are then partnered to an epitope binding assay as described herein to identify portions of a protein that bind well to one or many HLA proteins. Another method that can be coupled to the epitope binding test described here is a predictive database. A predictive database can indicate which peptides in which proteins might bind to HLA, and then the HLA binding test described herein can confirm or deny these predictions.

The above methods for identifying epitopes for the peptide binding assay are indirect methods. That is, the peptides that may be immunogenic are not directly identified as immunogenic. As such, the epitope testing assay described herein confirms which peptides actually do bind HLA molecules. The epitope testing assay also determines how well a peptide binds and to which HLA molecule(s) the peptide binds. Determining to which HLA molecule(s) a peptide binds is important because the population is heterogeneous for HLA. Therefore, a peptide which binds many HLA is a good vaccine candidate because a vaccine incorporating that peptide will work in a broader range of the population. The peptide binding assay therefore indicates how many HLA and how well to each HLA a peptide epitope binds.

The peptide binding assay can also be coupled with direct epitope discovery methods. For example, peptide epitopes unique to infected and cancerous cells can be directly identified by producing sHLA molecules in cancerous and infected cells and then sequencing the epitopes unique to the cancerous or infected cells. Such epitopes can then be tested for their binding to various HLA molecules to see how many HLA molecules these epitopes might bind. This direct method of epitope discovery is described in detail in U.S. Ser. No. 09/974,366 and is briefly described hereinbelow.

In summary, a number of methods can be used to select peptides which may bind to HLA and may be immune targets. The epitope binding assay can determine whether the putative peptide target actually binds to a specific HLA molecule and how well this epitope binds the specific HLA in comparison to other known peptides that bind to the specific HLA. The epitope binding assay can also be used to screen panels of overlapping synthetic peptides to help sift through large numbers of potential vaccine/diagnostic candidates. Those peptides that bind well can then be tested for immunogenicity. Finally, the epitope binding assay can determine if a particular peptide binds multiple HLA molecules as well as the peptide's relative affinity for various HLA molecules.

Methods of Epitope Discovery and Comparative Ligand Mapping

As stated above, peptides utilized in the peptide binding assay can be identified by direct epitope discovery methods.

For example, peptide epitopes unique to infected and cancerous cells can be directly identified by producing sHLA molecules in cancerous and infected cells and then sequencing the epitopes unique to the cancerous or infected cells. Such epitopes can then be tested for their binding to various HLA molecules to see how many HLA molecules these epitopes might bind. This direct method of epitope discovery is described in detail in U.S. Ser. No. 09/974,366 and is briefly described hereinbelow.

The method of epitope discovery included in the present invention (and described in detail in U.S. Ser. No. 09/974,366) includes the following steps: (1) providing a cell line containing a construct that encodes an individual soluble class I or class II MHC molecule (wherein the cell line is capable of naturally processing self or nonself proteins into peptide ligands capable of being loaded into the antigen binding grooves of the class I or class II MHC molecules); (2) culturing the cell line under conditions which allow for expression of the individual soluble class I or class II MHC molecule from the construct, with such conditions also allowing for the endogenous loading of a peptide ligand (from the self or non-self processed protein) into the antigen binding groove of each individual soluble class I or class II MHC molecule prior to secretion of the soluble class I or class II MHC molecules having the peptide ligands bound thereto; and (3) separating the peptide ligands from the individual soluble class I or class II MHC molecules.

The method described in parent application U.S. Ser. No. 09/974,366 further relates to a novel method for detecting those peptide epitopes which distinguish the infected/tumor cell from the uninfected/non-tumor cell. The results obtained from the present inventive methodology cannot be predicted or ascertained indirectly; only with a direct epitope discovery method can the unique epitopes described therein be identified. Furthermore, only with this direct approach can it be ascertained that the source protein is degraded into potentially immunogenic peptide epitopes. Finally, this unique approach provides a glimpse of which proteins are uniquely up and down regulated in infected/tumor cells.

Figure 2:
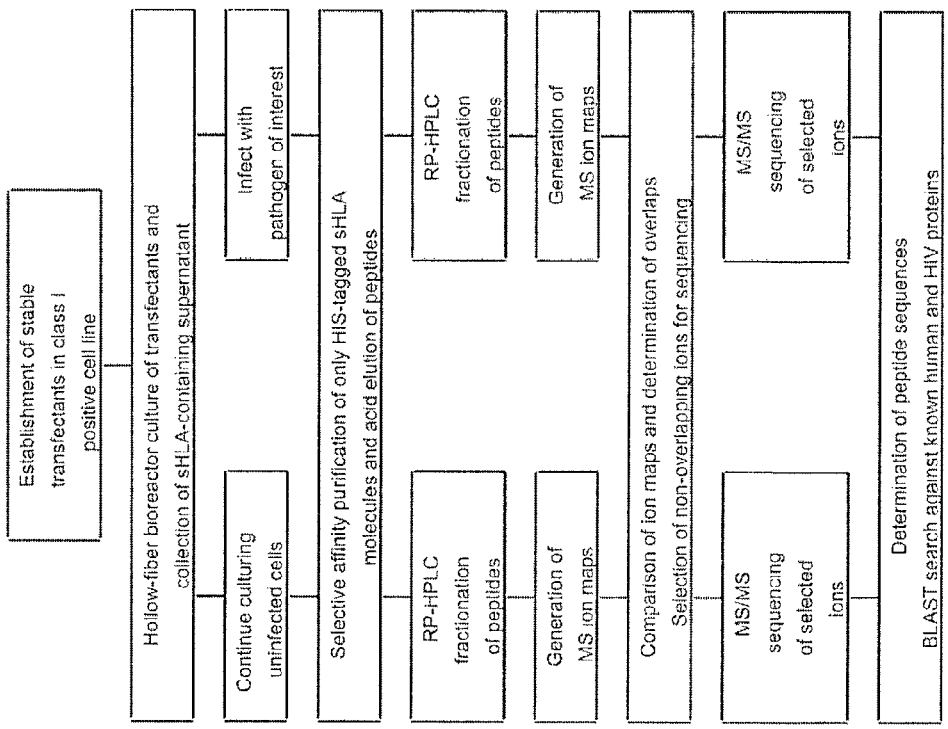
FIG. 2 is a flow chart of the epitope discovery of C-terminal-tagged sHLA molecules. Class I positive transfectants are infected with a pathogen of choice and sHLA preferentially purified utilizing the tag. Subtractive comparison of MS ion maps yields ions present only in infected cell, which are then MS/MS sequenced to derive class I epitopes.

The parent application U.S. Ser. No. 09/974,366 describes, in particular, peptide epitopes unique to HIV infected cells. Peptide epitopes unique to the HLA molecules of HIV infected cells were identified by direct comparison to HLA peptide epitopes from uninfected cells by the method illustrated in the flow chart of FIG. 2. Such method has been shown to be capable of identifying: (1) HLA presented peptide epitopes, derived from intracellular host proteins, that are unique to infected cells but not found on uninfected cells, and (2) that the intracellular source-proteins of the peptides are uniquely expressed/processed in HIV infected cells such that peptide fragments of the proteins can be presented by HLA on infected cells but not on uninfected cells.

The method of epitope discovery and comparative ligand mapping also, therefore, describes the unique expression of proteins in infected cells or, alternatively, the unique trafficking and processing of normally expressed host proteins such that peptide fragments thereof are presented by HLA molecules on infected cells. These HLA presented peptide fragments of intracellular proteins represent powerful alternatives for diagnosing virus infected cells and for targeting infected cells for destruction (i.e., vaccine development).

In accordance with the present invention, Table I lists peptide ligands that have been identified as being presented by the B*0702 class I MHC molecule in cells infected with the HIV MN-1 virus but not in uninfected cells, and also lists one peptide ligand that has been identified as not being presented by the B*0702 class I MHC molecule in cells infected with the HIV MN-1 virus that is presented in uninfected cells. As one of ordinary skill in the art can appreciate the novelty and usefulness of the present methodology in directly identifying such peptide ligands and the importance such identification has for numerous therapeutic (vaccine development, drug targeting) and diagnostic tools. Column 1 of Table I indicates the ion selected for sequencing, column 2 is the HPLC fraction, column 3 is the peptide sequence, column 4 is the predicted molecular weight, column 5 is the molecular weight obtained, column 6 is the source protein for the epitope sequenced, column 7 is where the epitope starts in the sequence of the source protein, column 8 is the accession number, and column 9 is a descriptor which briefly indicates what is known of that epitope and/or its source protein.

The methodology used herein is to use sHLA to determine what is unique to unhealthy cells as compared to healthy cells. Using sHLA to survey the contents of a cell provides a look at what is unique to unhealthy cells in terms of proteins that are processed into peptides. The data

TABLE I

| ION | FRACTION | SEQUENCE | MW | OBS'D MW | SOURCE PROTEIN | START AA | ACCESSION # | CATEGORY | SEQ ID NO: |
|---|---|---|---|---|---|---|---|---|---|
| Peptides Identified on Infected cells that are not present on Uninfected Cells | | | | | | | | | |
| 612.720 | 32INF | EQMFEDIISL | 1223.582 | 1223.418 | HIV MN-1, ENV | 101 | | HIV-DERIVED | 1 |
| 509.680 | 31INF | IPCLUSFL | 1017.601 | 1017.334 | CHOLINERGIC RECEPTOR, ALPHA-3 POLYPEPTIDE | 250 | | | 2 |
| 469.180 | 31INF | STTAICATGL | 936.466 | 936.360 | UBIQUITIN-SPECIFIC PROTEASE | 152 | 10720340 | | 3 |
| 420.130 | 16INF | APAQNPEL | 838.426 | 838.259 | B-ASSOCIATED TRANSCRIPT PROTEIN 3 (BAT3) | | | MHC GENE PRODUCT | 4 |
| 500.190 | 28INF | LVMAPRTVL | 998.602 | 998.396 | HLA-B HEAVY CHAIN LEADER SEQUENCE | 2 | 4566550 | MHC GENE PRODUCT | 5 |
| 529.680 | 31INF | APFI[NS]PADX | 1057.388 | | UNKNOWN, CLOSE TO SEVERAL cDNA's | | | UNKNOWN | 6 |
| 523.166 | 12INF | TPQSNRPVm | 1044.500 | 1044.333 | RNA POLYMERASE II POLYPEPTIDE A | 527 | 4505939 | RNA MACHINERY/ BINDING PR | 7 |
| 444.140 | 16INF | AARPATSTL | 887.495 | 887.280 | EUK, TRANSLATION INITIATION FACTOR 4 | 1073 | Q04637 | RNA MACHINERY/ BINDING PR | 8 |

TABLE I-continued

| ION | FRACTION | SEQUENCE | MW | OBS'D MW | SOURCE PROTEIN | START AA | ACCESSION # | CATEGORY | SEQ ID NO: |
|---|---|---|---|---|---|---|---|---|---|
| 470.650 | 16INF | MAMMAALMA | 940.413 | 939.410 | SPARC-LIKE PROTEIN | 19 | 478522 | TUMOR SUPPRESSOR GENE? | 9 |
| 490.620 | 16INF | IATVDSYVI | | 979.240 | TENASCIN-C (HEXABRACHION) | 1823 | 13639246 | TUMOR SUPPRESSOR GENE? | 10 |
| 563.640 | 16INF | SPNQARAQAAL | 1126.597 | 1126.364 | POLYPYRIMIDINE TRACT-BINDING PROTEIN 1 | 141 | 131528 | RNA MACHINERY/ BINDING PR | 11 |
| | 30INF | GPRTAALGLL | 968.589 | 968.426 | RETICULOCALBIN | 4 | 4506457 | TUMOR SUPPRESSOR GENE? | 12 |
| 556.150 | 16INF | NPNQNKNVAL | 1111.586 | 1111.300 | ELAV (HuR) | 188 | 4503551 | RNA MACHINERY/ BINDING PR | 13 |
| | | RPYSNVSNL | | | SBF-1 | | | | 14 |
| | | LPQANRDTL | | | MgcRacGap | | | | 15 |
| | | QPRYPVNSV | | | TCP-1 | | | | 16 |
| | | APAYSRAL | | | HSP27 | | | | 17 |
| | | APKRPPSAF | | | HMG-1 or HMG-2 | | | | 18 |
| | | AASKERSGVSL | | | histone H1 family member | | | | 19 |
| Peptides Identified on Uninfected cells that are not present on Infected cells | | | | | | | | | |
| | 16UNINF | GSHSMRY | | | MHC CLASS I HEAVY CHAIN (could derive from multiple alleles. I.e., HLA-B*0702 or HLA-G, etc.) | variable | multiple | MHC Class I Product | 20 | summarized in TABLE I shows that the epitope discovery technique described herein is capable of identifying sHLA bound epitopes and their corresponding source proteins which are unique to infected/unhealthy cells.

Likewise, and as is shown in Table I, peptide ligands presented in individual class I MHC molecules in an uninfected cell that are not presented by individual class I MHC molecules in an uninfected cell can also be identified. The peptide "GSHSMRY" (SEQ ID NO:20), for example, was identified by the method of the present invention as being an individual class I MHC molecule which is presented in an uninfected cell but not in an infected cell.

The methods of epitope discovery and comparative ligand mapping described herein are not limited to cells infected by a microorganism such as HIV. Epitope discovery with sHLA as described herein can be completed on cells infected with intact pathogens, cancerous cells or cell lines, or cells into which a particular cancer, viral, or bacterial gene has been transferred. In all these instances the sHLA described here will provide a means for detecting what changes in terms of epitope presentation and the source proteins for the epitopes.

Example of Epitope Binding Assay Using Radiolabeled Peptide and Comparison of sHLA to Detergent Lysate-Prepared HLA A specific assay for the A*0201T allele was used to test the feasibility of a competitive binding assay to measure the binding of defined synthetic antigenic peptides using sHLA class I molecules. A peptide derived from HBV that is known to strongly bind A*0201T was used to replace the endogenous peptide in solution. An irrelevant p53 peptide was used as a negative control in that it does not compete with the endogenous peptide for specifically binding to A*0201T.

In the reaction, different concentrations of individual sHLA having endogenous peptide bound therein was incubated with (1) a standard concentration of HBV peptide (positive reaction), or (2) p53 peptide (negative reaction), and after incubation for 48 hours at room temperature, the sHLA complexes were immobilized on a solid support using the HLA specific antibody W6/32. The A*0201T-HBV peptide complex was detected using a highly specific antibody (mouse anti-human MHC/HBV peptide antibody 5H9/1-2H) that only recognizes this particular conformation (i.e., A*0201T with HBV peptide bound therein), and A*0201T-endogenous peptide complexes are not recognized by the antibody. To visualize the replacement event, a secondary anti-mouse antibody conjugated to HRP was used.

The assay was performed using a sHLA amount of 1.5 µg A*0201T at a final volume of 20 µl (75 ng/µl) and a final peptide amount of 2 µl at a final volume of 20 µl (100 ng/µl). After incubation, the reaction was 75× diluted, and titrating amounts of sHLA-peptide complexes were captured with the W6/32 antibody coated to an ELISA plate.

FIG. 3 illustrates that saturation of the W6/32 coated ELISA plate could be achieved using the HBV peptide, demonstrating the successful replacement of the endogenous peptide with the HBV peptide. However, no saturation could be detected using the irrelevant peptide p53, thereby supporting the specificity of HBV peptide binding to sHLA A*0201T.

In addition, the sHLA molecules used herein were compared to an HLA prepared by the prior art method of detergent lysate using the above described method. FIG. 4 is a comparison of the saturation curves of the sHLA allele A*0201T and the detergent lysate preparation of A*0201 obtained through cell extraction. This figure demonstrates that a much lower concentration of sHLA-A*0201 gives a detectable and useful signal as compared to the detergent solubilized class I A*0201. This may be because the detergent solubilized class I A*0201 is really a mixture of class I molecules, or it may be because the detergent solubilized class I does not have a full mixture of endogenous loaded peptides. The peptides in the detergent solubilized A*0201 might represent only a subset of the endogenously loaded peptides; purification of A*0201 from other class I in the lysate can bias the peptides.

However, the method of assaying epitope binding described herein above is only applicable using the A*0201T allele loaded with HBV because of the involvement of a highly specific antibody recognizing only this specific conformation. Therefore, a more direct measurement of epitope binding to sHLA has been identified that eliminates the need to isolate and produce an antibody specific for a particular peptide bound in each class I allele. The method of Fluorescence Polarization involves labeling the peptide of interest and will be described in detail herein below.

Epitope Binding Assay Using Fluorescence Polarization (FP)

One of the most attractive features of binding assays is their simplicity. Developing a binding assay is to demonstrate that the labeled probe binds to the molecule of interest. The following series of criteria, however, must be met in order to validate the binding assay: (1) binding should be saturable, indicating a finite number of binding sites; (2) the binding should have the requisite specificity, where the binding affinity, defined as the dissociation constant ($K_d$), should be consistent with values determined for physiological molecules; and (3) ligand binding should be reversible, reflecting the dynamic nature of the chemical transmission process and reaching equilibrium when the ligand association rate is equal to the dissociation rate.

However, while the execution of a routine binding assay appears trivial, the development of such an assay requires many hours of testing to establish validity. Numerous factors can influence the specificity of ligand binding. Inorganic ions can influence the attachment site of a ligand and factors such as time, temperature, pH, and peptide concentration influence the kinetic properties, and possibly the specificity, of a binding assay. Other considerations include the stability of the fluorescent dye in the incubation medium and, even more fundamentally, the biological activity of the peptide.

Figure 5:
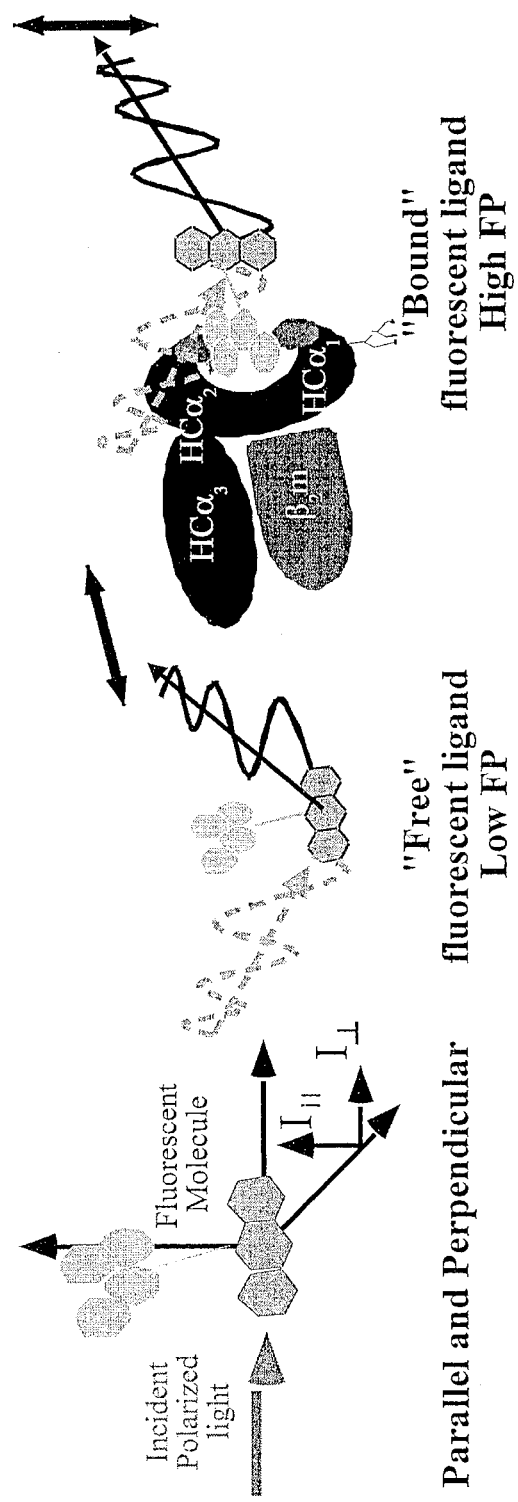
FIG. 5 is a pictorial representation showing a fluorescence polarization (FP) scheme allowing the detection of bound and free peptides to the sHLA complex in solution without separation using radiometric measurements of parallel and perpendicular fluorescent intensities. Free peptides created a low FP signal whereas bound peptides show high FP values.

Fluorescence polarization (FP) allows the direct measurement of the ratio between free and bound labeled ligand in solution without any separation steps (FIG. 5). Most importantly, FP allows real time measurements of single reactions to determine binding kinetics as well as equilibriums. Such constants can be used to directly establish the quality of sHLA molecules and also allow the comparison to native HLA molecules.

Fluorescein is one of the most often used molecules to produce fluorescent labels to localize antigen, receptors or other moieties with affinity for the labeled molecules. FITC (fluorescein isothiocyanate) is very fluorescent in aqueous environments and it gives high sensitivity under UV light; however, its fluorescence is pH-dependent. Its green fluorescence disappears in acid, but reappears in neutral or basic solutions. The $pK_a$ of FITC is approximately 6.5, and it gives its best fluorescent signal above pH 8. FITC has a molecular weight (MW) of 473.4; excitation and emission wavelengths at 494 nm and 520 nm, respectively; and a molar extinction coefficient of 72,000 $M^{-1}$ $cm^{-1}$ in an aqueous buffer, pH 8. Thus, FITC shifts in color from a blue-to-green fluorescent product. FITC fluorescence has a tendency to fade, but this fading may be overcome through the use of agents such as n-propyl gallate or phenylenediamine to stabilize the color. However, these reagents are toxic to living cells and cannot be used in all applications. Isothiocyanates also react with a variety of metal ions to form colored complexes. Therefore, metals such as $Fe^{3+}$, $Cu^{1+}$, and $Ag^{1+}$ should be avoided in reaction mixtures.

Fluorescence is characterized by a process of absorption of incident radiation at a wavelength, $\lambda_{abs}$, followed by the emission of radiation at another wavelength, $\lambda_{emiss}$. This behavior was first described by G. G. Stokes (1852) in the form of Stokes' Law of Fluorescence in which he stated that fluorescence (emission) always appears at a wavelength greater than the wavelength of the incident (excitation) radiation.

This behavior was successfully explained by A. Einstein (1905) using Planck's quantum hypothesis. A quantum of incident light with an energy of $E_{excit}$ is absorbed by the fluorescent molecule raising its energy to $E_{excit}$. This is quickly followed by a downward transition of the molecule to one of the vibration levels in the ground state, $E_{emiss}$, with the emission of a quantum of light.

The phenomenon of absorption and fluorescence can be described in terms of an energy level diagram showing the transitions between the vibration levels of the ground state ($s_0$) and the vibration levels of the first excited state ($s_1$).

In order to describe fluorescence and fluorescence polarization an incident beam strikes a fluorescent molecule (absorption) whereupon the molecule then emits fluorescent radiation. The parallel and vertical intensities of this fluorescence are represented by $I_{\parallel}$ and $I_{\perp}$, respectively, which serve as the components used in the experimental configuration to observe fluorescence polarization.

The technique of FP is based on the fact that if excited with plane-polarized light, the light emitted by a fluorophore is polarized as well. The primary parameter used in the field of the fluorescence polarization to describe the polarization of fluorescence is the degree of polarization, P. This parameter is a very useful way of summarizing the polarization state of fluorescence.

The equation for the degree of polarization, P is:

$$\text{Polarization} = (I_{\parallel} - I_{\perp})/(I_{\parallel} + I_{\perp})$$

where $I_{\perp}$ is the intensity of the fluorescence measured in the perpendicular (⊥) or vertical (V) direction and $I_{\parallel}$ is the intensity of the fluorescence measured in the parallel (∥) or horizontal (H) direction. These measurements are carried out using a polarizer rotated to the vertical and horizontal directions, respectively.

By using a fluorescent dye to label a small molecule, its binding to another molecule of equal or greater size can be monitored using fluorescence polarization (FP). FP operates on the principle that small molecules rotate faster than large molecules. If a molecule is labeled with a fluorophore, this rotation can be measured by exciting the fluorophore with plane polarized light and then measuring the emitted light with polarizers parallel and perpendicular to the plane of excitation to determine if it is still oriented in the same plane as it was when excited. If a fluorescent-labeled peptide binds to the sHLA molecule of higher molecular weight, the average angle (composed of the distribution of all angles between the optical planes) will decrease due to the slower molecular rotation of the bound probe (FIG. 5). Therefore, the ratio between the bound and free probe can be measured by FP directly in solution. This advantage makes FP an excellent tool for the fast and precise determination of molecular interactions between sHLA and peptide.

If a fluorophore is labeled on a small molecule, it will rotate in the time between excitation and emission and the light emitted will be depolarized. If the labeled molecule binds to a large molecule (effectively increasing its overall size), the molecule will not rotate in the time between excitation and emission, and the light emitted will be polarized, resulting in a polarization change between the free and bound forms. For convenience, units are usually 1000 mP=P.

The maximum theoretical mP value obtainable is 500 mP. Hence any experimental value greater than this suggests an artifact within the assay. The assumed theoretical mP for fluorescein is 27. When a small free tracer is bound to a large molecule, the mP is expected to increase. A good FP assay usually has an mP change of 100 or more.

A number of factors can contribute to the lowering of the maximum obtainable polarization value. Some factors that can influence this are quenching of the fluorophore by the molecules themselves, buffer quenching, adsorption onto surfaces, rotational spin (the "propeller effect") and low affinity of interaction between the components.

Polarization methods are used to measure affinities of FITC-labeled peptide probes for purified sHLA molecules. Equilibrium results contributed to the prediction of a efficacious dose ($IC_{50}$) and clarified the strong correlation of in vitro potency to the form of the sHLA molecule used in the assay. Such results also demonstrated that equilibrium polarization measurements are feasible after optimization of assay parameters. In addition, kinetic measurements are possible with FP.

Advantages of FP measurements include: homogeneous measurements, equilibrium and kinetic binding data, plate readers available with improved sensitivity and reduced minimum volume for detection, and competitor affinity data. FP uses one label only and has a truly homogeneous format, i.e., no solid phase to prepare or suspend and no washing steps required, and rapid kinetic data can be obtained. In addition, no radioactivity is required, and the ratiometric reading resists color quenching.

Minimization of the contribution of assay components to non-specific fluorescence polarization is very important. Quality factors include purity of tracer (fluorescent peptide), purity of binder (sHLA), buffer intrinsic fluorescence and ability of buffer components such as carrier proteins to bind the tracer. Some microplate materials such as polystyrene can bind free tracer, thereby increasing the polarization.

Because of the ease with which fluorescence can be detected it is also important to know that it is the compound of interest that is being traced and not a fluorescent impurity. Thus, manufacturers provide data on the specificity and purity of their products. Tracer should be >90% labeled and >95% pure. Failure to purify free fluorophore from tracer means an increased portion of the total fluorescence will not be able to change its polarization.

The dye most commonly used for labeling peptides is fluorescein. A fluorescent labeled substance is biologically not identical to the unlabeled compound and it may not behave in a manner similar to the parent molecule.

Because large proteins, cell membranes and cellular debris scatter light, causing a net increase in total polarization, impurities should be minimized, and only highly purified binder should be used. In some cases, the impurities may be corrected in part by appropriate background subtraction, but it is preferable to minimize the contribution to signal by using purified molecules.

A mixture of protease inhibitors has to be considered if degradation occurs during incubation. A simple cocktail is often sufficient to protect the molecule, such as the use of a protease inhibitor cocktail (Gibco BRL Cat #20012-043) dissolved in PBS pH 7.4 or a final concentration of 1 mM PMSF, 73 mM pepstatin A, and 8 mM EDTA. In the sHLA assay, highly purified sHLA molecules will be used which are also not susceptible to degradation through proteases and thus do not require the addition of protease inhibitors or calcium-chelating salts (EDTA or EGTA) to the buffer system.

In addition, buffer contribution to signal should be minimized. Increased buffer fluorescence background is due to contaminants that fluoresce at the wavelength of interest. Attention to raw materials, cleanliness of mixing and storage vessels and buffer preparation methods should reduce this to acceptable levels. High background counts due to buffer or non-fluorophore components can seriously affect the signal-to-noise ratios of an assay as well as the ultimate sensitivity of an assay.

Buffers for proteins often include carrier proteins, such as bovine albumin (BSA). Albumin may bind some fluorophores, and binding of BSA to the tracer could spuriously increase the baseline polarization, thereby reducing assay range. However, this problem can be overcome by avoiding carrier proteins or using low binding alternatives such as bovine gamma globulin (BGG).

In any case, it is useful to evaluate the contribution of buffer proteins to the net polarization of the tracer by comparing polarization in buffer with and without added protein. Alternatively, the final concentration of BSA can be reduced to minimize these effects.

Finally, likely sources of imprecision which increase the standard deviation of the assay include pipeting, instrument, buffer, tracer, and protein; each component contributes to total imprecision.

A critical feature of the recombinant sHLA molecule is the ability to load the peptide binding portion with a peptide of interest. Results obtained from acid eluted peptide pools indicate that the majority of recombinant sHLA complexes are folded around undefined "bulk peptides" derived from the cell line in which they are produced. It is necessary to replace these endogenous peptides with single, well-defined, labeled standard peptides. Endogenous sHLA molecules having endogenous peptide or no peptide bound will probably be present in a majority, but will not have any interference with the outcome of the assay. The peptide should be highly purified, as small contaminants in synthesized peptides can inhibit peptide loading.

Several peptide loading protocols have been described. A simple method involves passive loading of excess peptide in solution with sHLA. Passive loading works particularly well in the case of high-affinity peptides. For lower-affinity peptides, an increase in the molar ratio of peptide to HLA may improve loading. For each peptide, parameters such as the dose of HLA, molar ratio of peptide to HLA and peptide loading time need to be empirically determined by the investigator.

In order for the MHC class I alleles to be capable of binding peptides, recent peptide loading experiments indicated that β2-microglobulin (β2m) must be present. In general, MHC class I molecules are passively loaded over a several-day time course (in a range of from about 2 to about 5 days). Optimal peptide loading may vary for specific MHC class I alleles. While passively loaded complexes are generally sufficient to work with, they are not necessarily optimally loaded. Parameters and minimal requirements for peptide binding to HLA have been reported. (Khilko et al. *Measuring interactions of MHC class I molecules using surface plasmon resonance.* J Immunol Methods 183 (1):77-94 (1995); Parker et al. *Peptide binding to HLA-A2 and HLA-B27 isolated from Escherichia coli. Reconstitution of HLA-A2 and HLA-B27 heavy chain/ beta 2-microglobulin complexes requires specific peptides.* J Biol Chem. 267 (8):5451-9 (1992); Parker et al. *Sequence motifs important for peptide binding to the human MHC class*

*I molecule*, HLA-A2. J. Immunol. 149 (11):3580-7 (1992), all of which are hereby expressly incorporated herein by reference).

HLA complexes are also successfully loaded by a short alkaline stripping procedure followed by slow refolding at neutral pH. Peptide stripping can also be done in the presence of excess β2m under mildly acidic conditions.

There are three basic types of binding experiments: (1) saturation experiments in which a saturation curve is generated, by holding either the amount of fluorescent peptide (tracer) or sHLA (binder) constant and varying the concentration of sHLA in case of constant tracer or the labeled peptide in case of constant binder in order to determine the affinity constant ($K_d$); (2) competition experiments in which the amount of a competing, unlabeled compound for the receptor, included in the incubation, is the only variable, and the affinity ($K_i$) of that drug can be determined; and (3) kinetic experiments from which the forward ($k_{on}$) and reverse ($k_{off}$) rate constants of the binding process can be determined if the amount of sHLA and peptide are held constant and the time varied. The ratio of these constants provide an independent estimate of the $K_d$.

Description of Saturation Experiments: Passive loading of excess peptide in solution with sHLA is used in the saturation assays. For each peptide, parameters such as the dose of HLA, molar ratio of peptide to HLA and peptide loading time need to be empirically determined. MHC class I molecules are passively loaded over a several-day time course (in a range of from about 2 to about 5 days). Optimal peptide loading may vary for specific MHC class I alleles.

Titration assay to establish optimal sHLA concentration: The assay determines the sHLA concentration necessary to yield a sufficient peptide binding. Specific binding of various concentrations of sHLA (dose range: 0.1 nM-1000 nM) in the presence of a fixed concentration (5 nM) of fluorescent-labeled synthetic peptide should be tested. The fixed fluorescent-labeled synthetic peptide should be evaluated in preliminary experiments including biochemical considerations: the concentration of the tracer should be less than the $K_d$ and less than the concentration of available binder (sHLA) allowing peptide binding. It is recommended that the binder (sHLA) should be at a higher concentration than tracer (fluorescent-labeled synthetic peptide).

Comparison of free tracer with free fluorophore (by running free fluorescein in parallel) establishes the suitability of tracer size. If the tracer mP is significantly greater than that of the comparable fluorophore, the tracer may not be optimal for the use in FP. For adequate net polarization change, evaluation of several tracers must be conducted.

The purpose of titrating binder (sHLA) with appropriate controls is to determine the optimal concentration of binder and tracer. The acceptable range of concentrations of tracer include all concentrations giving a polarization value (in mP) near to the prescribed 27 mP. If the integration time is 100,000 microseconds, the counts per second should be at least 100,000.

Use of appropriate controls allows accurate estimation of specific polarization. The background signal is the contribution to the measurement from sources other than the fluorescent label. It is most easily seen taking a measurement on a well containing all test components except the fluorescent label. Background signals may arise from the microplate plastic, solution contaminants, leakage of light through the optical filters, or other sources generated in the instrument. If the background is highly predictable, i.e., constant from well to well, it can largely be eliminated by subtracting the signal from a control well lacking fluorescent label. Subtracting this constant signal will yield useful information from wells generating signals that are close to background levels.

Specific control groups utilized in the assay include: (1) Buffer only, (2) Tracer only, (3) Protein only and (4) Protein+Tracer. The purpose of each of the specific control groups is discussed in detail herein below.

The "Buffer only" control indicates the contribution of buffer alone to the S and P signals, especially when interfering molecules are present in the buffer. Since the binder may contribute to net signal, binder without tracer serves as a proper control and is used as background subtraction for "Tracer only". For multiple concentrations of binder, each should have the "Buffer only" control.

In the "Tracer only" control, S and P values for free tracer are background-subtracted with "Buffer only" controls and used for G factor calculation. G factors are calculated using the assumed theoretical mP (27 for fluorescein). S (parallel) and P (perpendicular) are the background subtracted intensity measurements when the polarizers are in parallel or perpendicular direction.

$$G \text{ factor} = \frac{S}{P} * \frac{\left(1 - \frac{27}{1000}\right)}{\left(1 + \frac{27}{1000}\right)}$$

G should be a very stable value which corrects for the contribution of the measurement pathway to the observed total polarization. Optical pathways, particularly those with reflective components, pass light of different polarization with varying efficiencies. Instrumental elements that impact this correction factor include the dichroic mirror, excitation and emission filters, polarizing filters and attenuators. Other elements that influence the G factor include the assay plate and buffer/assay components.

Essentially the G factor functions as a scaling (correction) factor, taking relative polarization measurements and making them appear absolute (relative to a known standard). The G factor is typically a value ranging from 0.8 to 1.2. Obtaining a G factor very different from 1 suggests that the filters and dichroic mirror may not be optimized for fluorescence polarization, although meaningful results may be obtained.

Once a G factor has been determined, it can be entered into the associated fluorescence polarization method. The calculated mP from the Criterion Host software will now report "corrected" mP values. Using the established G factor, calculate the mP value for the free tracer. The mP values are generally obtained by subtracting the mean S and P background values from the individual S and P values of the free tracer. As a control, the free fluorophore should have an mP value close to the theoretical value and serves as the minimal polarization value ($mP_{min}$).

$$mP = \frac{S - (P*G)}{S + (P*G)} * 1000$$

The "Protein only" control indicates contribution of light scattering by the specific protein binder. This is used as background subtraction for "Protein+Tracer". Since several concentrations of protein will be used, each should be tested in the absence of tracer.

For "Protein+Tracer", the S and P values are background subtracted with "Protein only" controls to determine the maximal mP for a given concentration. For background subtraction, the mean S and P "Protein only" values are calculated, and the appropriate mean from individual S and P values of wells containing "Protein+Tracer" are subtracted. The calculated G factor is used.

$$mP = \frac{S - (P*G)}{S + (P*G)} * 1000$$

As an additional check on the system, it is advisable to re-read the plate in the Fluorescence Intensity mode. If the same amount of tracer is present in each well, then there should be equal intensity values across the plate in the Fluorescence Intensity mode. Re-reading the plate in intensity mode allows evaluation of the extent of quenching. Quenching effects can affect the ultimate sensitivity of a fluorescence-based assay. The comparison of the molar fluorescence intensity of the fluorophore-labeled peptide and the fluorophore itself in free solution can be used to determine the degree of quenching caused by the chemical coupling process itself. If there is no quenching, the signal for 1 nM fluoresceinated peptide should be the same as that of the free fluorescein. It is not expected that fluorescein coupled to another molecule would be more fluorescent than free fluorescein, so this could indicate that the tracer may have an incorrect concentration assigned. Fluorescence polarization often results in the loss of about 10-90% of fluorescence intensity. This in itself may reduce the sensitivity of fluorescence polarization as opposed to direct intensity measurements.

Method of Epitope Binding Assay Using Flouorescence Polarization

The FITC-labeled peptides are prepared by dissolving the lyophilized powder in 90% Acetonitrile/10% water to a final concentration of 0.25 mM (this measurement should be as precise as possible). It is important to make sure everything is gone into solution. If there is still precipitate present, incubate overnight at room temperature with shaking. Seal the tube with parafilm and protect from light. (Some peptides will dissolve only by adding $NH_4HCO_3$ at a final concentration of 25 mM to convert the acidic environment into a more basic state).

The FITC labeled peptide solution is divided into 800 µl aliquots and added to sealable screw cap tubes. The aliquots are then lyophilized overnight at room temperature. Each tube should finally contain 0.2 µmol of peptide. Each tube is closed tightly, and parafilm is used to wrap the top. The tube is then labeled appropriately and stored at −80° C. until use.

For an adequate net polarization change, several FITC-labeled peptide tracers are evaluated. For optimal evaluation of FP data, 5 independent reaction types need to be mixed, as described in Table II.

Multiple concentrations of sHLA are tested for specific binding in a range of 0.1-1000 nM. A first study may include rather broad concentration ranges for both tracer and binder, whereas a follow-up test may use only one concentration of tracer and a tightly spaced limited dilution series of the binder.

In order for the MHC class I alleles to be capable of binding peptides, recent peptide loading experiments indicated that additional β2-microglobulin must be present. The addition of an extra amount of β2m in a ratio of β2m:sHLA between about 0.5 to about 2.0 are reasonable. Desirably, a ratio of β2m:sHLA of about 1.0 is utilized in the beginning and then adjusted if required.

TABLE II

| A | Reaction Mix | "Protein + peptide Tracer" | sHLA; β-2-m; pFITC; PBS; (BGG) |
|---|---|---|---|
| B | Protein only control | "Protein only" | sHLA; β-2-m; PBS; (BGG) |
| C | Labeled peptide only control | "Free Peptide Tracer only" | pFITC; β-2-m; PBS; (BGG) |
| D | Free FITC tracer only control | "Free FITC Tracer only" | FITC; β-2-m; PBS; (BGG) |
| E | Buffer only control | "Buffer only" | β-2-m; PBS; (BGG) |

Suggested dilutions of sHLA and β2m are as shown in Table III:

TABLE III

| | sHLA dilutions | | β-2-m dilutions | |
|---|---|---|---|---|
| 1 | 50,000 ng/ml | 1060 nM | 12,402 ng/ml | 1060 nM |
| 2 | 10,000 ng/ml | 212 nM | 2,480 ng/ml | 212 nM |
| 3 | 5,000 ng/ml | 106 nM | 1,240 ng/ml | 106 nM |
| 4 | 1,000 ng/ml | 21.2 nM | 248 ng/ml | 21.2 nM |
| 5 | 500 ng/ml | 10.6 nM | 124 ng/ml | 10.6 nM |
| 6 | 250 ng/ml | 5.3 nM | 62 ng/ml | 5.3 nM |
| 7 | 125 ng/ml | 2.65 nM | 31 ng/ml | 2.65 nM |
| 8 | 62.5 ng/ml | 1.32 nM | 15.5 ng/ml | 1.32 nM |
| 9 | 31.25 ng/ml | 0.66 nM | 7.75 ng/ml | 0.66 nM |
| 10 | 15.6 ng/ml | 0.33 nM | 3.88 ng/ml | 0.33 nM |
| 11 | 7.8 ng/ml | 0.16 nM | 1.94 ng/ml | 0.16 nM |
| 12 | 3.9 ng/ml | 0.08 nM | 0.97 ng/ml | 0.08 nM |

To prepare 2× dilutions of sHLA+excess β2m, a total volume of 550 µl is sufficient to perform 5 independent measurements for A ("Protein+Peptide tracer") and B ("Protein only") with a backup volume of 50 µl. The used dilution scheme will use up 81.4 µg µg of sHLA and 20.2 µg β2m for the (A) & (B) reactions.

PBS pH 7.4 is used as the buffer. Optionally, 0.05% (0.5 mg/ml) bovine gamma globulin (BGG) may be used as supplement to prevent non-specific binding of protein on tube walls or as carrier protein. When using BGG, prepare a volume of 33 ml of freshly mixed PBS/0.05% BGG (16.5 mg BGG/33 ml PBS).

To prepare the 2× dilutions, twelve "non-stick" 1.5 ml tubes are labeled with the numbers 1-12. Table IV below describes the dilutions. Each tube is mixed thoroughly after adding sHLA/β2m. Careful pipetting is required.

The first tube (tube #1) should originally contain 814 µl total volume with a sHLA concentration of 100,000 ng/ml and a β2m concentration of 24,804 ng/ml. Therefore, the amounts of sHLA and β2m to be added to tube #1 are calculated, and then the tube is filled up to 814 µl.

$$\mu l\ sHLA \text{ to add} = \frac{100\ \mu g/ml\ final\ conc. * 814\ \mu l\ total\ volum}{[\mu g/ml\ stock\ sHLA]}$$

$$\mu l\ b2m \text{ to add} = \frac{24.8\ \mu g/ml\ final\ conc. * 814\ \mu l\ total\ volum}{[\mu g/ml\ stock\ b2m]}$$

To prepare 2× control dilutions of excess β2m only, a total volume of 800 µl is sufficient to make up the rest of the controls necessary for C ("Free peptide tracer only"), D ("Free FITC tracer only") and E ("Buffer only") with a backup volume of 50 µl. The used dilution scheme will use about 29.4 µg β2m for the (C), (D) & (E) reaction.

To prepare the 2× dilutions, twelve "non-stick" 1.5 ml tubes are labeled with the numbers 1-12. Table V describes the dilutions. Each tube is mixed thoroughly after adding sHLA/β2m. Careful pipetting is required.

The first tube (tube #1) should originally contain 1184 µl total volume with a β2m concentration of 24,804 ng/ml. The amount of β2m to be added to tube #1 is calculated, and then the tube is filled to 1184 µl.

$$\mu l\ b2m\ to\ add = \frac{24.8\ \mu g/ml\ final\ conc. * 1184\ \mu l\ total\ volume}{[\mu g/ml\ stock\ b2m]}$$

TABLE IV

| Tube # | Volume of PBS/0.05% BGG to add | Tube # or stock to use | Volume of sHLA/β-2-m sample to add | 2x dilutions (ng/ml) |
|---|---|---|---|---|
| 1 | see above | see above | see above | 100,000/24,804 |
| 2 | 1056 µl | Tube 1 | 264 µl | 20,000/4,961 |
| 3 | 770 µl | Tube 2 | 770 µl | 10,000/2,480 |
| 4 | 880 µl | Tube 3 | 220 µl | 2,000/496 |
| 5 | 550 µl | Tube 4 | 550 µl | 1,000/248 |
| 6 | 550 µl | Tube 5 | 550 µl | 500/124 |
| 7 | 550 µl | Tube 6 | 550 µl | 250/62 |
| 8 | 550 µl | Tube 7 | 550 µl | 125/31 |
| 9 | 550 µl | Tube 8 | 550 µl | 62.5/15.5 |
| 10 | 550 µl | Tube 9 | 500 µl | 31.25/7.75 |
| 11 | 550 µl | Tube 10 | 550 µl | 15.6/3.88 |
| 12 | 550 µl | Tube 11 | 550 µl | 7.8/1.94 |

TABLE V

| Tube # | Volume of PBS/0.05% BGG to add | Tube # or stock to use | Volume of b-2-m sample to add | 2x dilutions (ng/ml) |
|---|---|---|---|---|
| 1 | see above | see above | see above | 24,804 |
| 2 | 1536 µl | Tube 1 | 384 µl | 4,961 |
| 3 | 1120 µl | Tube 2 | 1120 µl | 2,480 |
| 4 | 1280 µl | Tube 3 | 320 µl | 496 |
| 5 | 800 µl | Tube 4 | 800 µl | 248 |
| 6 | 800 µl | Tube 5 | 800 µl | 124 |
| 7 | 800 µl | Tube 6 | 800 µl | 62 |
| 8 | 800 µl | Tube 7 | 800 µl | 31 |
| 9 | 800 µl | Tube 8 | 800 µl | 15.5 |
| 10 | 800 µl | Tube 9 | 800 µl | 7.75 |
| 11 | 800 µl | Tube 10 | 800 µl | 3.88 |
| 12 | 800 µl | Tube 11 | 800 µl | 1.94 |

Finally, a stock solution of FITC-labeled peptide tracer (pFITC) is prepared using a pre-measured tube (0.2 µmol) and stored at 80° C. 20 µl of DMSO is added to 0.2 µmol of FITC-labeled peptide powder pre-measured in a microtube to receive a stock concentration of 10 mM and pipetted up and down until the tracer is completely dissolved. Optionally, 20 µl of DMF may be used for peptides containing methionine (M) which are known to oxidize more likely in DMSO than DMF. To protect from moisture, the FITC-labeled peptide and DMSO are allowed to equilibrate to room temperature before opening.

To obtain a 100 µM working dilution, 980 µl of PBS is added to the original DMSO stock, and then the working concentration is further diluted to a 1 µM solution (10 µl working dilution to 990 µl PBS). The 100 µM working dilution is aliquoted and stored at 25° C.

Acceptable concentrations of FITC-labeled peptides in FP experiments are in a 0.75 to 50 nM range. A mP range of free FITC tracer is expected to be between 30-50 mP. Intensities for parallel and perpendicular fluorescence for the concentration range of 0.75 to 50 nM FITC is 0.3 to 30 $10^6$ cps. Unpolarized fluorescence intensity will be 10× over the polarized intensities. An optimal starting concentration of FITC-labeled peptide would be 5 nM. Consider running more than one concentration of tracer initially.

To prepare 20 ml of 5 nM pFITC used in (A) ("Protein+Peptide tracer") and (C) ("Free peptide tracer only"), 100 µl of the 1 µM pFITC is added to 19.9 ml buffer. Free peptide tracer is compared with free fluorophore by running free FITC in parallel to establish the suitability of the tracer and as a control if the correct concentration was assigned to the peptide tracer. If there is no quenching the signal for the selected fluoresceinated peptide concentration should be the same as that of the FITC control.

A stock solution of FITC is prepared using pre-measured FITC (Fluorescein Isothiocyanate) Microtubes (Pierce #51004; 6×1 mg). (1 mg/ml is 2.112 mM). FITC has a molecular weight (MW) of 473.4. 211.2 µl of DMSO is added to 1 mg of FITC powder pre-measured in a microtube to receive a stock concentration of 10 mM. The FITC labeling reagent is reconstituted by puncturing the foil and adding 211.2 µl of DMSO and pipetting up and down until the FITC is completely dissolved. To protect from moisture, the FITC and DMSO are allowed to equilibrate to room temperature before opening.

To obtain a 100 µM working dilution, 980 µl of PBS is added to the original DMSO stock. The working concentration is further diluted to a 1 µM solution (10 µl working dilution to 990 µl PBS). The 100 µM working dilution is aliquoted and stored at −25° C.

To prepare 10 ml of 5 nM pFITC used in (D) ("Free FITC tracer only"), 50 µl of the 1 µM pFITC is added to 9.95 ml buffer.

Figure 6:
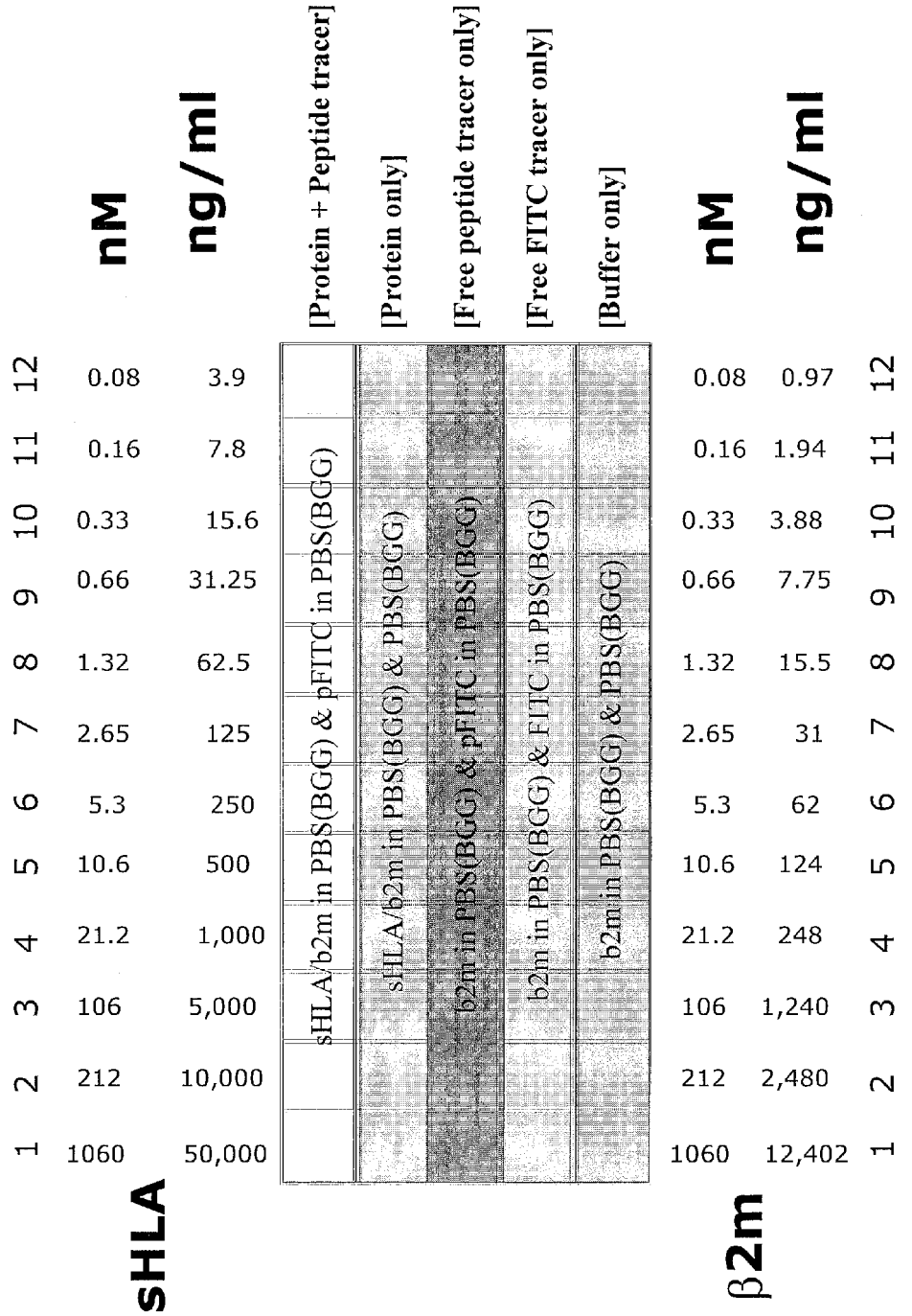
FIG. 6 is a diagrammatic scheme of the peptide exchange reaction using Fluorescence Polarization.

To start the peptide exchange reaction, mix 50 µl of each solution prepared above according to the scheme shown in FIG. 6. 50 µl buffer (PBS/(BGG) is added in row 1-12 of B & E. 50 µl of FITC solution is added in row 1-12 of D, and 50 µl of pFITC is added in row 1-12 of A & C. The serial dilutions of the β2m series are added only to C, D & E starting with 12 and ending with 1. Finally, the serial dilutions of the sHLA/β2m series are added to A & B, also starting with 12 and ending with 1. The dilutions are then kept at 4° C. in the dark.

The meniscus is checked to make sure they are uniform and are evened out by gentle tapping if necessary. Air bubbles, which may be present in some wells, are removed.

The usual incubation time for a peptide exchange reaction is about 48 hours. However, to determine optimal binding times, the course of binding should be observed, by reading the plate several times during incubation. Start the first reading at t=0 hours.

A fluorescence polarization detection method is prepared with the following parameters:
Lamp: continuous lamp
Plate format: as appropriate for the plate to be evaluated
Switch polarization after each well
Select wells: specify all the wells to be read
G factor: 1
Z Height: 1 mm
Filters: fluorescein excitation and emission
(also use the fluorescein dichroic in the top optics head)
Timing, Continuous Lamp:
Readings per Well: 1
Integration Time: 100,000 µsec
Raw Data Units: counts/sec
Attenuator mode: out
Polarizers:
excitation polarizer in the S position
emission polarizer as dynamic
PMT setup: SmartRead, sensitivity 2
Plate agitation: none Kinetic timing:
Delay Before First Read: 0
Delay Between Reads: 0
Number of Reads: 1.
Plate Settling Time: 25 ms The plate is re-read in Fluorescence Intensity mode to determine the degree of quenching caused by the chemical coupling process of sHLA and peptide. Without quenching and equal amount of tracer present in each well, the intensity values across the plate should be the same. Note that fluorescence intensity reaches a 10-90% higher signal than fluorescence polarization.

A fluorescence intensity detection method is then prepared with the following parameters:
Optics: top, continuous lamp
Plate format: as appropriate for the plate to be evaluated
Select wells: specify all the wells to be read
Z Height: 1 mm
Filters: fluorescein excitation and emission
(also use the fluorescein dichroic in the top optics head)
Timing, Continuous Lamp:
Readings per Well: 1
Integration Time: 100,000 μsec
Raw Data Units: counts/sec
Attenuator mode: out
Polarizers: none
PMT setup: SmartRead, sensitivity 2
Plate agitation: none
Kinetic timing:
Delay Before First Read: 0
Delay Between Reads: 0
Number of Reads: 1.
Plate Settling Time: 25 ms After reading the plate, the plate is covered with a lid and sealed with parafilm. To protect from light, the plate is additionally covered with aluminum foil. The plate is then incubated at assigned temperature until next reading. Each reading is recorded as follows:

| Date: | Time: No. | Incubation period | Current incubation time |
|---|---|---|---|
| | $t_1$ | 0 hours | 0 hours |
| | $t_2$ | hours | hours |
| | $t_3$ | hours | hours |
| | $t_4$ | hours | hours |
| | $t_5$ | hours | hours |
| | $t_6$ | hours | hours |
| | $t_7$ | hours | hours |
| | $t_8$ | hours | hours |
| | $t_9$ | hours | hours |
| | $t_{10}$ | hours | hours |

The data is evaluated using a spread-sheet program, such as Microsoft's EXCEL™. The net increase in polarization is determined upon addition of sHLA to the peptide. The "Free peptide tracer only" values provide the basis to calculate the G factor. "Tracer only" gives the lowest attainable mP (minimum tracer binding) not using a G factor to correct values to a theoretically assumed value. The "Buffer only" control provides a background control, indicating the contribution of buffer only to the S and P signals, especially when interfering molecules are present in the buffer. The background signal is the contribution to the measurement from sources other than the fluorescent label. It is most easily seen taking a measurement on a well containing all test components except the fluorescent label. Background signals may arise from the microplate plastic, solution contaminants, leakage of light through the optical filters, or other sources generated in the instrument. S and P values for "Free peptide tracer only" and "Free FITC tracer only" are background-subtracted with "Buffer only" controls before calculating mP and G factor.

If there are several concentrations of (unlabeled) components present (i.e., multiple β2m concentrations), there should be a background well for each concentration. Experiments with homogenous buffer systems are background corrected by subtracting the mean values.

G factors are calculated using the assumed theoretical mP (27 for fluorescein). S (parallel) and P (perpendicular) are the background subtracted intensity measurements when the polarizers are in parallel or perpendicular direction.

$$G\ \text{factor} = \frac{S}{P} * \frac{\left(1 - \frac{27}{1000}\right)}{\left(1 + \frac{27}{1000}\right)}$$

Using the calculated G factor will adjust all results to the assumed theoretical mP of 27 as the lowest attainable mP value (minimum tracer binding). The signal to background ratios is determined to assure the quality of the G factor.

"Free peptide tracer only"/"Buffer only"

and "Free FITC tracer only"/"Buffer only"

A representative value for signal/background can be calculated from the Parallel (S) value of signal "Free peptide tracer only" to background "Buffer only" values. Ideally, signal to background values of at least 10-fold should be targeted. Errors become usually large at low concentration as background noise dominates the intensities.

Noise relates to the uncertainty in measurements and usually determines the ultimate sensitivity of an instrument. To determine signal to noise ratios, the mP values are divided by the standard deviation where the mP value corresponds to signal and the imprecision (standard deviation) corresponds to the "noise". Ideally, signal to noise values of at least three times the background standard deviation should be targeted.

As additional check on the system, it is advisable to re-read the plate in the Fluorescence Intensity mode. Re-reading the plate in intensity mode allows evaluation of the extent of quenching. Quenching effects can affect the ultimate sensitivity of a fluorescence-based assay.

The comparison of the molar fluorescence intensity of the fluorophore-labeled peptide and the fluorophore itself in free solution can be used to determine the degree of quenching caused by the chemical coupling process itself. Compare "Free peptide tracer only" fluorescence intensities with "Free FITC tracer only" fluorescence intensities re-read in fluorescence intensity mode. If there is no quenching, the signal for 1 nM fluoresceinated peptide should be the same as that of the free fluorescein. It is not expected that fluorescein coupled to another molecule to be more fluorescent than free fluorescein, so this could indicate that the tracer may have an incorrect concentration assigned. In addition, the obtained fluorescence intensity results are confirmed by G factor comparison between "Free peptide tracer only" and "Free FITC tracer only".

The S and P "Protein+Peptide tracer" values determine the highest attainable mP (maximum tracer binding) for a chosen concentration. Before calculating mP, the background is subtracted with "Protein only" controls, and the calculated G factor is used.

The "Protein only" control indicates the contribution of light scattering by the specific protein binder. Since several concentrations of protein will be used, each should be tested in the absence of tracer.

$$mP = \frac{S - (P*G)}{S + (P*G)} *1000$$

A dose-response curve will be obtained by plotting bound fluorescence values (mP) against total concentration of the sHLA molecule on a log-log plot. There should be a plateau effect, with supraoptimal concentrations of binder yielding no further increase in mP. Data points are fitted to the dose-response model using the dose-response equation. Reproducibility can be shown by averaging the value from 3 independent measurements.

No binding should be detected in the case of using an irrelevant fluorescent-labeled MHC molecule. No binding should be detected in the case of using an irrelevant fluorescent-labeled peptide.

Imprecision is the standard deviation of the mean of each group of mP values. This should generally be less than 10 mP. The signal to background ratios is determined to assure the quality of the results.

"Protein+Peptide tracer"/"Protein only"

A representative value for signal/background can be calculated from the Parallel (S) value of signal ("Protein+Peptide tracer") to background ("Protein only") values. Ideally, signal to background values of at least 10-fold should be targeted.

The assay range as the change in polarization is calculated by subtracting the mean mP of ("Free peptide tracer only") from the mean mP of the ("Protein+Peptide tracer"). Ideally, the net change in polarization should be greater than 70 mP. Maximum measurable binding is determined to be the ("Protein+Peptide tracer") values background subtracted with ("Protein only") controls (maximum sHLA and tracer binding allowed, which gives a high mP) minus the "Free peptide tracer only" (minimum tracer binding, which gives a very low mP). The difference between these two conditions is the maximum delta m P.

Each background-corrected mP value obtained is normalized at a specific sHLA concentration by dividing by the maximum delta mP. To calculate % of maximum binding, multiply by 100%. Optimal sHLA concentration is chosen by comparing the results according to their best signal-to-background ratio and highest polarization value.

Given milligram to gram quantities of sHLA for the many HLA alleles in the population, it is possible to automate fluorescent epitope binding assays with sHLA and thousands to millions of various peptides. Robotics or other high throughput methods introduce various peptides to the various sHLA molecules, incubate at the time and temperatures described herein, and determine those peptides that bind to a given sHLA molecule and the relative affinity of those peptides for a sHLA molecule. For example, all the possible overlapping peptides in 50 different viral pathogens could be synthesized and tested for their binding to 50 different sHLA molecules. The resulting data would provide a database of those viral peptides that bind to HLA molecules for possible presentation to the immune response. Such data would be useful for viral vaccine discovery. In a similar test, all peptides encoded by genes known to be upregulated in tumor cells are tested for their binding to sHLA molecules. The resulting data would indicate peptides for potential use in tumor vaccines. Finally, all human proteins could have overlapping peptides synthesized and tested for binding to sHLA molecules. The resulting data, combined with gene expression studies, is useful in determining those epitopes which are involved in autoimmune disorders. The resulting data could then be used to design therapies and diagnostics.

Results from Epitope Binding Assay Using Fluorescence Polarization

Figure 7:
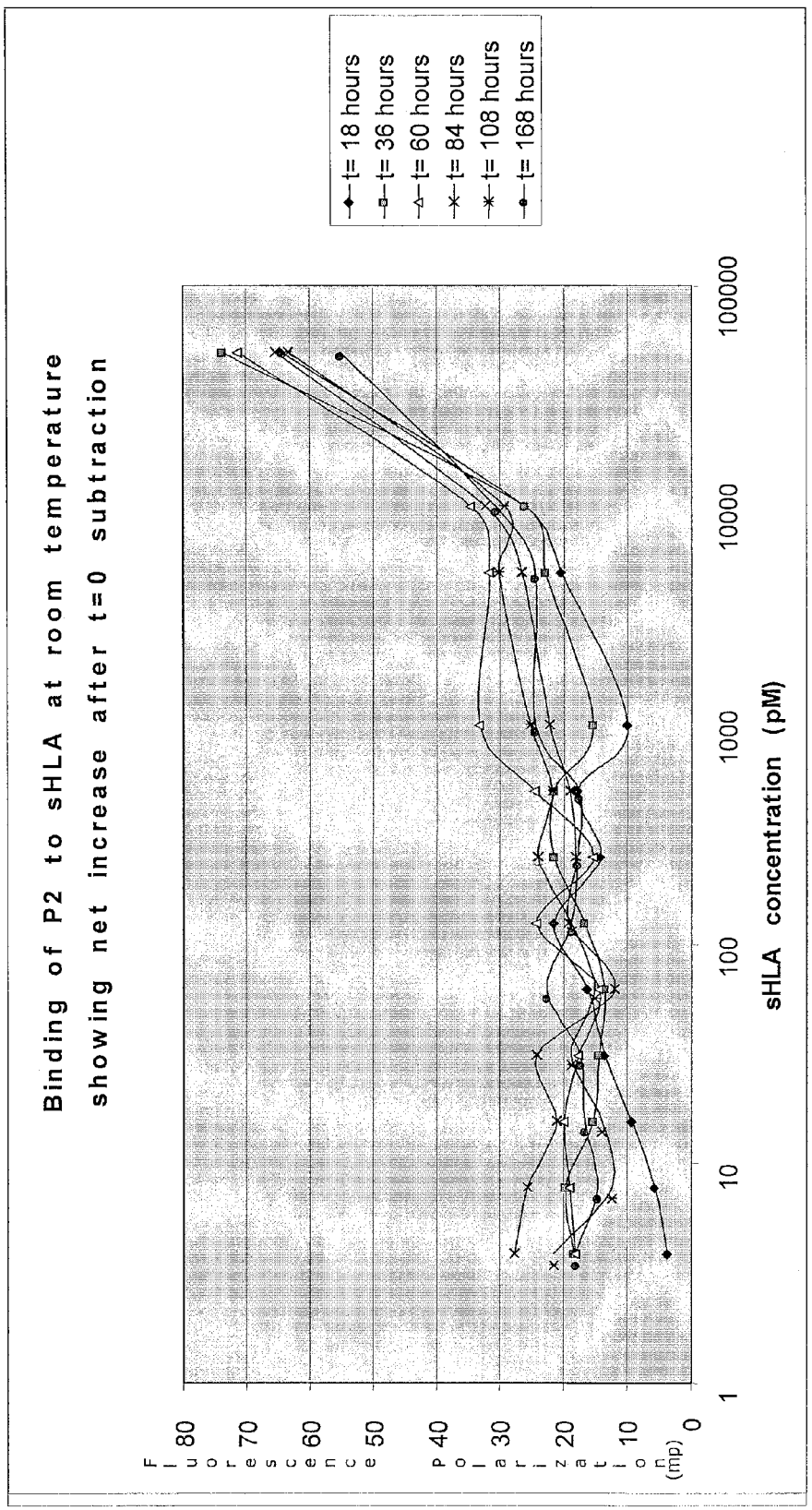
FIG. 7 illustrates the binding of P2 to sHLA at room temperature showing net increase after t=0 subtraction.

Methods for published peptide binding assays with detergent lysate HLA or with bacterial produced HLA typically incubate peptides and HLA at room temperature. FIG. 7 illustrates that incubating various concentrations of sHLA with a fixed concentration of peptide at room temperature requires 10,000 to 100,000 picomoles to obtain significant binding of fluorescent peptide as detected by fluorescent polarization. Baseline levels of FP are approximately 20 mp while maximum FP at room temperature incubation is approximately 70; a difference of 50 is the minimum required to differentiate between a positive and negative binding peptide.

Figure 8:
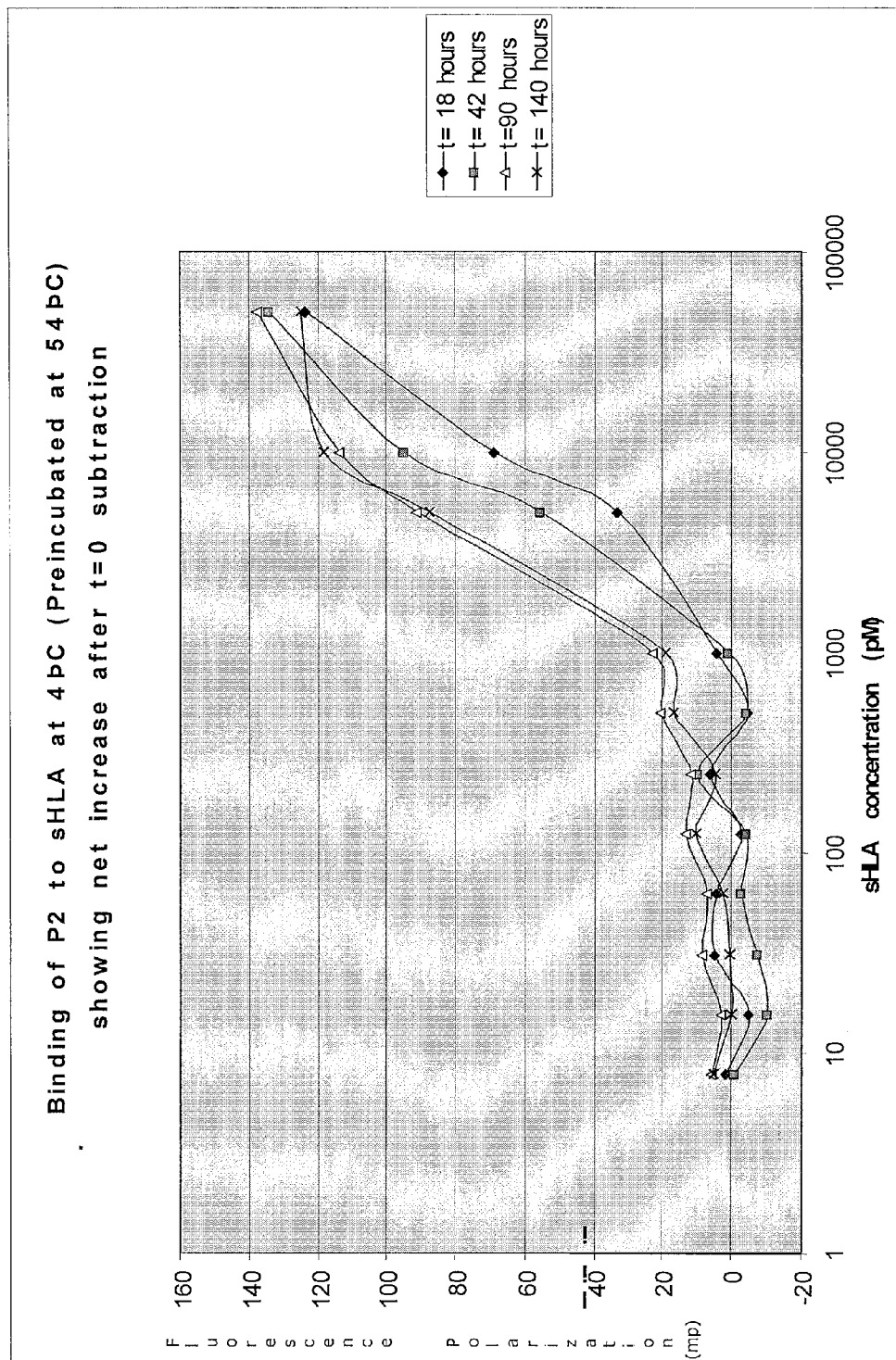
FIG. 8 illustrates the binding of P2 to sHLA at 4° C. (preincubated at 54° C.) showing net increase after t=0 subtraction.

By comparison to the incubation of peptide and sHLA at room temperature, as shown in FIG. 8, it can be seen that heating the sHLA to 54° C. for 45 minutes followed by incubation of the sHLA with the same peptide at 4° C. produces a much stronger FP signal at the same concentrations of sHLA. The difference between background and the strongest signal was approximately 130 mp. A greater difference between the baseline and the positive allows us to use less sHLA to get a signal difference of 50 mp and also allows the assay to provide greater differentiation among the various binding affinities of different peptides.

Figure 9:
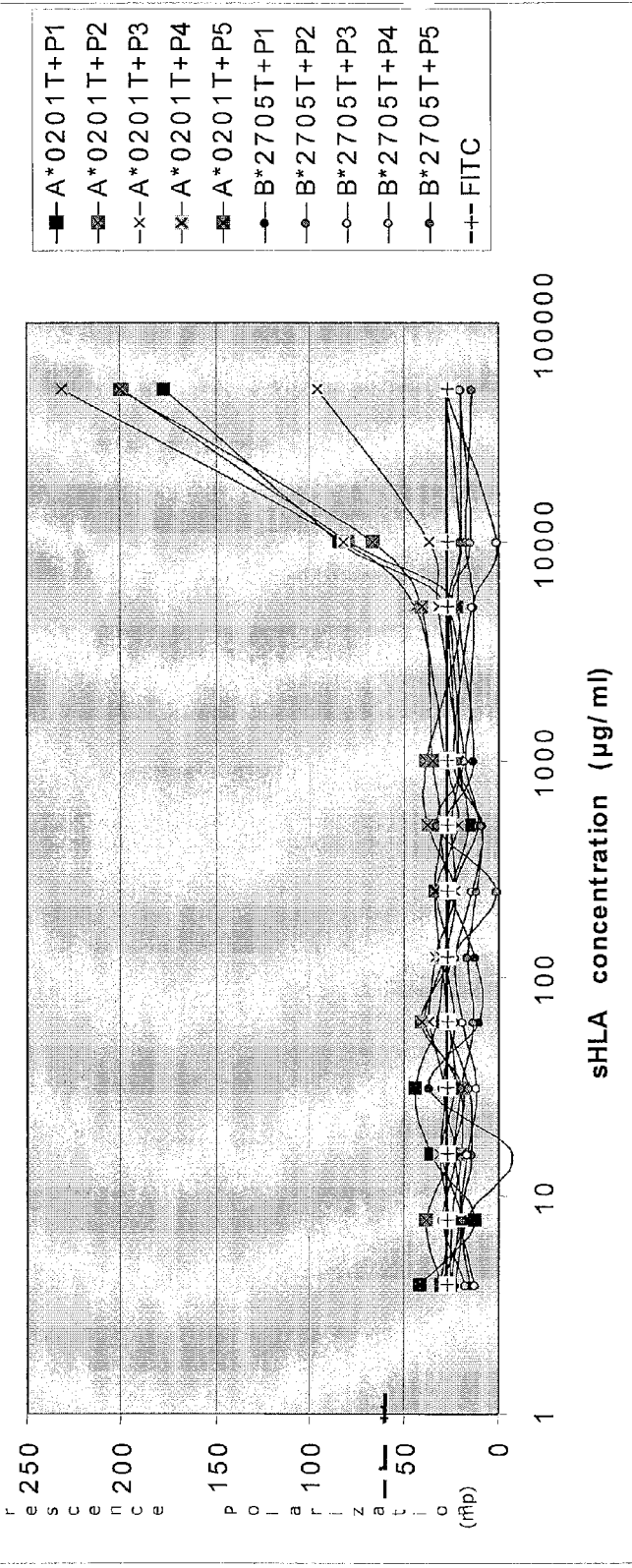
FIG. 9 illustrates the binding of various peptides (P1-P5) to sHLA A*0201T over a range of concentration detected by Fluorescence Polarization at time 45 hours after mixing.

FIG. 9 demonstrates that sHLA molecules bind fluorescent peptides in a manner specific to the sHLA being tested. In this Figure, the sHLA molecule A*0201 was tested for its ability to bind 5 peptides specific for A*0201 (+P1 to +P5) and five peptides specific for the HLA molecule B*2705. The sHLA A*0201 was heated to 54° C. for 45 minutes and then added to a reaction mixture at 4° C. that contained the various peptides. The data shows that the sHLA-A*0201 specifically binds A*0201 peptides as detected by FP.

Figure 10:
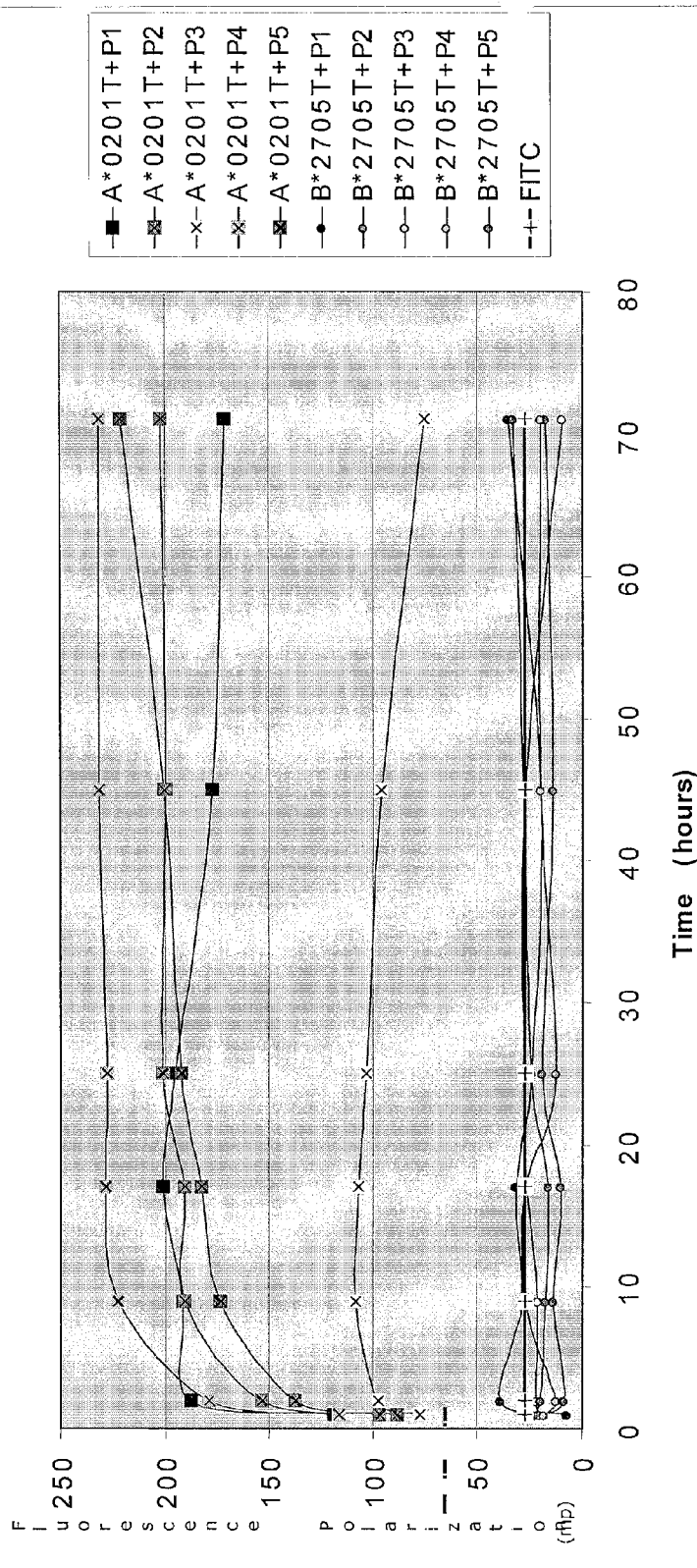
FIG. 10 illustrates the binding of various peptides (P1-P5) to sHLA A*0201T using Fluorescence Polarization at a concentration of 50 µg/ml sHLA.

FIG. 10 demonstrates that sHLA A*0201 at a concentration of 50 micrograms per milliliter bind peptides specific for A*0201. Furthermore, this data demonstrates that most peptides specific for A*0201 bind to their maximum extent within 24 hours. This assay shows that peptides bind to the sHLA molecules in a specific way with an FP difference of up to 200 mp. Therefore reaction conditions have been identified herein that quickly detect a peptide's ability to bind sHLA molecules. The strong FP difference allows us to compare peptide binding affinities of various peptides for the sHLA molecules.

Figure 11:
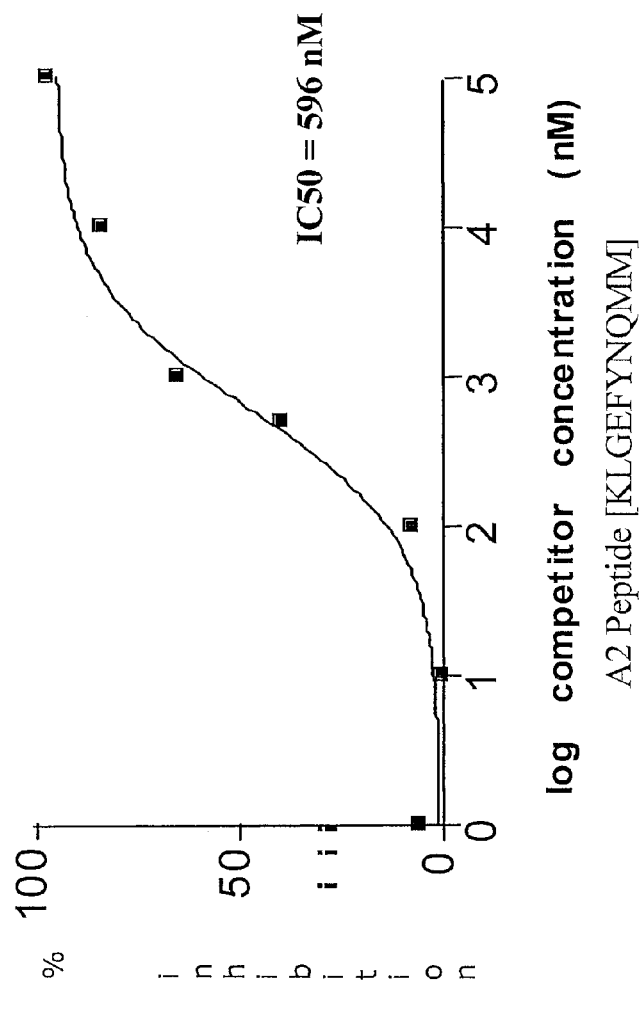
FIG. 11 illustrates a competition assay for sHLA A*0201T loaded with the specific standard peptide P5 (FITC) (ALMDKVLK(FITC)V (SEQ ID NO:22)), competing with a competitor peptide A2 peptide (KLGEFYNQMM (SEQ ID NO:21)).

In the previous figures of this application, it has been demonstrated that A*0201 specific peptide ligands bind to sHLA A*0201. In FIG. 11, a peptide was added that is also specific for A*0201 (A2 peptide (KLGEFYNQMM) (SEQ ID NO:21)). This "cold" competitor peptide is mixed with the "hot" fluorescent peptide (peptide P5, having the sequence ALMDKVLK (FITC)V (SEQ ID NO:22)) at various concentrations of the cold peptide. The sHLA which has been heated to 54° C. for 45 minutes is added to the mixture of peptides which is at 4° C. The mixture is then incubated at 4° C. In FIG. 11 it can be seen that increasing concentrations of the cold peptide prevent the hot peptide from binding to sHLA A*0201. The less the hot peptide binds, the less FP is obtained. Thus, it has been demonstrated herein that peptides specific for sHLA A*0201 can compete with labeled peptides specific for A*0201. In this way it is possible to determine the comparative affinity of various peptides for A*0201: the lower the concentration needed to complete the hot peptide means that the cold competitor has a higher affinity.

Results of Real-Time Kinetic Measurements of Peptide Binding to sHLA Using Fluorescence Polarization The determination of in vitro equilibrium and kinetic data for specific peptide/HLA class I interactions is a primary means of identifying viral, bacterial, and cancer vaccine candidates. Many different methodologies have been reported with the common theme of assessing the ability of synthetically defined peptide epitopes to associate with specific class I complexes.

In the present invention, the co-incubation of purified, recombinant sHLA molecules with FITC-labeled peptides that have been previously reported to have a high affinity for A*0201 as unlabeled peptides is described. Allele A*0201 was chosen because it is found at a high frequency in the population and is the most extensively studied HLA class I antigen. The resulting data demonstrate that an FP-based HLA/peptide binding assay is feasible, quantitative, and does not depend on radioactivity. Because of the real-time nature of the assay, kinetic measurements are readily obtainable. By testing the A*0201-specific peptide ligands against various class I, it has been demonstrated herein that individual sHLA molecules maintain their peptide binding behavior using the described method. This assay is relatively simple to conduct, can be standardized to different FP readers, and is amenable to the unbiased study of many different peptide/HLA interactions.

Materials and Methods:

Synthetic Peptides. FITC-labeled peptides (Table VI) were commercially synthesized by Synpep (Dublin, Calif.) or American Peptides (Sunnyvale, Calif.) using solid-phase strategies and purified with reverse-phase HPLC. Purity was determined to be greater than 95%. The composition was ascertained by mass spectrometric analysis. Peptides were ordered in aliquots of 0.2 μmol amounts and stored dry. Lyophilized peptide aliquots used in binding assays were originally dissolved in 100% DMSO at a concentration of 10 mM. Subsequent dilutions were done in 1× bovine λ-globulin in PBS (BGG/PBS, 0.5 mg/mL, 0.05%; Sigma, St. Louis, Mo.). Aliquoted working dilutions (200 μM) for FITC-labeled peptides were kept at −20° C. and reused for a period of up to 4 months without a measurable decline in signal.

TABLE VI

FITC-Labeled Peptide Sequences[a]

| name | sequence | SEQ ID NO: |
|---|---|---|
| A*0201/P1 | F L P S D K F P S V | 23 |
| A*0201/P2 | S L Y N K V A T L | 24 |
| A*0201/P3 | N L S K L S L D V | 25 |
| A*0201/P4 | L V F G K E V V E V | 26 |
| A*0201/P5 | A L M D K V L K V | 27 |

[a]Amino acid positions carrying the FITC label are in bold type.

Protein Expression and Large-Scale Production of Recombinant sHLA Class I Molecules. All sHLA molecules used within this study were cloned and expressed according to the techniques described previously herein. Briefly, truncating PCRs were performed using specific primer sets and template DNA from reliable full-length cDNA clones of the HLA alleles of interest. The resultant PCR products contained the leader peptide, as well as the α1, α2, and α3 coding domains of the HLA heavy chain resulting in the removal of the portion encoding the membrane-spanning region and the cytoplasmic tail. PCR products were directly subcloned into the mammalian expression vector pcDNA3.1(−) (Invitrogen; Carlsbad, Calif.) and sequenced to confirm allelic specificity. The class I negative, EBV-transformed Blymphoblastoid cell line 721.221 was transfected with a cloned DNA construct by electroporation, and stable transfectants were selected using 1.5 mg/mL $G_{418}$. Upon establishment of confluent growth after approximately 3 weeks, putative transfectant wells were screened for sHLA production using a sandwich ELISA (Prilliman et al, 1997). Transfectant wells positive for sHLA production were then subcloned by limiting dilution. Satisfactorily subcloned transfectants were expanded, frozen in RPMI-1640, 20% FCS, and 10% DMSO, and stored at 135° C.

After high-level producers were established, the CP-2500 CELL PHARM® System (Biovest International, Minneapolis, Minn.) was applied in order to produce large quantities of sHLA. Transfected 721.221 cells were first expanded over a time period of approximately 21 days before seeding two hollow-fiber bioreactor units of the CELL PHARM®. After inoculation, a typical production run lasting between 4 and 6 weeks produced approximately 30-40 L of secreted sHLA product, which was collected as crude harvest.

Affinity Purification of sHLA Molecules. Upon completion of a bioreactor run, sHLA complexes were affinity purified from the harvests obtained using the pan-HLA class I antibody W6/32 (25) coupled to a SEPHAROSE® 4B matrix (Amersham, Piscataway, N.J.). Harvests were applied to the column using a peristaltic pump system (Amersham) with a speed of 5 mL/min at 4° C. After the column was extensively washed with phosphate-buffered saline (PBS), bound sHLA molecules were eluted with 0.1 M glycine (pH 11.0) and immediately neutralized by addition of 1 M Tris-HCI, pH 7.0, to preserve the activity of the eluted molecules. Under these conditions, sHLA molecules were recovered with a 75-85% yield. Purified molecules were buffer exchanged with PBS at pH 7.2 and concentrated using 10 kDa cutoff Macrosep centrifugal concentrators (Pall Filtron, Northborough, Mass.). The final product was filter-sterilized and stored at 4° C. until further use.

The concentration of the purified molecules was determined by the colorimetric detection method using the Micro BCA protein assay kit (Pierce, Rockford, Ill.) using BGG as a standard. Gel electrophoresis-sodium dodecyl sulfate polyacrylamide gel electrophoresis (SDS-PAGE) was performed, which confirmed the size of the subunits and their purity (data not shown).

ELISA-Based Stability Testing. For stability evaluation, a specific HLA sandwich ELISA approach was adopted as described earlier herein with minor modifications. Briefly, to detect the antigen sHLA-A*0201, the wells of a microtiter plate were coated with the specific (capture) antibody W6/32 (8 μg/mL) followed by the incubation with test solutions containing the antigen. Unbound antigen was then washed away, and a second antigen-specific antibody (anti-β2m) (DAKO, Glostrup, DK) conjugated to HRP (detector) was added. After addition of the HRP substrate OPD, the degree of substrate hydrolysis was measured. ELISA data were finally transformed to percent relative stability using the nonheated solution of sHLA-A*0201 (4° C.) as reference (100%). Data are graphed against hours of incubation, and the half-lives were determined by applying a one-phase exponential decay model.

FP-Based Peptide Binding Assays. In a first step, the three components of the binding reaction (peptide, sHLA, and β2m) were prepared as concentrates. The fluorescent-labeled peptide (pFITC), listed in Table VI, and the sHLA component of the reaction were diluted to appropriate 4× and 2× solutions, respectively. The β2m component (Fitzgerald Industries International, Concord, Mass.) was prepared as a 4× mix and always added in a 2× molar excess of the used sHLA concentration. For all preparations, 1×BGG/PBS was used as buffer. In a second step, each individual well of a black 96-well UL HE PS microplate (Molecular Devices) was loaded with 10 μl of the prepared 4×β2m and 10 μL of 4×pFITC. To start the peptide exchange procedure, the 2×sHLA mix was activated by incubation at 53° C. for 15 min before addition of 20 μL to the previously loaded wells, reaching a final volume of 40 μL. All reagents were added to the wells of the microtiter plate sequentially using manual pipettors. Immediately after addition of all fluids, the plate was spun down for 1 min at 2500 rpm to even the meniscus and remove possible air bubbles. The plates were incubated at room temperature until no further increase in polarization was observed, indicating that equilibrium was reached (24-48 h). After each reading, the plate was covered with a lid and sealed with parafilm to protect from light and to prevent evaporation of the constituents. The use of appropriate controls allowed accurate estimation of specific polarization. Specific control groups included (a) protein only, (b) tracer only, and (c) buffer only. The protein only control indicated the background signal contributed from sources other than the fluorescent peptide, which was eliminated by subtraction from the experimental sample. For proper analysis, S (parallel) and P (perpendicular) intensities were background corrected. Background signals can arise from the microplate plastic, solution contaminants, leakage of light through the optical filters, or other sources generated in the instrument. Background-subtracted with the buffer only control, the tracer only control measured S and P values for free fluorescent peptide. As described by Herron and Voss (1981) and according to the instructions of the manufacturer of the Analyst AD, these corrected values serve in the calculation of the G factor [G factor] $I_S/I_P (1-(^{27}/_{1000}))/(1+(^{27}/_{1000}))$, which is a scaling (correction) factor, taking relative polarization measurements and making them appear absolute (relative to the theoretical mP (27 for fluorescein). Within this study, G factors were very stable values typically ranging from 0.9 to 1.1. Once a G factor had been determined, it was entered into the formula to calculate polarization: $mP=(I_S-I_P G)/(I_S+I_P G)\times 1000$.

FP measurements were performed on the Analyst AD assay detection system (Molecular Devices, Sunnyvale, Calif.) using a continuous high-intensity, xenon-arc lamp as light source with the following filter settings: excitation wavelength of 485 nm and emission wavelength of 530 nm. In a standard FP configuration, the static excitation polarization filter was set in S position whereas the dynamic emission polarization filter polarized the light in either the S or P orientation. A dichroic mirror (50/50 beam splitter) was used to direct the polarized light into the assay well. Emitted polarized light was detected by the fluorescence photomultiplier tube with the SmartRead, sensitivity 2 setup option in counts per second (cps). The two intensity measurements collected for each well, one when the polarizers were parallel to each other (S and S) and one when the polarizers were perpendicular to each other (S and P), were used to calculate polarization in millipolarization units (mP).

Time-Course Analysis of sHLA/Peptide Association.

Peptide kinetics of the ternary complex formation was investigated by monitoring the association of FITC-labeled peptides to sHLA molecules by FP, which allows direct measurement of the time course of the reaction. To determine the association kinetics, the purified sHLA molecules (50 μg/mL) and various concentrations of fluorescent-labeled peptides were incubated in the presence of excess β2m (24.8 μg/mL) in a final volume of 40 μL. Changes in FP were monitored starting shortly after addition of the activated sHLA at time 0, until equilibrium was reached. Reactions were setup directly in 96-well black plates. Measurements were performed on the Analyst AD as described above.

Binding parameters were achieved by fitting all data points to a monoexponential association model $[FP] FP_{max}(1-e^{-kt})$. FP is binding and t is time. The variable k in the exponential association equation is the observed rate constant ($k_{ob}$), expressed in units of inverse time, which is concentration dependent. To calculate absolute rate constants for association ($k_{on}$) and dissociation ($k_{off}$), $k_{ob}$ values were graphed versus the ligand concentration. Extrapolation of the plot to zero ligand determined the intercept, which is equal to $k_{off}$. The slope of the graph corresponded to $k_{on}$.

Results:

State-of-the-art biochemical assays are comprised of technologically advanced platforms and cutting edge reagents. Such assays must also be practical in many laboratory environments and, in this case, amenable to many different peptide/HLA combinations. Here, a FP-based system was developed for real-time peptide binding analysis with the overall objective of providing a robust and highly sensitive assay for the better characterization of HLA/peptide interactions.

FITC Labeling of Synthetic Peptide Candidates. The initial step toward assay development was the selection of high affinity peptide candidates and the attachment of a fluorescein isothiocyanate (FITC) label to these peptide candidates. Because the assay represents a quantitative characterization of FITC-labeled peptides, it was important to maintain insofar as possible the native reactivity of the candidate molecules. This goal implies that the functional groups involved when the peptide reacts with the sHLA molecule remain fully active and unimpeded and that the fluorescent label itself does not become involved in, or perturb, the reaction. The chemical addition of a FITC molecule to a peptide requires distinct amino acid residues, and only side chains containing primary amines (lysines, K) or sulfhydryl groups (cysteins, C) can be fluorochrome-labeled. Therefore, the fluorescent labeling of peptide candidates makes it mandatory to perform amino acid substitutions if these amino acids are absent within the primary structure of the peptide candidate. However, substitution of amino acids is not without risks as these residues can exert important effects on the binding capacity of a peptide. Therefore, considering only sequence positions with known permissiveness (Ruppert et al., 1993), positions P4, P5, and P8 for 9-mers and positions P5 and P6 for 10-mers were selected to allow the chemical coupling to the primary amine of a lysine side chain (Table VI). Important to mention is that labeling of an internal K residue for A*0201 peptides is not considered a conservative substitution. Such a modification will likely affect the interaction in a negative way as the FITC-coupling reaction changes the positively charged residue to a hydrophobic group, thus losing its capability for electrostatic interaction.

Figure 12:
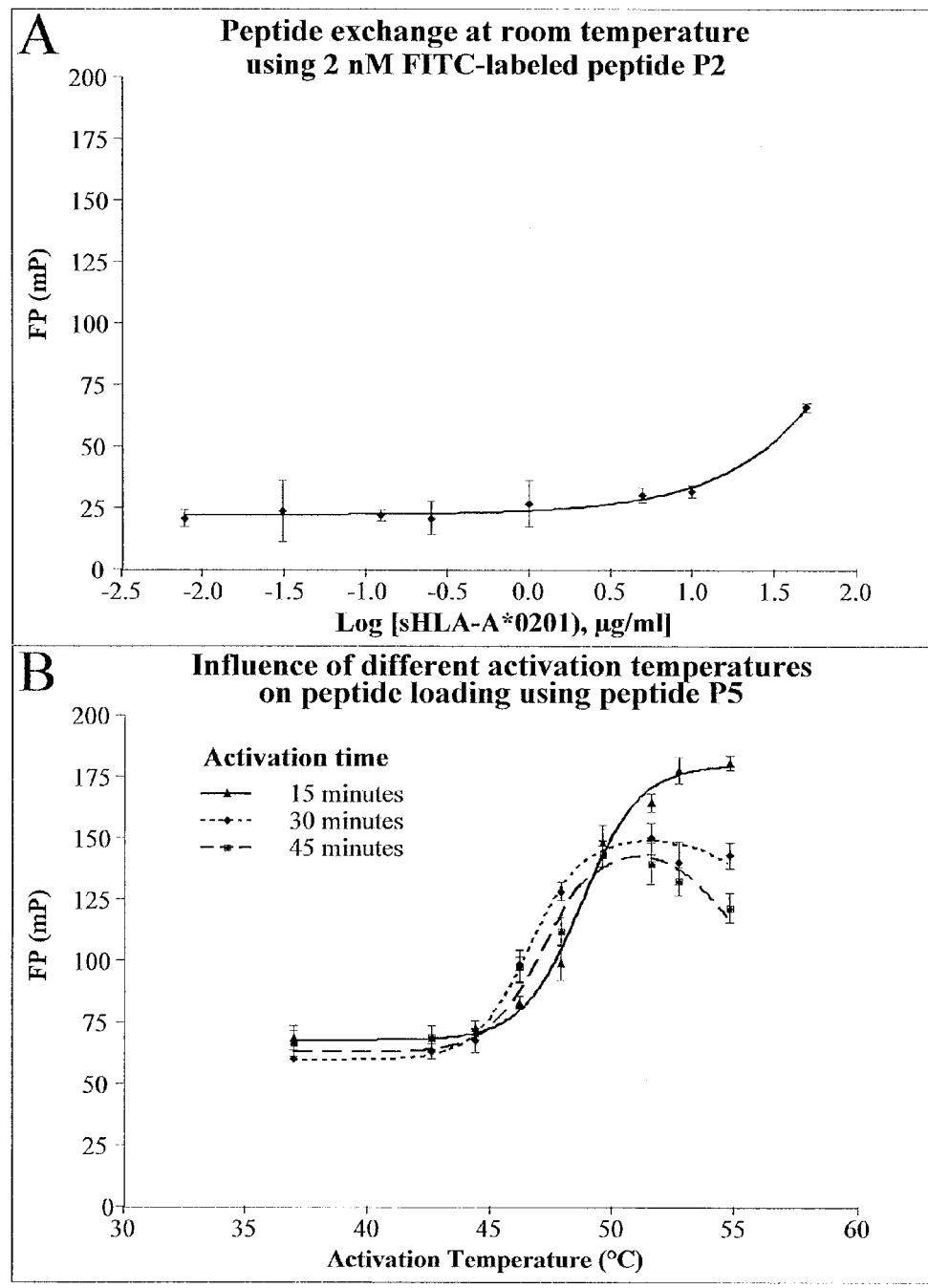
FIG. 12 illustrates a peptide exchange analysis. (A) Peptide exchange was monitored at room temperature over a sHLA concentration range of 0.01 to 50 µg/ml. Results demonstrate a low signal output making passive loading highly inefficient. (B) The influence of different activation temperatures on peptide exchange efficiency was tested by activating 50 µg/ml sHLA followed by incubation with 10 nM of the pFITC P5. Most optimal conditions were established using an activation temperature of 53° C. for 15 minutes to achieve maximal polarization levels. Longer activation times are shown to be sub-optimal for highest loading efficiency.

Peptide Exchange Procedure. Since the recombinant sHLA class I proteins used for this study are loaded with endogenous peptides, binding of FITC-labeled peptides can only occur through a peptide exchange procedure in which the original endogenous peptide is first released from the HLA binding groove. Therefore, the second but most challenging step in the development of the A*0201 peptide binding assay was the design of an effective loading procedure for FITC-labeled peptides. Because difficulties of loading native HLA molecules with synthetic peptides are well-known, several protocols have been designed. One of the simplest methods described in the literature was passive loading in which the peptide exchange is observed at room temperature. However, initial testing of multiple sHLA concentrations incubated with pFITC P2 demonstrated that passive loading did not work particularly well (FIG. 12A). The measured change in polarization values upon binding under equilibrium conditions was only 40 mP, reaching a maximal polarization level of 66 mP for the highest concentration used. These results corroborate with earlier findings showing experimental difficulties in demonstrating peptide binding to complexes that contain endogenous peptides. The low loading efficiency was attributed to the stability of the endogenous peptide/class I molecule complex. Other methods described included the stripping of peptides through alkaline or mild acid treatment followed by gel filtration and slow refolding at neutral pH to obtain HLA class I heavy chains without the presence of the endogenous peptides or $\beta2m$. However, the heavy chains prepared through these procedures were found to be unstable and only useable for a short amount of time, which makes such stripping procedures ill-suited for more advanced and standardized binding assays as stability has a direct impact on assay quality and reproducibility. Since most effective loading seems to be attained only when empty class I proteins become available, a novel approach was developed herein to increase the fraction of empty, peptide-receptive class I molecules. The approach of the present invention was based on the idea that peptide loading efficiency can be improved through the activation of sHLA molecules by thermal energy. Incubating sHLA samples temporarily at higher temperatures should thermodynamically destabilize the sHLA complex, allowing more peptide-receptive sHLA molecules to participate in the peptide exchange. However, the extent of energy employed has to be carefully controlled to ensure that the majority of the molecules are capable of restoring proper conformation after the reinstatement of original conditions.

As seen in FIG. 12B, sHLA activation as a function of temperature and time was tested to identify optimal peptide loading conditions. Identical sHLA samples (50 µg/mL) were incubated at various temperatures over a period of 15, 30 and 45 min. After activation, the samples were immediately combined with 10 nM pFITC P5 to initiate the experiment. The association of labeled peptides was monitored in real time to ensure that equilibrium was reached. Results obtained showed a steady increase in polarization with higher activation temperatures. Short-term activation for 15 min was found to be more advantageous than activation for 30 or 45 min as a much higher polarization level could be achieved. With longer activation periods, a decline in polarization was observed at temperatures above 50° C. This decline is due to partial denaturation of the complex by applying too much thermal energy. Most optimal conditions for peptide exchange activation were established by incubating sHLA complexes at 53° C. for 15 min. These parameters were kept constant and were applied for all further experiments. Only a low net increase in polarization was observed at temperatures below 43° C., and the loading efficiency was comparable to the results obtained through passive loading at room temperature. This observation indicates that the sHLA complexes are very stable and do not efficiently dissociate at temperatures below 43° C.

Figure 13:
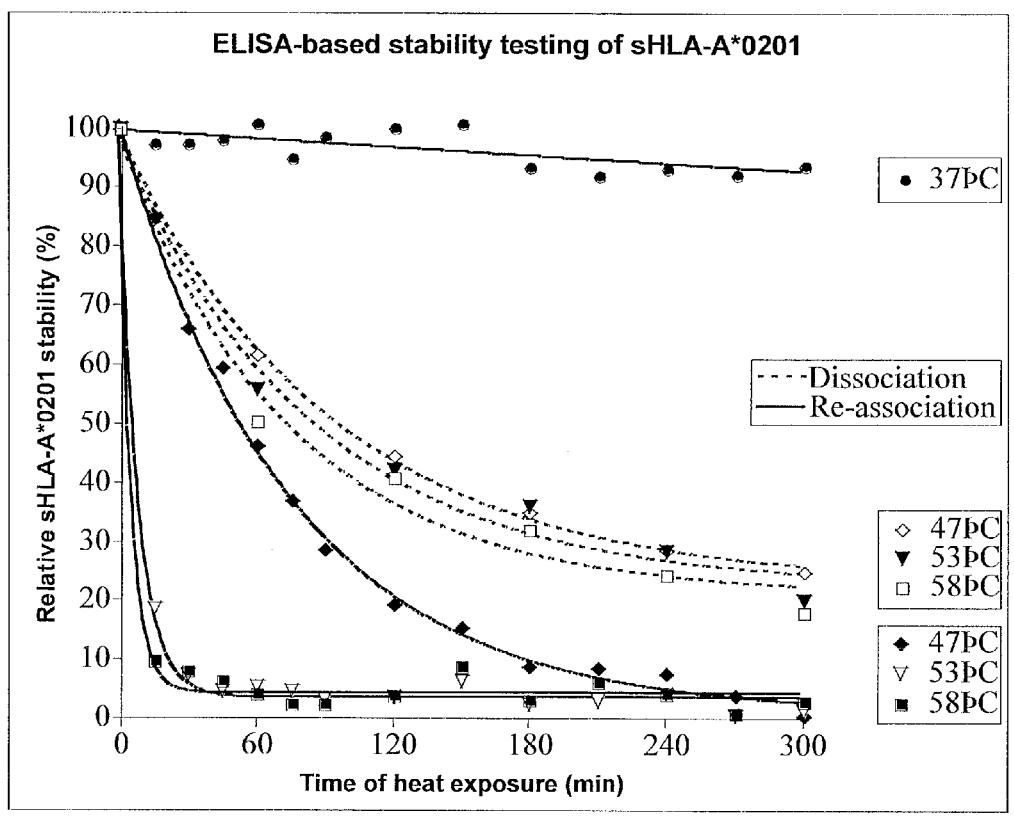
FIG. 13 illustrates an ELISA-based sHLA-A*0201 stability determination using conformational epitope-recognizing antibody W6/32. An assay procedure consisting of the monoclonal antibody W6/32 as capturing reagent and anti-β2m (HRP) as the detector antibody was developed to test sHLA-A*0201 complex stability at various temperatures during a period of 5 hours in 3% BSA. After incubation, the solutions were immediately tested on ELISA preventing reformation of destructed/destabilized molecules. ELISA data are transformed to % relative stability using a sample hold at 4° C. as 100%. Data are graphed against time of heat exposure and half-lives determined applying a one-phase exponential decay model (solid lines). In addition, a selection of heated samples were re-evaluated after a 72 hour incubation time at 4° C. to determine complex re-formation (dashed lines) and added to the graph.

To further validate the thermal activation procedure, the structural integrity of sHLA-A*0201 molecules during and after thermal destabilization was monitored using an ELISA based procedure which uses the conformation-dependent monoclonal antibody W6/32. For this stability testing, samples of sHLA-A*0201 were incubated at 58, 53, 47, and 37° C. for various lengths of time. After data transformation to percent relative stability using the nonheated solution (4° C.) of sHLA-A*0201 as reference (100%), data were graphed against time of heat exposure and the half-lives determined (FIG. 13). It is shown that the sHLA-A*0201 stability curve rapidly declines at higher temperatures (58 and 53° C.) with half-lives of only 3.7 and 5.7 min, respectively, indicating fast dissociation of the complex into its subunits. After 45 min, the conformational antibody was unable to detect any significant amounts of intact sHLA molecules. This effect was drastically reduced at 47° C. where complete denaturation of most molecules occurred after 3 h and showed a half-life of 51.6 min. Incubation of sHLA-A*0201 at 37° C. demonstrated little effect, and more than 95% of all molecules still maintained their structural integrity.

Figure 14:
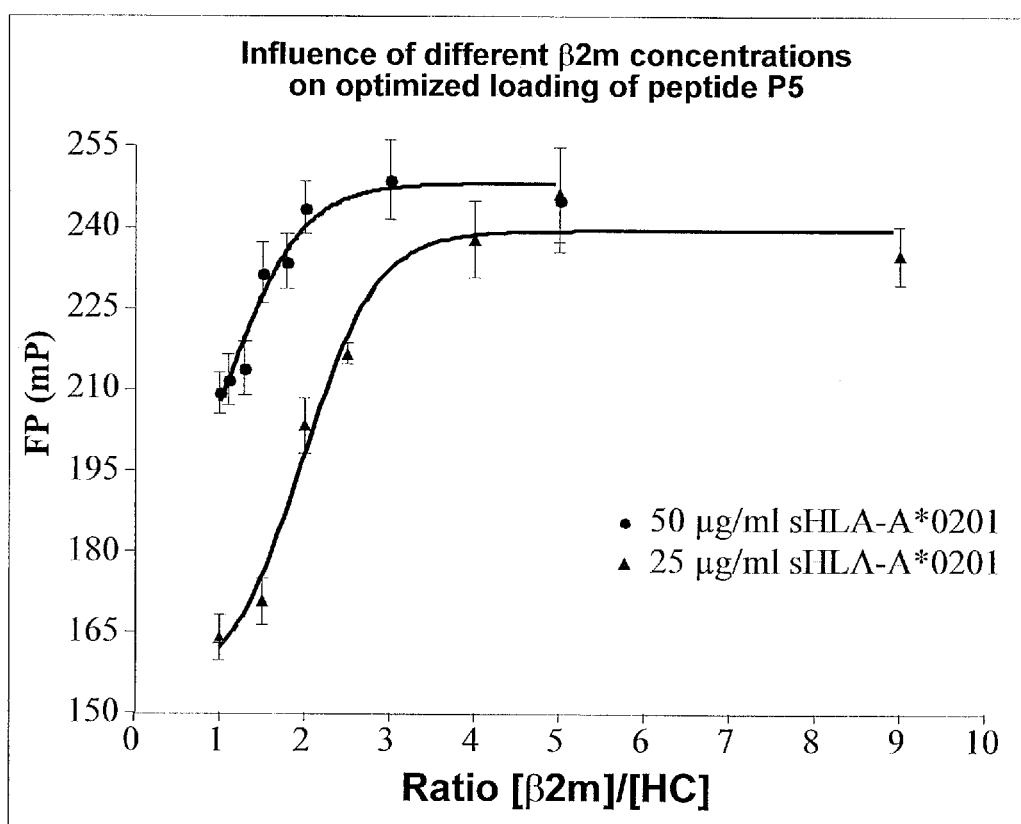
FIG. 14 illustrates the influence of variable β2m concentrations on maximal performance. Fixed amounts of sHLA-A*0201 (50 and 25 µg/ml) and 10 nM of pFITC P5 were incubated with varying amounts of β2m expressed as ratio of β2m] per [HC] under equilibrium conditions. Results show that peptide loading efficiency was highly increased using excess β2m. An optimal ratio of 3 was determined for both sHLA concentrations meaning that a 2× excess β2m over sHLA has to be supplemented to achieve maximal polarization levels.

After heat exposure, selected sHLA preparations were immediately brought to 4° C. and allowed to reassociate for 72 h without supplementation of exogenous peptides or $\beta2m$. As seen in FIG. 14, a re-formation process of subunits occurred as demonstrated above. Data show that the reassociation of sHLA-A*0201 complexes happens more effectively by using short activation times compared to extensive heat exposure. Incubations over 2 h seem to destroy more than 60% of the molecules, rendering them unusable for FP assays. Interestingly, temperature variance had a lesser effect than the time of heat exposure. Overall, this ELISA approach confirms and validates the thermal activation results obtained by FP experiments. Furthermore, it could also be demonstrated that, under the established conditions for optimal peptide exchange activation (53° C. for 15 min), more than 85% of sHLA-A*0201 molecules are available for the exchange process.

Influence of $\beta2m$ on Peptide Loading. In order for HLA class I alleles to be able to efficiently bind peptides, recent peptide loading experiments indicated that excess $\beta2m$ must be present in order to enhance peptide binding. To further improve the sensitivity of the assay, the influence of variable $\beta2m$ concentrations on maximal performance was tested. Fixed amounts of sHLA-A*0201 complexes (25/50 µg/mL) were allowed to react with varying amounts of $\beta2m$. As shown in FIG. 14, addition of higher concentrations of $\beta2m$ improved binding of the FITC-labeled reference peptide P5 by increasing the dynamic range by 15% for 50 µg/mL and by 30% for 25 µg/mL of sHLA-A*0201, respectively. The response curve for 50 µg/mL µg/ml compared to the curve generated by 25 µg/mL is higher as more sHLA molecules are available to participate in the binding event. An optimal ratio of three $\beta2m$ molecules per single HLA heavy chain was determined. Addition of more $\beta2m$ did not result in a more efficient loading.

As part of the optimization process, another goal was to minimize the contribution of assay components to nonspecific FP. High background counts due to buffer or nonfluorophore components can seriously affect the sensitivity of an assay. By using purified molecules, light scattering through cell membranes and cellular debris was not a problem, and therefore no contribution of the sHLA protein to the final signal could be detected. However, to further improve signalto-background ratios, bovine 5-globulin (BGG) was included as carrier protein, which drastically decreased baseline fluorescence intensity signals. A concentration of 0.05% BGG was sufficient to prevent nonspecific binding of the FITC-labeled peptides to other assay components and the walls of incubation vessels. In contrast, bovine serum albumin (BSA) completely failed as an alternative because of its ability to bind the fluorescent-labeled peptides, an interaction which greatly increased baseline polarization and reduced assay range (data not shown). Incubation of free FITC molecules with sHLA did not increase FP values, demonstrating that the fluorescent label does not impact the assay. Additional optimization experiments such as testing of various buffer systems did not result in further improvements of the assay protocol and are therefore not presented.

Figure 15:
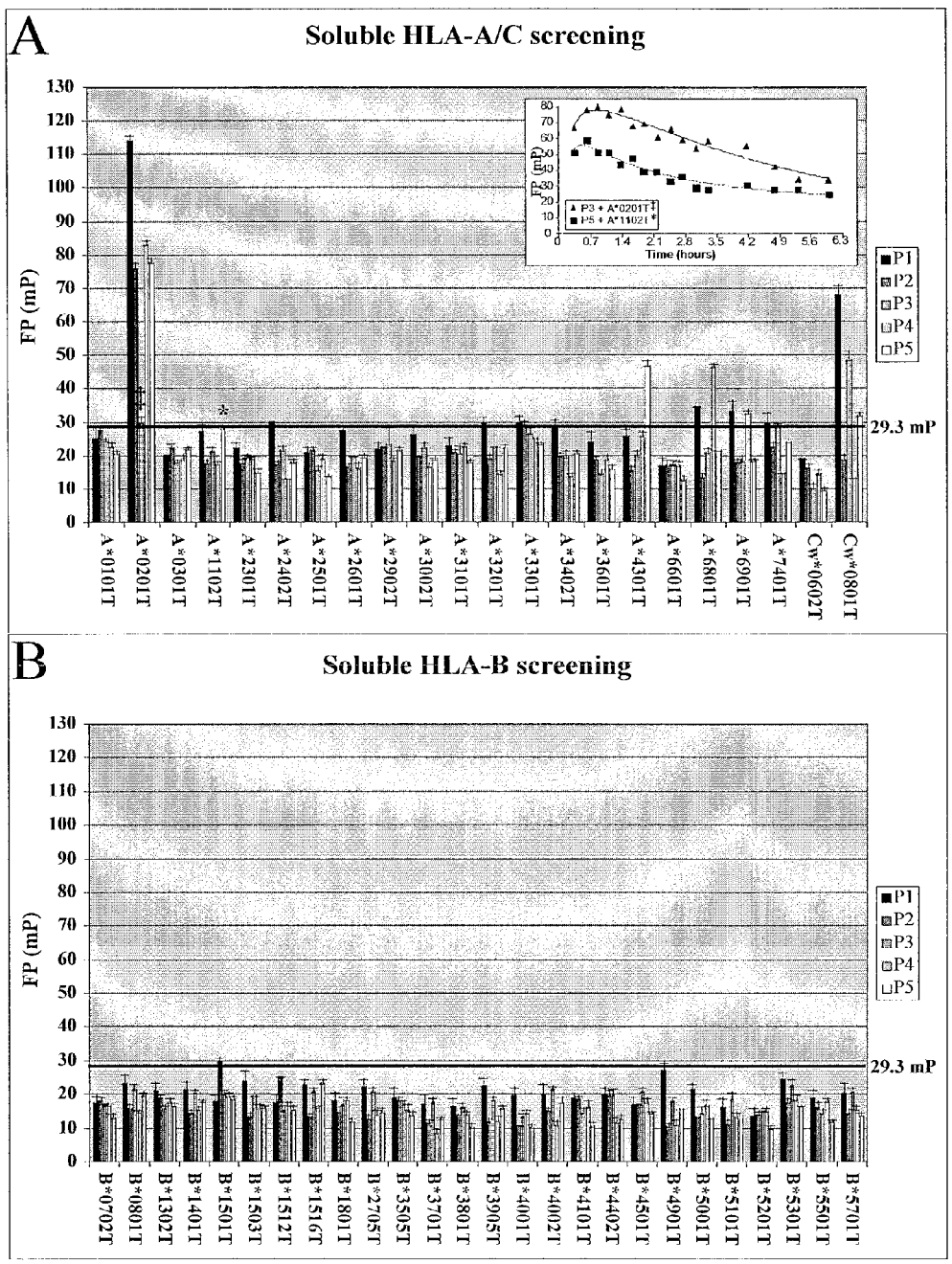
FIG. 15 illustrates the screening of HLA A, B and C alleles for cross-reactivity evaluation. A panel of 48 distinct sHLA alleles was tested to determine the specificity of the present invention's designed peptides to sHLA-A*0201 and to elaborate cross-reactivity to other sHLA allele specificities. FP values are obtained using a more simplified binding protocol without addition of β2m. Each peptide candidate (10 nM) was incubated with 100 μg/ml of activated sHLA and peptide/HLA interaction was monitored over time. Final equilibrium polarization levels indicating the extent of binding to each allele after incubation with each of the five test peptides is shown. A threshold line of 29.3 mP was introduced, which corresponds to the completely free state (and lowest polarization value) of the labeled ligand. (A) In this graph, twenty HLA-A

Multiple Specificity Screening. To determine the specificity for sHLA-A*0201 as well as potential cross-reactivity to other sHLA alleles, 48 different sHLA alleles were screened for binding with the A*0201 pFITC constructs (FIG. 15). For screening purposes, each peptide candidate (10 nM) was incubated with 100 μg/mL activated sHLA, and the peptide/HLA interaction was monitored over time. As expected, no significant binding was detected to any of the B-alleles tested (FIG. 15B), whereas a high binding affinity was observed between sHLA-A*0201 and the pFITC candidates. An exception was pFITC P3 (FIG. 15A). This peptide failed to attain a higher polarization level compared to the other candidates. A more detailed investigation showed that, at an early time point of association, this peptide was capable of binding to sHLA-A*0201 (FIG. 15A, insert). The significant decrease in association kinetics recorded after 0.8 h seems to imply that the HLA class I molecule is not stabilized following exposure to this peptide, irrespective of whether it attempted to bind. This effect was possibly caused by the integration of the fluorescent tag into the structure as the native peptide is published to have a high affinity to sHLA-A*0201. Thus, modification of the residue at the P4 nonanchor position of pFITC P3 may not affect the specificity and association kinetics of peptide binding but rather seems to affect the stability of the class I peptide interaction.

In addition to a successful interaction with sHLA-A*0201, high to medium binding affinities could also be observed between sHLA-Cw*0801 and peptides P1 and P3. Interestingly, the stability of the sHLA-Cw*0801/P3 interaction was not disrupted as it was for sHLA-A*0201/P3, indicating that positions most suitable for FITC labeling in A*0201 molecules may not be the same as those for Cw*0801. Peptide P5 was also found to bind sHLA-Cw*0801 but to a much lesser extent. However, binding was still significantly over the threshold line (29.3 mP), which corresponds to the determined baseline value where all pFITC conjugates are in a free state. No G factor correction was applied for the screening analysis, explaining a threshold of 29.3 mP rather than 27 mP. Comparing the structural characteristics of the designs to each other showed that only those peptides bound to Cw*0801 carrying a leucine (L) at position 2 and valine (V) at the C-terminus. These findings allowed us to propose an initial Cw*0801 binding specificity. Peptides P2 and P4 which did not concur with this rudimentary P2L/P9V motif were not able to bind sHLA-Cw*0801 (Table VII).

Furthermore, binding of peptides P4 and P1 to sHLA-A*6801 and sHLA-A*6901 as well as binding of peptide P5 to sHLA-A*4301 and sHLA-A*1102 could additionally be detected. In case of the interaction of P5 with sHLA-A*1102, the same observation was made as for peptide P3 binding to sHLA-A*0201, showing that this interaction was not stable at equilibrium (FIG. 15A, insert). The possibility of having monitored the effect of peptide degradation, however, can be ruled out, as both peptides were capable of binding to other alleles under equal conditions. To support these findings, it has been reported previously that HLA-A*6901 could bind certain A*0201-restricted antigenic peptides. Among those peptides is the nonmodified version of the P1 peptide which was also reported to bind A*6802 in addition to A*0201, A*0202, A*0205, and A*0206. However, these alleles were not available for this study.

Generally, screening data showed that four out of the five peptides demonstrated cross-reactivity with at least 2 of the 48 alleles tested, confirming but also extending the cross reactivity pattern found in other studies. More specifically, P1 and P5 bound to four different sHLA alleles, A*0201, A*6801, A*6901, and Cw*0801 and A*0201, A*4301, Cw*0801, and A*1102, respectively. P4 bound to three different sHLA alleles, A*0201, A*6801, and A*6901, and P3 bound two of the sHLA alleles, A*0201 and Cw*0801, tested. P2 was the only peptide not showing any cross reactivity and solely interacting with sHLA-A*0201.

Figure 16:
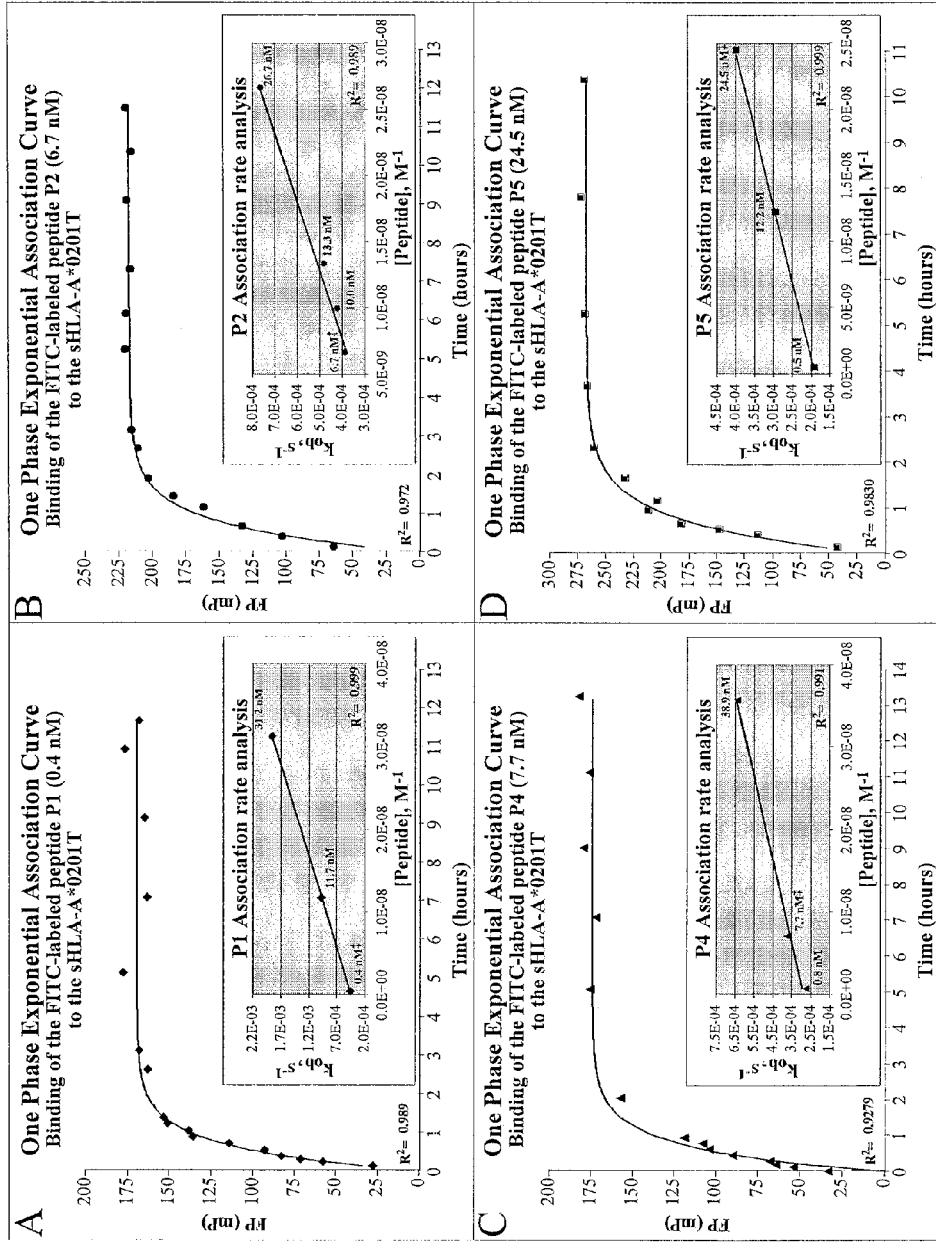
FIG. 16 illustrates the association of FITC-labeled peptides (A) P1, (B) P2, (C) P4, and (D) P5 with sHLA-A*0201. The association profiles for pFITC conjugates with sHLA were recorded at 20° C. at various periods of time in which the FP signals corresponding to the ratio of bound to free pFITC ligand were plotted versus time. Peptide binding to sHLA was rapid and stable and reached a maximum within several hours of incubation depending on the concentration tested. The data were fitted to a mono-exponential association model to determine apparent rate constants ($k_{ob}$). Concentration dependence of pFITC binding kinetics to HLA-A*0201/β2m are shown as inserts. Extrapolation of the plot to zero ligand allowed calculating absolute rate constants for association ($k_{on}$) and dissociation ($k_{off}$) as well as equilibrium dissociation constants ($K_d^{kin}$).

Kinetics of sHLA-A*0201/Peptide Interactions. A series of experiments to determine the kinetic rate constants to four of the five derivatized peptides were performed. In these experiments, different concentrations of the pFITC ligand were applied by using 50 μg/mL sHLA-A*0201 combined with an excess of β2m at room temperature (20° C.). Under such conditions, peptide replacement kinetics was shown earlier to be independent of the complex or β2m concentrations, therefore reflecting a pseudo-first-order reaction. After initiation of the reaction, typical curves of peptide binding time courses were recorded following the association of the FITC-labeled peptides to the class I sHLA complex A*0201 (FIG. 16). Starting from 27 mP, which corresponds to the free peptide condition, the FP values increased primarily during the first 3 h of the experiment. After this period, values reached a maximum plateau, where no further increase was monitored, indicating that equilibrium had been reached. The observed (apparent) association rate constant ($k_{ob}$), which is concentration dependent and expressed in units of inverse time, was obtained by fitting all data points to a monoexponential association model (see Materials and Methods section). As expected, the apparent dissociation rates were slower for low concentrations and faster for higher concentrations. Since the observed association rate constant was increasing linearly with the concentration of peptide, the data obtained allowed the calculation of absolute rate constants for association ($k_{on}$) and dissociation ($k_{off}$). Extrapolation of the plot to zero ligand as presented in the FIG. 16 inserts, determined the intercept, which equals $k_{off}$.

TABLE VII

Motif Comparison of Alleles Showing Positive Binding Capacity with A*0201-Specific Peptides

| | position 1 2 3 4 5 6 7 8 9 10 | binding | SEQ ID NO: |
|---|---|---|---|
| A*0201[a] | L<br>M<br>V | V<br>L | |
| P1 | F L P S D K F P S V | + | 23 |
| P4 | L V F G K E V V E V | + | 26 |
| P5 | A L M D K V L K V | + | 27 |
| P2 | S L Y N K V A T L | + | 24 |
| P3 | N L S K L S L D V | (+) | 25 |
| A*6801[b] | D V<br>E T | R<br>K | |

TABLE VII-continued

Motif Comparison of Alleles Showing Positive
Binding Capacity with A*0201-Specific Peptides

```
          position
          1 2 3 4 5 6 7 8 9 10    binding   SEQ ID NO:
P4        L V F G K E V V E V        +         26
P1        F L P S D K F P S V        +         23
P5        A L M D K V L K V          -         27
P3        N L S K L S L D V          -         25
P2        S L Y N K V A T L          -         24

Cw*0801
P1        F L P S D K F P S V        +         23
P3        N L S K L S L D V          +         25
P5        A L M D K V L K V          +         27
P2        S L Y N K V A T L          -         24
P4        L V F G K E V V E V        -         26

A*6901ᶜ   V I     I         V
          T F         F     L
          A L         L
P4        L V F G K E V V E V        +         26
P1        F L P S D K F P S V        +         23
P5        A L M D K V L K V          -         27
P3        N L S K L S L D V          -         25
P2        S L Y N K V A T L          -         24
```

ᵃSee the following references for motifs: Ruppert et al. (1993) Cell 74: 929-937; Falk et al., (1991) Nature 351: 290-296; and Kubo et al., (1994) J Immunol 152: 3913-3924.
ᵇSee Guo et al., (1992) Nature 360: 364-366 for motifs.
ᶜSee Barouch et al., (1995) J Exp Med 182: 1847-1856 for motifs.

whereas the slope of the graph corresponds to $k_{on}$. As listed in Table VIII, peptide dissociation rate constants for A*0201 peptide designs tested with sHLA-A*0201 were found to be relatively consistent [$(1.9–4.3)\times10^{-4}$ s$^{-1}$]. This was not surprising considering that all peptides were considered to be high-affinity binders as well as good CTL responders, thus assuming the necessity of low dissociation rates for in vivo immunogenicity. Equally, the rate constants for association were also found to be very similar [$(1.0–8.7)\times10^{4}$ M$^{-1}$ s$^{-1}$]. Such a close range of association rate constants indicates that all peptides seem to use the same association mechanism.

TABLE VIII

Summary of Kinetic and Equilibrium Constants

| | | A*0201T | | | |
|---|---|---|---|---|---|
| | | P1 | P2 | P4 | P5 |
| association rate constants | $k_{on}$ | 4.52 | 1.94 | 0.99 | 8.68 $10^4$ M$^{-1}$ s$^{-1}$ |
| dissociation rate constants | $k_{off}$ | 4.33 | 2.40 | 2.84 | 1.88 $10^{-4}$ s$^{-1}$ |
| equilibrium dissociation constants (kinetics) | $K_d^{kin}$ | 9.6 | 12.4 | 28.5 | 21.6 $10^{-9}$ M |
| equilibrium dissociation constants (titration) | $K_d^{titr}$ | 10.7 | 21.1 | 21.8 | 17.3 $10^{-9}$ M |

In addition, the kinetic data presented also allow for the estimation of the equilibrium dissociation constant ($K_d^{kin}$), which is the ratio of the dissociation and association rate constant ($K_d^{kin}=k_{off}/k_{on}$). All constants determined were in very good agreement with the values obtained in titration experiments under equilibrium conditions ($K_d^{titr}$), further confirming the accuracy of FP-based binding assays (Table VIII).

Development and Validation of Fluorescence Polarization-Based Competitive Peptide-Binding Assay for HLA-A*0201

Materials and Methods:

Synthetic Peptides. FITC-labeled peptides were commercially synthesized as described herein previously. Unmodified unlabeled peptides were synthesized and purified by the Molecular Biology Resource Facility of the Warren Medical Research Institute at OUHSC (Oklahoma City, Okla.). Purity of all synthetic peptides was greater than 95%, and their composition was ascertained by mass spectrometric analysis. Peptides were stored dry in prealiquoted amounts of 0.2 and 0.4 μmol for labeled and unlabeled peptides, respectively. Each pFITC preparation was standardized using a molar fluorescence intensity curve generated by a premeasured FITC standard (Pierce) reconstituted in 1×BGG (0.5 mg/mL). Aliquoted working dilutions for FITC-labeled peptides (200 μM) were kept at 20° C. and reused for a period of up to 4 months without a measurable decline in the signal.

Large-Scale Production and Purification of Recombinant sHLA Molecules. Production and purification of recombinant sHLA molecules was performed as described herein above. The molecular weight of sHLA-A*0201 was determined to be 47.2 kDa, and the molecular weight of β2m was determined to be 11.7 kDa.

FP-Based Peptide Competition Assay. FP measurements were performed as described herein above. For a standardized assay setup, each individual well of a black 96-well UL HE PS microplate (Molecular Devices) was loaded with 5 μL of a 16 β2m solution (198.7 μg/mL; 16 936 nM) (Fitzgerald Industries International, Concord, Mass.), 10 μL of 4× competitor at various dilutions, and 5 μL of an 8×pFITC preparation (16 nM). After addition of all fluids, a final ratio [β2m]/[heavy chain] of 3:1 was achieved, where 2 parts of β2m are derived from the added β2m solution and 1 part from the sHLA complex. Note that the labeled and unlabeled ligand was presented simultaneously to the activated sHLA.

Specific control groups included (a) protein only, (b) tracer only, and (c) buffer only, which are used for background correction and calculation of the G factor as described earlier (86). The G factor $\{G \text{ factor}=S/P(1-(^{27}/_{1000}))/(1+(^{27}/_{1000}))\}$ is a scaling (correction) factor, taking relative polarization measurements and making them appear absolute. For this study, the theoretical value for free fluorescein (27 mP) was used for G-factor determination with a value of 1.00±0.01. This value slightly dropped to 0.98±0.02 for readings beyond 72 h, probably caused by minor evaporation of the reactant solution. Baseline polarization values determined for all pFITCs in their free state (average 30.3±4.3) were not significantly different from the theoretical value used resulting in close to identical G-factor values. Once the G factor was determined, FP values given as mP (millipolarization) were calculated by the equation: polarization (mP)=1000(S−GP)/(S+GP), where S and P are background-subtracted intensities of the fluorescence measured in the S and P directions.

For assay stability testing, plates containing binding experiments were measured at an extended time period of 3-7 days. No change in maximal polarization levels could be observed, indicating good stability of all constituents. As additional check on the system, the plates were also read in the fluorescence intensity mode to control fluorescent peptide concentrations according to the established standard curve for single peptides.

Competition Assay Data Analysis. Competition experiments were analyzed by plotting $FP_{max}$ (maximal polarization) values as a function of the logarithms of competitor concentrations. The binding affinity of each competitor peptide was expressed as the concentration that inhibits 50% binding of the FITC-labeled reference peptide. Observed inhibitory concentrations ($IC_{50}$) were determined by nonlinear curve fitting to a dose-response model with a variable slope using the specific software Prism (Graph Pad Software, Inc., San Diego, Calif.). The appropriate values for $FP_{max}$ were extracted from curve fittings of single-association reactions of FITC-labeled peptides to sHLA molecules in the presence of the competitor using a monoexponential association model as described herein previously.

Epitope Screening. Experimental epitope screening at a threshold concentration of 80 µM was performed as described for the competition assay above with only minor modifications. Briefly, 10 µL of 4 competitor peptides (320 µM) (Table IX) were added to individual wells of a black 96-well microplate. Additional components such as 5 µL of a 16 β2m solution and 5 µL of an 8×pFITC preparation were added before starting peptide exchange with 20 µL of activated 2×sHLA solution, reaching a final volume of 40 µL. After equilibrium was reached, FP values were collected on the Analyst AD (Molecular Devices) and transformed into percent inhibition values by choosing the reaction without the inhibitor as 0% inhibition.

Results:

Competition binding assay methodologies have become exceedingly popular for assessing the ability of synthetically defined peptide epitopes to associate with specific HLA class-I complexes. This has been accomplished by comparing the relative affinities of multiple peptide ligands for the same HLA receptor. Experimentally, $IC_{50}$ values, representative of the affinity of the ligand-recognition site, have been determined by incubating HLA molecules from various sources with a labeled peptide in the presence of different concentrations of the competitor. However, results presented from various assay systems have shown a high variability rate, and thus, difficulties have been encountered in obtaining reproducible data. To further enhance the capabilities of such assays and better facilitate epitope discovery for MHC class-I molecules, a novel peptide competition assay has been developed based on the interaction between recombinant, sHLA molecules A*0201 and a fluorescence-labeled peptide reference using the technique of fluorescence polarization. To demonstrate feasibility but also increase the sensitivity and reproducibility of the assay, a detailed analysis of all parameters critical for the standardization of the assay was initially conducted. This analysis was also intended to elucidate critical factors for interassay data comparisons.

Influence of Different Reference Peptides on $IC_{50}$ Values. A primary requirement for the development of a more advanced competition assay is the careful selection of a reference peptide. The binding characteristics of several pFITC ligands to sHLA-A*0201 through kinetics experiments has been described herein, which seem to be well-suited to act as a reference peptide. The labeled peptide candidates were derived from peptides originally identified as naturally presented class-I ligands, CTL epitopes, or constructed from the A*0201 consensus sequence. All designs were made by substituting at various positions at nonanchor residues for a FITC-conjugated lysine (Table VI).

Figure 17:
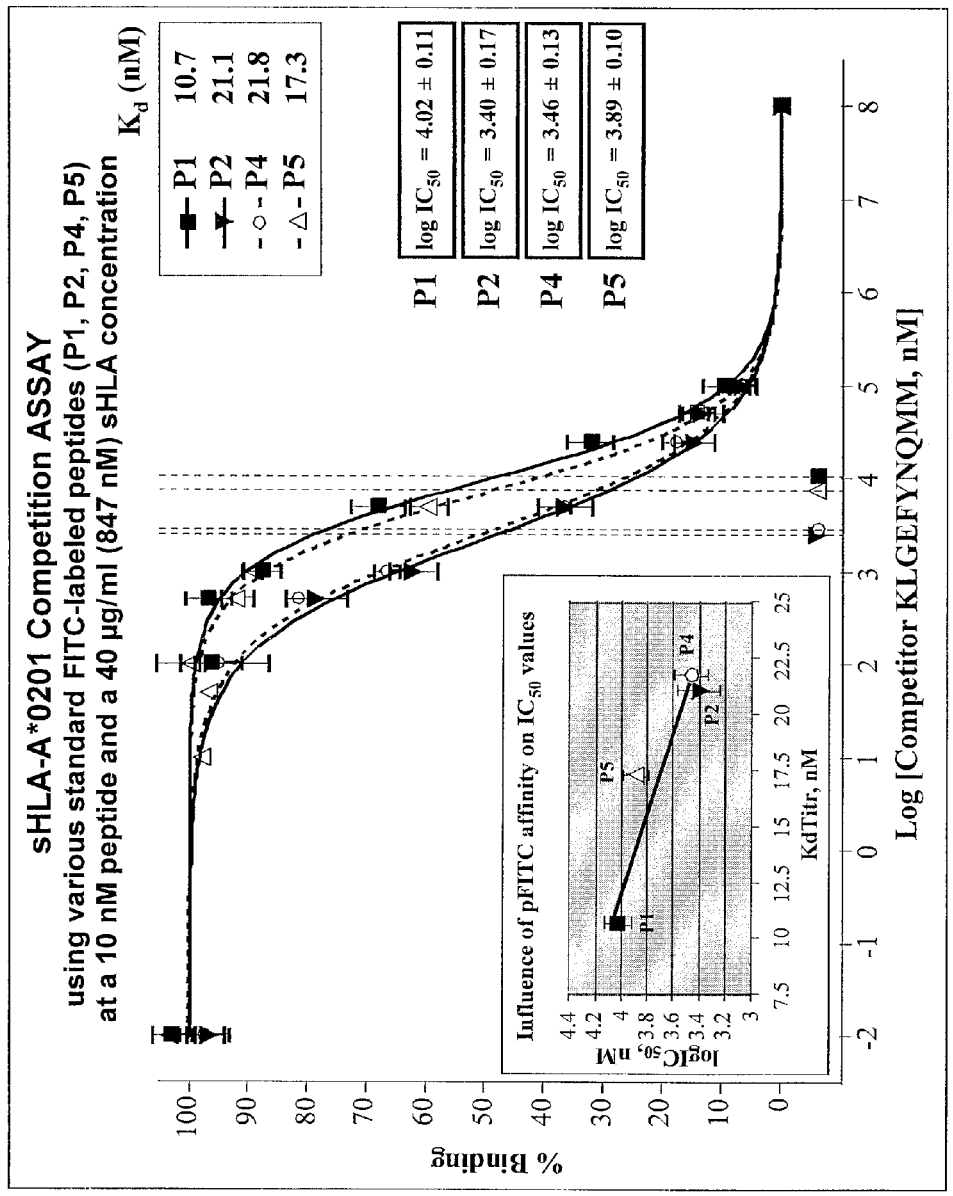
FIG. 17 illustrates soluble HLA-A*0201 competition assays testing the influence of various pFITC reference peptides on the $IC_{50}$ value for the unlabeled competitor KLGEFYNQMM (SEQ ID NO:21). Serial dilutions of competitor were prepared in 96-well plates and incubated with a constant concentration of activated sHLA-A*0201, excess β2m and FITC-labeled reference peptides P1, P2, P4, and P5. After reaching equilibrium at room temperature, FP of each well was read on an Analyst AD using a filter set appropriate for fluorescein. The $IC_{50}$ for the competitor was calculated from nonlinear regression analysis using the software program Prism. The X-axis plots the logarithm of the concentration of the test-peptide, where the Y-axis plots the response expressed in % binding of the pFITC to sHLA. To better compare data, maximum and minimum responses were normalized expressing $FP_{max}$ as 100% and $FP_{min}$ (27 mP) as 0% binding. The $IC_{50}$ concentrations of unlabeled competitor that produces pFITC binding half way between the upper and lower plateaus are indicated. A linear relationship (inset) is shown plotting $IC_{50}$ values as a function of the various $K_d$ values of the pFITC reference peptides.

To visualize the effect of pFITC molecules with different equilibrium dissociation constants ($K_d$) on $IC_{50}$ determinations, FP-based competition assays were performed using a constant concentration of activated sHLA (40 µg/mL; 847 nM), excess β2m (1694 nM), and labeled peptide (10 nM) in the presence of different concentrations of the unlabeled ligand KLGEFYNQMM (SEQ ID NO:21) as a test competitor (FIG. 17). The selected A2-related competitor peptide was derived from the influenza B virus chosen because of its successful use in several HLA studies. For each of the assays shown in FIG. 17, bound fluorescent peptide was displaced from the sHLA molecule. The top of each curve represents a plateau at a value equal to binding in the absence of the competing unlabeled peptide that was set as 100% binding. Because a log axis cannot accommodate a concentration of zero [log(0) is undefined], a value for a very low competitor concentration was entered (−2). The bottom of the curve is a plateau equal to the values for free labeled peptide, which indicates almost complete competition at higher concentrations of the competitor (set as 0% binding). Because of the usage of the G factor, which corrects for the contribution of the measurement pathway to the observed total polarization, the value for nonspecific binding (0%) is equal to the assumed theoretical value of 27 mP. High ratios between the maximum and minimum signals were observed for all competition experiments, with maximal FP values from 183.3 to 224.9 mP depending on the pFITC used (data not shown).

The concentration of the unlabeled competitor that produced 50% inhibition of fluorescent-labeled peptide binding (halfway between the upper and lower plateaus of the obtained curve) and defined as the inhibitory concentration ($IC_{50}$) was calculated by nonlinear regression analysis using the software program Prism. The obtained $IC_{50}$ values for the labeled pFITC ligands ranged from 2480 to 10,500 nM, demonstrating the specific nature of the interaction. No competition was observed testing a nonrelated peptide over the same concentration range used (data not shown). When the $IC_{50}$ values were plotted as a function of the various $K_d$ values of the pFITC tracers, a linear relationship was found (inset of FIG. 17), confirming that the competitive displacement of a reference peptide from its binding site depends on the affinity of the labeled pFITC ligand. Conclusively, it takes more unlabeled competitor peptide (high $IC_{50}$) to compete for a tightly bound tracer peptide (low $K_d$) than for a loosely bound tracer peptide (high $K_d$), which makes it mandatory to assign a single peptide to be used as the reference peptide in a standardized assay environment.

Figure 18:
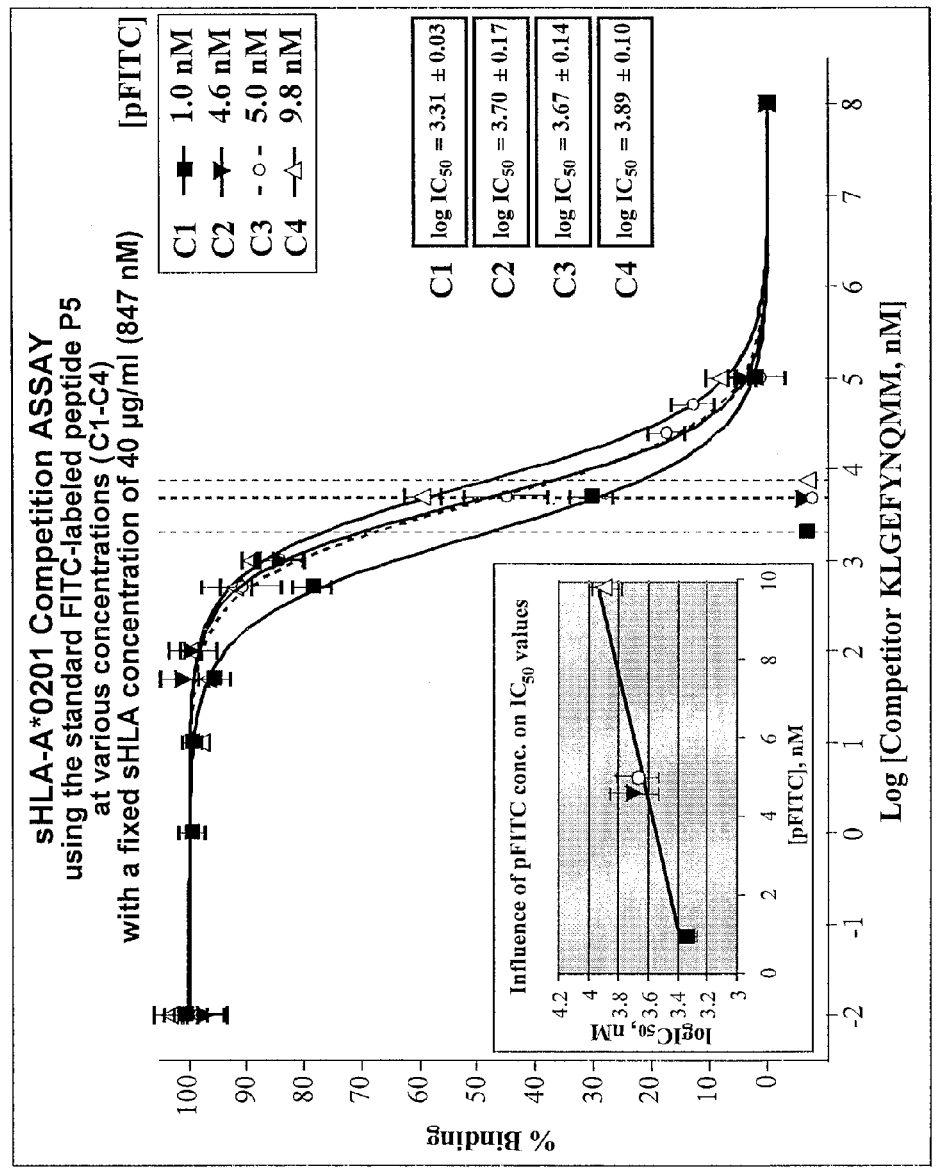
FIG. 18 illustrates soluble HLA-A*0201 competition assays testing the influence of different pFITC concentrations on the $IC_{50}$ value of the unlabeled competitor peptide KLGEFYNQMM (SEQ ID NO:21). Serial dilutions of competitor were incubated together with a constant concentration of activated sHLA-A*0201, excess β2m and the FITC-labeled reference peptide P5 at concentrations of 1.0, 5.0 and 10 nM. After reaching equilibrium at room temperature, polarization values were read and $IC_{50}$ values for the competitor calculated. A linear relationship (inset) was found by plotting $IC_{50}$ values as a function of the pFITC concentration.

Influence of pFITC Concentrations on $IC_{50}$ Values. To fully assess the influence of the pFITC concentration on $IC_{50}$ values in FP-based competition assays, the model competitor KLGEFYNQMM 9SEQ ID NO:21) was tested at several nanomolar concentrations of pFITC P5 utilizing a constant concentration of 40 µg/mL (847 nM) activated sHLA and excess β2m (1694 nM) (FIG. 18). Final analysis showed declining $IC_{50}$ values with reducing pFITC concentrations confirming a linear relationship between the fluorescent-labeled tracer peptide concentration and $IC_{50}$ determinations (inset of FIG. 18). As seen, choosing a higher concentration of tracer will take a larger concentration of unlabeled peptide to compete for half the binding sites. Therefore, to achieve higher accuracy and consistency during the assay performance, working concentrations of pFITC reference peptides have to be standardized and constantly controlled.

Figure 19:
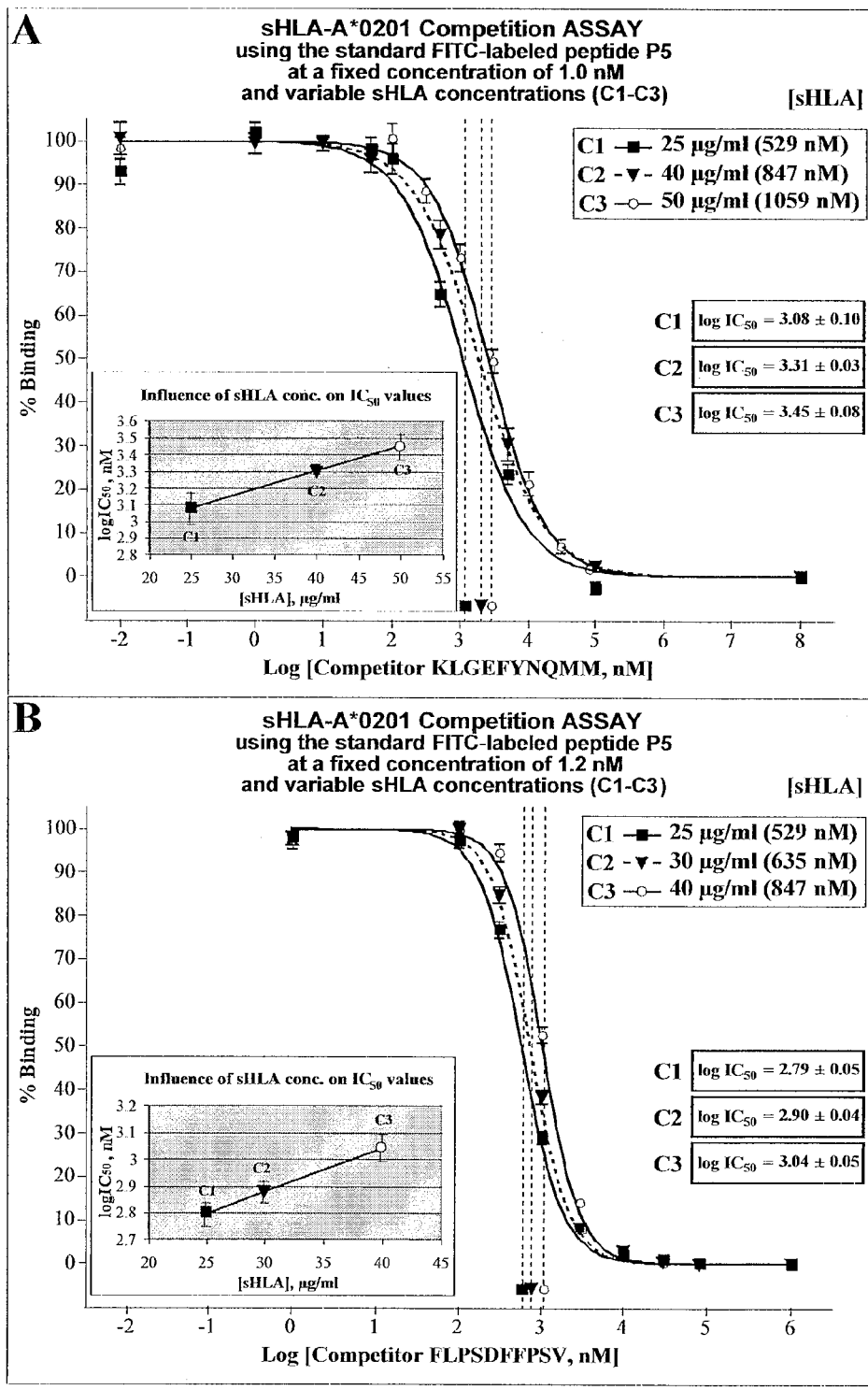
FIG. 19 illustrates the effect of sHLA concentration on competition binding data. Competition binding curves were obtained when the FP readout adjusted to % binding was plotted as a function of competitor concentration. Experiments were performed using variable sHLA-A*0201 concentrations with excess β2m, 1 nM fluorescent peptide P5 and increasing amounts of either (A) competitor peptide KLGEFYNQMM (SEQ ID NO:21) or (B) competitor peptide FLPSDFFPSV (SEQ ID NO:28). Data were collected and $IC_{50}$ values calculated by the nonlinear curve-fitting program in Prism. Insets show the linear relationship between sHLA and $IC_{50}$ determinations.

Influence of sHLA Concentrations on $IC_{50}$ Values. The effect of the sHLA concentration on binding competition curves for the unlabeled peptide KLGEFYNQMM (SEQ ID NO:21) is shown in FIG. 19A. It is evident that increasing the concentration of sHLA caused a significant shift of the competition curve to the right, considerably increasing the concentration of unlabeled competitor required to inhibit 50% of the binding of the FITC-labeled reference peptide P5. Regression analysis showed that the $IC_{50}$ values obtained from the competition binding curves vary as a linear function of the receptor concentration (inset of FIG. 19). Doubling the sHLA concentration caused nearly a 2.5 times increase in $IC_{50}$ values for peptide KLGEFYNQMM (SEQ ID NO:21). Results were further elaborated by testing the peptide FLPSDFFPSV (SEQ ID NO:28) under equal conditions (FIG. 19B). This competitor peptide was derived from an epitope located between residues 18-27 of the hepatitis B nucleocapsid core protein and known to bind A*0201 with high affinity. Indeed, results differ in that the regression lines do not concur to each other and the x variable for peptide KLGEFYNQMM (SEQ ID NO:21) is twice of that for peptide FLPSDFFPSV (SEQ ID NO:28), indicating that the FLPSDFFPSV (SEQ ID NO:28) affinity is 2-fold higher than KLGEFYNQMM (SEQ ID NO:21) for sHLA-A*0201. A direct comparison of $IC_{50}$ values at identical sHLA concentrations confirmed these findings. These results clearly demonstrate the effect of the HLA component on the assay outcome and show the necessity of utilizing high-quality HLA molecules, which have to be applied under standardized conditions to guarantee reproducibility.

DMSO/DMF Tolerance and Assay Stability. HLA-A2 peptides are quit-biased toward hydrophobicity, given the hydrophobic peptide-binding pocket of the HLA-A2 molecule and the preference for hydrophobic residues throughout. This bias inevitably leads to differences in solubility and, therefore, bioavailability in the assay. Therefore, dissolving HLA peptide candidates is a critical first step in a successful screening application because the wrong choice of solvent can lead to inaccurate or complete lack of performance. One of the most powerful solvents currently used, which is able to minimize these effects, is DMSO, widely accepted in many end-use applications for peptides. However, under certain circumstances, DMSO can be a weak oxidizing agent, and its use may result in gradual oxidation of C-containing peptides to dimers or polymers through disulfide bridge formation during long-term storage. Peptides containing M or W in their primary sequences may also be affected. For these particular cases, DMF replaced DMSO helping to avoid such oxidation effects. Accordingly, all peptides used for $IC_{50}$ determinations were diluted following these guidelines.

Figure 20:
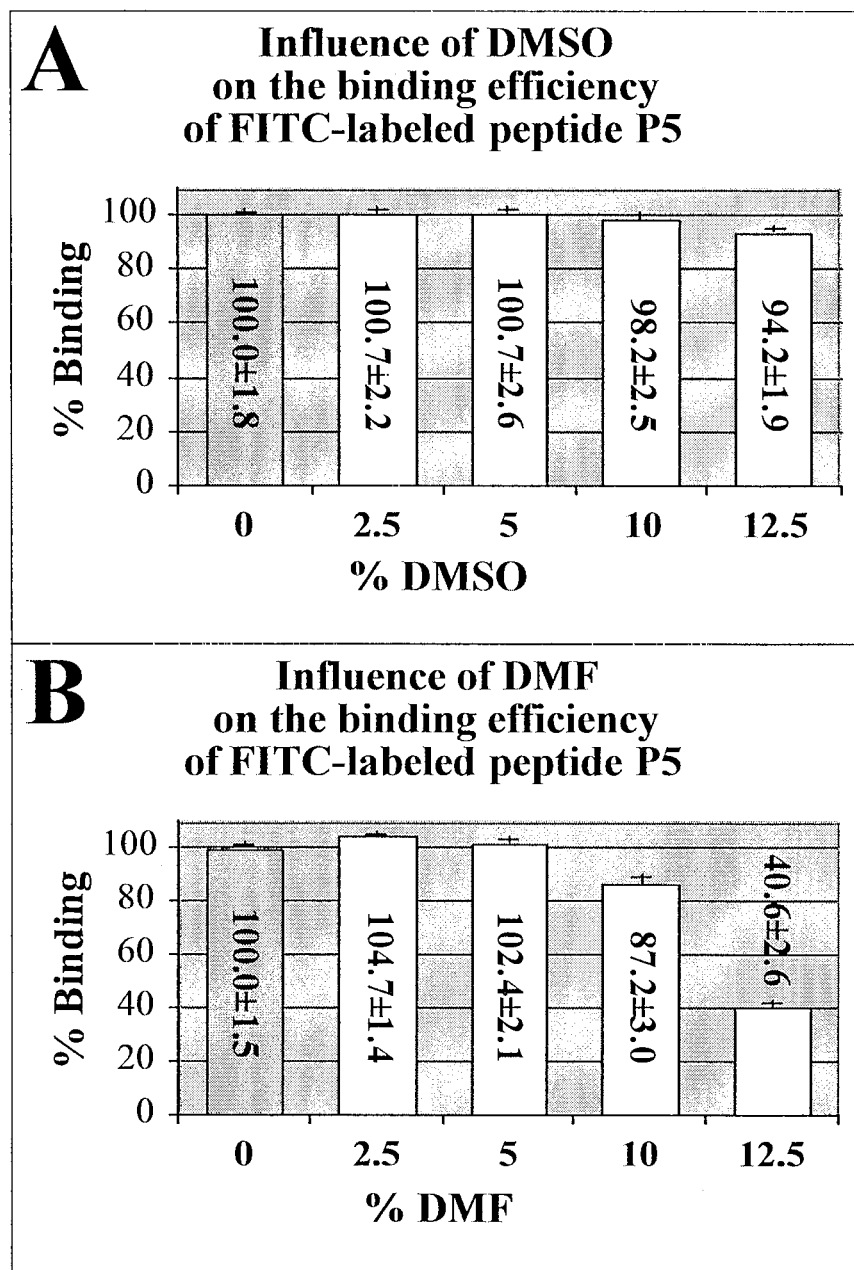
FIG. 20 illustrates the effects of (A) DMSO and (B) DMF on signal output for the sHLA-A*0201 and pFITC P5 interaction. Detergent (0-12.5%) was incubated with FP assay solution containing 1 nM fluorescein-labeled peptide P5, 50 μg/mL (1,059 nM) sHLA and excess β2m (2,117 nM). The FP signal was read after reactions reached equilibrium. As seen, the assay can withstand detergent concentrations of up to 5% without any perceptible effect on pFITC binding.

Because screening platforms must be capable of withstanding DMSO/DMF concentrations of 1-5%, sensitivity of the FP signal to DMSO and DMF was quantified (FIG. 20). The FP assay for the interaction of pFITC peptide P5 was chosen as a model system to test the effect of these solvents using concentrations between 0 and 12.5%. Results showed that concentrations up to 5% of DMSO or DMF had no significant effect on maximum polarization and are well tolerated by comparing maximum signals with control reactions free of solvent. At higher concentrations, the FP signal was nearly insensitive to DMSO up to 12.5%, whereas DMF detectably influenced the binding interaction of sHLA with the fluorescein-labeled peptide, resulting in a decrease in the FP signal to 40% binding. Nonetheless, both solvents tested for this approach were found to be highly compatible with the assay. For overall quality assurance, dilution schemes for competitors were chosen so that the highest concentration of a titration did not exceed a final assay concentration of 4% DMSO/DMF.

During assay development, it was also of interest to determine complex stability under applied assay conditions, a critical aspect in approaching high-throughput applications. Therefore, a variety of competition reactions were chosen to test for the stability of the maximal FP signal over time (data not graphed). The plates were incubated at room temperature, and FP was measured over a period of 7 days. Typically, the assay reactions reached equilibrium within the first 24-48 h, and no further change in polarization signal or calculated $IC_{50}$ value was detected. For plates that were not carefully sealed with Parafilm, a slight increase of signal could be observed because of evaporation of the reaction solution. However, this evaporation artifact had no visual effect on the $IC_{50}$ value itself. Ultimately, the results showed that the assay is extremely robust, because $IC_{50}$ values remained unchanged during the investigation period of 7 days.

Determination of $IC_{50}$ Values on Established Allele-Specific Test Peptides. At this point, a standardized procedure was applied and optimized according to the results obtained from the titration experiments, which clearly demonstrated that $IC_{50}$ values depend on (1) the affinity, (2) the concentration of the tracer peptide, (3) the amount of binding sites available (sHLA concentration), as well as (4) the affinity of the competitor itself. To achieve maximal performance in sensitivity and accuracy, the FITC-labeled reference peptide P5 ALMDKVL-K(FITC)-V (SEQ ID NO:27) was selected, which showed the largest dynamic range between the bound and the free fluorescent-labeled peptide, thus allowing the sensitive detection of small decreases in polarization when adding a competitor peptide. For the procedure, a concentration of 1 nM of FITC-labeled peptide was adopted, which lies within the dynamic range of the FP detector and showed minimal signal fluctuations. Finally, to obtain consistent affinity values, a fixed amount of 50 µg/mL (1059 nM) sHLA-A*0201 was selected for all validation experiments. The addition of a 2-fold excess of β2m (2117 nM) over sHLA resulting in a β2m/heavy-chain ratio of 3:1 was established herein above as the most optimal combination for maximum signal output and was automatically included in all experiments throughout this study. Competitor peptides were typically tested at concentrations ranging from 100 nM to 80 µM. Data were visualized by plotting the logarithm of the concentration of the competitor on the x axis, where the y axis plotted the response, which were changes in fluorescence polarization (mP) monitoring the binding of the reference peptide to sHLA-A*0201. All $IC_{50}$ values were calculated applying nonlinear regression analysis by fitting the inhibition data to a dose-response model as described earlier in the text.

Because FP has no actual zero value because the minimum polarization depends on the fluorescent ligand used (27 mP for fluorescent), signal-to-noise ratios were calculated by interpreting noise as the variability in measured FP and interpreting signal as the maximum change in FP. Typically, a 8 mP standard deviation in replicate assay wells compared to a maximal signal of 220-230 mP was achieved. This low noise compared to the maximal signal allows for sensitive detection of the effects of competitors and thus accurate determination of potencies. Experiments performed under suboptimal conditions, as seen in FIGS. 17-19, showed somewhat higher deviation values of ~12 mP. They are expressed in percentages of maximal binding.

Figure 21:
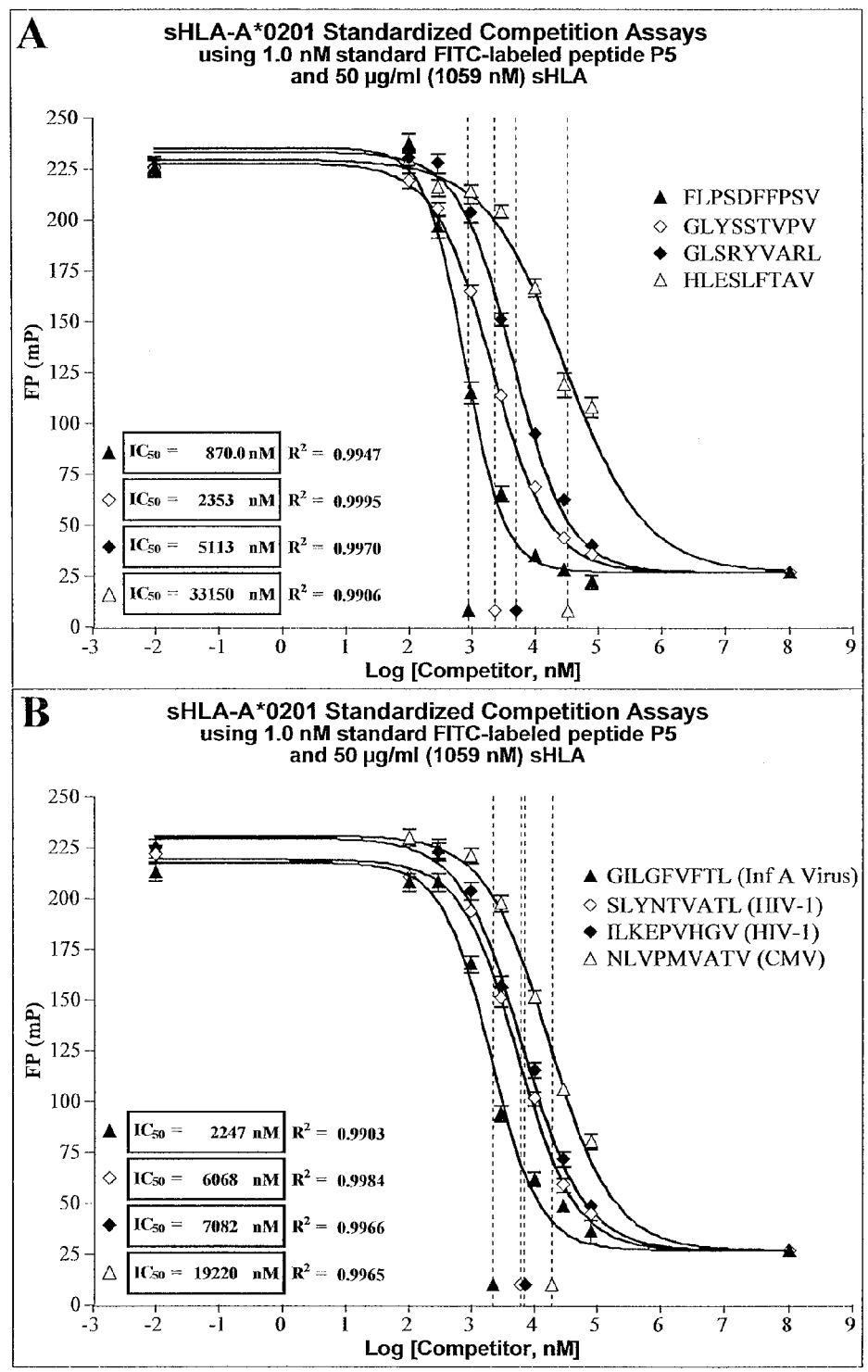
FIG. 21 illustrates standardized competition assays for sHLA-A*0201. Peptides from HBV (A) and multiple other viral sources (B) were tested with the standardized peptide competition assay for sHLA-A*0201. Peptides from HBV in panel A are: FLPSDFFPSV (SEQ ID NO:28), GLYSSTVPV (SEQ ID NO:33), GLSRYVARL (SEQ ID NO:35), and HLESLFTAV (SEQ ID NO:40). Peptides from other viral sources in panel B are: GILGFVFTL (SEQ ID NO:32) from influenza A Virus, SLYNTVATL (SEQ ID NO:36) from HIV-1, ILKEPVHGV (SEQ ID NO:37) from HIV-1, and NLVPMVATV (SEQ ID NO:39) from cytomegalovirus (CMV). The unlabeled peptides were titrated in 8 serial dilutions (100 nM-80 μM) in competition to the FITC-labeled peptide P5. Fluorescence polarization expressed in mP was measured with the Analyst AD. $IC_{50}$ values for the peptides were determined by fitting the data to a dose-response model using the software Prism. Since a log axis cannot accommodate a concentration of zero (log(0) is undefined), a value for a very low competitor concentration was entered (−2). The value for non-specific binding was set to be equal to the assumed theoretical value of 27 mP defining the bottom of the curve. Results of one representative experiment of at least three performed are shown. $R^2$ values indicate the goodness of fit.

For the proposed validation approach, a panel of 15 peptides was selected to represent binders that reflect several orders of magnitude of A*0201 binding affinity (Table IX). The peptides were derived from various sources, including HBV nucleocapsid- and polymerase-derived peptides, two variants of a CTL epitope from HIV-1, the influenza matrix protein Flu-M1 peptide, as well as several other peptides of which the relative binding affinity for HLA-A*0201 was reported previously. Because each competition assay system is generally defined by different internal parameters, such control peptides had to be carefully selected. Only candidates previously evaluated through direct cell-free $^{125}$I-radioligand assay systems or through cellular-based fluorescence assay procedures were accepted, with the additional constraint that $IC_{50}$ determinations for each system were performed under similar assay conditions. For some peptides, more than one $IC_{50}$ value was found. In the FP evaluation process, each test competitor generated its own binding isotherm from which $IC_{50}$ values were determined. Parts A and B of FIG. 21 present a selection of multiple reaction curves obtained from the competition experiments, whereas Table IX summarizes assessed $IC_{50}$ values for the peptides along with their exact amino acid sequences. All test peptides were able to inhibit at least 50% binding of the FITC-labeled reference peptide covering a spectrum of HLA A*0201 binding affinities spanning over 4 orders of magnitude, with $IC_{50}$ values ranging from 500 to 365,000 nM. To mention is that only a partial competition curve was observed for the weak binder DLVHFASPL (SEQ ID NO:49) over the concentration range used, and therefore, the $IC_{50}$ value is given as an approximation. No competition was detected in the case of using irrelevant unlabeled competitor peptides (data not shown).

To be in line with previously published results, the cell-free $^{125}$I-radioligand assay systems and the cellular-based fluorescence assay procedures were used as guidelines to define an FP-based classification system (Table X), where peptides with an FP-based $IC_{50}$ value of 5000 nM and lower were considered high-affinity binding, 5000-50 000 nM $IC_{50}$ values were considered medium-affinity binding, 50,000-1,000,000 nM $IC_{50}$ values were judged low-affinity binding, and $IC_{50}$ values above 1 mM were regarded as no binder. Additionally, low-affinity binders were further subdivided into a low- (50,000-350,000 nM) and very low-affinity category (350,000-1,000,000 nM) because quantitative analysis of very low binders was usually less accurate and generally based on only a few data points at the upper end of the dose-response curve. According to the FP-based classification system, eight test peptides belonged to the high affinity category; six to the medium, and one was identified as a very low binder.

TABLE IX

Summary of Peptide Competition Data Obtained in Association with HLA-A*0201
Including Specific Information on the Peptides Origin and Position

| sequence[a] | peptide origin[b] | position[c] | sequence ID[d] | peptide length (aa) | StD comp assay[e] (FP) IC50 (nM) | cell-free systems[f] ($^{125}$I) IC50 (nM) | references[g] (cell-free systems) | cellular systems[h] (fluorescence) IC50 (nM) | references[i] (cellular systems) | SEQ ID NO: |
|---|---|---|---|---|---|---|---|---|---|---|
| YLLPAIVHI | human; probable RNA-dependent helicase p72 | 146-154 | Q92841 | 9 | 509.8 | 18 | 131 | | | 29 |
| YMDDVVLGA | hepatitis B virus (HBV); Pol | 538-546 | P03156 | 9 | 823.1 | 200 | 40, 95, 97 | | | 30 |
| FLPSDFFPSV | hepatitis B virus (HBV); core | 18-27 | P03146 | 10 | 870 | 0.57; 1.2; 2.5; 2.8; 3.0; 3.3j | 40, 48, 56, 94, 96, 97 | 400; 500j | 49, 82, 118 | 28 |
| YLVSFGVWI | hepatitis B virus (HBV); core | 118-126 | P03146 | 9 | 1742 | 1.9 | 48 | | | 31 |
| GILGFVFTL | influenza A virus; matrix protein M1 | 58-66 | P21429 | 9 | 2247 | 6; 12.4j | 56, 132 | 4000 | 100 | 32 |
| GLYSSTVPV | hepatitis B virus (HBV); Pol | 61-69 | P03156 | 9 | 2353 | 20; 33j | 48, 99 | 4500 | 49 | 33 |
| KLGEFYNQMM | influenza B virus; NP | 85-94 | P13885 | 10 | 2820 | | | 5500 | 49 | 21 |
| LLSSNLSWL | hepatitis B virus (HBV); Pol | 407-415 | P03156 | 9 | 3828 | 455 | 99 | 19 500 | 49 | 34 |
| GLSRYVARL | hepatitis B virus (HBV); Pol | 442-450 | P03156 | 9 | 5113 | 71; 76; 79j | 40, 97, 99 | | | 35 |
| SLYNTVATL | human Immunodeficiency virus type 1 (HIV-1); Gag p17 | 77-85 | P05888 | 9 | 6068 | 50 | 133 | 1500 | 49 | 36 |
| ILKEPVHGV | human Immunodeficiency virus type 1 (HIV-1); Pol | 476-484 | P03368 | 9 | 7082 | 192; 242j | 40, 56 | 8000 | 49, 100 | 37 |
| NLQSLTNLL | hepatitis B virus (HBV); Pol | 400-408 | P03156 | 9 | 9389 | 1000; 2000j | 48, 99 | 22 000 | 49 | 38 |
| NLVPMVATV | cytomegalovirus (CMV); pp65 | 495-503 | P06725 | 9 | 19 220 | | | 12 500 | 100 | 39 |
| HLESLFTAV | hepatitis B virus (HBV); Pol | 551-559 | P03156 | 9 | 33 150 | 5000; 10 000j | 81, 99 | | | 40 |
| DLVHFASPL | hepatitis B virus (HBV); Pol | 817-825 | CAA46352 | 9 | 365 600 | 16 667 | 81 | | | 41 |

[a]Nonlabeled parental peptide sequence synthesized for IC50 evaluation.
[b]Protein source including species and category.
[c]Peptide position within the original protein.
[d]Swiss Prot reference link.
[e]Data represent IC50 values obtained by fluorescence polarization using the standardized assay conditions described within the text.
[f]Data represent IC50 values published for cell-free (HLA lysate) competition systems using 125I as peptide tracer.
[g]Peptide references for cell-free systems.
[h]Data represent IC50 values published for cellular systems (cell-bound HLA) using a fluorescence-labeled peptide reference.
[i]Peptide references for cellular systems.
jMultiple values from different publications listed.

TABLE X

Definition of IC50 Categories for Different Assay Systems

| Assay Systems | High affinity | Medium affinity | Low affinity | Very Low affinity | No affinity | | References |
|---|---|---|---|---|---|---|---|
| StD FP Comp Assay | < 5,000 < 3.7 | 5,000 50,000 3.7 4.7 | 50,000 350,000 4.7 5.5 | 350,000 1,000,000 5.5 6.0 | 1,000,000 > > 6.0 | $IC_{50}$ (nM) $log(IC_{50};$ nM) | |
| Cell-free $I^{125}$ Radioassays[a] | < 50 < 1.7 | 50 500 1.7 2.7 | 500 50,000 2.7 4.7 | — — — | 50,000 > 4.7 > | $IC_{50}$ (nM) $log(IC_{50};$ nM) | ENRfu(34, 48, 81, 99) |
| Cellular Fluorescence Assays[a] | < 5,000 < 3.7 | 5,000 15,000 3.7 4.2 | 15,000 1,000,000 4.2 6.0 | — — — | 1,000,000 > 6.0 > | $IC_{50}$ (nM) $log(IC_{50};$ nM) | ENRfu(49, 66, 100, 118) |

Figure 22:
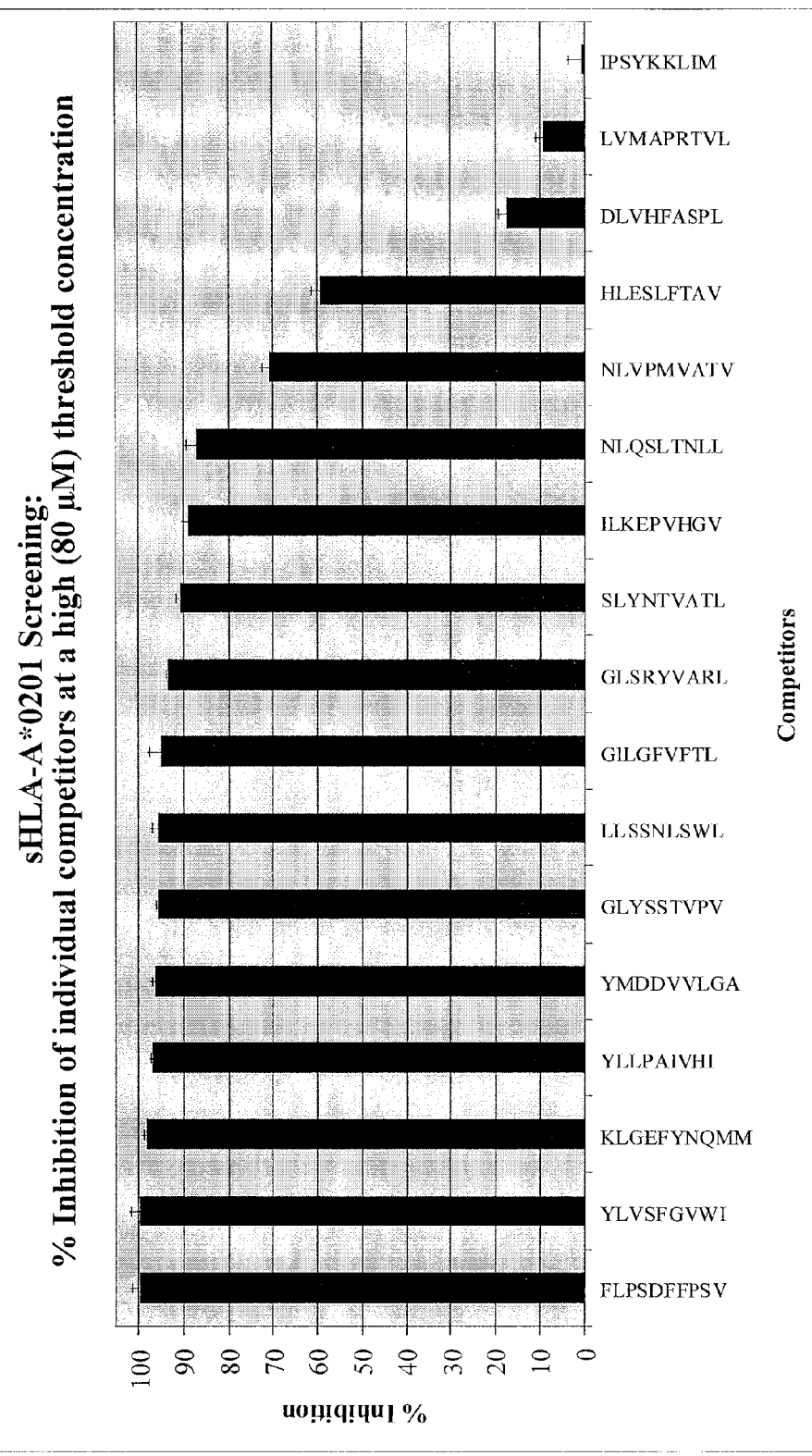
FIG. 22 illustrates epitope screening at a selected high threshold concentration of 80 μM. The panel of A2-specific peptides including two negative controls related to HLA allele B7 were screened at a single threshold concentration applying the peptide competition assay for sHLA-A*0201. The competitor peptides are, from right to left, FLPSDFFPSV (SEQ ID NO:28), YLVSFGVWI (SEQ ID NO:31), KLGEFYNQMM (SEQ ID NO:21), YLLPAIVHI (SEQ ID NO:29), YMDDVVLGA (SEQ ID NO:30), GLYSSTVPV (SEQ ID NO:33), LLSSNLSWL (SEQ ID NO:34), GILGFVFTL (SEQ ID NO:32), GLSRYVARL (SEQ ID NO:35), SLYNTVATL (SEQ ID NO:36), ILKEPVHGV (SEQ ID NO:37), NLQSLTNLL (SEQ ID NO:38), NLVPMVATV (SEQ ID NO:39), HLESLFTAV (SEQ ID NO:40), DLVH-FASPL (SEQ ID NO:41), LVMAPRTVL (SEQ ID NO:5), and IPSYKKLIM (SEQ ID NO:41). Among the competitor peptides, LVMAPRTVL (SEQ ID NO:5) and IPSYKKLIM (SEQ ID NO:41) are B7-specific peptides while the rest 15 peptides are A2-specific peptide. The unlabeled peptides (80 µM) were incubated with a constant concentration of activated sHLA-A*0201 (50 µg/mL; 1,059 nM), excess β2m (2,117 nM) and 1 nM FITC-labeled reference peptides P5. After reaching equilibrium, fluorescence polarization was measured with the Analyst AD and transformed in % inhibition relative to the control reaction without competitor. Results demonstrate the feasibility of a high-throughput approach for epitope discovery enabling the screening of a large number of peptides with the goal to identify high affinity binding peptides.

Epitope Screening. Recent reports show that peptides possessing good binding characteristics are a prerequisite for successful candidate CTL epitopes. In this matter, the availability of a high-throughput peptide screening method would be practical to discover novel MHC-restricted epitopes by screening large panels of candidate peptides. To test the feasibility of such a high-throughput approach, the standard competition assay procedure described herein was converted into a rapid screening process with the ultimate goal of identifying peptides not capable of binding to sHLA-A*0201. At a selected high threshold concentration of 80 μM, various peptides were used for this screen test including the same A2-specific peptides utilized earlier in addition to the B7-specific peptides LVMAPRTVL (HLA-B*0702 signal sequence) (SEQ ID NO:5) and IPSYKKLIM (prostatic acid phosphatase precursor) (SEQ ID NO:42). Experimentally, each peptide candidate (80 μM) was incubated with activated sHLAA*0201 (50 μg/mL; 1059 nM) in the presence of 1 nM FITC labeled reference peptides P5 and excess β2m (2117 nM) and peptide/MHC interactions were monitored over time. Final equilibrium polarization levels were transformed in percent inhibition to indicate the extent of binding to sHLAA*0201. Representative screening data are shown in FIG. 22. As expected, all A2-specific peptides showed positive screening results, whereas both B7-specific peptides were not able to efficiently compete against the FITC-labeled reference peptide. Statistically, no significant difference among screening values for high-affinity peptides was detected, showing an average inhibition level of 97.2±1.9%. This observation can be explained by the fact that high affinity peptides reach complete inhibition below the 80 μM threshold concentration causing saturation of the system. As such, a systematic ranking of these candidate epitopes within this affinity category is not possible. However, a correct order within this group can be obtained by either screening at a lower threshold concentration or by performing a complete $IC_{50}$ analysis as shown in FIG. 21. In contrast, the rank order for medium- to low-affinity peptides was consistent with the previous results, allowing a ranking procedure without further analysis. Most important, the screening procedure clearly showed only minor to no inhibition capacity for the B7-specific peptides LVMAPRTVL (SEQ ID NO:5) and IPSYKKLIM (SEQ ID NO:42), respectively, which provides the key for future screening applications, allowing the immediate identification of negative binders and their elimination from subsequent functional studies.

Figure 23:
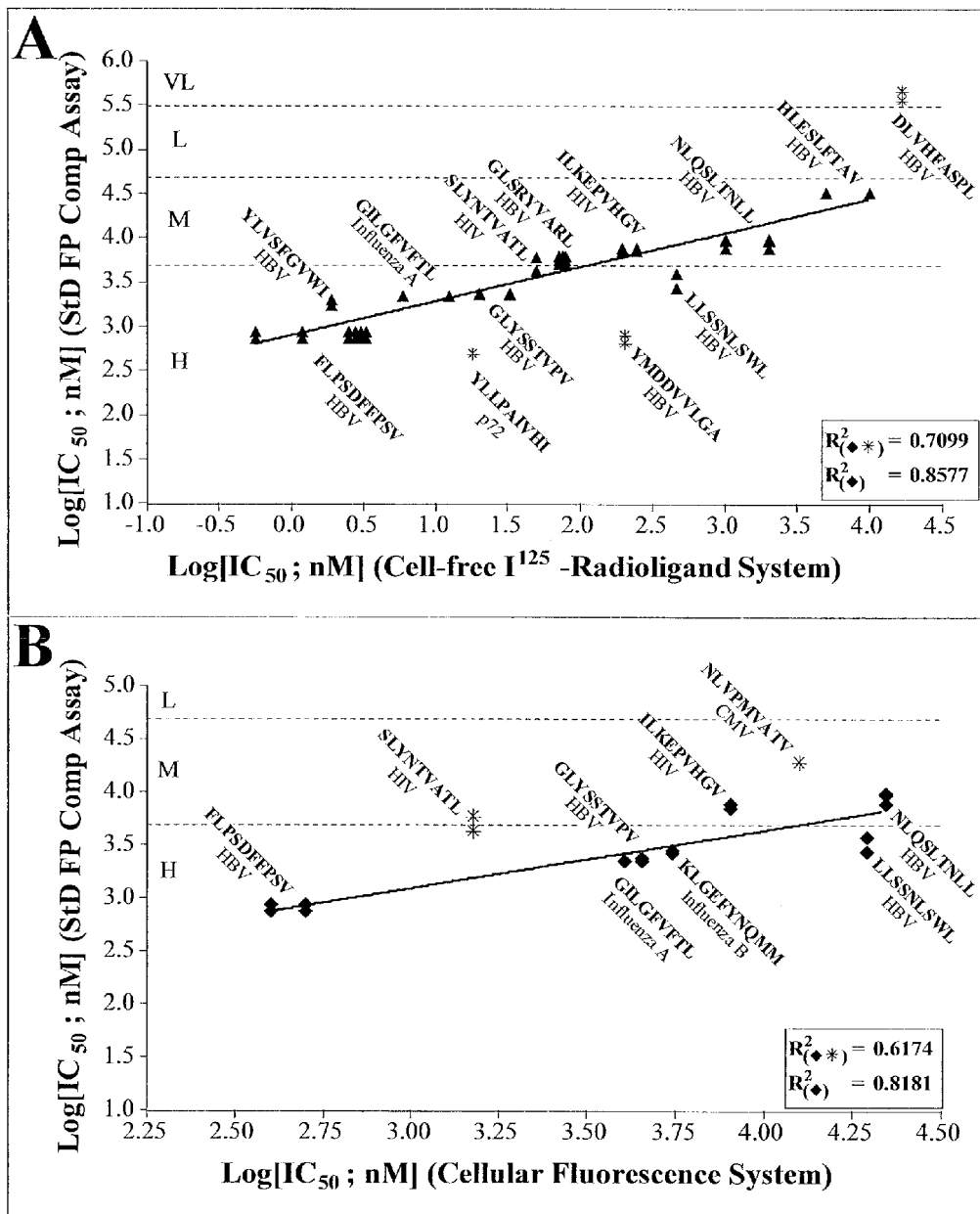
FIG. 23 illustrates a system to system affinity comparison using a variety of established peptide epitopes. The relationship between peptide binding affinity determinations for the HLA class I molecule A*0201 assessed through the FP system and values from (A) direct cell-free $I^{125}$-radioligand assay systems or from (B) cellular based fluorescence assay procedures was evaluated. Peptides used in panel A are: DLVHFASPL (SEQ ID NO:41), HLESLFTAV (SEQ ID NO:40), NLQSLTNLL (SEQ ID NO:38), ILKEPVHGV (SEQ ID NO:37), GLSRYVARL (SEQ ID NO:35), SLYNTVATL (SEQ ID NO:36), GILGFVFTL (SEQ ID NO:32), YLVSFGVWI (SEQ ID NO:31), LLSSNLSWL (SEQ ID NO:34), YMDDVVLGA (SEQ ID NO:30), GLYSSTVPV (SEQ ID NO:33), YLLPAIVHI (SEQ ID NO:29), and FLPSDFFPSV (SEQ ID NO:28). Peptides used in panel B are: NLVPMVATV (SEQ ID NO:39), ILKEPVHGV (SEQ ID NO:37), GLYSSTVPV (SEQ ID NO:33), SLYNTVATL (SEQ ID NO:36), FLPSDFFPSV (SEQ ID NO:28), NLQSLTNLL (SEQ ID NO:38), LLSSNLSWL (SEQ ID NO:34), KLGEFYNQMM (SEQ ID NO:21), and GILGFVFTL (SEQ ID NO:32). Logarithmic $IC_{50}$ values were graphed against each other and a correlation factor was determined using linear regression analysis. Affinity values are distributed over several orders of magnitude. The classification of the peptide binding affinity into high (H), medium (M), low (L) and very low (VL) are comparable to the classifications published by other investigators using the same reference peptides. In addition, specific outcomes were subdivided into two groups: very well correlating peptides (♦) and poorly correlating peptides (*) contributing to a much lower correlation factors.

System-System Affinity Comparison. To determine whether the peptide-binding data that obtained is in general agreement with other studies in addition to be able to better judge the quantitative differences of $IC_{50}$ values of the set of congeners, FP-derived binding values were compared to the peptide-binding data extracted from the literature. To simplify the problem of direct comparison of absolute $IC_{50}$ values, all affinity determinations were transformed logarithmically and plotted against each other in a log-log format. Results displayed strong linear correlations throughout the measurable range between the FP format and the cell-free $^{125}$I-radioligand assay system (FIG. 23A) as well as between the cellular-based fluorescence assay procedure (FIG. 23B). Regression analysis delivered a regression line for the cell-free $^{125}$I-radioligand assay system with a slope and intercept of 0.37 and 2.91, respectively. A similar linear first-order relationship was found for the cellular-based fluorescence assays with a slope of 0.55 and an intercept of 1.45, respectively. Specific outcomes were subdivided into two groups: very well-correlating peptides with an overall correlation factor 0.86 and 0.82, respectively, and poorly correlating peptides, which contributed to a much lower correlation factor of only 0.71 and 0.62. The occurrence of outliers was, however, not surprising, considering the variety of peptide-binding values collected from independent experimental procedures. Overall, the difference in performance between these particular systems seems to be only minor, considering the highly selective choice of comparative data. Conclusively, such an attribute suggests that accurate assessment of peptide binding can be obtained and the FP based assay can be used for successful validation of unknown peptide candidates for their potential to bind sHLA-A*0201 molecules.

Equilibrium Study Monitoring Specific Peptide Binding to Soluble HLA-A*0201

In this report, critical factors in the development and standardization of peptide binding applications were elaborated using the FP-based assay methodology as a model system. By monitoring specific peptide binding to sHLA-A*0201 under a variety of different physical conditions, individual designs of fluorescein isothiocyanate-labeled high affinity peptide (pFITC) probes were not only used to establish improved assay settings but were also applied to elucidate potential pitfalls for future assay designs. During the study, the potency, selectivity and efficacy of the pFITC probes were determined as well as the performance of the sHLA molecules in FP-based assay formats. The concept of the assay can be adapted to basically every HLA class I allele of interest.

Materials and Methods:

Synthetic peptides. FITC-labeled peptides (Table VI) and unmodified peptides were synthesized, purified and stored as described herein above.

Production and purification of recombinant soluble MHC class I molecules was as described herein above. FP-based peptide binding assays were conducted as described herein above.

Data Analysis.

Titration experiments with variable sHLA concentrations were analyzed by plotting FP readings as a function of sHLA concentration at a fixed concentration of fluorescein-labeled peptide. The observed binding constant ($EC_{50}$), better defined as the concentration provoking a response half way between the baseline and maximum response, was determined by non-linear curve fitting using the specific software Prism (Graph Pad Software Inc.; San Diego, Calif.).

Titration experiments with variable pFITC concentrations were analyzed by applying the FP $K_d$ model to the obtained data set as described previously (Prystay et al., 2001; Binz et al., 2003). A hypothetical saturation curve was generated using the basic equations (1) and (2) shown below where variable x is equivalent to the total pFITC concentration and variable y to the corresponding polarization signal for equilibrated sHLA/pFITC binding. Since the FP $K_d$ model is based on the principle that measured polarization signals are a weighted sum of unbound pFITC ($mP_{min}$) and pFITC signals when fully bound to sHLA ($mP_{max}$), $mP_{min}$ can be set to 27 mP since all values are relative to the theoretical mP for fluorescein. The appropriate values for $mP_{max}$ can be extracted from the titration experiments with variable sHLA concentrations performed within this study at the point where they reached saturating conditions. The polarization signal of free pFITC and nonspecific binding ($mP_d$) was approximated to be that for free fluorescent-labeled ligand. Finally, RL corresponds to the specifically bound pFITC concentration and $L_{free}$ to the free pFITC concentration, both values used to obtain the classical saturation binding profiles.

$$RL = x*((mP_{max}-mP_{min})-mP_d+mP_{min})*(y-mP_d)/(mP_{max}-mP_{min})^2 \quad (1)$$

$$L_{free} = x*((mP_{max}-mP_{min})-mP_d+mP_{min})* ((mP_{max}-mP_{min})+mP_d-y)/(mP_{max}-mP_{min})^2 \quad (2)$$

Equations (1) and (2) were further simplified into equation (3) and (4) integrating the value 27 mP for $mP_d$ and $mP_{min}$.

$$RL = x*(y-27)/(mP_{max}-27) \quad (3)$$

$$L_{free} = x*(mP_{max}-y)/(mp_{max}-27) \quad (4)$$

Transformed data were fitted by the computer-aided, non-linear regression analysis package from Prism (Graph Pad). A one site binding (hyperbola) model was applied to extract the equilibrium dissociation constant ($K_d$) (concentration of ligand required to reach half-maximal binding) and $B_{max}$ (maximal binding) from the data sets. Furthermore, a Klotz plot was used to better visualize data at lower peptide concentrations. Important to mention is that binding analysis under these conditions are not limited by ligand depletion.

Competition Assay.

Similar to the procedure described above, individual wells of a black microplate (Molecular Devices) were loaded with 5 µl of a prepared 8×β2m (Fitzgerald) solution, 10 µl of the 4× competitor at various dilutions and 5 µl of 8×pFITC preparation. The peptide exchange procedure was started by adding 20 µl of the activated 2×sHLA mix to the other components. Note that the labeled and unlabeled ligand is added simultaneously to the sHLA. The competition reaction was incubated at room temperature until equilibrium was reached (24-48 hours).

Competition experiments were analyzed by plotting FP readings as a function of the logarithms of competitor concentrations at a fixed concentration of the FITC-labeled reference peptide and sHLA. The binding affinity of each competitor peptide was expressed as the concentration that inhibits 50% binding of the FITC-labeled reference peptide. Observed inhibitory concentrations ($IC_{50}$) were determined by fitting data sets to a dose-response model.

Results:

Design of synthetic FITC-labeled, motif-bearing peptides. Many peptide binding approaches utilize labeled peptide candidates to determine kinetics, equilibrium or cross-reactivity characteristics (Buchli et al., 2004). In addition, labeled peptides are often used as references in competition-based assays (Buchli et al., 2005). In this matter, the first and perhaps most critical step is the labeling of these contenders with a fluorophore which involves a number of considerations relating to both, their biological and chemical nature in order to maintain their potential to bind HLA-A*0201. Parameters such as the affinity to the HLA allele under investigation, the peptide length, the position of the fluorescence-linkage to the peptide, the solubility, and the stability of the design are most important for optimal performance. In contrast, the selection process for suitable reference peptides for competition assays is somewhat different as these assays do not require that specific peptide candidates maintain their native biologic reactivity.

To elaborate potential pitfalls in peptide design, various labeling strategies were selected, which included the choice of candidates with different amino acid sequences as well as various labeling positions. The initial selection focused on nonameric and decameric molecules representing recently published high affinity A*0201 binders. Peptide P1, was derived from an epitope that contains an HLA-A2-binding motif located between residues 18-27 of the hepatitis B nucleocapsid core protein. This peptide is known to bind A*0201 with high affinity and is well described by several authors (Ruppert et al., 1993; Kast et al., 1994; Kubo et al., 1994; Sette et al., 1994a). This particular HBV peptide is also strongly recognized by CTL's derived from both acute and chronic hepatitis patients (Bertoletti et al., 1991; Bertoletti et al., 1993; Nayersina et al., 1993). Peptide P3 is a derivative from the HBV pol (411-419) epitope (Vitiello et al., 1997), whereas P4 is related to the melanoma-associated antigen 2 (MAGE-2; 160-169) (Keogh et al., 2001). The last candidate in this category, peptide P2, derived from the HIV-1 CTL epitope gag (76-84) (van der Burg et al., 1995), was selected because of its successful use in HLA tetramer studies capable of staining CTL's in the peripheral blood of HIV-infected individuals (Goulder et al., 2001; Scott-Algara et al., 2001). Finally, a different strategy was adapted for peptide P5, which was designed based on specific anchor motifs (Falk et al., 1991; Henderson et al., 1992; Hunt et al., 1992; Rotzschke et al., 1992; Rammensee et al., 1993; Kubo et al., 1994; Sudo et al., 1995) and a frequency table for A*0201 (Ruppert et al., 1993), showing amino acid groups at different non-anchor positions which seem to be associated with good or poor binding. The sequences of all peptide candidates are summarized in Table I.

Considering a possible interference in binding caused by sterical hindrance, substitutions at various positions were made (Table VI). The goal was to conservatively exchange amino acids with a fluorescein isothiocyanate (FITC)-conjugated lysine at positions 4, 5 and 8 for 9-mers and positions 5 and 6 for 10-mers, respectively. These positions are known for their permissiveness (Ruppert et al., 1993), in the sense that substitutions seem not to lead to significant changes in the binding capacity. In contrast, positions 2 and 9 in nonamers (2 and 10 in decamers) were not considered for FITC-labeling as they represent the major anchors of the peptide (Falk et al., 1991; Henderson et al., 1992; Hunt et al., 1992; Rotzschke et al., 1992; Rammensee et al., 1993; Kubo et al., 1994; Sudo et al., 1995). Furthermore, positions 3, 6, and 7 in nonamers or 7 and 8 in decamers were not utilized as they seem to act as secondary anchors for A*0201 and strongly correlated to the peptides affinity (Ruppert et al., 1993). In addition, modifications at these positions may affect â2m exchange kinetics (Morgan et al., 1998). Amino acids at position 1 were also excluded, which are generally seen to be buried within the HLA binding groove and therefore hard to access.

Results for sHLA/pFITC interactions showed that direct attachment of the FITC conjugate at selected positions from four out of the five peptide designs did not significantly interfere with binding to sHLA-A*0201 and that the overall stability of the complex could be maintained (Table XI). However, despite the fact that the native (not modified version of P3) is a known and well characterized binder for A*0201 (Sette et al., 1994a; van der Burg et al., 1996; Vitiello et al., 1997), a major problem in the creation of fluorescence-labeled peptides remains in that interferences cannot readily be predicted.

Evaluation of FP signals using serial dilutions of FITC-labeled peptides: Important preliminary tasks for high quality data output are the evaluation of the sensitivity and dynamic range of the assay detection system as well as the assessment of concentration accuracy of the synthetic FITC-labeled peptides. To determine sensitivity and dynamic range, serial dilutions of pFITC P2 were used that extended beyond the expected working range. Two intensity measurements were collected for each well, one when the polarizers were parallel (S and S) and one when the polarizers were perpendicular to each other (S and P). As seen in FIGS. 25A and 25B, the optimal concentration range for parallel and perpendicular fluorescence intensities was between 0.15 and 1000 nM following a linear relationship with lowest variation around the mean fluorescence. Above and below this range, values were no longer in good correlation to the linear regression curve showing a steady increase of standard deviation values in the direction of lower concentrations (inserts). In contrast to the parallel and perpendicular intensities, fluorescence measurements without polarization filters (FIG. 25C) were on a linear scale up to only 200 nM after which saturation was reached. In addition to the mean intensity values obtained to formulate the range of the assay, all experimental intensity values obtained for P2 during this study were added to the graphs. Best fit analysis showed that data sets were within close proximity of the standard curve and had an $R^2$ of 0.98, indicating the reproducibility of the technique.

Noteworthy to mention is that FP operates differently than other methods of fluorescence detection. Instead of simply being a measure of the amount of FITC present, it gives a direct measure of the bound/free ratio. FP values are independent of concentration and a given bound/free ratio remains constant over several orders of magnitude. This characteristic provides a definite advantage for this type of assay in that the essential measurements can be made without any physical separation of bound and free species. As seen in FIG. 25D, the baseline ratio was monitored over a wide range of pFITC P2 concentrations. The lower limit was determined at 0.15 nM, producing a constant signal of 29.3 mP, which is near to the prescribed value of 27 mP for fluorescein. This FP value stayed constant up to the highest concentration tested (4 µM) defining a concentration range, which is over 4 orders of magnitude. At lower concentrations, errors became large as background noise dominated the intensities as seen in FIGS. 25A and 25B. This uncertainty in measurement ultimately determined the sensitivity of instrument and assay.

Figure 26:
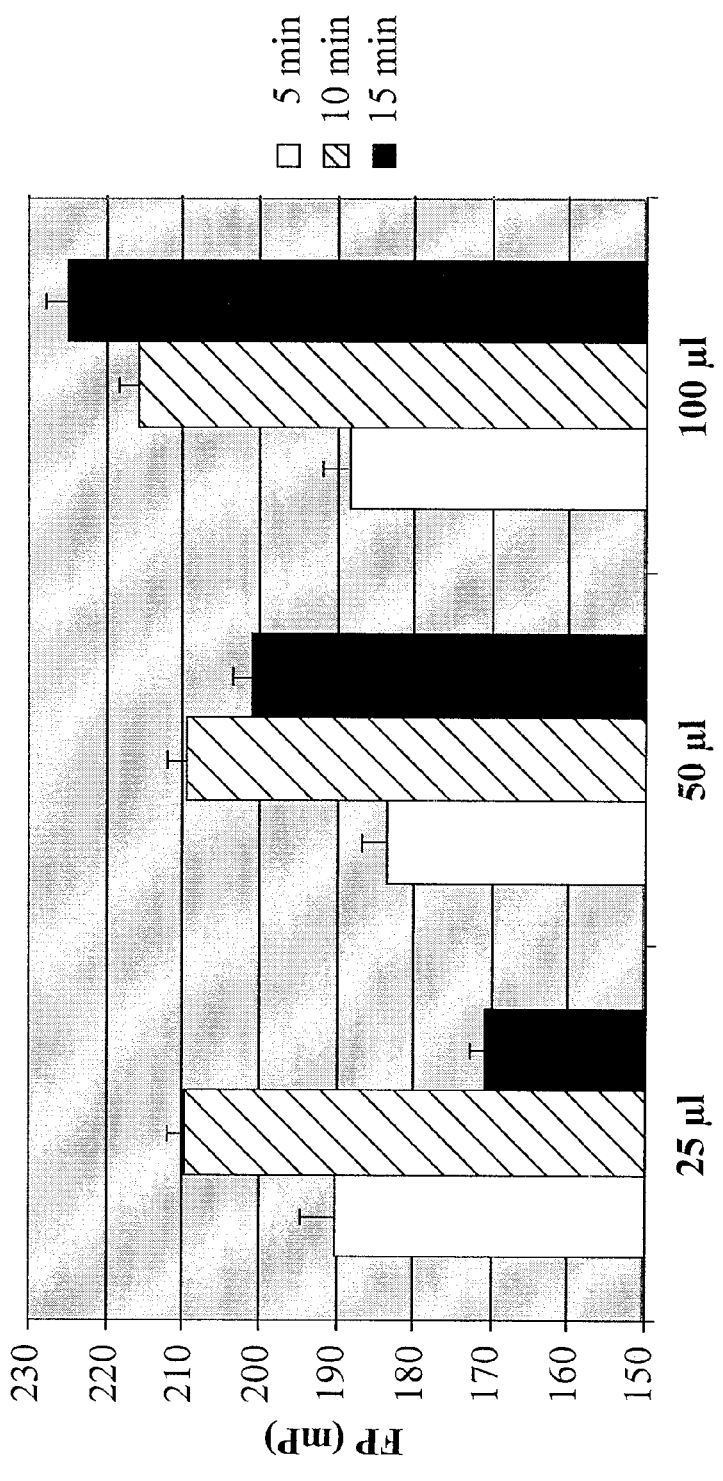
FIG. 26 illustrates the FP response of FITC-labeled peptide P5 as a function of sample volume and activation time. Parameters for optimal sHLA activation for small sHLA sample volumes at a temperature of 53° C. were investigated in order to maintain maximal polarization levels. Identical sHLA samples (25, 50, and 100 µl) were incubated over a period of 5, 10 and 15 minutes before added to a 2 nM pFITC P5 solution containing excess β2m to start the loading process. Polarization values (mP) were graphed after reaching equilibrium.

Optimization of peptide exchange procedures: As demonstrated herein above, to enable the loading of exogenous peptides into a fully assembled HLA-A*0201 complex, a thermal destabilization procedure was established demonstrating that the peptide exchange procedure does not require the removal of endogenous peptides from the reaction environment. A temperature of 53° C. was established earlier as optimal for peptide exchange activation by incubating sHLA complexes for 15 minutes where 85% of sHLA-A*0201 molecules were available for the exchange process. These parameters including volume were kept constant and applied for all experiments. In order to maintain experimental flexibility while still allowing for miniaturization of such peptide binding approaches, however, different volumes of activated sHLA are needed. Because the total amount of thermal energy to be applied depends not only on temperature and time but also on the volume, the initial activation study described herein was extended. As seen in FIG. 26, sHLA activation as a function of sample volume and activation time was investigated at a temperature of 53° C. to identify optimal peptide exchange conditions for various sample volumes. Identical sHLA samples (40 µg/ml) were incubated at volumes of 25, 50, and 100 µl over a period of 5, 10 and 15 minutes, respectively. After activation, the samples were immediately added to a solution containing 2 nM of the pFITC P5 and excess β2m to order to initiate the pFITC loading process.

Results obtained for the 100 µl sample showed a steady increase in polarization reaching highest polarization levels at 15 min indicating that incubation times below 15 min are not activating all sHLA molecules present for exchange. In contrast, the two other samples, 25 and 50 µl, reached highest polarization levels at 10 minutes of activation immediately followed by a decline in signal due to partial denaturation of the complex by applying too much thermal energy. It was noted that the maximal polarization level as seen for the 100 µl sample was not matched, indicating that volumes below 100 µl are much harder to control and optimization protocols utilizing smaller volumes require much narrower test intervals. Additional tests in the range between 100 to 300 µl volumes were found to be similar to the 100 µl values with no visual effect on the maximal polarization levels at 15 minutes activation time (data not shown). Overall, results show that different incubation times have to be applied for different volumes to prevent partial denaturation or lack of activation of the sHLA complex leading to decreased polarization levels.

Figure 27:
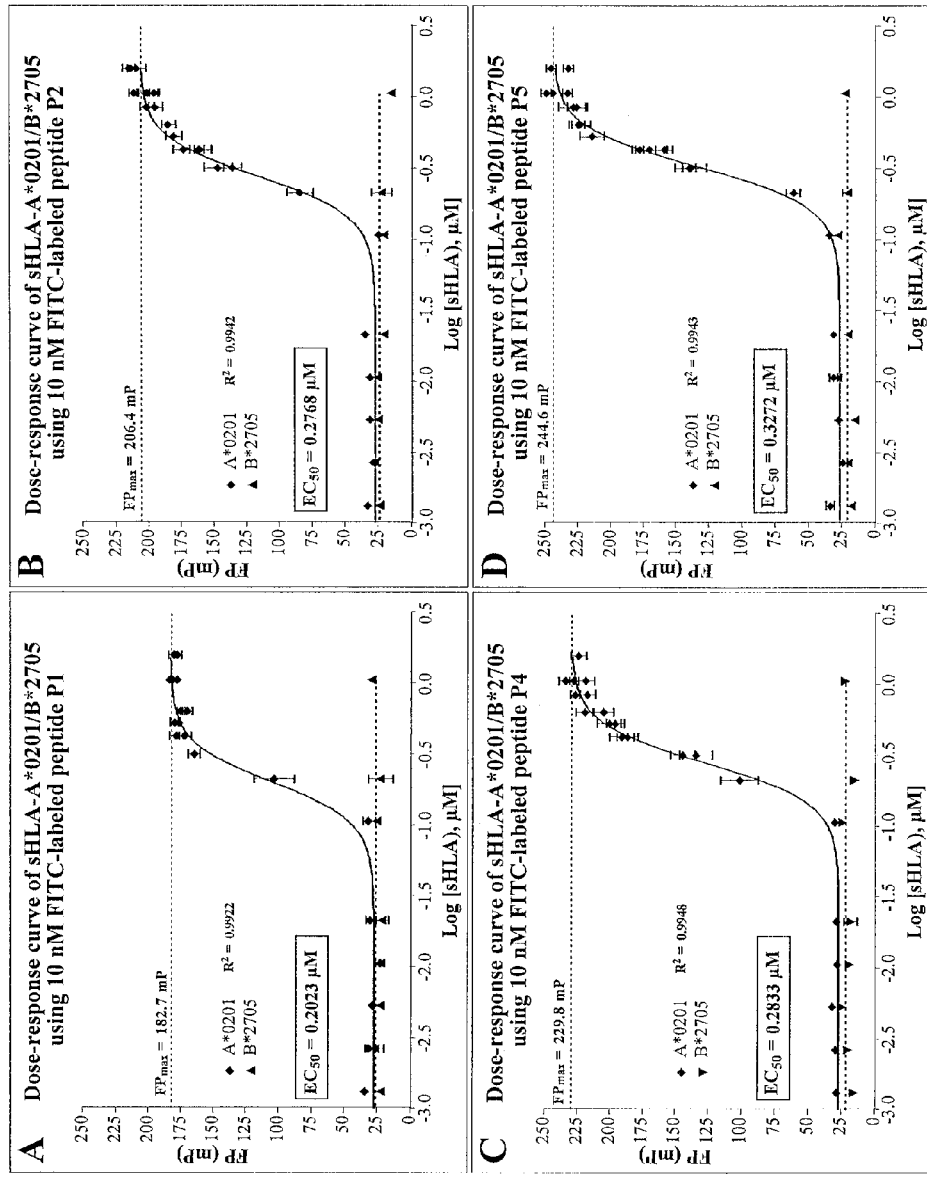
FIG. 27 illustrates the FP response of FITC-labeled peptides as a function of the logarithm of the molar concentration of sHLA. To maximize assay performance, various concentrations of sHLA in the presence of 10 nM of the fluorescence-labeled synthetic peptide were tested. Typical titration curves for the binding of pFITC conjugates P1 (A), P2 (B), P4 (C) and P5 (D) to sHLA were obtained, all reaching a plateau yielding no further increase in mP at supraoptimal concentrations. As negative binding control, the sHLA-A*0201 molecule was exchanged with sHLA-B*2705. Data from the experiments were imported into Prism to determine the maximum binding range for each peptide. $EC_{50}$ values were calculated applying the equation for a sigmoidal dose-response. $R^2$ values indicate the goodness-of-fit. Maximal mP values obtained are indicated.
Figure 28:
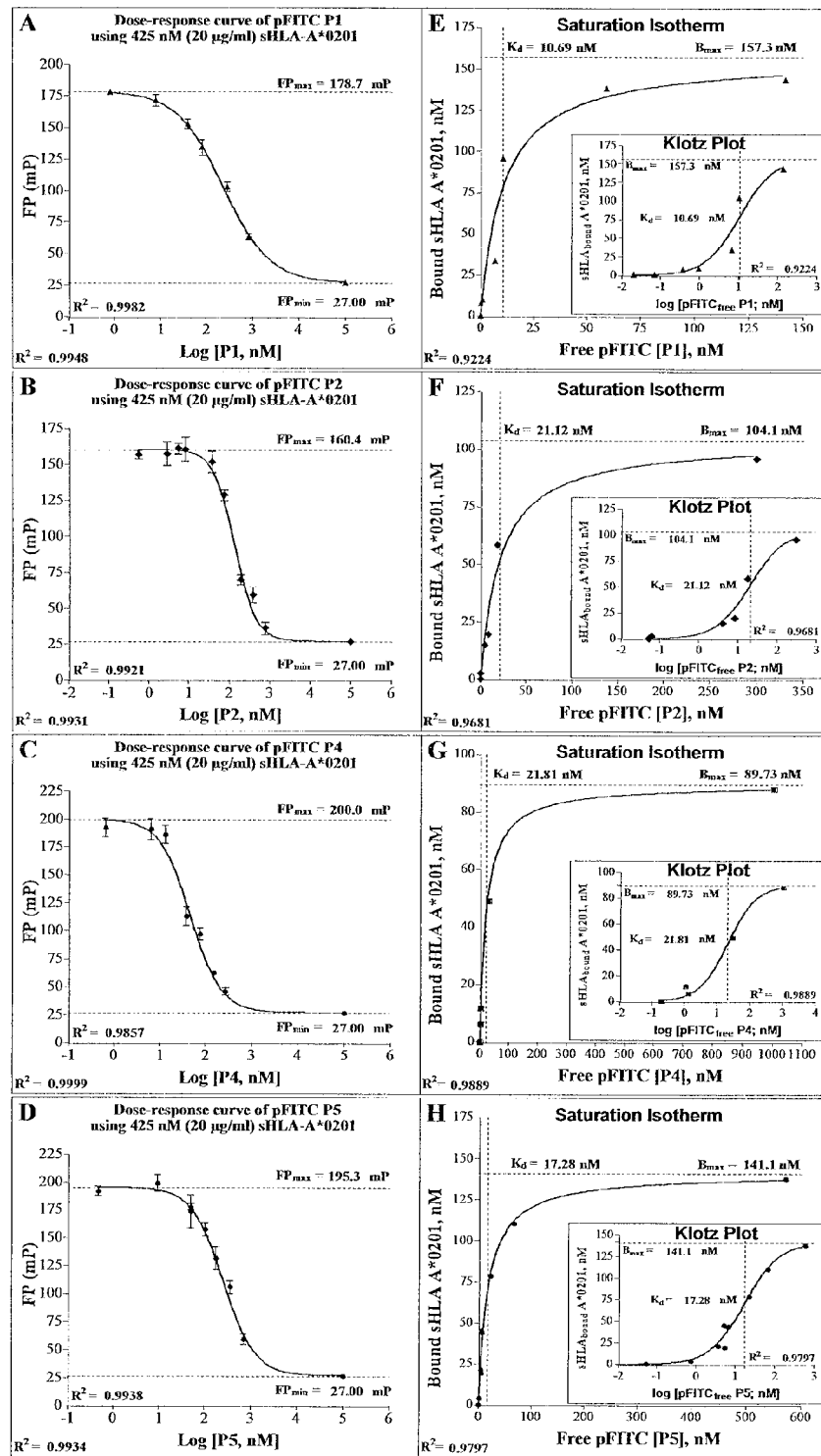
FIG. 28 illustrates binding isotherms for pFITC/sHLA A*0201 interactions. (A-D) The specificity of peptide binding to HLA-A*0201 was evaluated using a set of different FITC-labeled peptides. Polarization values for fluorescent peptides bound to sHLA were tested against increasing concentrations of pFITC by holding the concentration of sHLA constant at a fixed concentration of 425 nM (20 µg/ml) at 20° C. Binding curves were analyzed by non-linear least squares regression using the Prism software package (Graph Pad, Inc.). (E-H) Transformation of original data sets to obtain saturation curves showing the specific binding of the pFITC ligand (ordinates) as a function of the free concentration of ligand (abscissa). The binding isotherms were analyzed by non-linear regression using a one site binding (hyperbola) model to extract $K_d$ and $B_{max}$ from the transformed data sets. Semi-logarithmic saturation curves (Klotz plot) are shown as insets.

Optimization of FP signal strength employing titration experiments with variable sHLA concentrations: Another critical step in assay optimization is the amount of sHLA present during the binding reaction. In this matter, the most effective number of molecules had to be determined in order to achieve high FP binding signals. Therefore, the goal within this section was to maximize peptide binding by employing titration experiments, where sHLA-A*0201 was titrated against a fixed concentration of labeled ligand (10 nM). To assure full data coverage at the lower and higher end of the binding curve, a broad spectrum of concentrations was selected. Results showed that with the exception of pFITC P3, all pFITC candidates were able to generate saturation curves reaching a plateau ($FP_{max}$) at supraoptimal concentrations of sHLA yielding no further increase in mP signal. Conclusively, the selection of appropriate HLA concentrations should preferably occur within the linear range of the titration curve to prevent distortions by protein overload. In contrast, control experiments performed in parallel using sHLA-B*2705 in exchange for sHLA-A*0201 did not result in a gradual increase in polarization, indicating that the enhanced polarization seen for sHLA-A*0201 was a result of specific binding. This was expected, as HLA-B*2705 was reported to bind a much different ligand repertoire compared to HLA-A*0201 (Jardetzky et al., 1991; Rotzschke et al., 1994; Boisgerault et al., 1996; Fiorillo et al., 1997). Typical titration curves are presented in FIG. 27, where data of single titration experiments were fitted by a dose-response model. Additionally, various degrees in maximum signal output between the four FITC-labeled ligands were detected. Highest signals were seen for pFITC P5 (FIG. 27D) with a maximum polarization signal of 244.6 mP for the bound state representing the top dynamic range (217.7 mP) with an increase of signal upon binding of more than 900%. With a dynamic range of only 155.7 mP, pFITC P1 still performed acceptably with an increase of signal still above 500% (FIG. 27A). Peptide P2 (FIG. 27B) and P4 (FIG. 27C) also showed very good binding ranges with values of 179.4 mP and 202.8 mP, respectively. Because FP signals are standardized, the polarization value corresponding to the unbound state is set as a constant with a value of 27 mP. In case of pFITC P3, experimental data showed that this peptide was not able to form stable complexes with sHLA-A*0201. Association analysis showed initial binding of the peptide, but within a few hours the binding levels dropped to the ground state (Buchli et al., 2004). This effect is most likely caused by interferences of the FITC label as peptide competition data referenced within the literature suggest high affinity A*0201 binding capabilities (Vitiello et al., 1997). Optimization of FP signal strength employing titration experiments with variable pFITC concentrations: Because FP is a simple solution-based assay, it was possible to obtain binding profiles under a number of different conditions to assess their effect on peptide binding. After optimization of the sHLA concentration, another approach was to test variable peptide concentrations by holding the concentration of sHLA constant at a fixed low concentration of 425 nM (20 µg/ml). FIG. 28 (A-D) shows typical binding curves where FP readings were plotted as a function of pFITC concentrations and fitted by nonlinear regression analysis using a dose-response model. Unlike the classical binding curve profile, the FP signal is greater for low ligand concentration because both bound and free fluorescent ligand contribute to the signal. Therefore, binding of pFITC conjugates to sHLA is characterized by an initial upper plateau for the bound state with highest polarization values followed by a steady polarization decrease as a result of the presence of increasing amounts of free fluorescent-labeled peptide ligand. Consequently, to achieve maximal change in polarization, it is critical to use low fluorescent ligand concentrations as increasing pFITC concentrations would require increasing "free" sHLA to ensure that the same fraction of ligand is bound.

Determination of dissociation equilibrium constants: Determination of the dissociation equilibrium constant ($K_d$) can be an important component of an epitope validation process because it allows for the elucidation of the structure-activity relationship of the selected peptides with sHLA. However, a standard titration curve analysis is not directly applicable for FP, because the ratio between bound and free fluorescent-labeled ligand is detected as seen in FIG. 28 (A-D). Due to the contribution of free ligand to the detected polarization signal, a more complicated approach for data analysis is necessary. To obtain the $K_d$ for sHLA/pFITC interactions, the recently described FP $K_d$ model from Prystay et al. (Prystay et al., 2001) was used. FP titration data as above were transformed using the equations of the Prystay model (see Materials and Methods section), which generated a hypothetical saturation curve of bound vs. free ligand concentrations (FIG. 28 (E-H)). To better visualize binding data at lower peptide concentrations, fitted results were additionally displayed as Klotz plots (semi-logarithmic saturation curves) shown as inserts of FIG. 28 (E-H).

Titration results showed that the fluorescent-labeled ligands P1, P2, P4 and P5 could all be saturated and express high binding affinities within a range of 10.7 to 21.8 nM (Table XI). The affinity of the peptide P1 was highest, corresponding well to earlier publications using an iodinated (15.5 nM) molecule FLPSDY($^{125}$I)FPSV (Sette et al., 1994a) (SEQ ID NO:43). Maximal binding ($B_{max}$) for the sHLA-A*0201 protein was in the range of 90-160 nM indicating binding efficiencies of more than 20% for all peptide candidates tested. In addition, these efficiencies are much higher than reported by others using similar procedures to generate peptide receptive HLA molecules (Christinck et al., 1991; Abastado et al., 1993; Ojcius et al., 1993; Binz et al., 2003).

Peptide competition analysis: To further explore the specificity of peptide binding, it was determined whether the binding of the A*0201-related FITC-labeled peptides were inhibitable by an unlabeled peptide known to bind HLA-A*0201 with high affinity. The affinity of the unlabeled A*0201-related control peptide KLGEFYNQMM (SEQ ID NO:21) was thus evaluated by a competition assay approach using pFITC peptides as labeled tracers. To determine the 50% inhibitory concentration ($IC_{50}$), which can be taken to be representative of the relative affinity of the ligand-recognition site, a constant concentration of activated sHLA (40 µg/ml), excess β2m and labeled peptide (10 nM) were incubated in the presence of different concentrations of the selected competitor.

Figure 29:
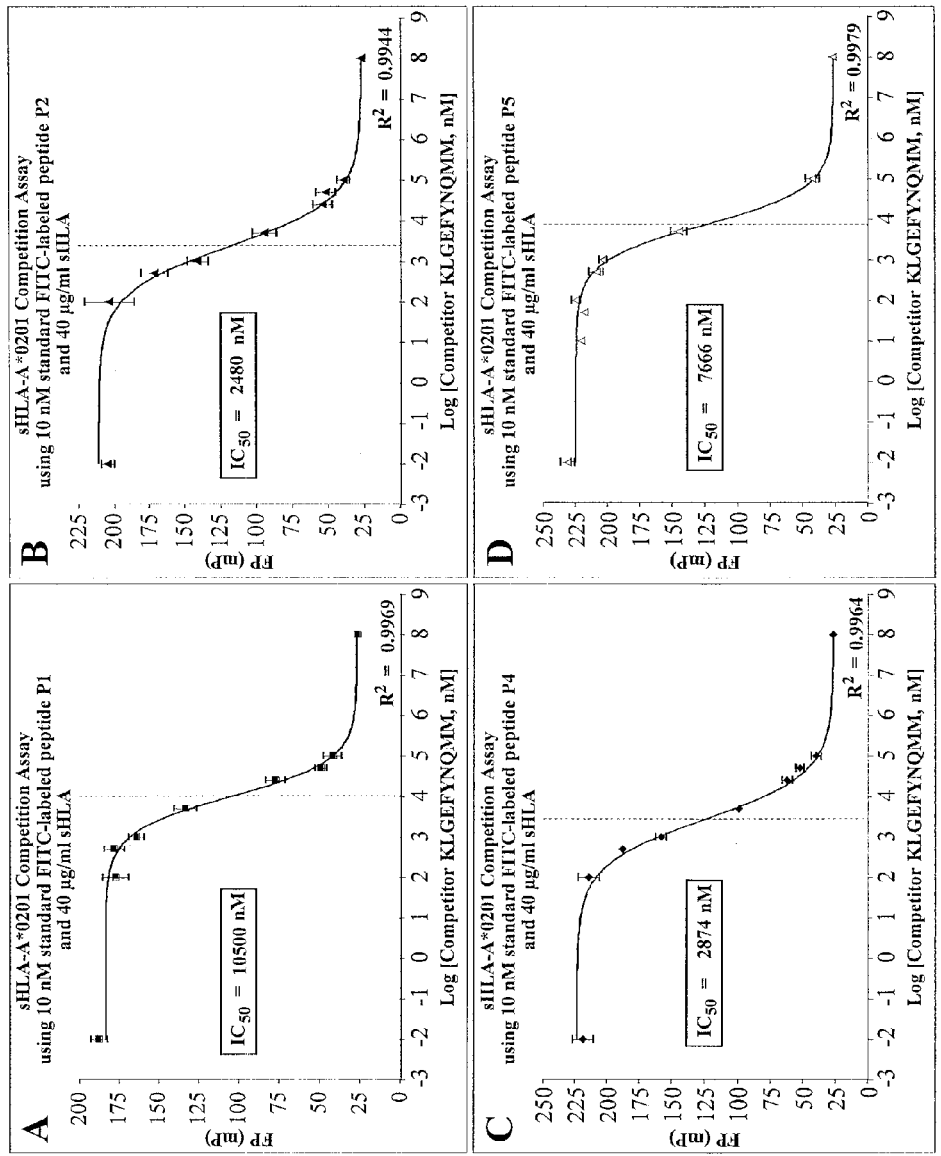
FIG. 29 illustrates competition curves obtained with the nonlabeled peptide KLGEFYNQMM (SEQ ID NO:21) and various pFITC tracer peptides. A constant concentration of activated sHLA-A*0201, excess β2m and HLA-A2-binding FITC-labeled reference peptides (A) P1, (B) P2, (C) P4, and (D) P5 were incubated with titrated amounts of the competitor peptide KLGEFYNQMM (SEQ ID NO:21) for 72 hours at room temperature. After equilibrium was reached, FP was measured and data analyzed by nonlinear regression analysis to determine $IC_{50}$ values. The X-axis plots the logarithm of the concentration of the test-peptide, where the Y-axis plots the response expressed in mP monitoring the binding of the pFITC to sHLA. Results of one representative experiment of at least three performed are shown. The goodness of curve fitting is expressed as $R^2$.
Figure 30:
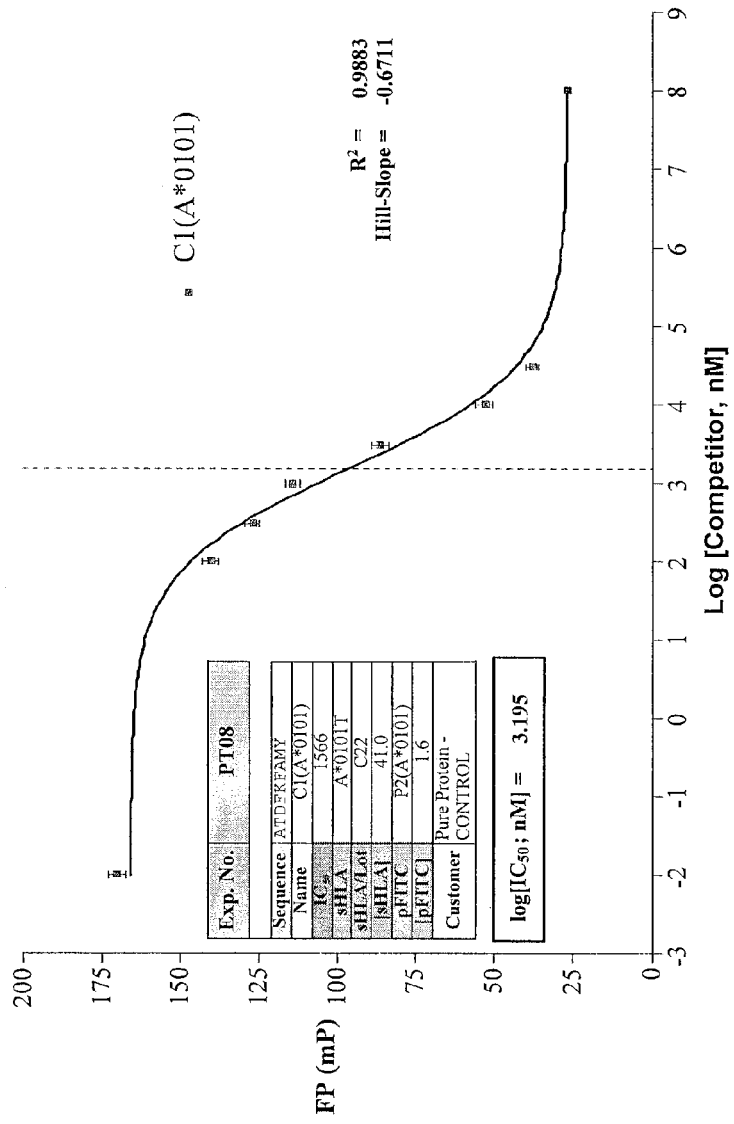
FIGS. 30 and 31 depict sHLA-A*0101 competition assay using FITC-labeled peptide P2(A*0101) and competing peptide ATDFKFAMY (SEQ ID NO:45) (FIG. 30) or peptide IADMGHLKY (SEQ ID NO:46) (FIG. 31).
Figure 31:
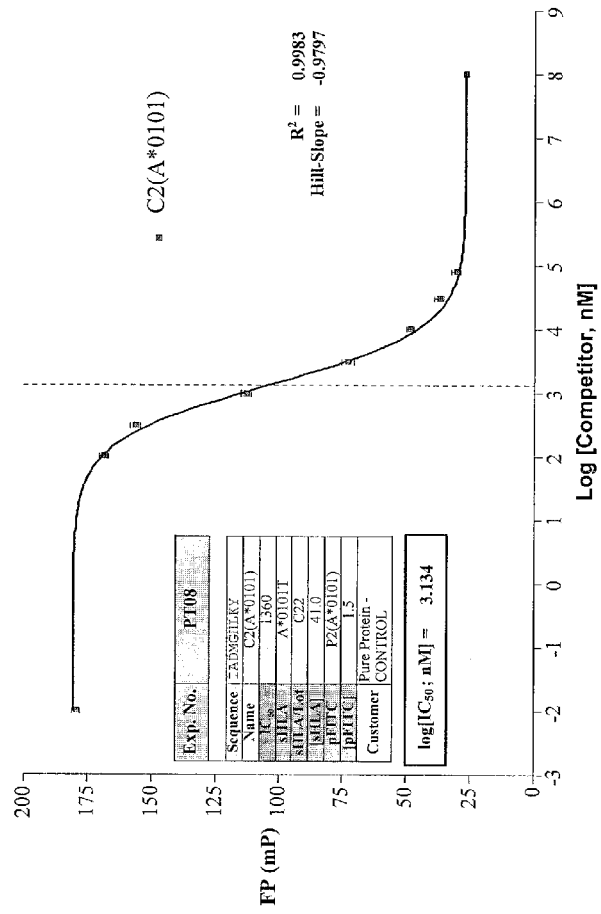
Figure 32:
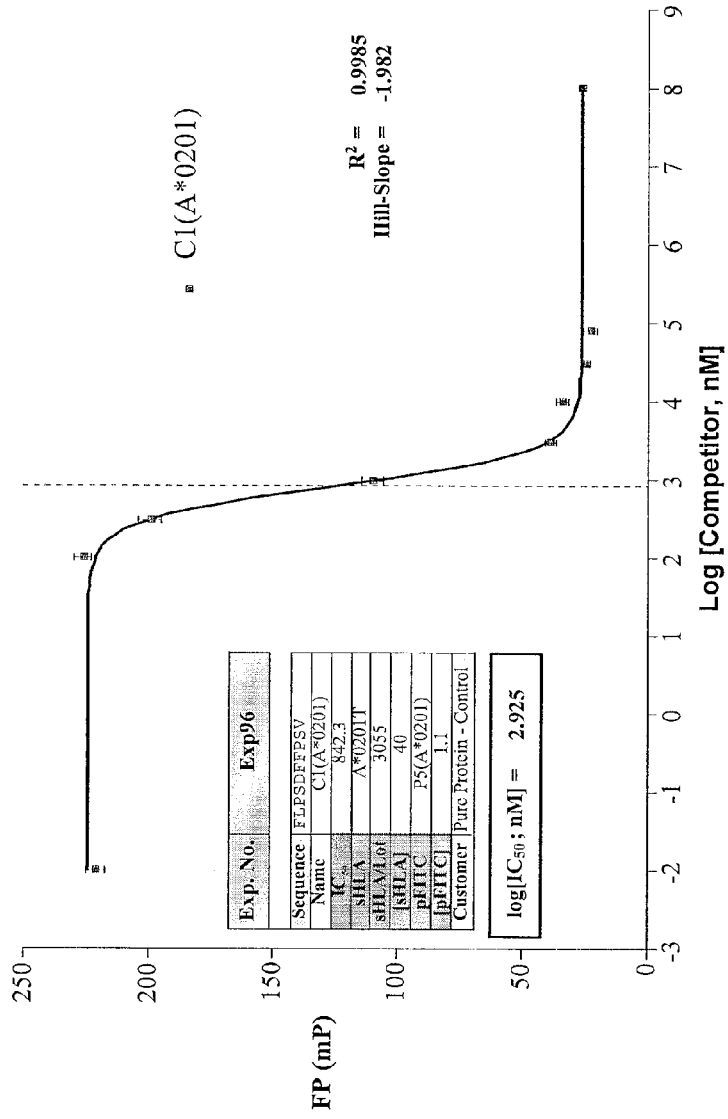
FIGS. 32 and 33 depict sHLA-A*0201 competition assay using FITC-labeled peptide P5(A*0201) and competing peptide FLPSDFFPSV (SEQ ID NO:28) (FIG. 32) or peptide KLGEFYNQMM (SEQ ID NO:21) (FIG. 33).
Figure 33:
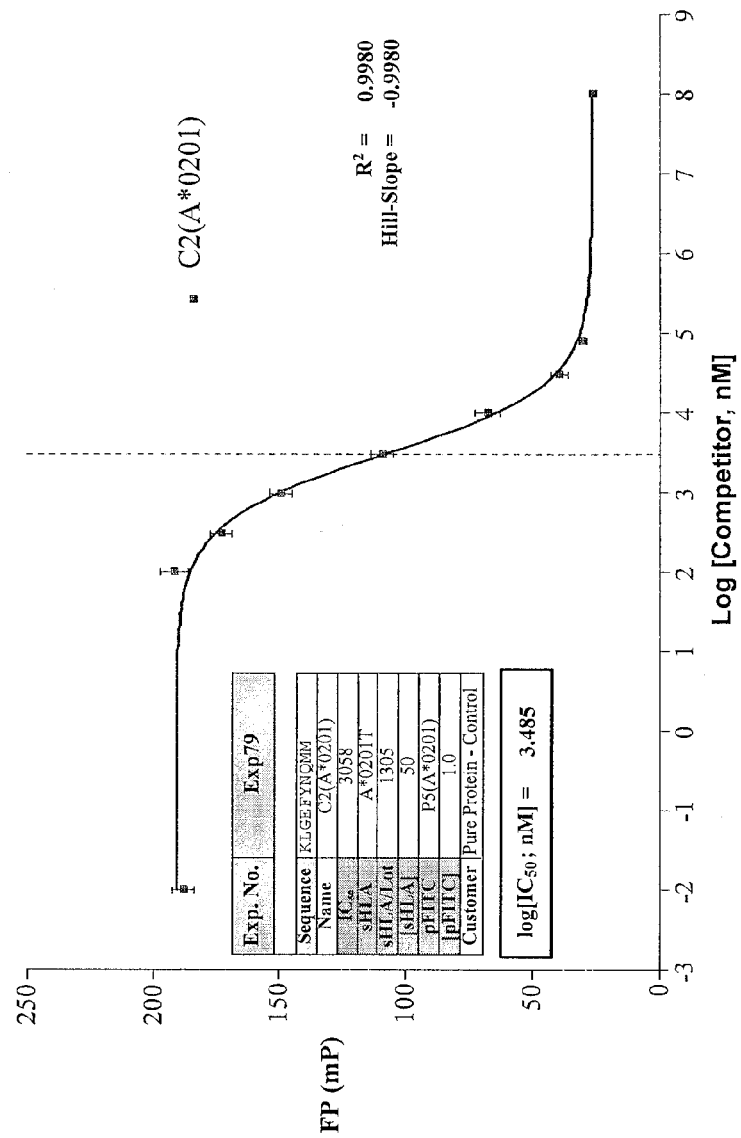
Figure 34:
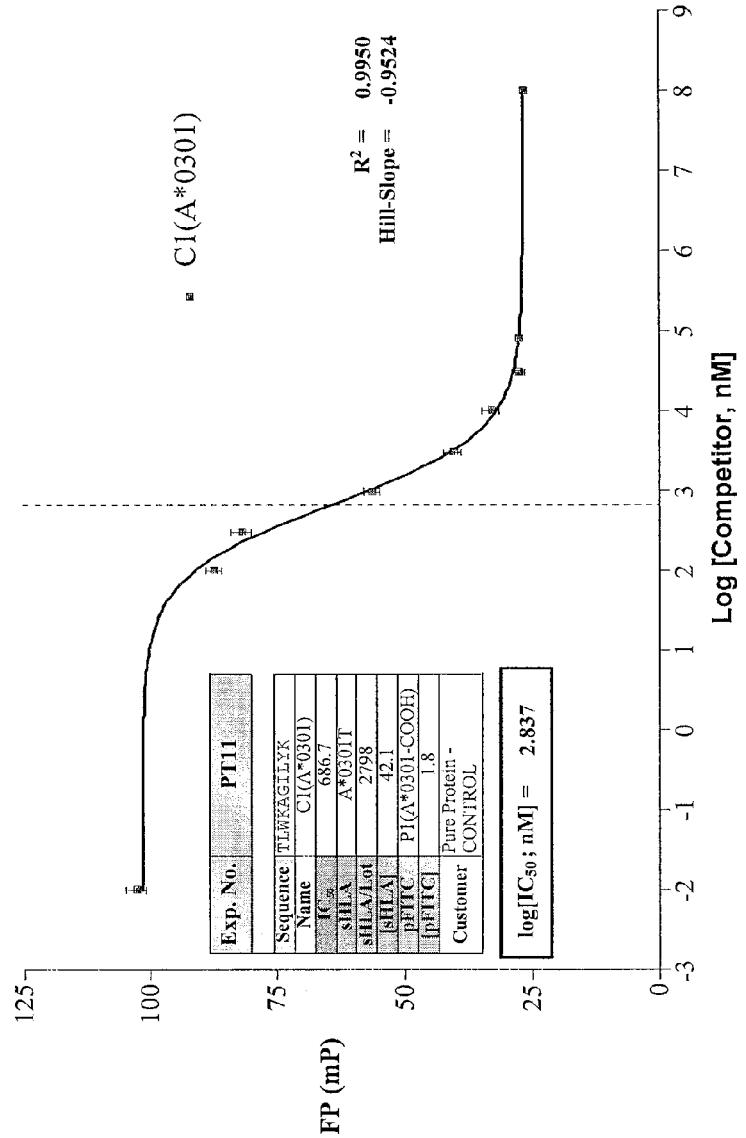
FIGS. 34 and 35 depict sHLA-A*0301 competition assay using FITC-labeled peptide P1(A*0301) and competing peptide TLWAGILYK (SEQ ID NO:47) (FIG. 34) or peptide SLFRAVITK (SEQ ID NO:48) (FIG. 35).
Figure 35:
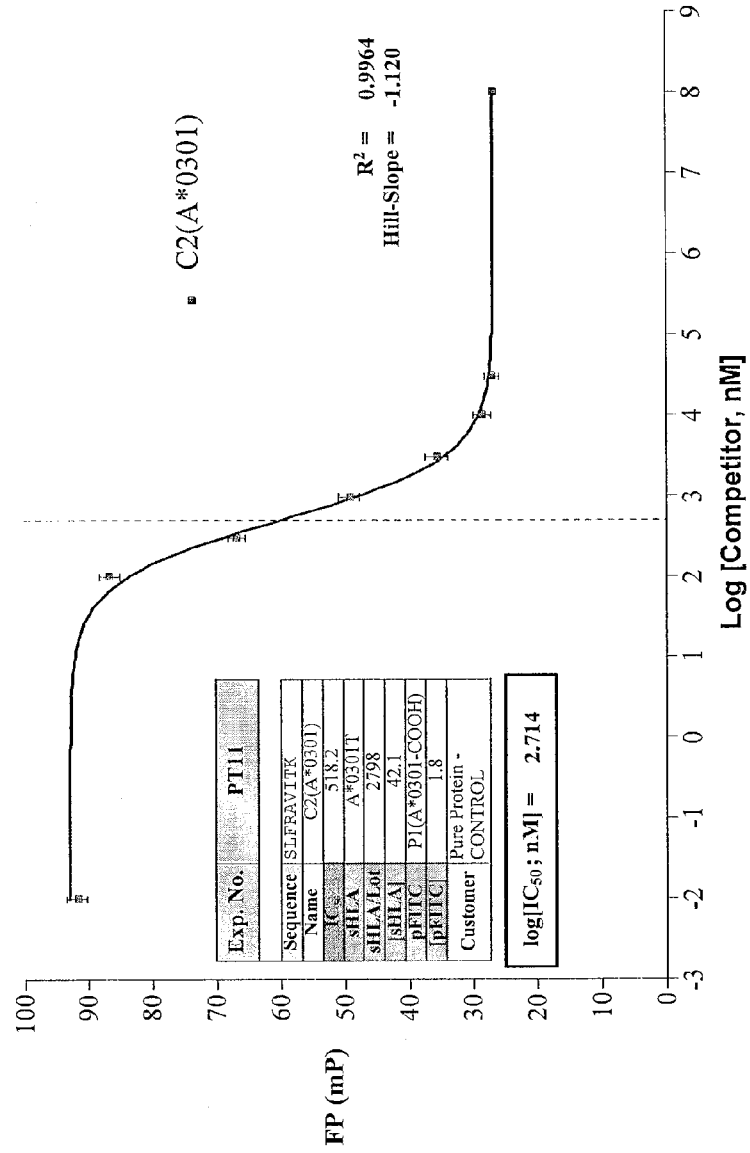
Figure 36:
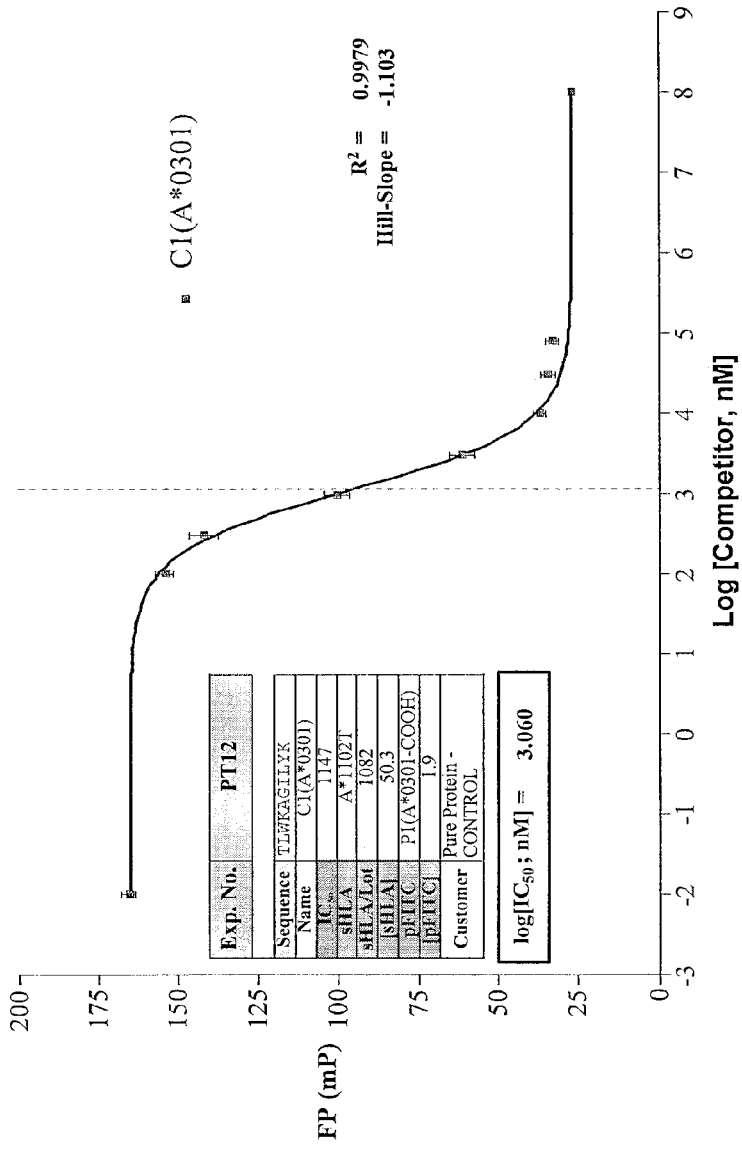
FIGS. 36 and 37 depict sHLA-A*1102 competition assay using FITC-labeled peptide P1(A*0301) and competing peptide TLWKAGILYK (SEQ ID NO:47) (FIG. 36) or peptide SLFRAVITK (SEQ ID NO:48) (FIG. 37).
Figure 37:
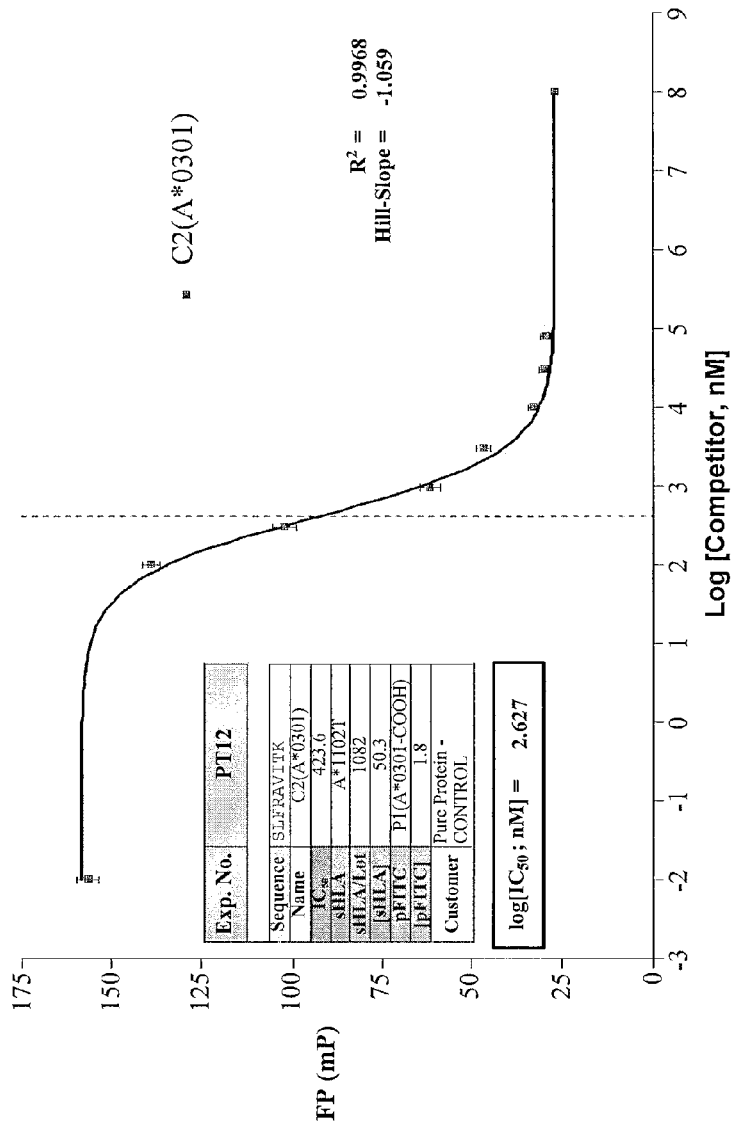
Figure 38:
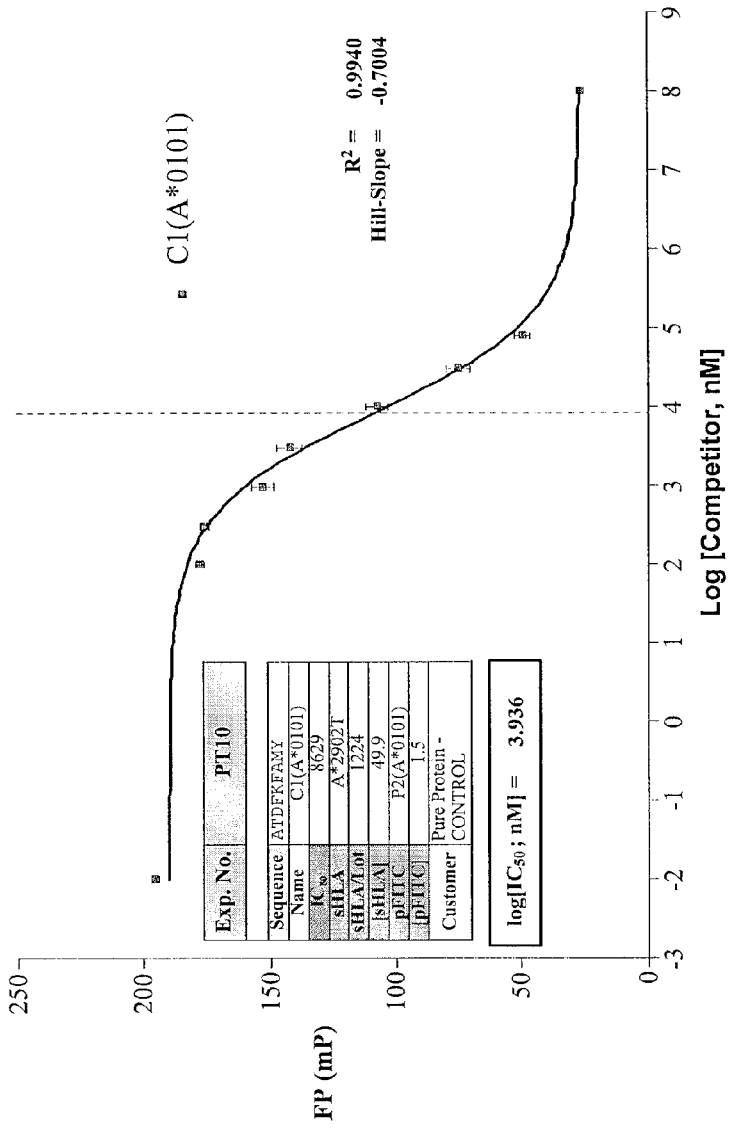
FIGS. 38 and 39 depict sHLA-A*2902 competition assay using FITC-labeled peptide P2(A*0101) and competing peptide ATDFKFAMY (SEQ ID NO:45) (FIG. 38) or peptide IADMGHLKY (SEQ ID NO:46) (FIG. 39).
Figure 39:
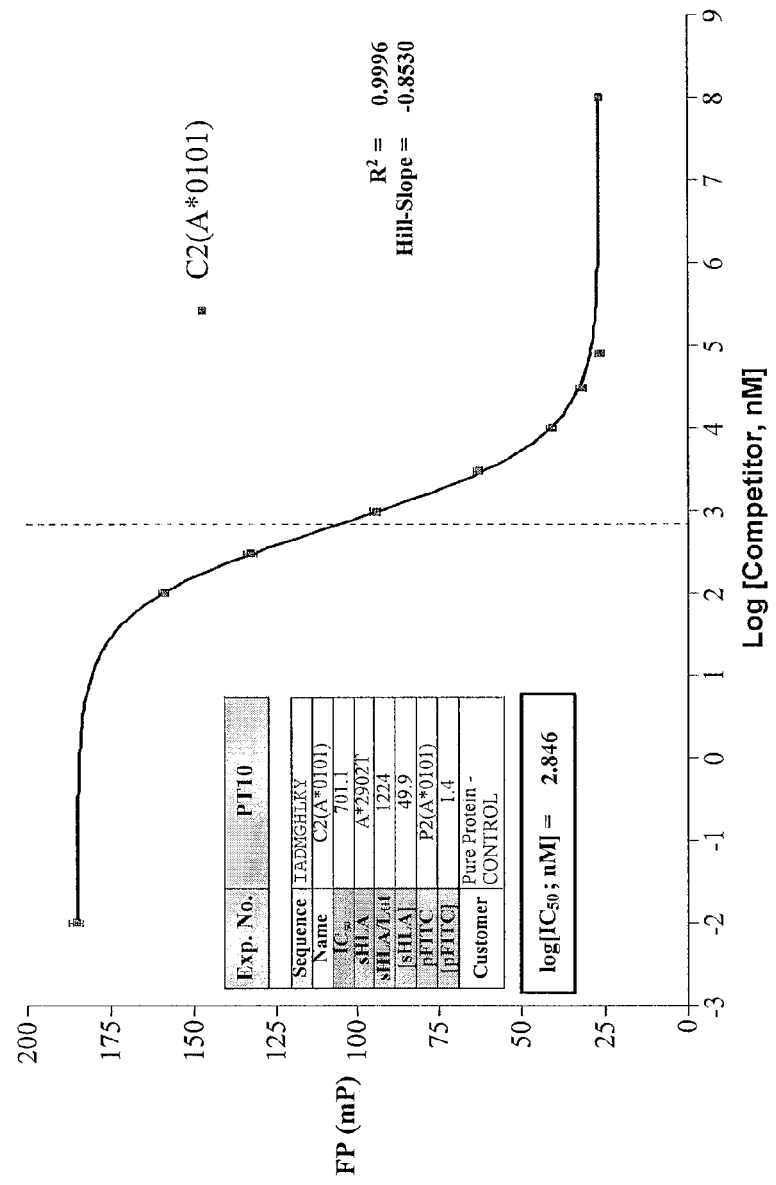
Figure 40:
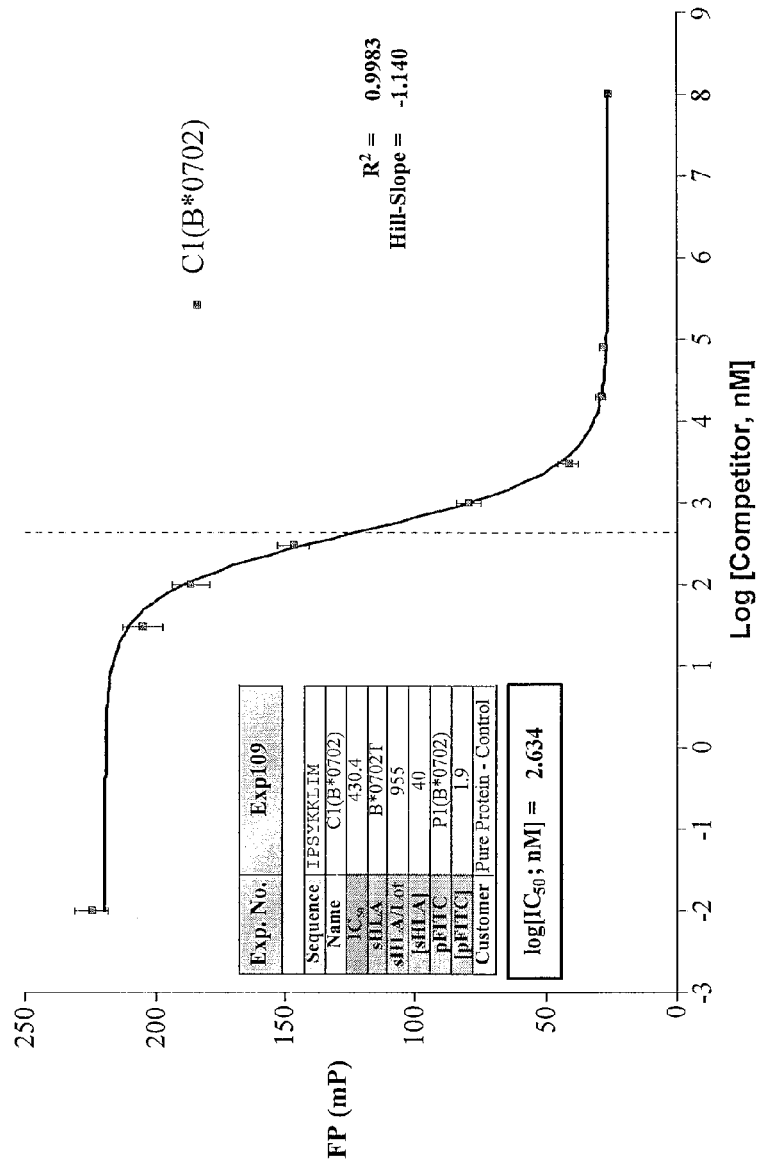
FIGS. 40 and 41 depict sHLA-B*0702 competition assay using FITC-labeled peptide P1(B*0702) and competing peptide IPSYKKLIM (SEQ ID NO:42) (FIG. 40) or peptide LVMAPRTVL (SEQ ID NO:5) (FIG. 41).
Figure 41:
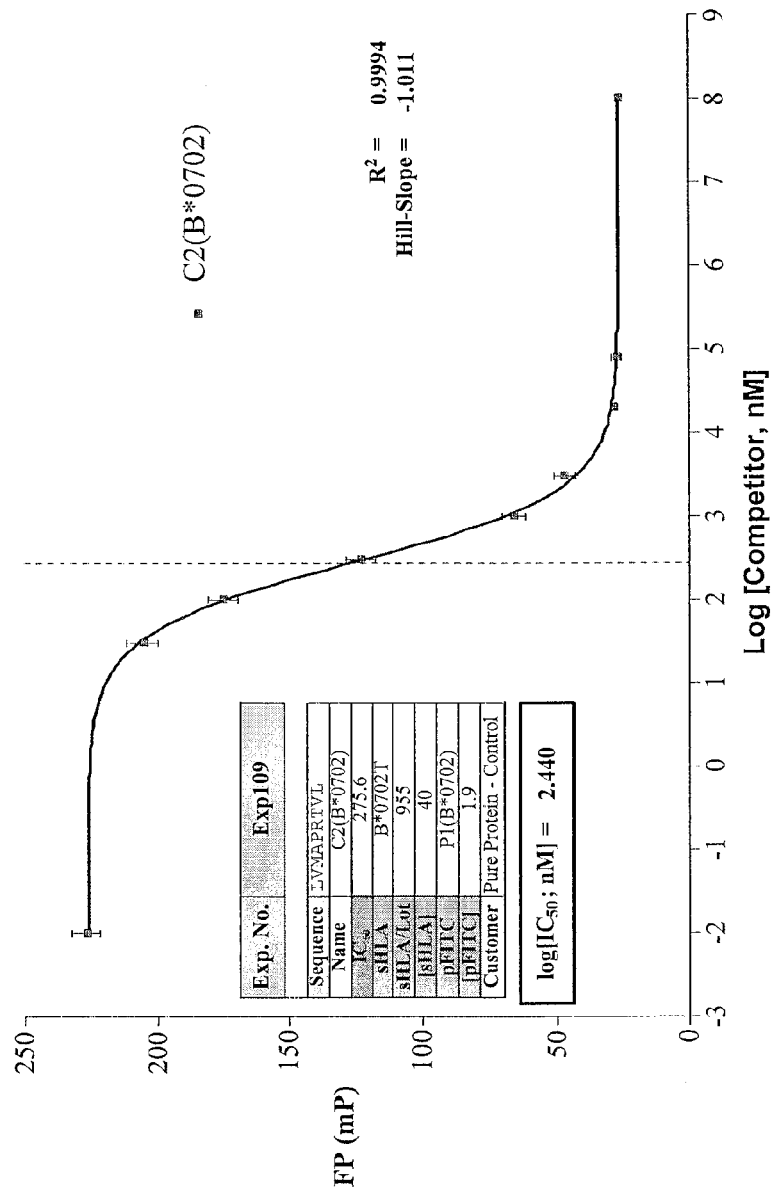
Figure 42:
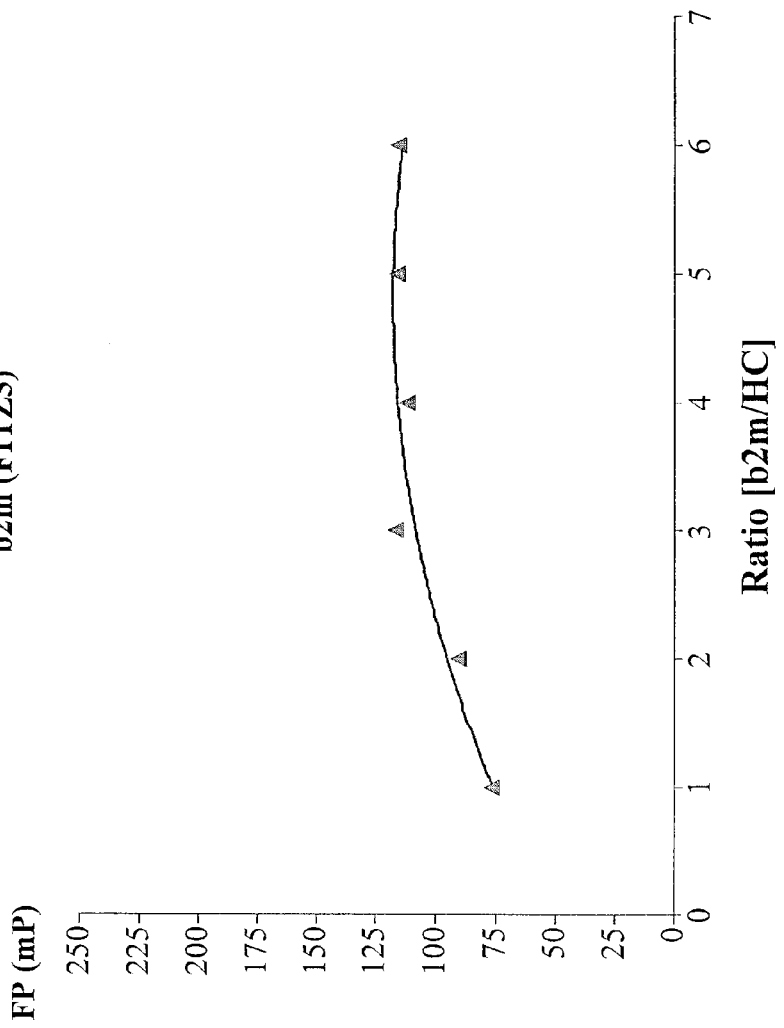
FIG. 42 illustrates a dose response curve of the β2m quality control assay of sHLA-A*0301T with FITC-labeled peptide P2(A*0301).
Figure 43:
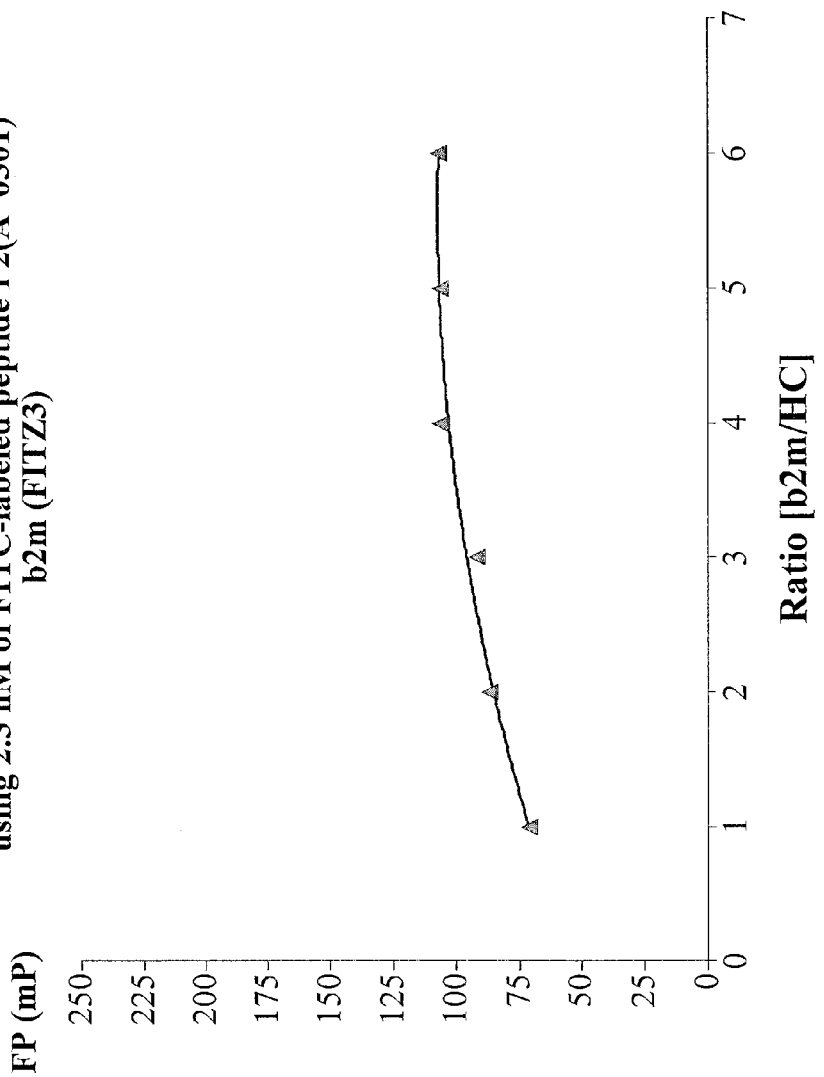
FIG. 43 illustrates a dose response curve of sHLA-A*03402T with FITC-labeled peptide P2(A*0301).
Figure 44:
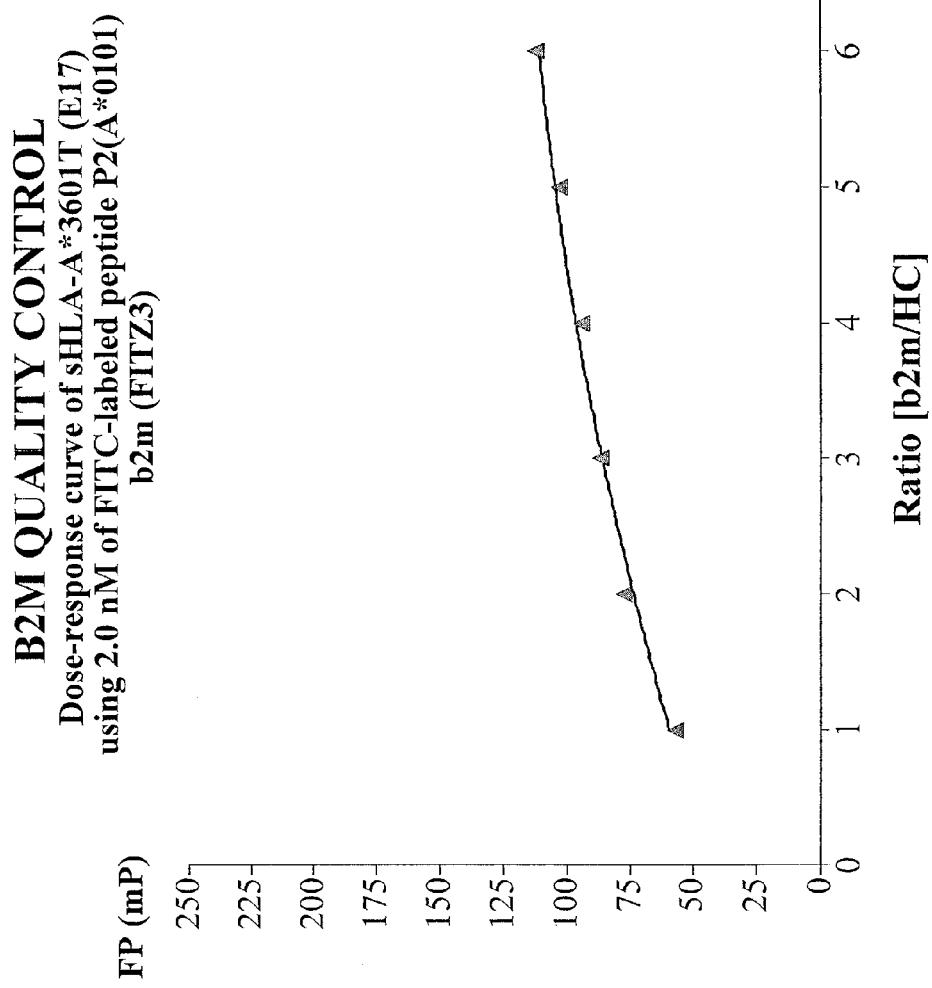
FIG. 44 illustrates a dose response curve of the β2m quality control assay of sHLA-A*3601T with FITC-labeled peptide P2(A*0101).
Figure 45:
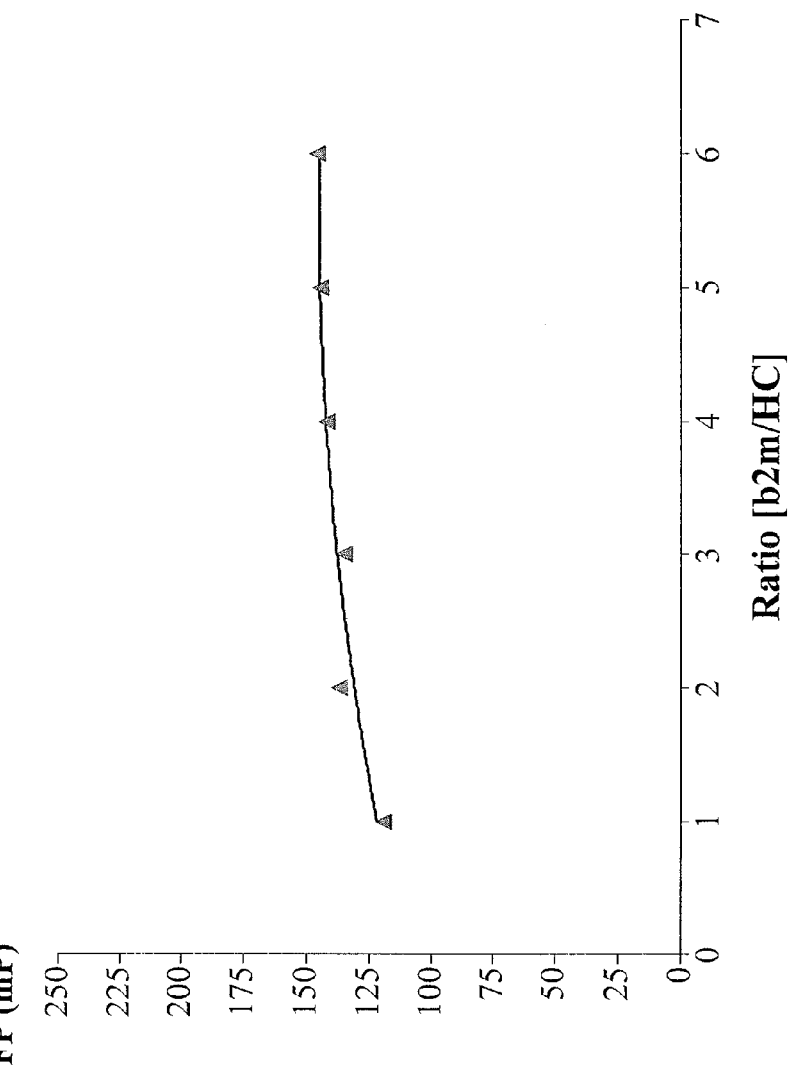
FIG. 45 illustrates a dose response curve of the β2m quality control assay of sHLA-A*0301T with FITC-labeled peptide P2(A*0301).
Figure 46:
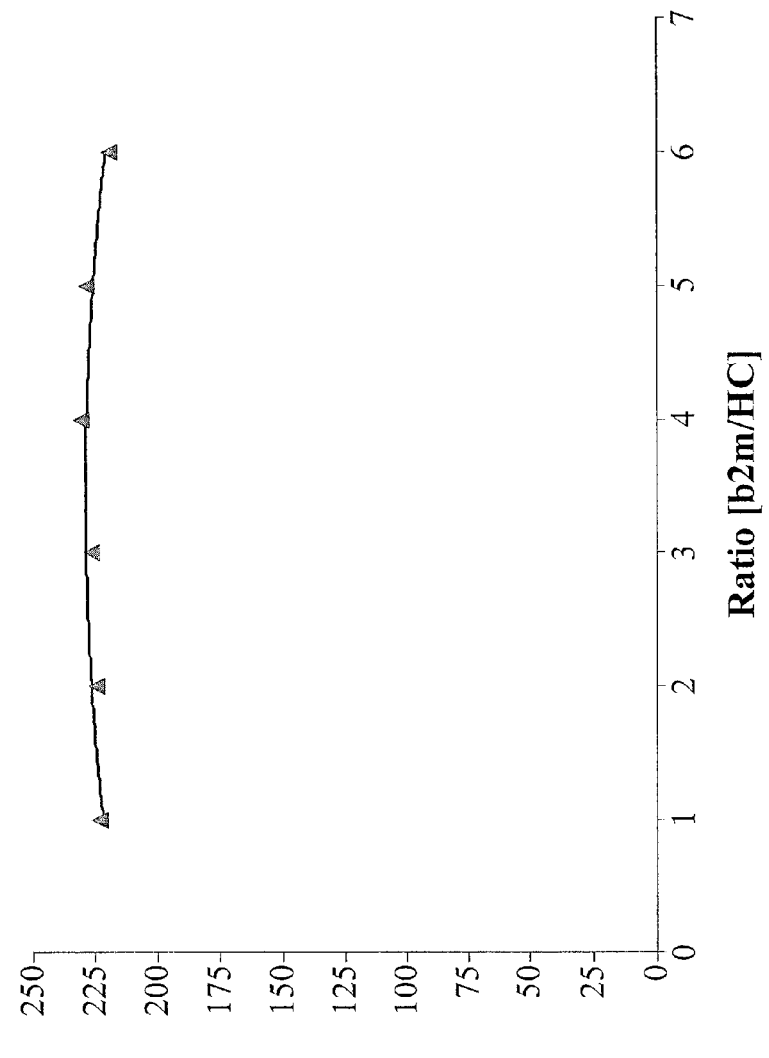
FIG. 46 illustrates a dose response curve of the β2m quality control assay of sHLA-A*6801T with FITC-labeled peptide P2(A*0301).
Figure 47:
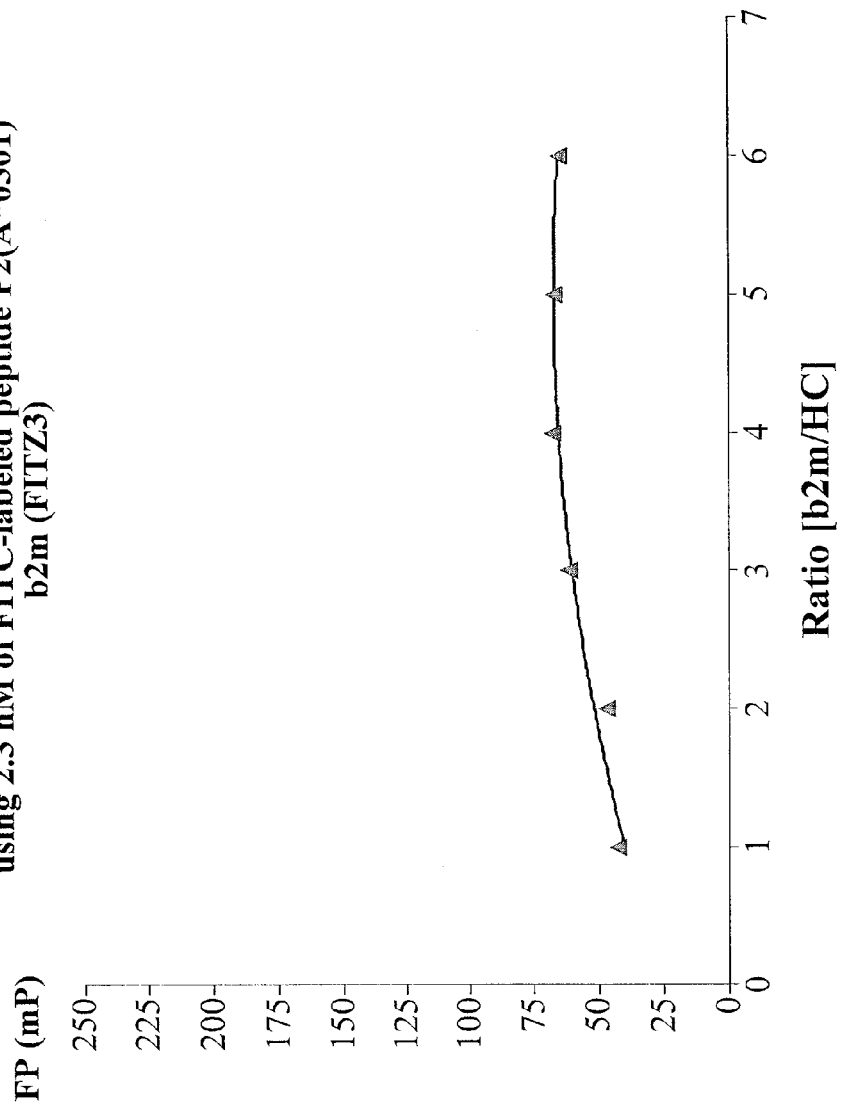
FIG. 47 illustrates a dose response curve of the β2m quality control assay of sHLA-A*7401T with FITC-labeled peptide P2(A*0301).
Figure 48:
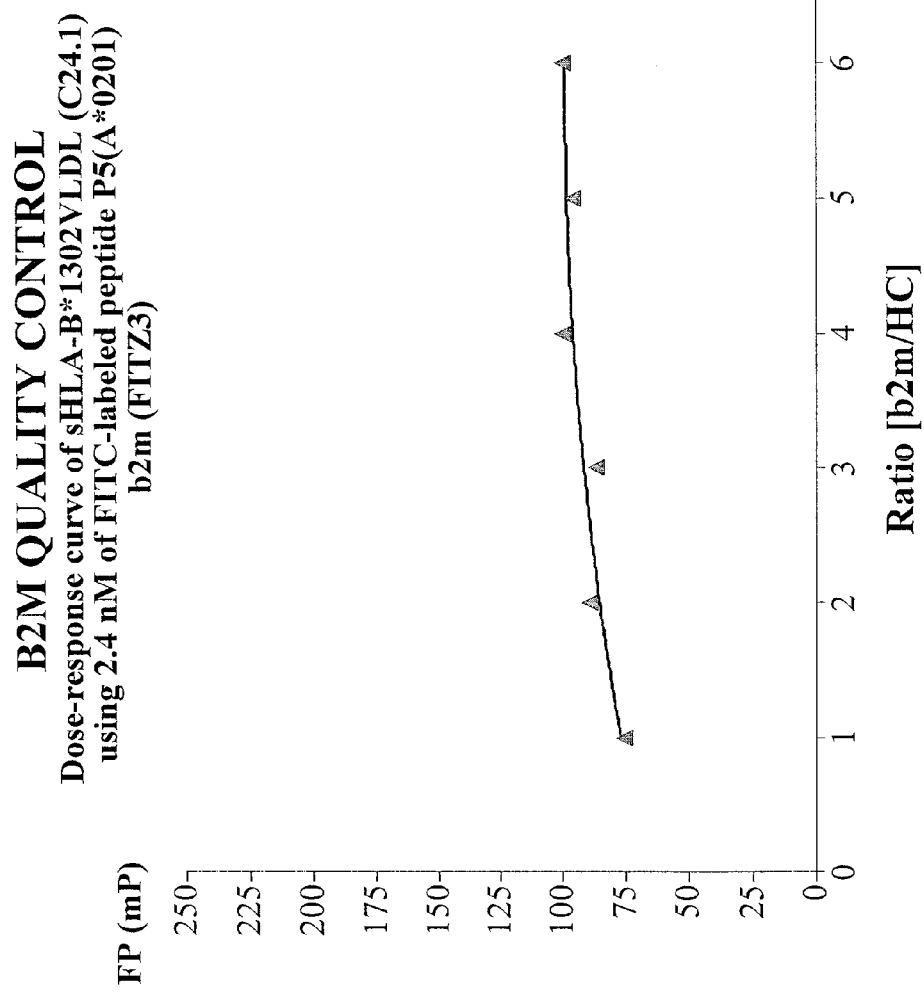
FIG. 48 illustrates a dose response curve of the β2m quality control assay of sHLA-B*1302VLDL with FITC-labeled peptide P5(A*0201).
Figure 49:
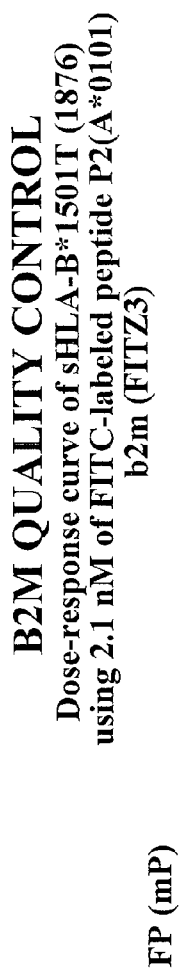
FIG. 49 illustrates a dose response curve of the β2m quality control assay of sHLA-B*1501T with FITC-labeled peptide P2(A*0101).
Figure 50:
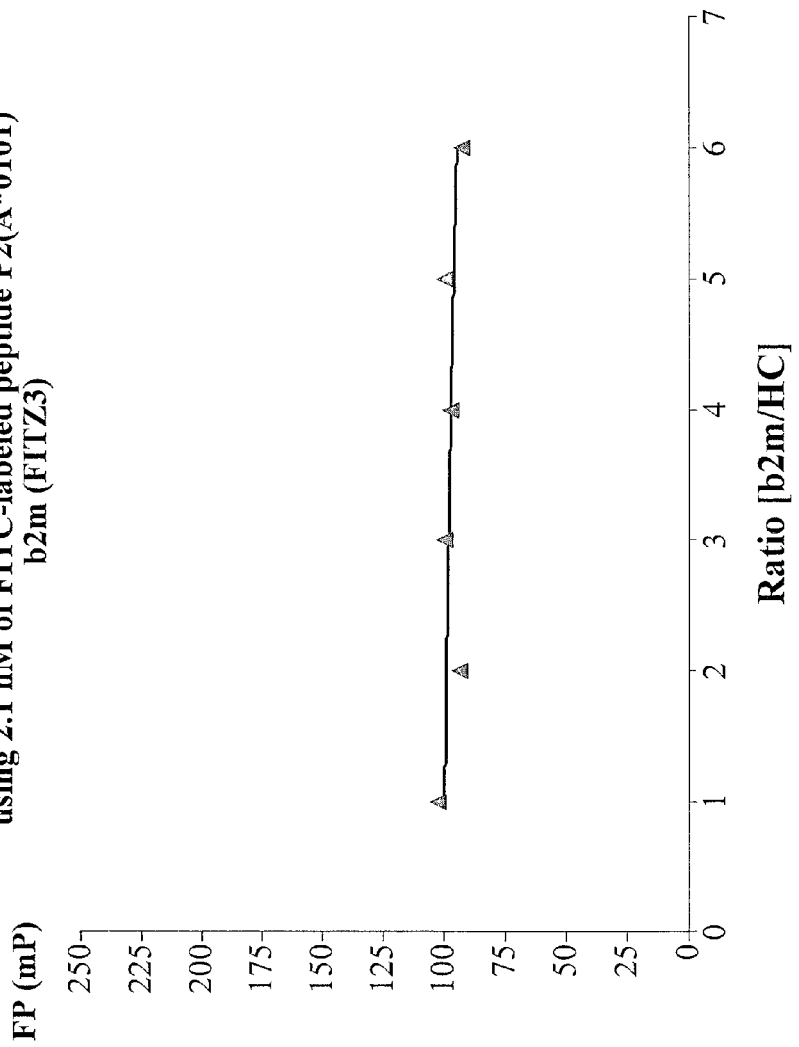
FIG. 50 illustrates a dose response curve of the β2m quality control assay of sHLA-B*1516T with FITC-labeled peptide P2(A*0101).
Figure 51:
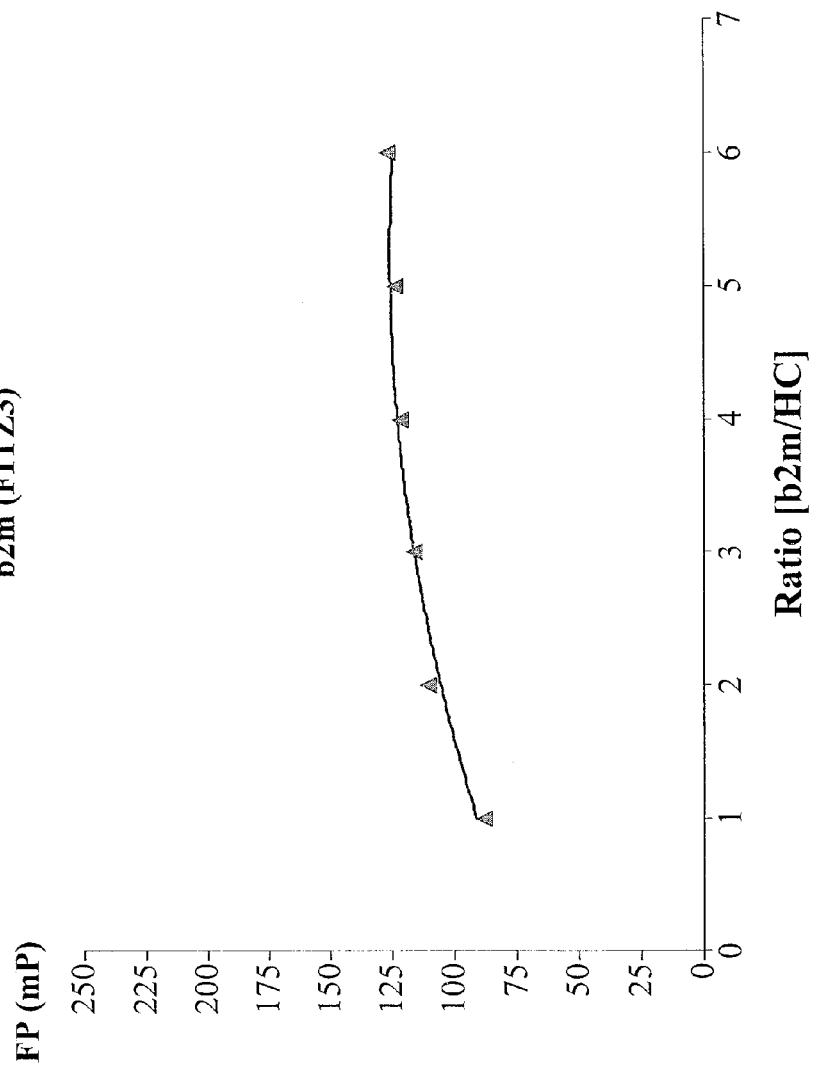
FIG. 51 illustrates a dose response curve of the β2m quality control assay of sHLA-B*1801T with FITC-labeled peptide P2(B*4402).
Figure 52:
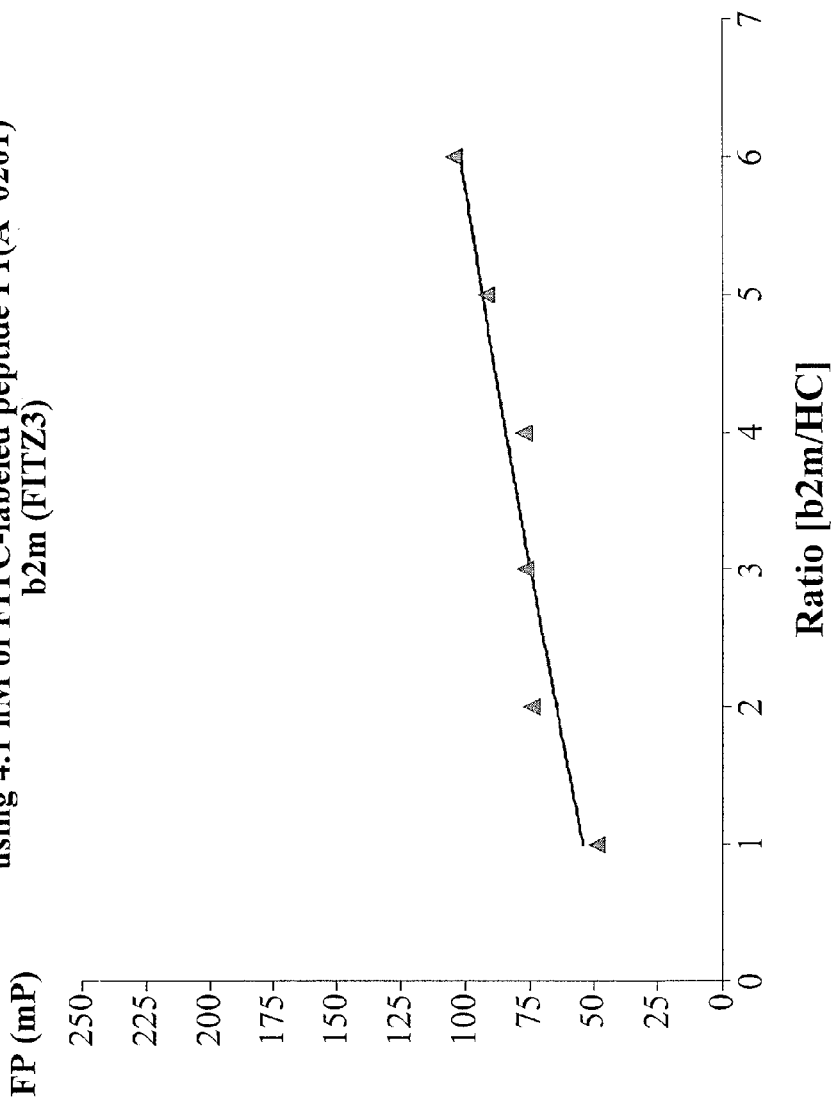
FIG. 52 illustrates a dose response curve of the β2m quality control assay of sHLA-B*3505T with FITC-labeled peptide P1(A*0201).
Figure 53:
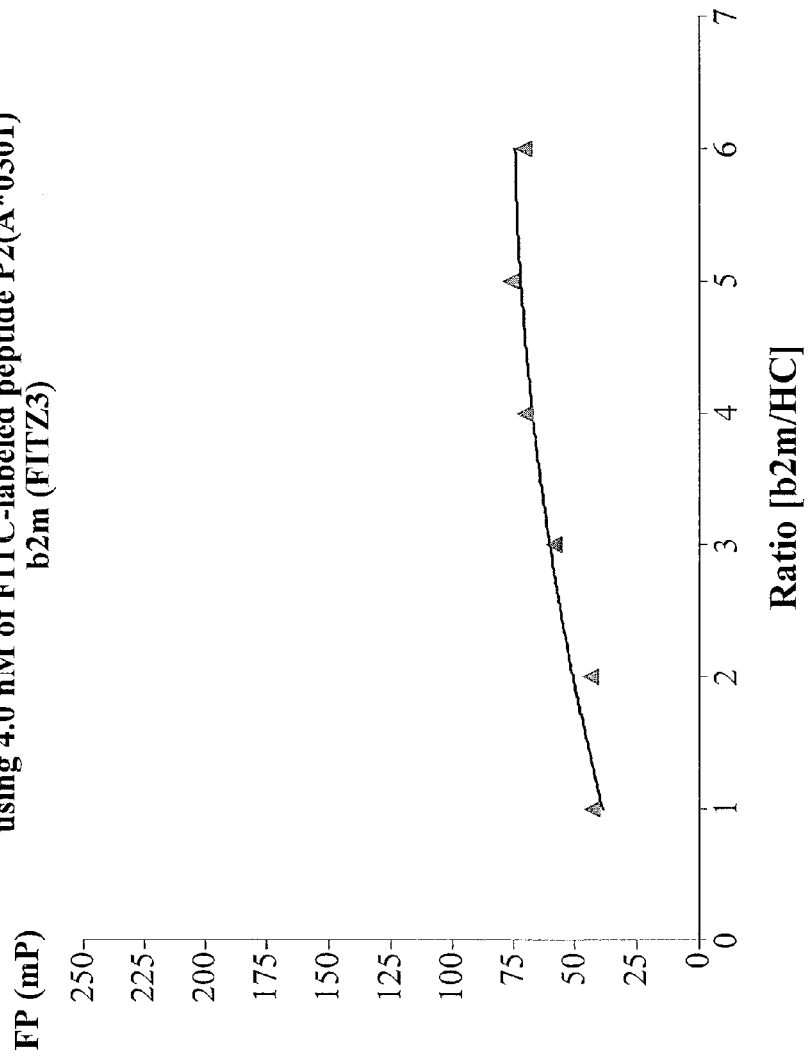
FIG. 53 illustrates a dose response curve of the β2m quality control assay of sHLA-B*5101T with FITC-labeled peptide P2(A*0301).
Figure 54:
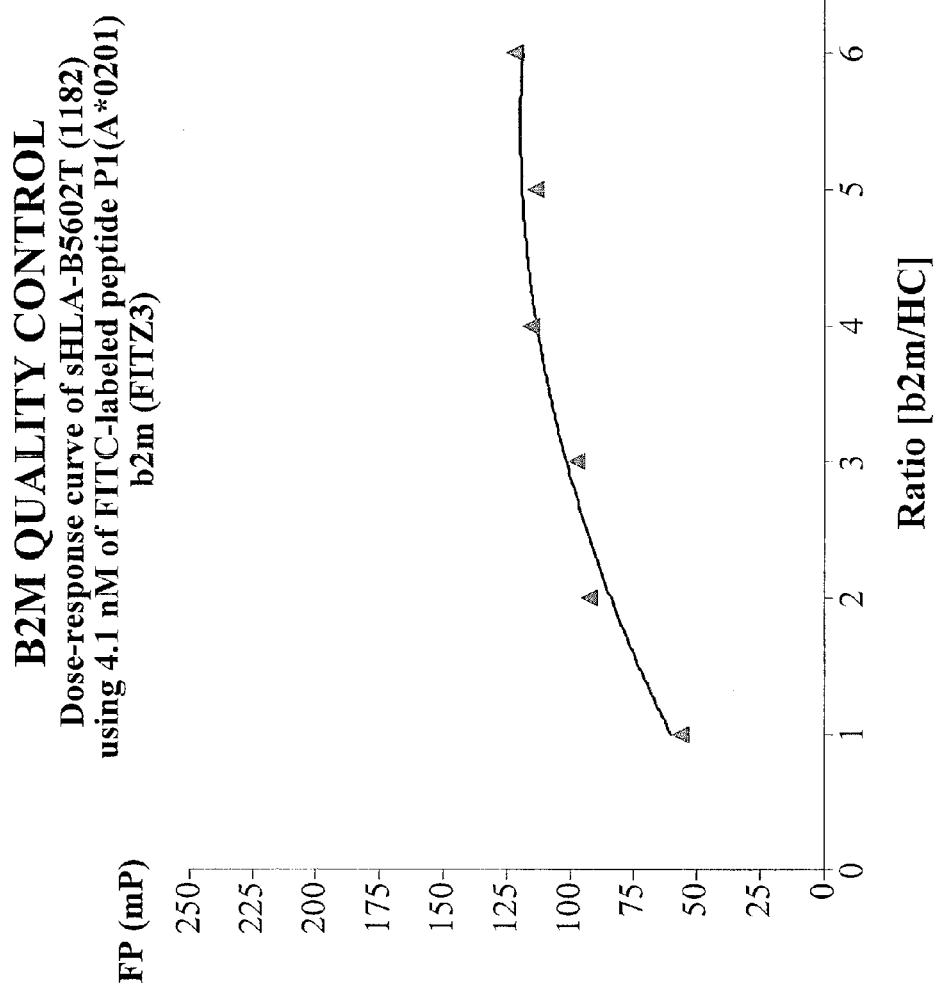
FIG. 54 illustrates a dose response curve of the β2m quality control assay of sHLA-B*5602T with FITC-labeled peptide P1(A*0201).
Figure 55:
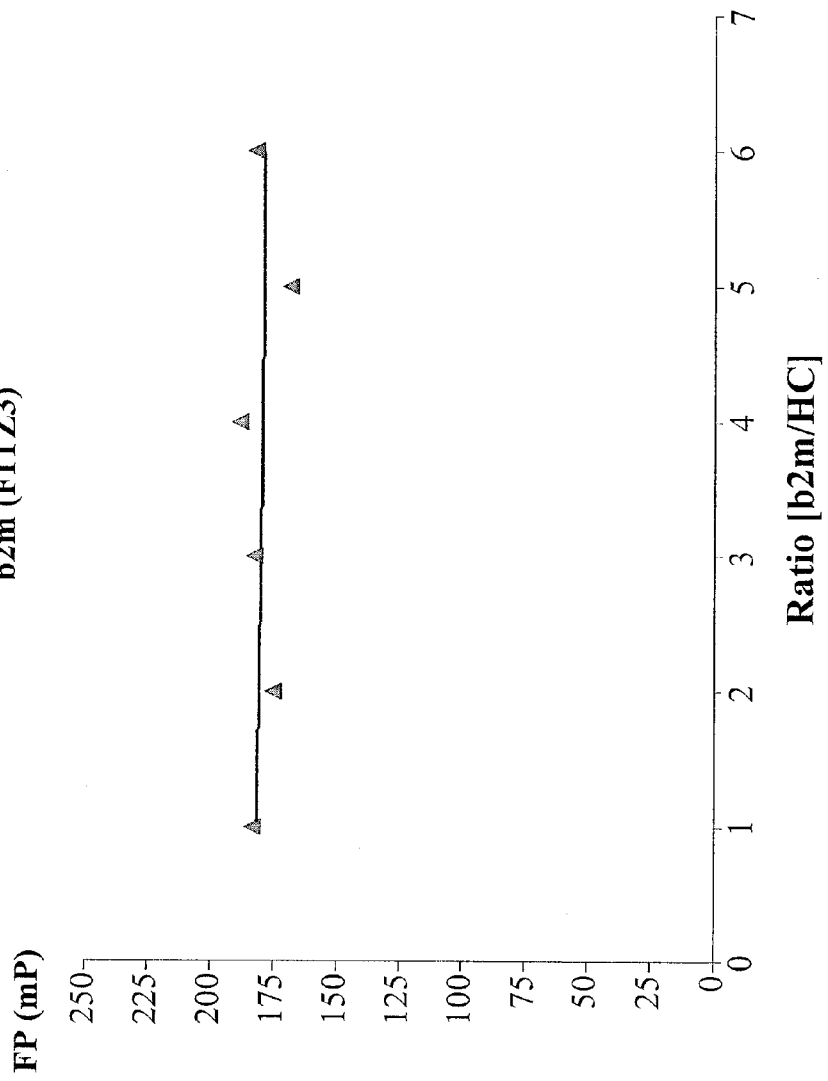
FIG. 55 illustrates a dose response curve of the β2m quality control assay of sHLA-Cw*0801T with FITC-labeled peptide P1(A*0201).
Figure 56:
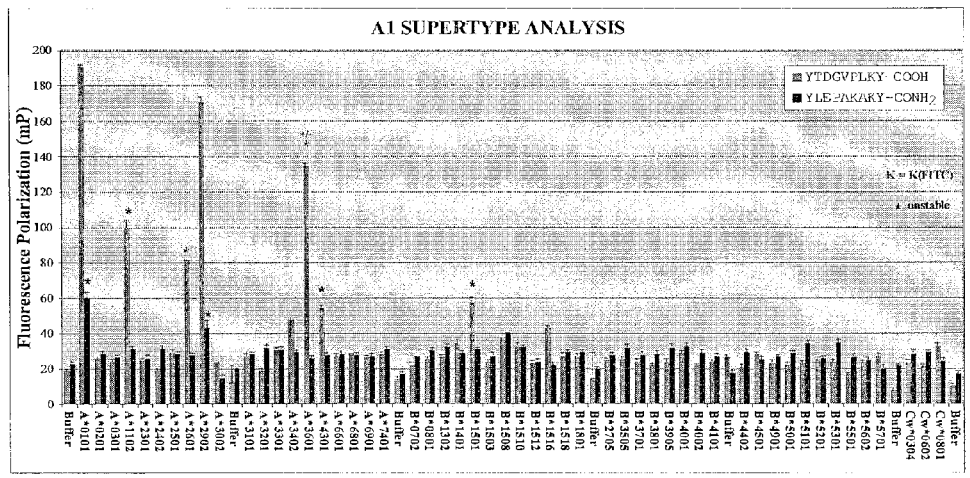
FIG. 56 illustrates the FP response of two A1-like peptides YTDGVPLKY (SEQ ID NO:50) and YLEPAKAKY (SEQ ID NO:51)) in a binding assay with 53 MHC class I molecules.
Figure 57:
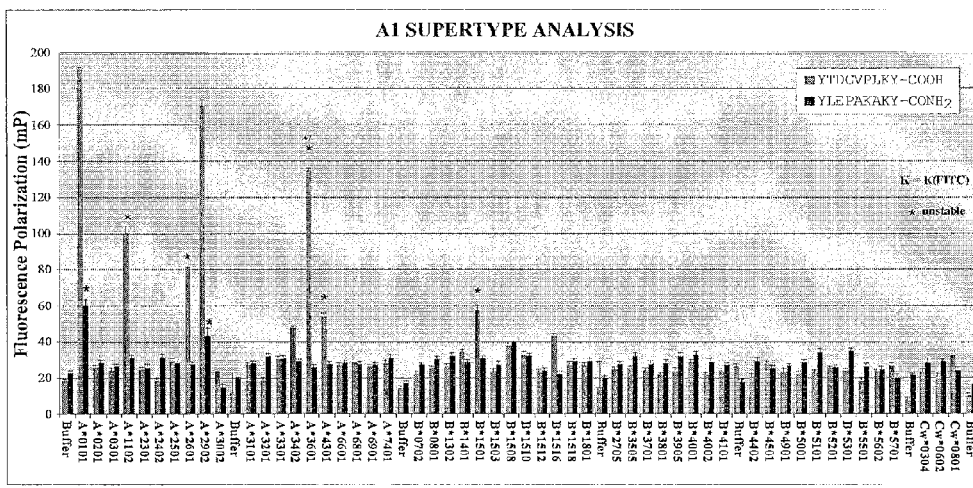
FIG. 57 illustrates the FP response of two A2-like peptides YTDGVPLKY (SEQ ID NO:50) and YLEPAKAKY (SEQ ID NO:51)) in a binding assay with 53 MHC class I molecules.
Figure 58:
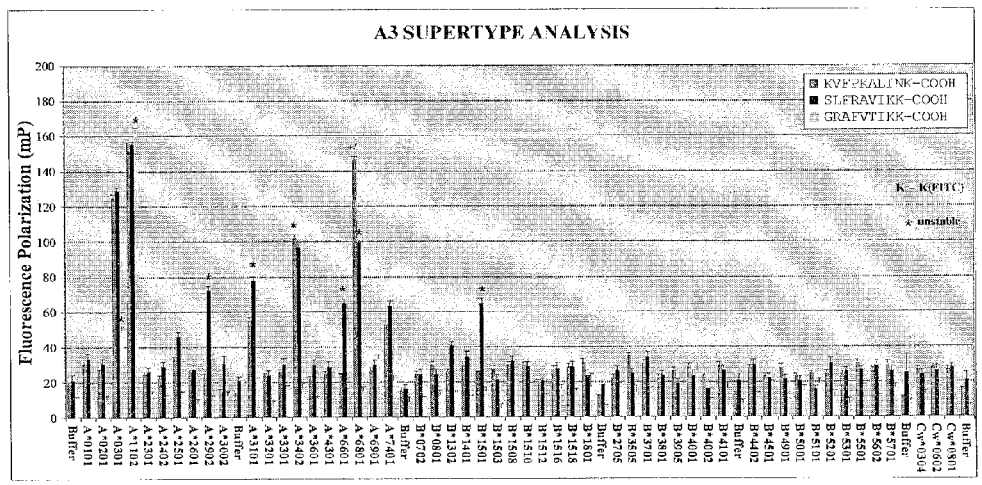
FIG. 58 illustrates the FP response of three A3-like peptides KVFPKALINK (SEQ ID NO:52) and SLFRAVIKK (SEQ ID NO:53), and GRAFVTIKK (SEQ ID NO:44)) in a binding assay with 53 MHC class I molecules.
Figure 59:
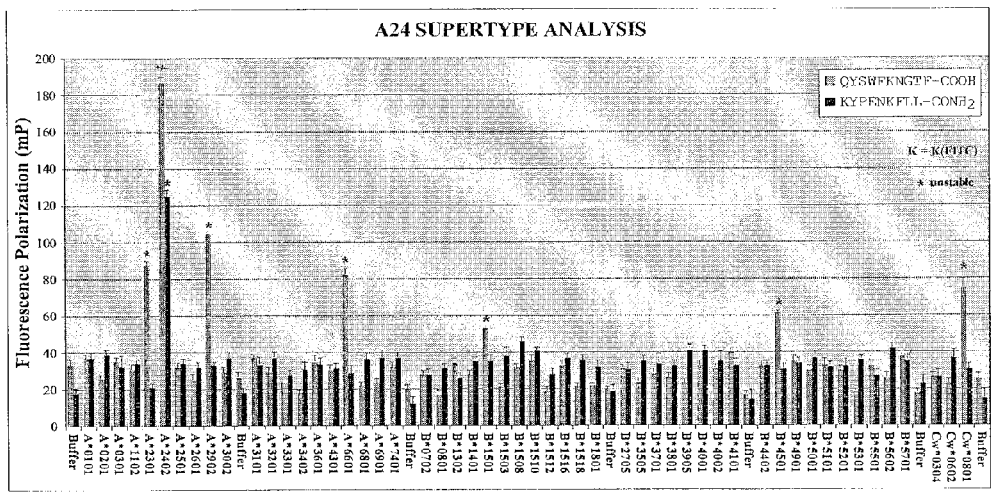
FIG. 59 illustrates the FP response of two A24-like peptides QYSWFKNGTF (SEQ ID NO:54) and KYPENKFLL (SEQ ID NO:55)) in a binding assay with 53 MHC class I molecules.
Figure 60:
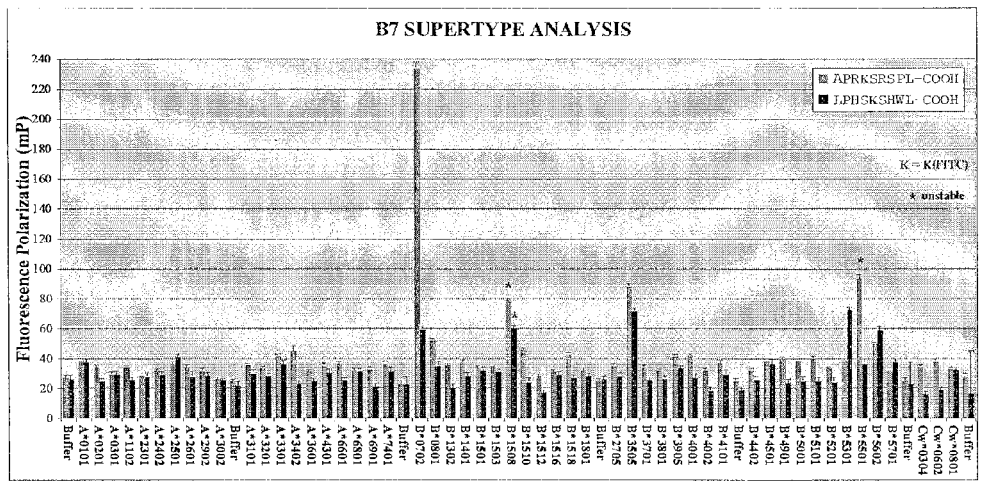
FIG. 60 illustrates the FP response of two B7-like peptides APRKSRSPL (SEQ ID NO:56) and LPHSKSHWL (SEQ ID NO:57)) in a binding assay with 53 MHC class I molecules.
Figure 61:
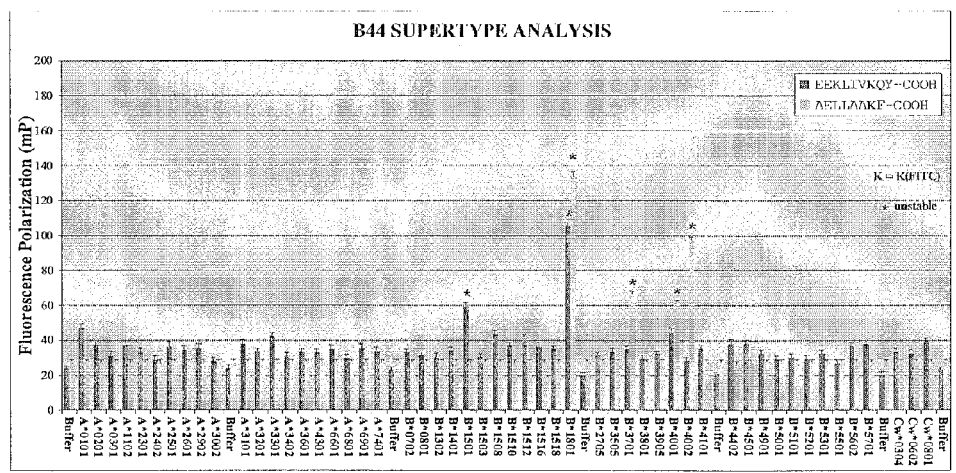
FIG. 61 illustrates the FP response of two B44-like peptides EEKLIVKQY (SEQ ID NO:58) and AELLAAKF (SEQ ID NO:59)) in a binding assay with 53 MHC class I molecules.

For each of the assays shown in FIG. 29, bound fluorescent peptide was displaced from the sHLA molecule using increasing amounts of unlabeled competitor. The top of the curves shown represent a plateau at a value equal to binding in the absence of the competing unlabeled peptide. No competition was observed testing a non-related peptide over the same concentration range (data not shown). The minimum FP values, which are comparable to the values for free labeled peptide, indicate almost complete competition for higher concentrations of the competitor. The $IC_{50}$ values determined within the different tracer systems ranged from 2.48 to 105 µM demonstrating the specificity of these peptide interaction. Moreover, it also shows a dramatic influence of different tracer molecules on the $IC_{50}$ value, which can be critical in the analysis of binding data derived from unrelated systems with different assay parameters. Additional parameters influencing $IC_{50}$ values have been described herein above.

Discussion of Development of FP-Based Peptide Binding Assays

Figure 24:
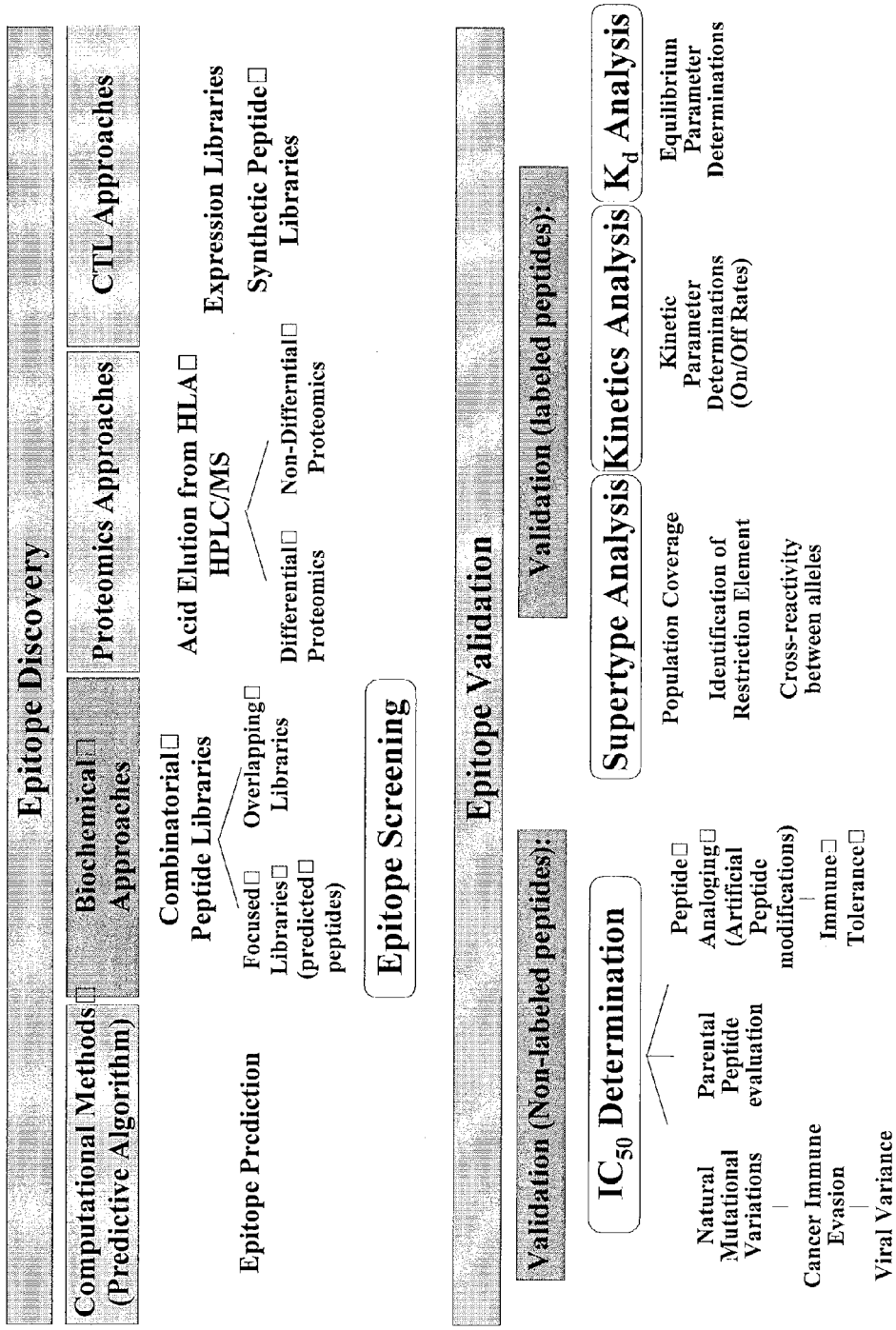
FIG. 24 illustrates epitope discovery and validation tools. The upper part of the scheme summarizes various methods currently applied in CTL-epitope discovery. The lower part shows approaches feasible for epitope validation using FP-based technologies, which are subdivided into systems using non-labeled versus labeled peptides as validation objects. Methodologies, which use standardized FP-based peptide binding assays for analysis, are circled.

Epitopes are the most concise piece of information required by the T cell to generate an immune response. Since it is the peptide-MHC interaction that serves to flag the T cell response, and only certain peptides fit each MHC, the problem of selecting the right peptides has been considered a major obstacle to the development of epitope-based vaccines and/or therapeutics. Therefore, much effort has been directed towards investigating the interactions between MHC proteins and their respective peptide ligands. As such, a body of knowledge enhancing the ability to identify and design peptides that bind across many HLA types has emerged over the past decade, and many different methodologies have been reported (FIG. 24).

A common approach for the identification of tumor antigen/virus-derived sequences recognized by CTLs consists of screening cDNA-based expression libraries or various forms of combinatorial synthetic peptide libraries in a cytotoxicity assay format. In parallel, proteomic approaches use high-performance liquid chromatography fractionation and mass spectrometry sequencing for identification of MHC peptides eluted from normal cells of specific tissues or presented by particular MHC alleles. This nondifferential method can also be used for analysis of peptides recovered from primary tumor cells and from cells involved with pathologies other than cancer, such as autoimmune diseases and viral infections, with the aim of identifying peptides of significance for treating these diseases. More recently, mapping studies were performed with the primary intent of characterizing differences between peptide elution maps, such as between pathogenically infected versus uninfected cell lines. Differential proteomics approaches can also be used for comparisons of MHC peptide patterns induced by mutations, as a result of cancer induction or metastatic progression, induced by changes in cell-growth conditions or stress. Also very common is the utilization of computer-based algorithms, which became quit common to select immunological targets for T-cell recognition. This predictive approach basically looks for nonameric or decameric peptide sequences within a target protein, which may potentially bind to MHC class-I molecules. The matrixes are usually based on a previously determined motif and/or individual ligand sequences. Overall, these procedures are often lengthy, labor intensive, and not free from pitfalls.

In order to be practical for many laboratory environments and amenable to many different peptide/HLA combinations, novel biochemical assay formats suitable for the better characterization of specific HLA/peptide interactions are presented. As summarized in FIG. 24, FP-based assay techniques combined with sHLA technology allow a broad spectrum of applications to be employed in epitope discovery and validation of CTL-based epitopes. A primary application is the screening of large numbers of peptides in order to identify novel epitopes at a selected high threshold concentration with the goal of eliminating peptides, which are not capable to bind to sHLA. Such screening approaches are generally using libraries of synthetic overlapping peptides at lengths between 8-11 amino acids, covering potential tumor-associated proteins or proteins of viral origin. Failing fast and cheap is highly desirable in the drug discovery world, meaning that less time and expense is wasted on compounds that would not have passed the next stage hurdles because of the lack of binding. As seen in FIG. 22, the newly developed epitope screening approach is highly flexible to identify peptides from any protein of interest, making this approach a key factor in early epitope discovery. The measurements provide data of very high precision and reproducibility.

For epitope validation, competition binding assay methodologies have become exceedingly popular for assessing the ability of synthetically defined peptide epitopes to associate with specific HLA class I complexes. High-affinity binding is thought to be a critical factor controlling immunogenicity of peptides. A common approach is the ranking of identified peptides according to their immunogenic potential with the assumption that high-affinity binding peptides are preferred over low-affinity candidates. However, definitions of target identification vary. In general, identification falls along a spectrum ranging from simply cataloging a molecule's existence to ascertaining a therapeutically relevant function in cell and animal models. Identification always comes back to unbiased searches, those that do not skew results toward a certain subset of targets. The quality of anyone data set is such that you can never choose the top one or two and be confident that the selection criteria have actually led you to the one or two best candidates. Therefore, any one of these candidates has generally the potential to be successful as vaccines. In addition, the $IC_{50}$ determination approach is also used to evaluate binding results achieved after introduction of sequence alterations thought to improve the potency of the peptide. Within the epitope discovery process, characterization of peptide and MHC interactions can be achieved using the same plate based assay format with slightly different assay conditions. This validation approach enables the determination of the inhibitory concentration $IC_{50}$ on positively identified peptide candidates (FIG. 21), with the goal to optimize data quality by higher resolution analysis. Furthermore, competition-based approaches are often used not only to validate screening results of parental epitopes but also to evaluate peptides whose sequence has been altered in order to overcome immune tolerance in cancer vaccine design or in determination of escape mutants in viral variance studies.

With the availability of more than 50 of the most common sHLA alleles, direct experimental detection of overlapping peptide-binding capacities (supertype analysis) among this large set of alleles became feasible, reflecting the ability of MHC class-I alleles with genetically more or less distinct peptide-binding sites to share the binding of identical peptides. Classification of allele overlapping peptide-binding specificities may become an important issue in vaccine design, with direct implications concerning population coverage. Dependent upon individual allelic composition, it is import to identify the binding capacity of single peptides to determine their usefulness for treating a larger subset of patients who express the MHC alleles that are capable of binding that specific peptide.

In addition, kinetics and equilibrium analysis deliver further validation for individual peptide epitopes, thus allowing for a direct judgment of the stability of a complex. Overall, these techniques allow the generation of layers of information, from MHC-type, peptide position, size of peptide, peptide sequence, binding constants, to cross-reactivity with other MHC-molecules. Ultimately, MHC epitope mapping will offer access to a large pool of peptide information that can be used to identify lead components for vaccine and therapeutic development.

To establish a real-time assay to directly evaluate the interaction of HLA class I molecules with synthetic peptides, genetically engineered sHLA class I analogues were combined with a state-of-the-art FP-based detection system to monitor molecular binding interactions. FP binding assays are based on the polarization of a FITC moiety covalently bound to a peptide of interest and differ from other types of binding studies in one important regard: they require no steps to separate free from bound and are therefore fast, simple, and accurate. Data acquisition is relatively simple and rapid, and results are of high quality for detailed analysis of HLA/peptide interactions. In order to obtain robust, sensitive and reproducible FP-based binding assay, a detailed analysis of parameters critical for assay standardization was conducted. Initially, a common issue with all fluorescent-based assays is the extent to which the size of the fluorescent label impacts the binding affinity of the peptide ligand. The introduction of a fluorescent label such as FITC involves the addition of 473.4

Da to the molecular structure, which makes the chemical and physical properties of the fluorescent conjugate different from those of the native molecules and may sterically hinder binding of this ligand to its HLA receptor (Wu et al., 1997). Experiments performed using iodine labeled peptides possesses a similar dilemma. Therefore, an important goal in introducing a fluorescent label is to maintain insofar as possible the native reactivity of the candidate molecule. This goal implies both that the functional groups which are involved when the ligand reacts with receptor remain fully active and unimpeded and that the fluorescent label itself does not become involved in the reaction. Several 3D-structures available for distinct peptides bound to the binding groove of various HLA molecules show that bulging out away from the class I binding cleft is sequence dependent (Guo et al., 1992; Parham, 1992). Thus, not every peptide will fold in the same manner indicating that a suitable amino acid position for fluorescent labeling in a particular peptide might not be shared in others. These results are supported by a variety of publications demonstrating the successful attachment of labels at position 5, 6, 7 and 8 in nonamers (Tsomides et al., 1991; Sette et al., 1994a; Khilko et al., 1995; Gakamsky et al., 2000) and position 5, 6, 7, 8 and 9 in decamers (Chen et al., 1994; Sette et al., 1994a; Khilko et al., 1995; van der Burg et al., 1996; Kessler et al., 2003). Ultimately, the interaction of HLA molecules with the functional groups introduced into the unlabeled ligand will have to be empirically determined for each sHLA allele/pFITC combination.

Figure 25:
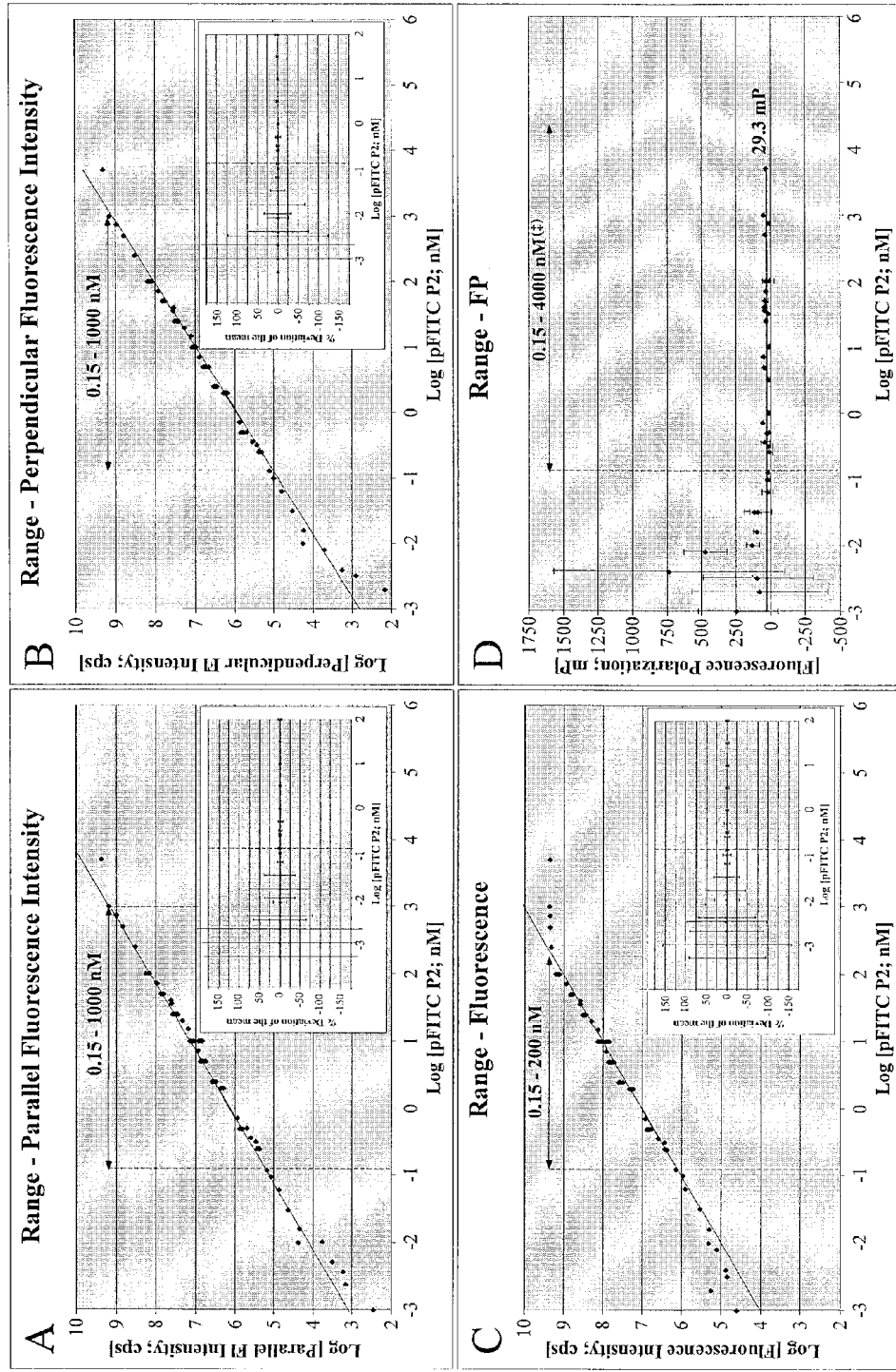
FIG. 25 illustrates a determination of dynamic range and sensitivity of the assay system. (A) Presentation of background-corrected parallel fluorescence intensity data obtained at various pFITC P2 concentrations demonstrating a linear relationship. The insert shows variations around the mean parallel fluorescence intensity values corresponding to the imprecision of the measurements. (B) The same analysis shown in A was performed for perpendicular fluorescence intensity values. (C) Detection of light intensities from the same sample in fluorescence mode without polarization filters. (D) The baseline ratio for FP was monitored over a wide range of pFITC P2 concentrations. This FP value stayed constant up to the highest concentration tested (t) defining a concentration range of over 4 orders of magnitude.

Evaluation of the sensitivity and dynamic range of the assay system showed that FP observations can be comfortably made at nanomolar concentrations, but become more difficult and less reliable at lower concentrations. As seen in FIG. 25, only minimal amounts of fluorescent-labeled peptide ligand are required for measurement. The one limitation in this method originated from the FP reader sensitivity, which only allowed precise detection of fluorescent ligand to concentrations of 0.15 nM and higher which is somewhat lower than mentioned previously (Prystay et al., 2001). It was determined that meaningful data can be acquired over at least 4 orders of magnitude. Furthermore, unlike other assays where the robustness of the assay depends on the magnitude of the signal-to-noise ratio, in FP assays the $\Delta P$ (highest signal-lowest signal) is of major importance. As definition, FP assays in which $\Delta P$ reaches 100 mP are considered "good" assays, whereas assays with $\Delta P$>200 mP are considered robust assays. Within the present study, differences in polarization between free and bound state were usually between 150 to 220 mP which is well above that found in other studies for equally sized molecules (Dedier et al., 2001) thus showing the robustness of the FP-based sHLA/peptide binding approach. In addition, because FP is a ratiometric technique, the assay is not as susceptible to background issues as intensity measurements, and nonspecific binding ratios present in FP are very small compared to radioligand assays (Wu et al., 1997; Prystay et al., 2001). This was also demonstrated by negative control experiments, where the nonspecific binding trace was approximately that for free fluorescent-labeled ligand suggesting insignificant background binding (data not shown).

Moreover, as an often underestimated but critical assay design factor, the contribution of background counts from the buffer system can seriously affect the sensitivity of an assay. As part of the optimization process shown earlier, PBS (pH 7.4) was used as the buffering system supplemented with 0.05% BGG as carrier protein, which not only decreased baseline fluorescence intensity signals but also had the capacity to stabilize sHLA.

Additional compatibility testing showed that peptide solvents such as DMSO and DMF (often used to dissolve hydrophobic HLA peptide candidates) were well tolerated by the system with concentrations up to 5% having no significant effect on maximum polarization. Such findings are particularly important in case for HLA-A*02 peptides which are quite biased toward hydrophobicity, given the hydrophobic peptide-binding pocket of the HLA-A*02 molecules and their preference for hydrophobic residues throughout. Therefore, dissolving HLA peptide candidates to guarantee their bioavailability in the assay is a critical step in successful screening and validation applications because the wrong choice of peptide solvent can lead to inaccurate or complete lack of performance.

One of the first challenges in the development of such a new procedure was the loading of exogenous synthetic peptides into a fully assembled sHLA complex. Since recombinant sHLA class I proteins are loaded with endogenous peptides (Prilliman et al., 1998; Prilliman et al., 1999; Hickman et al., 2003; Hickman et al., 2004), binding of exogenously added peptides can only occur through peptide exchange in which the original endogenous peptide is first released from the HLA binding groove. The concept of very slow dissociation of peptides from assembled class I molecules is consistent with the findings of minimal peptide binding in solution at room temperature (FIG. 12A) as well as under physiological conditions (FIG. 12B). Therefore, if a complex is held together by many bonds, then a fluctuation in which enough bonds are simultaneously ruptured to allow the complex to fall apart will be very rare. To overcome such barriers, a peptide exchange procedure was designed in which the original endogenous peptide is first released from the HLA binding groove by incubating sHLA samples for 15 min at 53° C. Peptide interactions have been described as a function of ionic forces, hydrophobic interactions, and hydrogen bond-type interactions. Thermal treatment can weaken these bonds and lead to enhanced peptide exchange. Temperature dependence of peptide binding to the heavy chain has been demonstrated earlier and is consistent with previous thermal stability studies showing that the degree of heavy chain unfolding is less than 10% at 53° C., and an HLA/peptide complex can exhibit proper refolding even after being heated to 80° C. As demonstrated, the extent of energy employed has to be carefully controlled to ensure that the majority of molecules are capable of restoring proper conformation after the reinstatement of original conditions. Too much denaturation caused irreversible damage as seen by prolonged incubations at higher temperatures (FIG. 12B and FIG. 13). Furthermore, sample volume, activation time and temperature are parameters critical for optimal exchange and have to be individually adjusted (FIG. 26). Other peptide loading methods were described which includes the stripping of peptides through alkaline or mild acid treatment followed by gel filtration and slow refolding at neutral pH (Tanigaki et al., 1993; Stryhn et al., 1996; Jensen et al., 1998; Reinelt et al., 2001). However, the heavy chains prepared through these procedures were found to be unstable and only useable for a short amount of time (Jensen et al., 1998). This makes such stripping procedures ill-suited for more advanced and standardized binding assays since stability has a direct impact on assay quality and reproducibility.

A number of groups have previously reported enhanced peptide binding by cell surface or purified class I molecules in the presence of excess free β2m. Since assembly of class I heavy chains with β2m is accompanied by a characteristic change in conformation of the α1 and α2 domains, it was suggested that β2m in excess can stabilize folding of the α1 and α2 domains of the heavy chain without addition of peptides and consequently enhance peptide binding. In addition, as shown earlier, peptide binding seems not to require β2m dissociation from the HLA heavy chain. Considering the presence of excess β2m combined with the fact that the rate constant of heavy chain association with β2m is much faster than that with peptides, the presence of a majority of heterodimers is very reasonable under such activated conditions. Therefore, heterodimers consisting of heavy chain and β2m may be sufficiently stable to allow reassembly of the A*0201 protein complex with labeled peptides without complete separation into single subunits. In such a reassociation reaction, the formation of a new complex seems to require only a collision between the heterodimer and the labeled peptide. The subsequent formation of just enough weak bonds to keep the complex together as more and more electrostatic interactions, hydrogen bonds, and hydrophobic interactions occur may gradually increase the stability of the complex. Comparison of experiments done with equimolar concentrations of the heavy chain and β2m with those done using an excess of β2m showed that excess β2m concentrations shift the polarization signal toward complex formation and therefore can dramatically enhance peptide binding. An optimal ratio of three β2m molecules per single HLA-A*0201 heavy chain was determined. However, additional testing showed that this dependency may vary depending on the quality of the preparation and the specific allele used (data not shown). Therefore, to maintain optimal performance of the assay, it is critical to adjust β2m concentrations for individual HLA preparations.

It is important to note that in contrast to most traditional binding experiments, it is very common in FP studies to extract $K_d$ values from receptor titrations (Wu et al., 1997; Sun et al., 2002; Zhang et al., 2002). For FP, the experiments are done this way in order to vary the labeled ligand response from the completely free state (lowest polarization value) to the completely bound state (highest polarization value). However, this method necessitates that the system complies with specific conditions in order to assume that the total receptor concentration graphed corresponds to the free receptor concentration, upon which $K_d$ values are based. To meet this constraint, the ligand concentration must be rather low, compared with the $K_d$ value ([Ligand]/$K_d$<<0.1). Higher ligand concentrations tend to bind significant amounts of sHLA leading to receptor depletion. Unfortunately, by facing the problem of receptor depletion within the presented experimental setup, free sHLA concentrations could not be approximated by the total sHLA concentration. Consequently, the system is unable to directly provide $K_d$ values from the saturation curves obtained and the observed effective concentrations (EC$_{50}$) calculated using a dose response model (FIG. 27) are therefore overestimations of the true $K_d$'s. To be able to determine accurate $K_d$ values, binding profiles were therefore assessed holding the concentration of sHLA constant and vary the pFITC ligand (FIG. 28). However, it is again important to keep in mind when performing titration experiments with variable pFITC concentrations the differences between classical and FP systems. Classical saturation isotherms consist of "total binding" values corresponding to the signal from specifically and nonspecifically bound ligand. FP saturation values consist of "total binding" values, which correspond to the signal from specifically and nonspecifically bound ligand as well as the remaining free ligand. Due to the contribution of free ligand to the detected polarization signal, binding values have to be transformed in order to allow proper analysis. As such, a more complicated approach for data analysis is necessary to obtain the $K_d$ for sHLA/pFITC interactions. Applying the recently described FP $K_d$ model from Prystay et al. (Prystay et al., 2001) delivered $K_d$ values which are well in agreement with values obtained using a kinetics approach.

The physiological relevance of the $k_{on}$ of peptides for preformed class I molecules is still unclear, because peptides can bind class I in vitro either during or after assembly of the heavy chain/β2m complex and may interact with free heavy chain prior to association with β2m. In contrast, $k_{off}$ seems to have more physiological relevance. The test results show that the dissociation rate constants for the interaction of sHLA-A*0201 with the derivatized peptides P1, P2, P4, and P5 were in a low range of $1.9 \times 10^{-4}$ to $4.3 \times 10^{-4}$ s$^{-1}$, supporting a relationship between $k_{off}$ rates and immunogenicity as native peptides for P1, P2, and P4 are known to be highly immunogenic. For peptide association, it is generally agreed that the interaction between peptide ligands and HLA molecules is a complex process involving multiple steps between the initial interaction and the fully complex state. Therefore, any process which would alter one or more of these binding steps would result in a change in the apparent association rate constant. Testing of several peptides using sHLA-A*0201 did not reveal major differences in association rate constants [$(1.0-8.7) \times 10^4$ M$^{-1}$s$^{-1}$], which would indicate that all peptides use the same association mechanism. Several studies have reported good correlation between binding kinetics and the degree of T cell activation, but an absolute correlation between binding kinetics and biological effect has still not been experimentally observed.

Overall, the obtained kinetic rate values of the engineered sHLA molecules are remarkably close to those previously obtained for native molecules in human as well as in murine systems, indicating that these soluble heterodimers bind in the same manner as the original molecules expressed on cells. In general, the reassembly pathway for sHLA/peptide complexes under the assay conditions seems to be best described by the binding of peptide to preformed heavy chain/β2m heterodimer as suggested in the K2 step described by Matsumura (1992). Finally, it is evident that labeling at positions P5 and P8 for 9-mers and at positions P5 and P6 for 10-mers, respectively, does not interfere significantly with ligand binding. These results are supported by a variety of publications demonstrating the successful attachment of a label at positions 5, 6, 7, and 8 in nonamer and positions 5, 6, 7, 8, and 9 in decamer peptides.

Competition assays measure the binding of a labeled ligand (also called reference or tracer peptide) in the presence of various concentrations of an unlabeled ligand (also called the competitor or inhibitor) to HLA. As each competitor generates its own binding isotherm, an affinity dependent IC$_{50}$ value, the concentration of competitor necessary to displace 50% of the labeled ligand, can be obtained and directly compared to other values derived from the same system. The advantage of this approach is that, because only a reference ligand is labeled, an adverse effect on affinity potentially caused by the labeling process does not affect the comparison of the unlabeled ligands. This type of assay is not only conceptually simple but also a sensitive and most viable alternative for high-throughput applications. A common practical problem encountered experimentally in a variety of competitive binding studies is the lack of standardization, seldom allowing direct comparison of IC$_{50}$ values between different assay approaches. As visualized in Tables IX and X, differences for IC$_{50}$ determinations between chosen systems range from 2- to 900-fold when comparing FP data to the $^{125}$I-radioligand assay systems and 0.2- to 5-fold when compared to the cellular-based fluorescence assay systems. As such, it seems apparent that the task of $IC_{50}$ determinations by competitive ligand-binding studies requires a more standardized approach than has been initially considered adequate, justifying the further development of such studies, particularly in view of identifying new potential epitopes for vaccine development.

Therefore, as a first step toward a more robust approach, it was attempted to better assess the factors influencing competition binding curves and consequently $IC_{50}$ values. One of the most critical factors found to affect $IC_{50}$ values is the HLA molecule itself, which was identified as generally the most variable assay component. The usage of HLA derived from homozygous cell lines, as lysate or intact cells, is common practice in competition assay studies. However, the problem of establishing suitable models and reliable data for MHC class-I/peptide interactions is vastly complicated when heterogeneity of alleles is present. In some cases, antibodies against an individual allele are available to achieve more specificity but required specialized purification procedures, which are cumbersome, time-consuming, and usually do not deliver sufficient quantities for experiments in a large scale. Another factor that influences the efficiency and reproducibility in studies utilizing HLA-expressing cell lines is the level of class-I expression that generally varies from cell line to cell line. Because the functional response to a ligand is related to receptor density, this variability can lead to a rather wide range of variation, which is not suitable for reliable data comparison. Therefore, the most important advantage of utilizing recombinant sHLA molecules produced in cell lines that do not spontaneously express HLA ("null" cell lines) reside in the capacity to standardize the amount of sHLA employing sHLA preparations of defined specificity and purity, as well as exhibit excellent stability on storage. When the focus was on standardization issues, a striking example of the effect of sHLA concentration on the $IC_{50}$ values of unlabeled peptides is shown in FIG. 19. It is evident that increasing the concentration of sHLA markedly increased the concentration of unlabeled competitor required to inhibit 50% of the binding of FITC-labeled reference peptide resulting in an underestimation of the potency of the displacing ligand. Therefore, to achieve experimental accuracy and reproducibility, it is necessary to work with a standardized quantity of sHLA molecules. The importance of receptor concentration in determining relative potencies of competitive inhibitors has been described earlier.

Furthermore, it was demonstrated that direct binding studies of ligand-receptor interactions of high affinity are subject to artifactual distortions because of the need to utilize high concentrations of the receptor. Therefore, it would be advantageous to design competition experiments such that the $[sHLA]/K_d$ ratio is much lower than 0.1. However, such conditions do not seem experimentally approachable for FP based peptide-binding experiments, because relatively high concentrations of sHLA receptors are needed to yield a significant change in polarization. Consequently, more inhibitor is required to see a 50% drop in the amount of tracer ligand during competition. The result is that the observed $IC_{50}$ values are an overestimation of the true dissociation constant for the unlabeled ligand ($K_i$). Overall, the FP system is affected by severe competitor depletion, explaining why $IC_{50}$ values are several orders of magnitude higher than their $K_i$ values, an effect also seen in other assay systems. Because of this depletion effect, the historically used method of Cheng and Prusoff (1973), transforming $IC_{50}$ values into $K_i$ values, is not applicable because the necessary substitution of total concentrations for free concentrations cannot be made without introducing significant errors in the calculation of $K_i$. In addition, the presence of unknown amounts of endogenous, class-I-associated peptides that could potentially compete with the tracer and test peptide during the course of the assay would even further complicate such mathematical transformations. Nevertheless, results derived from dose-response curves remain extremely useful in comparing relative affinities of ligands to the HLA receptor and in determining whether the ligand of interest in a series of compounds can cause the same maximal response (indicative of a closely similar interaction with the recognition site) as other ligands.

In addition to the effect of the HLA concentration, variations in the choice of the tracer peptide and the inconsistent usage of tracer concentrations are also contributing factors for inconsistent data output. The impact of different reference peptides on $IC_{50}$ values shown in FIG. 17 clearly indicates that the development of a standardized assay necessitates the consistent usage of the same reference peptide to deliver reproducible results. As such, a critical initial step toward development of any sHLA assay is the choice of a single FITC-labeled peptide candidate able to specifically bind to the allele of interest. Because of the specific nature of competition assays, the selection process for a suitable tracer involves considerations relating more to the chemical rather than the biological nature of the candidate. Because pFITC-labeled reference peptides are not under investigation in these assays, maintaining the native reactivity of the candidate reference peptides was not necessary. Therefore, to achieve most optimal assay performance qualities, the highest priorities are normally given to features such as stability and affinity of the design, as well as dynamic range of the polarization signal allowing sensitive detection of a small decrease in polarization upon the addition of a competitor peptide. Extensive analysis showed that the pFITC ligand ALMDKVL-K(FITC)-V (P5) (SEQ ID NO:27), an artificially designed peptide whose primary sequence was derived from sequence pools of naturally processed peptides, best met the requirements for an optimal A*0201 tracer candidate by showing a very high stability and a unique dynamic range of over 215 mP.

Furthermore, an optimal pFITC reference concentration had to be selected, to ascertain sensitivity but also guaranteeing maximal dynamic range. Unlike classical binding curve profiles, FP signals are greater for low ligand concentration because both the bound and free fluorescent ligand contribute to the final signal. Consequently, to achieve maximal change in polarization, it is necessary to use low fluorescent ligand concentrations because increasing pFITC concentrations would require increasing "free" sHLA to ensure that the same fraction of ligand is bound. Therefore, a low concentration of 1 nM FITC-labeled peptide was chosen, which enables a high ratio between maximum and minimum FP signals and also displays low standard deviation values. To control the accuracy of all fluorescent peptide concentrations used within this study, concentration values were normalized by comparing the molar fluorescence intensity of each fluorophore labeled peptide with the FITC fluorophore molecule itself. The importance of this task should not be underestimated, because inaccurate assignment of concentrations can cause high $IC_{50}$ fluctuations. As shown in FIG. 18, applying higher pFITC concentrations took larger concentrations of unlabeled peptide to compete for half of the binding sites and therefore increased the $IC_{50}$ values. According to the steepness of the regression line, it became obvious that a ±1 nM variance in concentration will cause a ±627 nM variance in the $IC_{50}$ value.

Another important step of the present invention besides standardization was to further explore the binding specificity of the HLA A*0201-restricted FP-based competition assay. For this reason, a panel of well-defined HLA class-I ligands from various sources covering a broad range of binding affinities was tested (Table IX). These peptides were almost all of viral origin except for a single peptide derived from an RNA dependent helicase p72. Results showed that, in all cases, the previously known A*0201 specificity was confirmed. More importantly, the assay was capable of measuring $IC_{50}$ values over a range of 4 orders of magnitude (from 500 to 365,000 nM), quantitatively characterizing the binding strength of various existing sequences. Because dose response curves are unable to confirm or disprove any mode of interaction of peptides with sHLA, they are only useful in comparing relative affinities of ligands with the HLA receptor as well as determining whether the ligand of interest in a series of compounds can cause the same maximal response (indicative of a closely similar interaction with the recognition site) as other peptides. Therefore, a common approach for peptide evaluation is the quantitative ranking of identified peptides according to arbitrarily defined categories along a spectrum of high-, medium-, and low-affinity binding to ascertain a therapeutically relevant function in cell and animal models. Built upon existing models earlier defined by Sette et al. and van der Burg et al., an FP-based $IC_{50}$ value classification scheme was created (Table X). When the focus was on the correlation between peptide-binding affinity and immunogenicity, all control peptides selected with known CTL activity showed, as expected, a high to medium-high affinity to sHLA-A*0201. Among the viral controls, the HBV-derived epitope FLPSDFFPSV (SEQ ID NO:28) was found to display very high-affinity values. As one of the most referenced peptides found in the literature, FLPSDFFPSV (SEQ ID NO:28) is known for high-affinity binding to A*0201 as well as the ability to induce potent and specific CTL responses. Additional members of the high-affinity category were the peptides SLYNTVATL (SEQ ID NO:36), another well studied HIV-derived CTL epitope, and the influenza matrix peptide GILGFVFTL (SEQ ID NO:32), found to be a major target of influenza-specific CTL, both in humans and in HLA-A2 transgenic mice.

As a final step in validating the FP system of the present invention, $IC_{50}$ determinations were compared to the two quantitative assay systems most commonly referred to in the literature, the direct cell free $^{125}$I-radioligand assay and the cellular-based fluorescence assay. A significant correlation between the logarithm of the $IC_{50}$ values from the FP-based system of the present invention and values from the two reference systems was found by linear regression analysis (FIG. 24). During analysis, some outlier values were noted for both systems, a discrepancy certainly expected considering the selection of affinity data from independent assay sources. As such, single differences found in affinity might rather be due to the lack of normalization in obtaining binding values as discussed above, which resembles a current problem in analysis of competition data between individual assay systems. In addition, the solubility of the peptide as well as the challenge of accurate weighing of solid peptides may further contribute to the inaccurate determination of binding values. Particularly, dissolving peptides is a critical step because the wrong choice of solvents and methodology can lead to inaccurate or complete lack of performance. As described earlier within the text, the usage of DMSO or DMF, which are widely accepted in many end-use applications for peptides, seems most appropriate for biochemical peptide-binding assay procedures. Nevertheless, results obtained clearly suggest that accurate assessment of peptide binding can be obtained by using the novel FP-based assay procedure of the present invention.

In conclusion, several lines of evidence, both at the biological and functional level, emphasize the biologic relevance of peptide-binding assays in the identification and evaluation of potential peptide candidates. The binding assays described and claimed herein comprise a number of significant advantages compared to existing other HLA class-I binding assays. The most important features are the excellent reproducibility and high sensitivity. Good reproducibility is a key parameter in screening extensive sets of peptides for their affinity to HLA, and crucial information is derived from comparisons of various peptides. Furthermore, FP is unique among methods used to analyze molecular binding because it gives a direct, nearly instantaneous measurement of a peptide tracer's bound/free ratio in solution. A truly homogeneous technique, which does not require the separation of bound and free species, makes the assay a very simple one-step procedure, which is particularly appropriate for high-throughput screening where all reagents remain in solution. Such assays are easily automated and have the ability to rapidly screen whole libraries for peptide candidates. Methods that depend on separation are not only more time-consuming, but they also disturb the reaction equilibrium and therefore prevent accurate quantification of binding. In addition, it is worthwhile to note that the assay is nonradioactive and can thus be performed in virtually any laboratory without the risk of radioactive contamination. With the utilization of purified, high-quality sHLA molecules, which are available in large quantities, this assay exceeds the current expectations of a quantitative peptide/HLA binding assay. These attributes will help to address critical roadblocks and knowledge gaps that currently constrain rapid progress in cellular immunotherapy by offering new possibilities for the identification and validation of an ever-burgeoning number of immunologically active peptide epitopes.

The concept of the assays of the present invention can be adapted for basically every HLA class-I allele of interest (FIGS. 30-55). Although the data presented herein were generated using sHLA-A*0201, additional studies indicate that this approach works equally well with other sHLA alleles. Numerous significant MHC restricted epitopes have already been defined for B*0702, and more studies are on the way. Therefore, the present invention is also an instruction for the development of class-I binding assays that are still lacking. This assay's capacity for high-throughput evaluation of peptide/HLA interactions, coupled with the ability of the immune system to recognize virus-infected or cancerous cells, will open new possibilities to identify an ever-burgeoning number of immunologically active peptide epitopes for the development of vaccines to treat or prevent various types of infectious diseases or cancers. Furthermore, the FP assay has great potential to provide new database information and help to increase missing knowledge, which can be utilized for the development of more sophisticated algorithms to predict and quantify the binding affinity to HLA class-I molecules.

Epitope Specific Supertyping Analysis

There are many different major histocompatibility complex (MHC) molecules, and these MHC molecules differ from person to person in the population. Particular MHC molecules bind peptide constituents that are quite like the peptides that bind another MHC molecule; particular MHC molecules bind peptides that are somewhat like the peptides that bind another MHC molecule; and particular MHC molecules bind peptides unlike the peptides that bind another MHC molecule. A spectrum or gradient of MHC molecules therefore exists in terms of peptide binding.

Understanding how MHC molecules do or do not overlap in their binding of peptides is key to the successful development of peptide and antigen based vaccines and immune therapeutics. Therapies and vaccines designed to encode or include peptide epitopes that are capable of binding to MHC molecules will only succeed if the various MHC molecules can bind the intended therapeutic or vaccine peptide. Differences in MHC molecules from person to person can interfere with the success of vaccines and immune therapies that encode or include peptide epitopes.

As MHC molecules represent a spectrum or gradient of differences in the peptides bound, it is possible to identify and subsequently include representative MHC molecules at different points in this gradient. If a vaccine or immune therapeutic includes peptides that bind to selected MHC molecules that are representative of enough points in the peptide binding gradient, then all MHC molecules, and therefore all individuals, in the gradient will be served by the vaccine or immune therapy.

The present invention includes a method of testing peptides that bind to various MHC molecules can be utilized to identify MHC molecules that represent overlapping points in the MHC peptide binding gradient. Using the peptide binding assay of the present invention to identify overlapping points in the spectrum of MHC peptide binding, the design of vaccines and immune therapies that are based on peptide binding to all MHC in the population can be facilitated. Herein is a way to test various peptides in multiple MHC molecules to identify a series of MHC molecules that constitute all the MHC molecules in the population is described. A vaccine or immune therapy that encodes or includes peptides that bind to this continuum of MHC molecules will then work in the entire population.

Past efforts have used the term "supertypes" to describe a system of grouping functionally similar MHC molecules. The terms "supertype", "supertypes" and "supertyping" as used herein will be understood to describe functionally overlapping clusters of MHC molecules located in the spectrum of MHC molecules that bind different peptides. The peptide binding assay of the present invention can readily identify functionally overlapping supertypes or supergroups and therefore facilitate the implementation of vaccines and immune therapies that encode or include peptides that will bind to all MHC molecules in a population. Thus, the goal of using sHLA in a peptide binding assay for supertypes is to determine what the MHC peptide binding gradient looks like and where the various MHC molecules fall in relation to one another in this gradient. Such knowledge will guide the design and implementation of vaccines and immune therapies that function in the context of many different MHC molecules.

Classification of major histocompatibility complex (MHC) molecules into functional supertypes on the basis of overlapping peptide-binding specificities has become an important issue, with direct implications for the development of epitope-based vaccines with wide population coverage. Unfortunately, direct experimental validation of multiple members of these super-types has been tremendously difficult because of lack of high quality human leukocyte antigen (HLA) molecules. In the present invention, a direct biochemical approach for classifying HLA molecules into super-types using recombinant soluble HLA (sHLA) proteins is described. Screen analysis showed various degrees of overlapping peptide binding capacities among the alleles tested, reflecting the ability of MHC class I alleles with genetically more or less distinct peptide binding sites to share the binding of identical peptides. As a result of the present invention, it was possible to not only able to better define super-type classification but also to include additional alleles not currently characterized. Taken together, this novel HLA screening procedure represents a versatile tool for super-type-binding analysis and will have profound use in the understanding of antigenic peptide selection, degeneration, and discrimination during T-cell mediated immune responses. A complete knowledge of this phenomenon finds utility in epitope design for the development of HLA based vaccines and immunotherapeutics.

Among the various elements of the immune system, T lymphocytes are probably the most adept to recognize and eliminate cells expressing foreign or tumor-associated antigens (TAAs). Cytotoxic T lymphocytes (CTLs) express the CD8+ cell surface marker and are specialized at inducing lysis of the target cells with which they react via the perforin/granzyme and/or the Fas/Fas-L pathways. The T-cell receptor (TCR) for antigen of CTLs binds to a molecular complex on the surface of the target cell formed by small peptides (8-11 residues) derived from processed viral antigens or TAAs, which associate with MHC class I molecules. Peptides are bound within a specific MHC binding groove, the shape and characteristics of which results in the binding of specific subsets of peptides sharing a common binding motif. As a consequence of TCR stimulation of naive CTLs by peptide/MHC complexes on antigen presenting cells, the CTLs mature into effector killer cells capable of lysing tumor or virus infected cells that express the corresponding peptide/MHC class I complex. Therefore, therapeutic vaccines based on the activation of CTLs hold a clear promise for the diagnosis and treatment of infectious, autoimmune, allergic, and neoplastic diseases.

In order for this promise to be realized, however, the scientific community must overcome an array of obstacles. A major challenge in the vaccine development process relates to the limitations on patient population coverage imposed by the rules of MHC restriction. MHC genes resemble the most polymorphic system in mammals, generated by systematic recombinatorial and point mutation events. As such, hundreds of different HLA types exist throughout the world's population, resulting in a large immunological diversity. Since class I expression is codominant, a single person may display up to six different HLA class I molecules upon his or her nucleated cells.

Depending upon allelic composition, it is import to identify the binding capacity of single peptides in order to determine its usefulness for treating a larger subset of patients who express the MHC allele product that is capable of binding that specific peptide. For that reason, the present invention focused on identifying peptide cross-reactivity patterns among the most common MHC class I alleles of the human population selected according to HLA gene frequencies in the North American population.

Methods:

Multiple-specificity screening of FITC-labeled peptides: To approach the problem of super-type analysis, a novel, state-of-the-art screening assay was developed that utilizes high quality soluble HLA and the technique of fluorescence polarization (FP). This assay combination allows the direct measurement of the ratio between free and bound labeled ligand in solution without any separation steps. The technique of FP is based on the principal that if a fluorescent-labeled peptide binds to the sHLA molecule of higher molecular weight, polarization values will increase due to the slower molecular rotation of the bound probe.

To elaborate peptide cross-reactivity among MHC class I molecules, a panel of 53 single-specificity sHLA receptors was screened for their binding capacity towards a series of fluorescent-labeled peptide ligands. During the process, each peptide candidate (2 nM) was incubated with 100 μg/ml of activated sHLA and peptide/MHC interaction was monitored over time on the Analyst™ AD Assay Detection System (Molecular Devices; Sunnyvale, Calif.). For optimal signal output, $b_2$-microglobulin was added in 2× molar excess of the used sHLA concentration. For all preparations, 1×BGG/PBS was used as buffer. The use of appropriate controls allowed accurate estimation of specific polarization. Specific control groups included: (a) [protein only], (b) [tracer only] and (c) [buffer only]. Data analysis was performed using the software package Prism (GraphPad), by fitting all data points to a mono-exponential association model using computer-aided, nonlinear regression analysis. Final polarization levels indicate the extent of binding to each allele.

Figure 63:
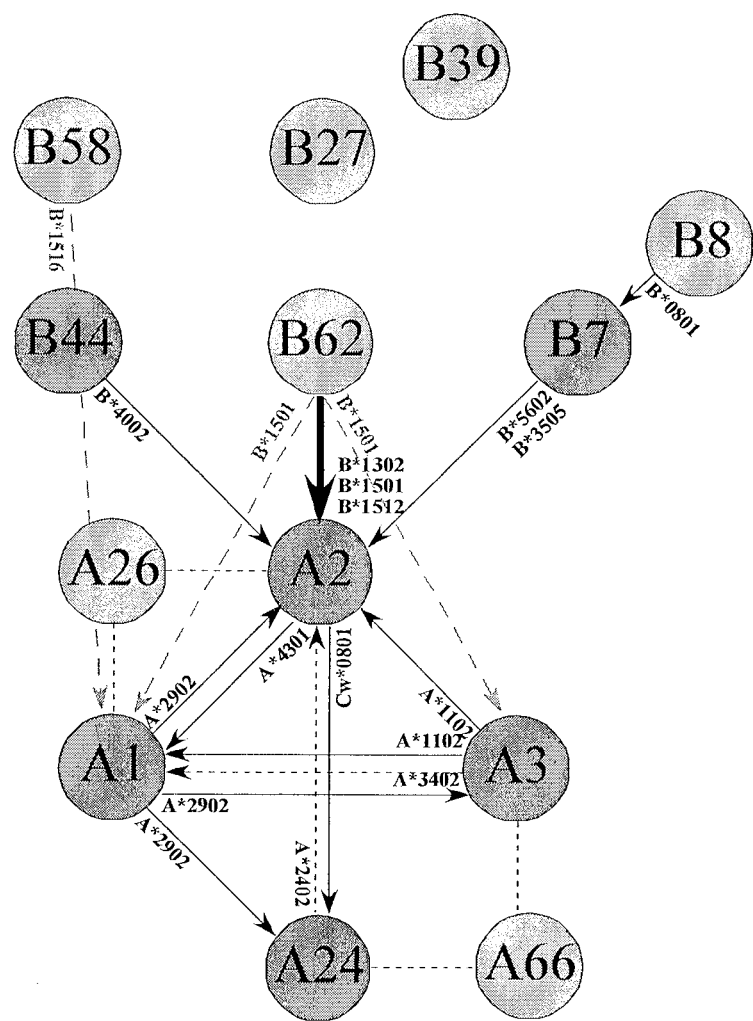
FIG. 63 illustrates a proposed map of relationships between common HLA alleles.

Results/Discussion:

A major challenge in peptide-based vaccine design is the integration of polymorphic diversity into epitope discovery by identification of promiscuous (supermotif bearing) peptides that bind a sufficient array of HLA molecules to give broader population coverage. To overcome this challenge a new screening strategy was developed that utilizes a novel FP-based peptide binding assay which directly reveals the binding spectrum of individual FITC-labeled peptide epitopes towards 53 MHC class I molecules. A variety of FITC-labeled peptides were evaluated which were known to be related to one of the six common HLA alleles, A1, A2, A3, A24, B7 and B44 (see FIGS. 56-61). Screening results obtained were classified into super-types (FIG. 62), as originally suggested by Sette and Sidney (1999), and found to disclose an extended picture of the currently proposed system (FIG. 63).

A1 Super-type (FIG. 56): Screening with two A1-like peptides showed characteristic binding interactions with various A-alleles previously assigned to this super-type. Most significant within this super-type is a strong correlation between HLA-alleles A*0101 and A*2902, showing the highest reactivity and stability. To mention is that A*2902 seems to possess more binding flexibility as it was also capable of interacting with A2-, A3-, and A24-like peptides. HLA A*3601 also exhibited a high binding activity but was found to be partially unstable. Furthermore, examination of HLA-A alleles A*3402, A*3601, and A*4301 for which no peptide binding motif is known, showed significant reactivity towards A1-like peptides, confirming their assignment to the A1 super-type. Minor reactivities for A*2601 was found for A1- and A2-like peptides making an assignment to one or the other rather difficult. As suggested by others, it seems likely that A26 resembles a new super-type, sharing overlap capability between A1 and A2 super-types. Overlap capabilities with B-alleles was rather limited.

A2/B62 Super-type (FIG. 57): The most prominent result in screening of A2-related peptides was the strong correlation to B62 assigned MHC-alleles consisting of HLA-alleles B*1302, B*1501 and B*1512. Particularly, the strong binding of all peptides to B*1302 suggests an A2-like motif for this currently not characterized allele. In addition, Cw*0801 shows an equally strong binding pattern most likely belonging to the A2/B62 super-type combination. Also characteristic for the A2 super-type is an extended reactivity overlap towards other A- and B-alleles from other super-type groupings, which is less extensive in other super-types. These findings make A*0201 studies even more valuable by vastly enhancing the prospective feasibility of peptide-based vaccination approaches with even greater population coverage than originally thought.

A3 Super-type (FIG. 58): The definition of this super-type provided herein largely overlaps with earlier definitions and is characterized by a strong correlation between A*0301 and A*1102 seen for all peptides tested. Interestingly, it was found that the peptide GRAFVTIKK (SEQ ID NO:44), originally thought to bind B*2705, did not bind to alleles listed for the B27 super-type, rather showing a distinct A3 pattern with high A*1102 binding capacity. Furthermore, definition of super-types for HLA molecules using clustering of specificity matrices by Lund et al. 2004 suggested a further split of B27 into B27 and B39. However, additional super-type analysis experiments are needed to confirm this hypothesis.

A24 Super-type (FIG. 59): The A24 super-type pattern is accompanied with strong reactivities toward A*2402 and A*2301 as originally seen. Additional binding reactions were seen with A*2902, A*6601 and Cw*0801 but also interactions to B-type alleles B*1501 and B*4501. HLA-allele A*3002, originally assigned to the A24 super-type was not reacting with the test panel. Recent study suggests, however, that this allele should be re-assigned to the A1 super-type. During the analysis, A*3002 did also not interact with A1-like peptides leaving a final assignment unresolved.

B7 Super-type (FIG. 60): Testing B7-like peptide candidates showed a similar high degree of overlap to the originally defined B7 super-type as seen for A3. All motifs within this group were characterized and feature proline in position 2 and hydrophobic residues at the C-terminus.

B44 Super-type (FIG. 61): Finally, the B44 super-type was originally defined on the basis of a shared specificity for peptides with negatively charged residues in position 2 and hydrophobic residues at the C terminus. Within this super-type B*1801 showed highest reactivity followed by B*4002 and B*4001 following closely the suggested motifs for this super-type. No cross-reactivity was detected towards HLA B*4402.

The capacity of this new assay design to accurately determine the extent of peptide binding cross-reactivity among 53 single-specificity alleles was evaluated by investigating multiple FITC-labeled peptides of various origins. The majority of peptide candidates were capable of binding with a broad range of affinities to multiple HLA class I molecules. In addition, peptides were judged to be highly promiscuous, showing unique reaction patterns toward the allele set used. HLA molecules belonging to the same super-type frequently bound multiple members but not in a predictable fashion. These results clearly demonstrate that super-type classification does not hold the promise of delivering a definitive answer of cross-reactivity capabilities. Even individual peptides generally stay within a certain super-type, but the grouping does not indicate which allele will actually be capable of efficient binding. As such, direct evaluation by an experimental approach is mandatory to accurately determine population coverage. This approach suggests that broadly cross-reactive peptide epitopes can be identified and greatly enhance the effectiveness of future vaccine designs by providing a more extensive population coverage.

Thus, in accordance with the present invention, there has been provided a method for assaying epitope binding to HLA that includes methodology for producing and manipulating Class I and Class II MHC molecules from gDNA as well as methodology for directing discovering epitopes unique to infected or tumor cells that fully satisfies the objectives and advantages set forth herein above. Although the invention has been described in conjunction with the specific drawings, experimentation, results and language set forth herein above, it is evident that many alternatives, modifications, and variations will be apparent to those skilled in the art. Accordingly, it is intended to embrace all such alternatives, modifications and variations that fall within the spirit and broad scope of the invention.

What is claimed is:

1. A method of assaying the affinity of a peptide of interest for binding to an individual MHC class I molecule, the method comprising the steps of:
   labeling a first peptide with a fluorescent label, wherein the first peptide is known to bind to a specific MHC class I molecule;
   activating individual soluble, specific MHC class I molecules by heating the individual soluble, specific MHC class I molecules for about 15 minutes at about 53° C. to cause the individual soluble, specific MHC class I molecules to release any endogenous peptide loaded therein, thereby activating the individual soluble, specific MHC class I molecules;
   mixing the labeled first peptide and the activated individual soluble, specific MHC class I molecules together with different concentrations of a second peptide, wherein the second peptide is a peptide of interest, to provide individual soluble, specific MHC class I molecule-labeled first peptide complexes and individual soluble, specific MHC class I molecule-second peptide complexes, wherein the individual soluble, specific MHC class I molecule-first peptide complexes are detectable by fluorescence polarization; and
   determining a binding affinity of the peptide of interest for the individual soluble, specific MHC class I molecule by determining an inhibitory concentration of the second peptide that inhibits 50% binding of the first peptide to the individual soluble, specific MHC class I molecule.

2. The method of claim 1 wherein, in the method of providing individual soluble, specific MHC class I molecules, the individual soluble, specific MHC class I molecules are produced by the method comprising the steps of:
   obtaining genomic DNA or cDNA encoding at least one MHC class I molecule;
   identifying an allele encoding an individual MHC class I molecule in the genomic DNA or cDNA;
   PCR amplifying the allele encoding the individual MHC class I molecule in a locus specific manner such that a PCR product produced therefrom encodes a truncated, soluble form of the individual MHC class I molecule;
   cloning the PCR product into an expression vector, thereby forming a construct that encodes the individual soluble, specific MHC class I molecule;
   transfecting the construct into a cell line to provide a cell line containing a construct that encodes an individual soluble, specific MHC class I molecule, the cell line being able to naturally process proteins into peptide ligands capable of being loaded into antigen binding grooves of MHC class I molecules;
   culturing the cell line under conditions which allow for expression of the individual soluble, specific MHC class I molecules from the construct, such conditions also allowing for endogenous loading of a peptide ligand into the antigen binding groove of each individual soluble, specific MHC class I molecule prior to secretion of the individual soluble, specific MHC class I molecules from the cell; and
   isolating the secreted individual soluble, specific MHC class I molecules.

3. The method of claim 2 wherein the construct further encodes a tag which is attached to the individual soluble, specific MHC class I molecule and aids in isolating the individual soluble, specific MHC class I molecule.

4. The method of claim 3 wherein the tag is selected from the group consisting of a HIS tail and a FLAG tail.

5. A method of assaying the affinity of a peptide of interest for binding to an individual HLA class I molecule, the method comprising the steps of:
   (a) activating a pool of isolated, functionally active, recombinantly produced, secreted, individual soluble HLA class I trimolecular complexes for peptide exchange by application of thermal energy to thermodynamically destabilize the trimolecular complexes and thus allow the trimolecular complexes to participate in peptide exchange, each secreted, recombinant HLA class I trimolecular complex produced in a human cell line and comprising a recombinantly produced, soluble HLA class I heavy chain, non-covalently associated beta-2-microglobulin, and peptide, wherein the peptide is naturally produced by the human cell line and endogenously loaded into the trimolecular complex by the human cell line, and wherein each complex present in the pool comprises the same truncated, soluble HLA class I heavy chain, and wherein the activation of the trimolecular complexes thermodynamically destabilizes the complexes and thus allows the complexes to participate in peptide exchange;
   (b) mixing together:
      (i) the pool of activated, secreted, recombinant HLA class I trimolecular complexes of (a);
      (ii) a labeled first peptide known to bind to the specific HLA class I molecule of the pool of HLA class I trimolecular complexes; and
      (iii) a second peptide, wherein the second peptide is a peptide of interest; and
      wherein the mixing of (i)-(iii) produces at least one of HLA class I trimolecular complexes containing the labeled first peptide and HLA class I trimolecular complexes containing the second peptide; and
   (c) determining a binding affinity of the second peptide for the specific HLA class I molecule by determining an inhibitory concentration of the second peptide that inhibits 50% binding of the labeled first peptide to the activated soluble HLA class I trimolecular complex.

6. The method of claim 5, wherein the step of activating a pool of isolated, functionally active, recombinantly produced, secreted, individual soluble HLA class I trimolecular complexes for peptide exchange by application of thermal energy is further defined as heating the pool of individual soluble, HLA class I trimolecular complexes for about 15 minutes at about 53° C. to cause the pool of individual soluble, HLA class I trimolecular complexes to release any endogenous peptide loaded therein, thereby activating the individual soluble, HLA class I trimolecular complexes.

7. The method of claim 5, wherein the first peptide is labeled with a radiolabel or a fluorescent label.

8. The method of claim 7, wherein the first peptide is labeled with a fluorescent label, and the HLA class I trimolecular complexes containing the labeled first peptide are identified by fluorescence polarization.

9. The method of claim 8, wherein the fluorescent label is fluorescein isothiocyanate (FITC).

10. The method of claim 8, wherein (i)-(iii) are mixed together in the presence of excess beta-2-microglobulin.

11. The method of claim 10, wherein the ratio of added beta-2-microglobulin to recombinant soluble HLA class I heavy chain is about 3:1.

12. The method of claim 10, wherein (i)-(iii) are mixed together in the presence of bovine gamma globulin.

\* \* \* \* \*

UNITED STATES PATENT AND TRADEMARK OFFICE
CERTIFICATE OF CORRECTION

Page 1 of 1

PATENT NO. : 9,110,080 B2
APPLICATION NO. : 13/116808
DATED : August 18, 2015
INVENTOR(S) : William H. Hildebrand and Rico Buchli It is certified that error appears in the above-identified patent and that said Letters Patent is hereby corrected as shown below:

In the Specification:
Column 41, line 15: Delete "UL" and replace with -- LJL --
Column 45, line 1: Delete "5-globulin" and replace with -- γ-globulin --
Column 48, line 29: Delete "UL" and replace with -- LJL --
Column 59, line 14: Delete "â2m" and replace with -- β2m --
Column 62, line 49: Delete "105" and replace with -- 10.5 --

In the Claims:
Column 93, line 7, Claim 10: Delete "claim 8," and replace with -- claim 5, --

Signed and Sealed this
Twenty-second Day of December, 2015

Michelle K. Lee
*Director of the United States Patent and Trademark Office*

```
                           SEQUENCE LISTING

<160> NUMBER OF SEQ ID NOS: 49

<210> SEQ ID NO 1
<211> LENGTH: 10
<212> TYPE: PRT
<213> ORGANISM: HIV MN-1

<400> SEQUENCE: 1

Glu Gln Met Phe Glu Asp Ile Ile Ser Leu
1               5                   10

<210> SEQ ID NO 2
<211> LENGTH: 9
<212> TYPE: PRT
<213> ORGANISM: Homo sapiens

<400> SEQUENCE: 2

Ile Pro Cys Leu Leu Ile Ser Phe Leu
1               5

<210> SEQ ID NO 3
<211> LENGTH: 10
<212> TYPE: PRT
<213> ORGANISM: Homo sapiens

<400> SEQUENCE: 3

Ser Thr Thr Ala Ile Cys Ala Thr Gly Leu
1               5                   10

<210> SEQ ID NO 4
<211> LENGTH: 8
<212> TYPE: PRT
<213> ORGANISM: Homo sapiens

<400> SEQUENCE: 4

Ala Pro Ala Gln Asn Pro Glu Leu
1               5

<210> SEQ ID NO 5
<211> LENGTH: 9
<212> TYPE: PRT
<213> ORGANISM: Homo sapiens

<400> SEQUENCE: 5

Leu Val Met Ala Pro Arg Thr Val Leu
1               5

<210> SEQ ID NO 6
<211> LENGTH: 9
<212> TYPE: PRT
<213> ORGANISM: Homo sapiens
<220> FEATURE:
<221> NAME/KEY: misc_feature
<222> LOCATION: (5)..(5)
<223> OTHER INFORMATION: n or s
<220> FEATURE:
<221> NAME/KEY: misc_feature
<222> LOCATION: (9)..(9)
<223> OTHER INFORMATION: any amino acid

<400> SEQUENCE: 6

Ala Pro Phe Ile Xaa Pro Ala Asp Xaa
```

```
1               5
```

<210> SEQ ID NO 7
<211> LENGTH: 9
<212> TYPE: PRT
<213> ORGANISM: Homo sapiens

<400> SEQUENCE: 7

```
Thr Pro Gln Ser Asn Arg Pro Val Met
1               5
```

<210> SEQ ID NO 8
<211> LENGTH: 9
<212> TYPE: PRT
<213> ORGANISM: Homo sapiens

<400> SEQUENCE: 8

```
Ala Ala Arg Pro Ala Thr Ser Thr Leu
1               5
```

<210> SEQ ID NO 9
<211> LENGTH: 9
<212> TYPE: PRT
<213> ORGANISM: Homo sapiens

<400> SEQUENCE: 9

```
Met Ala Met Met Ala Ala Leu Met Ala
1               5
```

<210> SEQ ID NO 10
<211> LENGTH: 9
<212> TYPE: PRT
<213> ORGANISM: Homo sapiens

<400> SEQUENCE: 10

```
Ile Ala Thr Val Asp Ser Tyr Val Ile
1               5
```

<210> SEQ ID NO 11
<211> LENGTH: 11
<212> TYPE: PRT
<213> ORGANISM: Homo sapiens

<400> SEQUENCE: 11

```
Ser Pro Asn Gln Ala Arg Ala Gln Ala Ala Leu
1               5                   10
```

<210> SEQ ID NO 12
<211> LENGTH: 10
<212> TYPE: PRT
<213> ORGANISM: Homo sapiens

<400> SEQUENCE: 12

```
Gly Pro Arg Thr Ala Ala Leu Gly Leu Leu
1               5                   10
```

<210> SEQ ID NO 13
<211> LENGTH: 10
<212> TYPE: PRT
<213> ORGANISM: Homo sapiens

<400> SEQUENCE: 13

```
Asn Pro Asn Gln Asn Lys Asn Val Ala Leu
1               5                   10
```

<210> SEQ ID NO 14
<211> LENGTH: 9
<212> TYPE: PRT
<213> ORGANISM: Homo sapiens

<400> SEQUENCE: 14

Arg Pro Tyr Ser Asn Val Ser Asn Leu
1               5

<210> SEQ ID NO 15
<211> LENGTH: 9
<212> TYPE: PRT
<213> ORGANISM: Homo sapiens

<400> SEQUENCE: 15

Leu Pro Gln Ala Asn Arg Asp Thr Leu
1               5

<210> SEQ ID NO 16
<211> LENGTH: 9
<212> TYPE: PRT
<213> ORGANISM: Homo sapiens

<400> SEQUENCE: 16

Gln Pro Arg Tyr Pro Val Asn Ser Val
1               5

<210> SEQ ID NO 17
<211> LENGTH: 8
<212> TYPE: PRT
<213> ORGANISM: Homo sapiens

<400> SEQUENCE: 17

Ala Pro Ala Tyr Ser Arg Ala Leu
1               5

<210> SEQ ID NO 18
<211> LENGTH: 9
<212> TYPE: PRT
<213> ORGANISM: Homo sapiens

<400> SEQUENCE: 18

Ala Pro Lys Arg Pro Pro Ser Ala Phe
1               5

<210> SEQ ID NO 19
<211> LENGTH: 11
<212> TYPE: PRT
<213> ORGANISM: Homo sapiens

<400> SEQUENCE: 19

Ala Ala Ser Lys Glu Arg Ser Gly Val Ser Leu
1               5                   10

<210> SEQ ID NO 20
<211> LENGTH: 7
<212> TYPE: PRT
<213> ORGANISM: Homo sapiens

<400> SEQUENCE: 20

Gly Ser His Ser Met Arg Tyr
1               5

<210> SEQ ID NO 21

-continued

```
<211> LENGTH: 10
<212> TYPE: PRT
<213> ORGANISM: Homo sapiens

<400> SEQUENCE: 21

Lys Leu Gly Glu Phe Tyr Asn Gln Met Met
1               5                   10

<210> SEQ ID NO 22
<211> LENGTH: 9
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: FITC label

<400> SEQUENCE: 22

Ala Leu Met Asp Lys Val Leu Lys Val
1               5

<210> SEQ ID NO 23
<211> LENGTH: 10
<212> TYPE: PRT
<213> ORGANISM: Homo sapiens

<400> SEQUENCE: 23

Phe Leu Pro Ser Asp Lys Phe Pro Ser Val
1               5                   10

<210> SEQ ID NO 24
<211> LENGTH: 9
<212> TYPE: PRT
<213> ORGANISM: Homo sapiens

<400> SEQUENCE: 24

Ser Leu Tyr Asn Lys Val Ala Thr Leu
1               5

<210> SEQ ID NO 25
<211> LENGTH: 9
<212> TYPE: PRT
<213> ORGANISM: Homo sapiens

<400> SEQUENCE: 25

Asn Leu Ser Lys Leu Ser Leu Asp Val
1               5

<210> SEQ ID NO 26
<211> LENGTH: 10
<212> TYPE: PRT
<213> ORGANISM: Homo sapiens

<400> SEQUENCE: 26

Leu Val Phe Gly Lys Glu Val Val Glu Val
1               5                   10

<210> SEQ ID NO 27
<211> LENGTH: 9
<212> TYPE: PRT
<213> ORGANISM: Homo sapiens

<400> SEQUENCE: 27

Ala Leu Met Asp Lys Val Leu Lys Val
1               5
```

```
<210> SEQ ID NO 28
<211> LENGTH: 10
<212> TYPE: PRT
<213> ORGANISM: Homo sapiens

<400> SEQUENCE: 28

Phe Leu Pro Ser Asp Phe Phe Pro Ser Val
1               5                   10

<210> SEQ ID NO 29
<211> LENGTH: 9
<212> TYPE: PRT
<213> ORGANISM: Homo sapiens

<400> SEQUENCE: 29

Tyr Leu Leu Pro Ala Ile Val His Ile
1               5

<210> SEQ ID NO 30
<211> LENGTH: 9
<212> TYPE: PRT
<213> ORGANISM: Homo sapiens

<400> SEQUENCE: 30

Tyr Met Asp Asp Val Val Leu Gly Ala
1               5

<210> SEQ ID NO 31
<211> LENGTH: 9
<212> TYPE: PRT
<213> ORGANISM: Homo sapiens

<400> SEQUENCE: 31

Tyr Leu Val Ser Phe Gly Val Trp Ile
1               5

<210> SEQ ID NO 32
<211> LENGTH: 9
<212> TYPE: PRT
<213> ORGANISM: Homo sapiens

<400> SEQUENCE: 32

Gly Ile Leu Gly Phe Val Phe Thr Leu
1               5

<210> SEQ ID NO 33
<211> LENGTH: 9
<212> TYPE: PRT
<213> ORGANISM: Homo sapiens

<400> SEQUENCE: 33

Gly Leu Tyr Ser Ser Thr Val Pro Val
1               5

<210> SEQ ID NO 34
<211> LENGTH: 9
<212> TYPE: PRT
<213> ORGANISM: Homo sapiens

<400> SEQUENCE: 34

Leu Leu Ser Ser Asn Leu Ser Trp Leu
1               5

<210> SEQ ID NO 35
```

```
<211> LENGTH: 9
<212> TYPE: PRT
<213> ORGANISM: Homo sapiens

<400> SEQUENCE: 35

Gly Leu Ser Arg Tyr Val Ala Arg Leu
1               5

<210> SEQ ID NO 36
<211> LENGTH: 9
<212> TYPE: PRT
<213> ORGANISM: Homo sapiens

<400> SEQUENCE: 36

Ser Leu Tyr Asn Thr Val Ala Thr Leu
1               5

<210> SEQ ID NO 37
<211> LENGTH: 9
<212> TYPE: PRT
<213> ORGANISM: Homo sapiens

<400> SEQUENCE: 37

Ile Leu Lys Glu Pro Val His Gly Val
1               5

<210> SEQ ID NO 38
<211> LENGTH: 9
<212> TYPE: PRT
<213> ORGANISM: Homo sapiens

<400> SEQUENCE: 38

Asn Leu Gln Ser Leu Thr Asn Leu Leu
1               5

<210> SEQ ID NO 39
<211> LENGTH: 9
<212> TYPE: PRT
<213> ORGANISM: Homo sapiens

<400> SEQUENCE: 39

Asn Leu Val Pro Met Val Ala Thr Val
1               5

<210> SEQ ID NO 40
<211> LENGTH: 9
<212> TYPE: PRT
<213> ORGANISM: Homo sapiens

<400> SEQUENCE: 40

His Leu Glu Ser Leu Phe Thr Ala Val
1               5

<210> SEQ ID NO 41
<211> LENGTH: 9
<212> TYPE: PRT
<213> ORGANISM: Homo sapiens

<400> SEQUENCE: 41

Asp Leu Val His Phe Ala Ser Pro Leu
1               5

<210> SEQ ID NO 42
<211> LENGTH: 9
<212> TYPE: PRT
```

<213> ORGANISM: Homo sapiens

<400> SEQUENCE: 42

Ile Pro Ser Tyr Lys Lys Leu Ile Met
1               5

<210> SEQ ID NO 43
<211> LENGTH: 10
<212> TYPE: PRT
<213> ORGANISM: Homo sapiens

<400> SEQUENCE: 43

Phe Leu Pro Ser Asp Tyr Phe Pro Ser Val
1               5                   10

<210> SEQ ID NO 44
<211> LENGTH: 9
<212> TYPE: PRT
<213> ORGANISM: Homo sapiens

<400> SEQUENCE: 44

Gly Arg Ala Phe Val Thr Ile Lys Lys
1               5

<210> SEQ ID NO 45
<211> LENGTH: 9
<212> TYPE: PRT
<213> ORGANISM: Homo sapiens

<400> SEQUENCE: 45

Ala Thr Asp Phe Lys Phe Ala Met Tyr
1               5

<210> SEQ ID NO 46
<211> LENGTH: 9
<212> TYPE: PRT
<213> ORGANISM: Homo sapiens

<400> SEQUENCE: 46

Ile Ala Asp Met Gly His Leu Lys Tyr
1               5

<210> SEQ ID NO 47
<211> LENGTH: 9
<212> TYPE: PRT
<213> ORGANISM: Homo sapiens

<400> SEQUENCE: 47

Thr Leu Trp Ala Gly Ile Leu Tyr Lys
1               5

<210> SEQ ID NO 48
<211> LENGTH: 9
<212> TYPE: PRT
<213> ORGANISM: Homo sapiens

<400> SEQUENCE: 48

Ser Leu Phe Arg Ala Val Ile Thr Lys
1               5

<210> SEQ ID NO 49
<211> LENGTH: 9
<212> TYPE: PRT
<213> ORGANISM: Homo sapiens

-continued

```
<400> SEQUENCE: 49

Asp Leu Val His Phe Ala Ser Pro Leu
1               5
```